(12) United States Patent
Breves et al.

(10) Patent No.: US 7,300,782 B2
(45) Date of Patent: Nov. 27, 2007

(54) GLYCOSYL HYDROLASES

(75) Inventors: Roland Breves, Mettmann (DE);
Karl-Heinz Maurer, Erkrath (DE);
Jürgen Eck, Heppenheim (DE);
Patrick Lorenz, Lorsch (DE); Holger Zinke, Zwingenberg (DE)

(73) Assignee: B.R.A.I.N. Biotechnology Research and Information Network AG, Zwingenberg (DE)

( * ) Notice: Subject to any disclaimer, the term of this patent is extended or adjusted under 35 U.S.C. 154(b) by 106 days.

(21) Appl. No.: 10/872,874

(22) Filed: Jun. 21, 2004

(65) Prior Publication Data

US 2005/0003419 A1    Jan. 6, 2005

Related U.S. Application Data

(63) Continuation of application No. PCT/EP02/14210, filed on Dec. 13, 2002.

(30) Foreign Application Priority Data

Dec. 21, 2001   (DE) ................................ 101 63 748

(51) Int. Cl.
C12N 9/24   (2006.01)
C12N 9/00   (2006.01)
C11D 3/386  (2006.01)
C07K 1/00   (2006.01)
C07H 21/04  (2006.01)

(52) U.S. Cl. .................. 435/200; 435/69.1; 435/183; 435/320.1; 510/114; 530/350; 536/23.2

(58) Field of Classification Search ............... 435/69.1, 435/183, 200, 320.1; 530/350; 536/23.2
See application file for complete search history.

(56) References Cited

U.S. PATENT DOCUMENTS

| | | | |
|---|---|---|---|
| 1,227,374 | A | 5/1917 | Boidin |
| 3,623,957 | A | 11/1971 | Feldman |
| 3,893,929 | A | 7/1975 | Basadur |
| 4,116,885 | A | 9/1978 | Derstadt et al. |
| 4,264,738 | A | 4/1981 | Stepanov et al. |
| 4,820,439 | A | 4/1989 | Rieck |
| 5,171,673 | A | 12/1992 | Sloma et al. |
| 5,318,733 | A | 6/1994 | Carduck et al. |
| 5,614,161 | A | 3/1997 | Wilkens et al. |
| 5,616,550 | A | 4/1997 | Kruse et al. |
| 5,705,169 | A | 1/1998 | Stein et al. |
| 5,730,960 | A | 3/1998 | Stein et al. |
| 5,783,545 | A | 7/1998 | Paatz et al. |
| 6,075,001 | A | 6/2000 | Wilde |
| 6,187,055 | B1 | 2/2001 | Kottwitz et al. |
| 6,193,960 | B1 | 2/2001 | Metzger et al. |
| 6,280,926 | B1 | 8/2001 | Short |
| 6,333,185 | B1 | 12/2001 | Barbeyron et al. |
| 6,379,394 | B1 | 4/2002 | Chilou et al. |
| 6,417,152 | B1 | 7/2002 | Kottwitz et al. |
| 6,703,357 | B1 | 3/2004 | Maurer et al. |

FOREIGN PATENT DOCUMENTS

| | | |
|---|---|---|
| CA | 2 306 376 | 10/2000 |
| CA | 2 452 029 | 1/2003 |
| DE | 1 940 488 | 2/1971 |
| DE | 1 617 141 | 4/1972 |
| DE | 2 121 397 | 11/1972 |
| DE | 2 253 063 | 5/1973 |
| DE | 2 200 911 | 10/1973 |
| DE | 28 57 292 | 2/1980 |
| DE | 33 24 258 A1 | 1/1984 |
| DE | 40 13 142 A1 | 10/1991 |
| DE | 44 43 177 A1 | 6/1996 |
| DE | 196 01 063 A1 | 9/1996 |
| DE | 196 16 693 A1 | 11/1997 |
| DE | 196 16 767 A1 | 11/1997 |
| DE | 196 16 769 A1 | 11/1997 |
| DE | 196 16 770 A1 | 11/1997 |
| DE | 197 09 284 A1 | 9/1998 |
| DE | 197 12 033 A1 | 9/1998 |
| DE | 199 18 267 A1 | 10/2000 |
| DE | 199 56 382 A1 | 5/2001 |
| DE | 101 31 441 A1 | 1/2003 |
| EP | 0 006 638 B1 | 4/1984 |
| EP | 0 066 944 B1 | 11/1986 |
| EP | 0 272 033 A2 | 6/1988 |
| EP | 0 164 514 B1 | 6/1989 |
| EP | 0 253 567 B1 | 12/1990 |
| EP | 0 241 985 B1 | 1/1991 |

(Continued)

OTHER PUBLICATIONS

Tsao et al. Accession S28179. Jan. 13, 1995.*

(Continued)

*Primary Examiner*—Ponnathapu Achutamurthy
*Assistant Examiner*—Christian L. Fronda
(74) *Attorney, Agent, or Firm*—Woodcock Washburn LLP

(57) ABSTRACT

The invention relates to a new glycosyl hydrolases with an amyloltic activity and nucleic acids coding for said gylcosyl hydrolases, A PCR-based method for identifying and preparing new gylcosyl hydrolases from metagenome DNA and several possible technical uses for such glycosyl hydrolases with an amylolytic activity. Washing and cleaning products containing such enzymes, and methods and possible uses corresponding thereto are particularly interesting.

6 Claims, 17 Drawing Sheets

FOREIGN PATENT DOCUMENTS

| | | |
|---|---|---|
| EP | 0 472 042 A1 | 2/1992 |
| EP | 0 185 427 B1 | 3/1992 |
| EP | 0 274 907 B1 | 8/1992 |
| EP | 0 241 984 B1 | 3/1994 |
| EP | 0 486 592 B1 | 6/1994 |
| EP | 0 628 630 A2 | 12/1994 |
| EP | 0 636 693 A2 | 2/1995 |
| EP | 0 564 476 B1 | 4/1995 |
| EP | 0 670 367 A1 | 9/1995 |
| EP | 0 357 280 B1 | 2/1996 |
| EP | 0 642 576 B1 | 7/1996 |
| EP | 0 727 485 A1 | 8/1996 |
| EP | 0 728 749 A2 | 8/1996 |
| EP | 0 525 239 B1 | 7/1997 |
| EP | 0 693 471 B1 | 1/1998 |
| EP | 0 694 521 B1 | 1/1998 |
| EP | 0 818 450 A1 | 1/1998 |
| EP | 0 410 498 B1 | 6/1998 |
| EP | 0 736 084 B1 | 9/1998 |
| EP | 0 755 944 B1 | 10/2001 |
| GB | 1 154 730 | 6/1969 |
| GB | 1 377 092 | 12/1974 |
| GB | 1 263 765 | 2/1984 |
| GB | 2 123 848 | 2/1984 |
| WO | WO 91/02792 A1 | 3/1991 |
| WO | WO 94/18314 A1 | 8/1994 |
| WO | WO 94/19454 A2 | 9/1994 |
| WO | WO 94/23005 A1 | 10/1994 |
| WO | WO 94/27970 A1 | 12/1994 |
| WO | WO 94/28102 A1 | 12/1994 |
| WO | WO 94/28103 A1 | 12/1994 |
| WO | WO 95/00626 A1 | 1/1995 |
| WO | WO 95/14075 A1 | 5/1995 |
| WO | WO 95/14759 A1 | 6/1995 |
| WO | WO 95/17498 A1 | 6/1995 |
| WO | WO 95/26397 A1 | 10/1995 |
| WO | WO 95/32232 A1 | 11/1995 |
| WO | WO 96/02633 A1 | 2/1996 |
| WO | WO 97/00324 A1 | 1/1997 |
| WO | WO 97/18287 A1 | 5/1997 |
| WO | WO 97/24177 A1 | 7/1997 |
| WO | WO 97/25399 A1 | 7/1997 |
| WO | WO 97/31085 A1 | 8/1997 |
| WO | WO 98/15617 A2 | 4/1998 |
| WO | WO 98/45396 A1 | 10/1998 |
| WO | WO 99/06515 A1 | 2/1999 |
| WO | WO 99/06516 A1 | 2/1999 |
| WO | WO 9920768 A1 | 4/1999 |
| WO | WO 99/43793 A1 | 9/1999 |
| WO | WO 99/63035 A1 | 12/1999 |
| WO | WO 99/63036 A1 | 12/1999 |
| WO | WO 99/63037 A1 | 12/1999 |
| WO | WO 99/63038 A1 | 12/1999 |
| WO | WO 99/63041 A1 | 12/1999 |
| WO | WO 00/39306 A2 | 7/2000 |
| WO | WO 00/42145 A1 | 7/2000 |
| WO | WO 03/002711 A2 | 1/2003 |

OTHER PUBLICATIONS

Crueger et al. Accession AAW76192, Nov. 26, 1998 (20060614_082549_us-10-872-874-3.rag).*

Crueger et al. Accession AAW76192, Nov. 26, 1998 (20061213_172159_us-10-872-874-6.n2p.rag).*

Database Swiss-Prot, "Alpha-amylase precursor", Accession No. 024781, XP002247832 (1998).

Arai, M., "Bacillus sp. DNA for alpha-amylase", Accession No. AB006823, XP002247833, Database EMBL/Genbank/DDBJ (1997).

Sumitani et al., "New type of starch-binding domain: the direct repeat motif in the C-terminal region of Bacillus sp. No. 195 α-amylase contributes to starch binding and raw starch degrading", Biochemical Journal, vol. 350, No. 2, pp. 477-484 XP009013936 (2000).

Seeger et al., "Putative bi-functional protein (Secreted alpha-amylase/dextrinase)", Accession No. Q9KZ11, XP002271703, Database EMBL/Genbank/DDBJ (2000).

Jespersen et al., "Starch- and Glycogen-Debranching and Branching Enzymes: Predition of Structural Features of the Catalytic (β/α),- Barrel Domain and Evolutionary Relationship to Other Amytolytic Enzymes", Journal of Protein Chemistry, Vo. 12, pp. 791-805 (1993).

Nakajima et al., "Comparison of amino acid sequences of eleven different α-amylases", Applied Microbiology Biotechnology, vol. 23, pp. 355-360 (1986).

Lexikon der Biochemie, Spektrum Akademischer Verlag, Berlin, vol. 1, pp. 267-271 (1999).

Lexikon der Biochemie, Spektrum Akademischer Verlag, Berlin, vol. 2, pp. 227-229 (1999).

Lipman et al., "Rapid and Sensitive Protein Similarity Searches", Science, vol. 227, pp. 1435-1441 (1985).

Zhou et al., "DNA Recovery from Soils of Diverse Composition", Appllied And Environmental Microbiology, vol. 62, No. 2, pp. 316-322 (1996).

Handbuch Fritsch, Sambrook und Maniatis, "Molecular cloning: a laboratory manual", Cold Spring Harbour Laboratory Press, New York (1989).

Zhang et al., "A new logic for DNA engineering using recombination in *Escherichia coli*", Nature Genetics, vol. 20, pp. 123-128 (1998).

Zhao et al., "Molecular evolution by staggered extension process (StEP) in vitro recombination", Nature Biotechnology, vol. 16, pp. 258-261 (1998).

Shao et al., "Random-priming in vitro recombination: an effective tool for directed evolution", Nucleic Acids Research, vol. 26, No. 2, pp. 681-683 (1998).

Stemmer, W., "Rapid evolution of a protein in vitro by DNA shuffling", Nature, vol. 370, pp. 389-391(1994).

Ness et al., "DNA shuffling of subgenomic sequences of subtilisin", Nature Biotechnology, vol. 17, pp. 893-896 (1999).

von H. Ihlig, Industrial enzymes and their applications, Wiley-Verlag, New York, (1998).

K. H. Wallhauber, "Praxis der Sterilisation, Desinfektion-Konservierung:Keimidentifizierung-Betriebshygiene", 5th Edition, Stuttgart-New York: thieme (1995).

P. Finkel, "Formulierung kosmetischer Sonnenschutzmittel", SOFW-Journal, vol. 11, pp. 543-548 (1996) [English summary included].

Georg van Raay et al., "Zur Bestimmung der proteolytischen Aktivitat in Enzymkonzentraten und Enzymhaltigen Wasch-, Spul- und Reinigungsmitteln", Tenside, vol. 7, pp. 125-132 (1970) [Eng summary on p. 131].

Gornall et al., "Determination of Serum Proteins By Means of the Biuret Reaction", Journal Biol. Chem. vol. 177, pp. 751-766 (1948).

Boos et al., "α-Amylase of *Escherichia coli*, Mapping and Cloning of the Structural Gene, malS, and Identification of Its Product as a Periplasmic Protein", Journal of Biological Chemistry, vol. 261, No. 6, pp. 2946-2953 (1986).

Stathopoulos et al., "Characterization of *Escherichia coli* expressing an Lpp'OmpA(46-159)-PhoA fusion protein localized in the outer membrane", Appl. Microbiol Biotechnol. vol. 45, pp. 112-119 (1996).

Altschul et al. "Basic Local Alignment Search Tool", Journal Mol. Biol. vol. 215, pp. 403-410 (1990).

Pearson et al., "Improved tools for biological sequence comparison", Proc. Natl. Acad. Sci., vol. 85, pp. 2444-2448 (1988).

Redenbach et al., "A set of ordered cosmids and a detailed genetic and physical map for the 8 Mb Streptomyces coelicolor A3(2) chromosome", Molecular Microbiology, vol. 21, No. 1 pp. 77-96 (1996).

Hofstetter et al., "Uber die Reduktion der 3,5-Dinitrosalicylsaure durch Zuker", Helvetica Chimica Acta, vol. 34, pp. 2133-2139 (1951).

Faβ et al., "Influence of Specific Signal Peptide Mutations on the Expression and Secretion of the α-Amylase Inhibitor Tendamistat in Streptomyces lividans", Journal of Biological Chemistry, vol. 271, No. 25, pp. 15244-15252 (1996).

Genbank Accession No. AB006823, Bacillus sp. DNA for alpha-amylase, Oct. 4, 2000, 5 pages.

Genbank Accession No. CAE48862, Putative secreted bifunctional (alpha-amylase and endo-alpglucosidase): starch degradation and integral membrane protein [Corynebacterium diptheria Nov. 6, 2003, 8 pages.

Genbank Accession No. Z85949, S. lividans am1B gene. Sep. 23, 1997, 4 pages.

* cited by examiner

|   |   |   |   |   |   |   |   |   |     |     |     |     |     |     |     |     |
|---|---|---|---|---|---|---|---|---|-----|-----|-----|-----|-----|-----|-----|-----|
| 1 | 2 | 3 | 4 | 5 | 6 | 7 | 8 | 9 | 10  | 11  | 12  | 13  | 14  | 15  | 16  | 17  |
|   | 18| 19| 20| 21| 22| 23| 24| 25|     |     |     |     |     |     |     |     |
| V | D | G | P | R | T | D | $X_1$ | $X_2$ | $X_3$ | $X_4$ | $X_5$ | $X_6$ | $X_7$ | $X_8$ | $X_9$ | $X_{10}$ |
| $X_{11}$ | $X_{12}$ | $X_{13}$ | $X_{14}$ | $X_{15}$ | $X_{16}$ | $X_{17}$ | $X_{18}$ | | | | | | | | | |

|    |    |    |    |    |    |    |    |    |    |    |    |    |    |    |    |    |
|----|----|----|----|----|----|----|----|----|----|----|----|----|----|----|----|----|
| 26 | 27 | 28 | 29 | 30 | 31 | 32 | 33 | 34 | 35 | 36 | 37 | 38 | 39 | 40 | 41 | 42 |
|    | 43 | 44 | 45 | 46 | 47 | 48 | 49 | 50 |    |    |    |    |    |    |    |    |
| $X_{19}$ | $X_{20}$ | $X_{21}$ | $X_{22}$ | $X_{23}$ | $X_{24}$ | $X_{25}$ | $X_{26}$ | $X_{27}$ | $X_{28}$ | $X_{29}$ | $X_{30}$ | $X_{31}$ | $X_{32}$ | $X_{33}$ | S | $X_{34}$ |
| $X_{35}$ | $X_{36}$ | $X_{37}$ | $X_{38}$ | $X_{39}$ | $X_{40}$ | $X_{41}$ | $X_{42}$ | | | | | | | | | |

|    |    |    |    |    |    |    |    |    |    |    |    |    |    |    |    |    |
|----|----|----|----|----|----|----|----|----|----|----|----|----|----|----|----|----|
| 51 | 52 | 53 | 54 | 55 | 56 | 57 | 58 | 59 | 60 | 61 | 62 | 63 | 64 | 65 | 66 | 67 |
|    | 68 | 69 | 70 | 71 | 72 | 73 | 74 | 75 |    |    |    |    |    |    |    |    |
| $X_{43}$ | $X_{44}$ | $X_{45}$ | $X_{46}$ | $X_{47}$ | $X_{48}$ | $X_{49}$ | $X_{50}$ | $X_{51}$ | $X_{52}$ | $X_{53}$ | $X_{54}$ | $X_{55}$ | $X_{56}$ | $X_{57}$ | $X_{58}$ | $X_{59}$ |
| $X_{60}$ | $X_{61}$ | $X_{62}$ | $X_{63}$ | $X_{64}$ | $X_{65}$ | $X_{66}$ | $X_{67}$ | | | | | | | | | |

|    |    |    |    |    |    |    |    |    |    |    |    |    |    |    |    |    |
|----|----|----|----|----|----|----|----|----|----|----|----|----|----|----|----|----|
| 76 | 77 | 78 | 79 | 80 | 81 | 82 | 83 | 84 | 85 | 86 | 87 | 88 | 89 | 90 | 91 | 92 |
|    | 93 | 94 | 95 | 96 | 97 | 98 | 99 | 100|    |    |    |    |    |    |    |    |
| $X_{68}$ | $X_{69}$ | $X_{70}$ | $X_{71}$ | $X_{72}$ | $X_{73}$ | $X_{74}$ | $X_{75}$ | $X_{76}$ | $X_{77}$ | $X_{78}$ | $X_{79}$ | $X_{80}$ | $X_{81}$ | $X_{82}$ | $X_{83}$ | $X_{84}$ |
| $X_{85}$ | $X_{86}$ | $X_{87}$ | $X_{88}$ | $X_{89}$ | $X_{90}$ | $X_{91}$ | $X_{92}$ | | | | | | | | | |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| 101 | 102 | 103 | 104 | 105 | 106 | 107 | 108 | 109 | 110 | 111 | 112 | 113 | 114 | 115 | 116 | 117 |
|     | 118 | 119 | 120 | 121 | 122 | 123 |     |     |     |     |     |     |     |     |     |     |
| $X_{93}$ | $X_{94}$ | $X_{95}$ | $X_{96}$ | $X_{97}$ | $X_{98}$ | $X_{99}$ | $X_{100}$ | $X_{101}$ | $X_{102}$ | $X_{103}$ | $X_{104}$ | $X_{105}$ | $X_{106}$ | $X_{107}$ | $X_{108}$ | V |
|     | D | N | H | D | T | E |     |     |     |     |     |     |     |     |     |     |

Figure 5A

| Position | Amino acid |
|---|---|
| 1 | V |
| 2 | D |
| 3 | G |
| 4 | F |
| 5 | R |
| 6 | I |
| 7 | D |
| 8 | $X_1$=A or T |
| 9 | $X_2$=G or I or V or T or L or A or S |
| 10 | $X_3$=K or E or R |
| 11 | $X_4$=H or A or R |
| 12 | $X_5$=I or M or V or L |
| 13 | $X_6$=H or D or R or T or P or S or A or Y or N or K |
| 14 | $X_7$=P or T or N or S or A or R or H or Q |
| 15 | $X_8$=P or R or T or S or G or A or D or E or F |
| 16 | $X_9$=F or Y or D |
| 17 | $X_{10}$=L or V or F or Y or I or W or T |
| 18 | $X_{11}$=S or N or A or K or R or E or C or t Q or H or L |
| 19 | $X_{12}$=R or A or H or E or D or W or N or G or K |
| 20 | $X_{13}$=W or I or V or F or L |
| 21 | $X_{14}$=F or L or M or K or R or V or N |
| 22 | $X_{15}$=Q or D or G or Y or C or T or N or S or A or R |
| 23 | $X_{16}$=E or A or K or H or L or R or G or D |
| 24 | $X_{17}$=V or L or M or A or I |
| 25 | $X_{18}$=K or R or T or S or G or N or H or A |
| 26 | $X_{19}$=G or A or Q or E or S or T or V or N or D or K or R or Y |
| 27 | $X_{20}$=T or P or E or A or K or N or H or S or G or R |
| 28 | $X_{21}$=S or N or T or F or Y or G or D or V or H or A or K or - |
| 29 | $X_{22}$=P or G or K or S or R or I or - |
| 30 | $X_{23}$=G or K or D or A or S or H or E or - |
| 31 | $X_{24}$=R or P or E or A or L or D or - |
| 32 | $X_{25}$=G or - |
| 33 | $X_{26}$=R or - |
| 34 | $X_{27}$=P or K or - |
| 35 | $X_{28}$=E or N or A or R or D or P or - |
| 36 | $X_{29}$=R or L or A or P or V or F or - |
| 37 | $X_{30}$=F or Y or I |
| 38 | $X_{31}$=A or G or L or I or W or V or N or Q or M or T |
| 39 | $X_{32}$=V or H or K or F or T or I |
| 40 | $X_{33}$=T or S or G or A or Q or H or L or M |
| 41 | E |
| 42 | $X_{34}$=F or A or Y or H or V or T or I |
| 43 | $X_{35}$=Y or W or I or F or V |
| 44 | $X_{36}$=D or F or S or E or Q or Y or H or G or P or N |

Figure 5B

| | |
|---|---|
| 45 | $X_{37}$=G or A or D or R or S or T or E or - |
| 46 | $X_{38}$=N or K or D or S or H or A or T or - |
| 47 | $X_{39}$=P or L or V or I or M or A or N or G or D |
| 48 | $X_{40}$=A or D or Q or N or E or T |
| 49 | $X_{41}$=H or Q or L or A or E or D or V or P or N |
| 50 | $X_{42}$=L or I or V or P or T |
| 51 | $X_{43}$=A or T or H or N or K or D or Q or R or S or G |
| 52 | $X_{44}$=T or A or D or N or G or K or S or R or P or Q or V |
| 53 | $X_{45}$=V or Y or G or S or T or D or A or Q or N or L or F |
| 54 | $X_{46}$=I or A or L or V or Q or W or E or D or S or T or R |
| 55 | $X_{47}$=D or K or T or N or A or S or Y or E or W or G |
| 56 | $X_{48}$=L or E or A or S or D or K or T or I or Y or F or R |
| 57 | $X_{49}$=Y or L or S or V or T or G or E or P |
| 58 | $X_{50}$=A or G or N or D or E or I or S or T or V or L or M |
| 59 | $X_{51}$=R or D or S or G or N or A |
| 60 | $X_{52}$=T or N or - |
| 61 | $X_{53}$=A or - |
| 62 | $X_{54}$=S or M or - |
| 63 | $X_{55}$=D or P or A or - |
| 64 | $X_{56}$=Q or R or A or K or V or G or T or M or - |
| 65 | $X_{57}$=S or T or M or V or L or D or W or - |
| 66 | $X_{58}$=H or R or S or K or Q or D or T |
| 67 | $X_{59}$=L or A or V or T or D |
| 68 | $X_{60}$=F or H or D or Q or T or L or Y |
| 69 | $X_{61}$=D or E or F |
| 70 | $X_{62}$=F or V or G |
| 71 | $X_{63}$=A or P or V or R or G or T or H |
| 72 | $X_{64}$=L or Y or F or V |
| 73 | $X_{65}$=H or G or A or S or F or K |
| 74 | $X_{66}$=F or Y or A or R or K or S or D or N or E |
| 75 | $X_{67}$=L or K or R or N or G or D or S or H or Q or A |
| 76 | $X_{68}$=L or F or I or V or A |
| 77 | $X_{69}$=Q or Y or E or M or H or R or L or F or K or A or S or G or I or V |
| 78 | $X_{70}$=R or G or Q or E or D or N or A or H or S or T |
| 79 | $X_{71}$=M or A or Q or V or R or F or E |
| 80 | $X_{72}$=S or A or F or L or V |
| 81 | $X_{73}$=A or N or R or K or Q or S or L or H or T or G |
| 82 | $X_{74}$=G or N or A or R or K or Q or S or Y or F |
| 83 | $X_{75}$=N or G or E or Q or D or K or - |
| 84 | $X_{76}$=R or - |
| 85 | $X_{77}$=G or R or K or E or N or Q or D or P or A |
| 86 | $X_{78}$=G or A or M or D or E or S or I or L or P |
| 87 | $X_{79}$=F or S or W or Y or K or A or H |
| 88 | $X_{80}$=D or W or Y or N or E or P |
| 89 | $X_{81}$=I or H or - |
| 90 | $X_{82}$=L or D or - |
| 91 | $X_{83}$=M or L or I |
| 92 | $X_{84}$=R or G or S or P or T or Q or K or A or N |

Figure 5C

| | |
|---|---|
| 93 | $X_{85}$=S or N or K or T or R or A |
| 94 | $X_{86}$=L or I or V or F or Y |
| 95 | $X_{87}$=R or K or L or P or G or A or Y |
| 96 | $X_{88}$=F or Q or T or D or A or E or S or P or R or L |
| 97 | $X_{89}$=G or A or R or N or S or T or - |
| 98 | $X_{90}$=S or G or T or W or D or L or - |
| 99 | $X_{91}$=S or G or D or - |
| 100 | $X_{92}$=D or L or P or - |
| 101 | $X_{93}$=D or Y or K or - |
| 102 | $X_{94}$=G or T or - |
| 103 | $X_{95}$=S or N or - |
| 104 | $X_{96}$=R or - |
| 105 | $X_{97}$=F or L or D or - |
| 106 | $X_{98}$=L or T or M or V or G or H or P |
| 107 | $X_{99}$=E or K or A or Q or R or G or S or Y or F or H or L or D |
| 108 | $X_{100}$=Q or A or E or W or D or R or G or V or M or L or I or T or S |
| 109 | $X_{101}$=H or N or Q or R or P or G or S or E or T |
| 110 | $X_{102}$=P or G or S or N or E or A or I |
| 111 | $X_{103}$=A or K or L or Q or T or D or S or G or H or Y |
| 112 | $X_{104}$=F or L or R or M or S or V or K or Q or G or N or A or E |
| 113 | $X_{105}$=A or S or T or L |
| 114 | $X_{106}$=V or A or M or G or S or I or N or L |
| 115 | $X_{107}$=T or V or A or S |
| 116 | $X_{108}$=Y or F |
| 117 | V |
| 118 | D |
| 119 | N |
| 120 | H |
| 121 | D |
| 122 | T |
| 123 | E |

Figure 5D

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
|   | 18 | 19 | 20 | 21 | 22 | 23 | 24 | 25 |   |   |   |   |   |   |   |   |
| V | D | G | P | R | I | D | $X_1$ | $X_2$ | $X_3$ | $X_4$ | $X_5$ | $X_6$ | $X_7$ | $X_8$ | $X_9$ | $X_{10}$ |
| $X_{11}$ | $X_{12}$ | $X_{13}$ | $X_{14}$ | $X_{15}$ | $X_{16}$ | $X_{17}$ | $X_{18}$ | | | | | | | | | |

| 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|
|   | 43 | 44 | 45 | 46 | 47 | 48 | 49 | 50 |   |   |   |   |   |   |   |   |
| $X_{19}$ | $X_{20}$ | $X_{21}$ | $X_{22}$ | $X_{23}$ | $X_{24}$ | $X_{25}$ | $X_{26}$ | $X_{27}$ | $X_{28}$ | $X_{29}$ | $X_{30}$ | $X_{31}$ | $X_{32}$ | $X_{33}$ | E | $X_{34}$ |
| $X_{35}$ | $X_{36}$ | $X_{37}$ | $X_{38}$ | $X_{39}$ | $X_{40}$ | $X_{41}$ | $X_{42}$ | | | | | | | | | |

| 51 | 52 | 53 | 54 | 55 | 56 | 57 | 58 | 59 | 60 | 61 | 62 | 63 | 64 | 65 | 66 | 67 |
|---|---|---|---|---|---|---|---|---|---|---|---|---|---|---|---|---|
|   | 68 | 69 | 70 | 71 | 72 | 73 | 74 | 75 |   |   |   |   |   |   |   |   |
| $X_{43}$ | $X_{44}$ | $X_{45}$ | $X_{46}$ | $X_{47}$ | $X_{48}$ | $X_{49}$ | $X_{50}$ | $X_{51}$ | $X_{52}$ | $X_{53}$ | $X_{54}$ | $X_{55}$ | $X_{56}$ | $X_{57}$ | $X_{58}$ | $X_{59}$ |
| $X_{60}$ | $X_{61}$ | $X_{62}$ | $X_{63}$ | $X_{64}$ | $X_{65}$ | $X_{66}$ | $X_{67}$ | | | | | | | | | |

| 76 | 77 | 78 | 79 | 80 | 81 | 82 | 83 | 84 | 85 | 86 | 87 | 88 | 89 | 90 | 91 | 92 |
|---|---|---|---|---|---|---|---|---|---|---|---|---|---|---|---|---|
|   | 93 | 94 | 95 | 96 | 97 | 98 | 99 | 100 |   |   |   |   |   |   |   |   |
| $X_{68}$ | $X_{69}$ | $X_{70}$ | $X_{71}$ | $X_{72}$ | $X_{73}$ | $X_{74}$ | $X_{75}$ | $X_{76}$ | $X_{77}$ | $X_{78}$ | $X_{79}$ | $X_{80}$ | $X_{81}$ | $X_{82}$ | $X_{83}$ | $X_{84}$ |
| $X_{85}$ | $X_{86}$ | $X_{87}$ | $X_{88}$ | $X_{89}$ | $X_{90}$ | $X_{91}$ | $X_{92}$ | | | | | | | | | |

| 101 | 102 | 103 | 104 | 105 | 106 | 107 | 108 | 109 | 110 | 111 | 112 | 113 | 114 | 115 | 116 | 117 |
|---|---|---|---|---|---|---|---|---|---|---|---|---|---|---|---|---|
|   | 118 | 119 | 120 | 121 | | | | | | | | | | | | |
| $X_{93}$ | $X_{94}$ | $X_{95}$ | $X_{96}$ | $X_{97}$ | $X_{98}$ | $X_{99}$ | $X_{100}$ | $X_{101}$ | $X_{102}$ | $X_{103}$ | $X_{104}$ | $X_{105}$ | $X_{106}$ | V | D | N |
| | H | D | T | E | | | | | | | | | | | | |

Position Amino acid

| Position | Amino acid |
|---|---|
| 1 | V |
| 2 | D |
| 3 | G |
| 4 | P |
| 5 | R |
| 6 | I |
| 7 | D |
| 8 | $X_1$=A or T |
| 9 | $X_2$=G or I or V or T or L or A or S |
| 10 | $X_3$=K or E or R |
| 11 | $X_4$=H or R |
| 12 | $X_5$=I or M or V or L |
| 13 | $X_6$=H or D or R or T or P or S or A or N |
| 14 | $X_7$=P or T or N or S or A or R |
| 15 | $X_8$=P or R or T or S or G or A or E or D |
| 16 | $X_9$=F or Y or D |
| 17 | $X_{10}$=L or V or F or Y or I or W |
| 18 | $X_{11}$=S or N or A or K or R or E or C or H |
| 19 | $X_{12}$=R or A or H or E or D or N |
| 20 | $X_{13}$=W or V or I or F |
| 21 | $X_{14}$=F or L or M or V or K or R or N |
| 22 | $X_{15}$=Q or D or G or Y or C or N or T or S or A |
| 23 | $X_{16}$=E or A or K or H or G or R or L |
| 24 | $X_{17}$=V or L or M or I |
| 25 | $X_{18}$=K or R or H or T or S or G or N |
| 26 | $X_{19}$=G or A or Q or E or T or S or V or N or D or K or R |
| 27 | $X_{20}$=T or P or E or A or K or H or S or G or R |
| 28 | $X_{21}$=S or N or T or F or V or G or D or A or - |
| 29 | $X_{22}$=P or G or K or S or R or - |
| 30 | $X_{23}$=G or K or D or A or H or - |

Figure 6A

| | |
|---|---|
| 31 | $X_{24}$=R or P or E or A or L or - |
| 32 | $X_{25}$=G or - |
| 33 | $X_{26}$=R or - |
| 34 | $X_{27}$=P or - |
| 35 | $X_{28}$=E or N or A or R or D or - |
| 36 | $X_{29}$=R or L or A or P or V or F |
| 37 | $X_{30}$=F or Y or I |
| 38 | $X_{31}$=A or G or I or V or L or W or Q |
| 39 | $X_{32}$=V or T or F or H or K |
| 40 | $X_{33}$=T or S or G or A or Q or H |
| 41 | E |
| 42 | $X_{34}$=F or A or Y or H or I or V or T |
| 43 | $X_{35}$=Y or W or F or I |
| 44 | $X_{36}$=D or F or S or E or P or Q or Y or H or N |
| 45 | $X_{37}$=G or A or D or R or S |
| 46 | $X_{38}$=N or K or D or S or H or A or T or - |
| 47 | $X_{39}$=P or L or V or I or A or N or G or D or - |
| 48 | $X_{40}$=A or D or Q or N or T or E |
| 49 | $X_{41}$=H or Q or L or A or E or D or P or V |
| 50 | $X_{42}$=L or P or I or V |
| 51 | $X_{43}$=A or T or H or N or K or D or R or Q or S or G |
| 52 | $X_{44}$=T or A or D or N or G or K or S or R or Q or P or V |
| 53 | $X_{45}$=V or Y or D or Q or G or S or T or A or N or L |
| 54 | $X_{46}$=I or A or L or V or E or D or Q or W or S |
| 55 | $X_{47}$=D or K or T or N or A or S or Y or E |
| 56 | $X_{48}$=L or E or A or S or D or K or Y or F or T or I |
| 57 | $X_{49}$=Y or L or S or V or T or G |
| 58 | $X_{50}$=A or G or N or D or E or T or I or S or V |
| 59 | $X_{51}$=R or D or S or G or N |
| 60 | $X_{52}$=T or - |
| 61 | $X_{53}$=A or - |
| 62 | $X_{54}$=S or M or - |
| 63 | $X_{55}$=D or P or - |
| 64 | $X_{56}$=Q or R or A or K or V or G or T or M or - |
| 65 | $X_{57}$=S or T or M or V or L or D or - |
| 66 | $X_{58}$=H or R or S or K or Q or D or T |
| 67 | $X_{59}$=L or A or V or T |
| 68 | $X_{60}$=F or L or H or D or Q |
| 69 | $X_{61}$=D or E |
| 70 | $X_{62}$=F or V |
| 71 | $X_{63}$=A or P or T or V or R or G |
| 72 | $X_{64}$=L or F or Y |
| 73 | $X_{65}$=H or A or G or F |
| 74 | $X_{66}$=F or Y or A or D or R or K or N |
| 75 | $X_{67}$=L or K or R or N or Q or D or G or S or A |
| 76 | $X_{68}$=L or F or V or I or A |
| 77 | $X_{69}$=Q or Y or E or M or H or R or L or F or K or A or S |
| 78 | $X_{70}$=R or G or Q or E or N or D or A or S or T or H |
| 79 | $X_{71}$=M or A or Q or V or F |
| 80 | $X_{72}$=S or A or F or L or V |
| 81 | $X_{73}$=A or N or R or K or Q or S or L or H or T |
| 82 | $X_{74}$=G or N or A or R or K or Q or S or H |
| 83 | $X_{75}$=N or G or E or Q or - |

Figure 6B

| | |
|---|---|
| 84 | $X_{76}$=R or - |
| 85 | $X_{77}$=G or R or K or E or N or D or Q or P |
| 86 | $X_{78}$=G or A or M or D or S or I or L or P |
| 87 | $X_{79}$=F or S or W or Y or A or K |
| 88 | $X_{80}$=D or N or W or Y or E |
| 89 | $X_{81}$=M or L |
| 90 | $X_{82}$=R or G or S or T or Q or K or A |
| 91 | $X_{83}$=S or N or K or T or A |
| 92 | $X_{84}$=L or I or V or F or Y |
| 93 | $X_{85}$=R or K or L or F or G |
| 94 | $X_{86}$=F or Q or T or D or A or E or S or P or R |
| 95 | $X_{87}$=G or A or R or N or S or T |
| 96 | $X_{88}$=S or G or T or W or D |
| 97 | $X_{89}$=S or G or D or - |
| 98 | $X_{90}$=D or L or Y or F or H or - |
| 99 | $X_{91}$=D or S or Y or - |
| 100 | $X_{92}$=G or T or - |
| 101 | $X_{93}$=S or - |
| 102 | $X_{94}$=R or - |
| 103 | $X_{95}$=F or L or D or - |
| 104 | $X_{96}$=L or T or M or V or H or - |
| 105 | $X_{97}$=E or K or A or Q or R or G or D or - |
| 106 | $X_{98}$=Q or A or E or W or D or R or G or T or L or V or M or I or S |
| 107 | $X_{99}$=H or N or Q or R or T or P or G or S or K |
| 108 | $X_{100}$=P or G or E or A or S or N or I |
| 109 | $X_{101}$=A or K or L or Q or T or D or S or G or H |
| 110 | $X_{102}$=P or L or R or M or S or V or K or N or D or Q or G or A |
| 111 | $X_{103}$=A or S or T |
| 112 | $X_{104}$=V or A or N or M or G or S or L |
| 113 | $X_{105}$=T or S or V or A |
| 114 | $X_{106}$=Y or F |
| 115 | V |
| 116 | D |
| 117 | N |
| 118 | H |
| 119 | D |
| 120 | T |
| 121 | E |

Figure 6C

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
|   | 18 | 19 | 20 | 21 | 22 | 23 | 24 | 25 |    |    |    |    |    |    |    |    |
| $X_1$ | $X_2$ | A | D | $X_3$ | V | $X_4$ | $X_5$ | $X_6$ | $X_7$ | $X_8$ | $X_9$ | $X_{10}$ | $X_{11}$ | $X_{12}$ | $X_{13}$ | $X_{14}$ |
|   | $X_{15}$ | $X_{16}$ | $X_{17}$ | $X_{18}$ | $X_{19}$ | $X_{20}$ | $X_{21}$ | $X_{22}$ |    |    |    |    |    |    |    |    |

| 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|
|   | 43 | 44 | 45 | 46 | 47 | 48 | 49 | 50 |   |   |   |   |   |   |   |   |
| $X_{23}$ | $X_{24}$ | $X_{25}$ | $X_{26}$ | $X_{27}$ | $X_{28}$ | $X_{29}$ | $X_{30}$ | $X_{31}$ | $X_{32}$ | $X_{33}$ | $X_{34}$ | $X_{35}$ | $X_{36}$ | $X_{37}$ | $X_{38}$ | $X_{39}$ |
|   | $X_{40}$ | $X_{41}$ | $X_{42}$ | $X_{43}$ | $X_{44}$ | $X_{45}$ | $X_{46}$ | $X_{47}$ |   |   |   |   |   |   |   |   |

| 51 | 52 | 53 | 54 | 55 | 56 | 57 | 58 | 59 | 60 | 61 | 62 | 63 | 64 | 65 | 66 | 67 |
|---|---|---|---|---|---|---|---|---|---|---|---|---|---|---|---|---|
|   | 68 | 69 | 70 | 71 | 72 | 73 | 74 | 75 |   |   |   |   |   |   |   |   |
| $X_{48}$ | $X_{49}$ | $X_{50}$ | $X_{51}$ | $X_{52}$ | $X_{53}$ | $X_{54}$ | $X_{55}$ | $X_{56}$ | $X_{57}$ | $X_{58}$ | $X_{59}$ | $X_{60}$ | $X_{61}$ | $X_{62}$ | $X_{63}$ | $X_{64}$ |
|   | $X_{65}$ | $X_{66}$ | $X_{67}$ | $X_{68}$ | $X_{69}$ | $X_{70}$ | $X_{71}$ | $X_{72}$ |   |   |   |   |   |   |   |   |

| 76 | 77 | 78 | 79 | 80 | 81 | 82 | 83 | 84 | 85 | 86 | 87 | 88 | 89 | 90 | 91 | 92 |
|---|---|---|---|---|---|---|---|---|---|---|---|---|---|---|---|---|
|   | 93 | 94 | 95 | 96 | 97 | 98 | 99 | 100 |   |   |   |   |   |   |   |   |
| $X_{73}$ | $X_{74}$ | $X_{75}$ | $X_{76}$ | $X_{77}$ | $X_{78}$ | $X_{79}$ | $X_{80}$ | $X_{81}$ | $X_{82}$ | $X_{83}$ | $X_{84}$ | $X_{85}$ | $X_{86}$ | $X_{87}$ | $X_{88}$ | $X_{89}$ |
|   | $X_{90}$ | $X_{91}$ | $X_{92}$ | $X_{93}$ | $X_{94}$ | $X_{95}$ | $X_{96}$ | $X_{97}$ |   |   |   |   |   |   |   |   |

| 101 | 102 | 103 | 104 | 105 | 106 | 107 | 108 | 109 |
|---|---|---|---|---|---|---|---|---|
| $X_{98}$ | D | G | F | R | I | D | A | $X_{99}$ |

Position Amino acid
1           $X_1$=V or -
2           $X_2$=Y or -
3           A
4           D
5           $X_3$=V or A
6           V
7           $X_4$=F or Y or I or N or L
8           $X_5$=N or -
9           $X_6$=H or -
10          $X_7$=L or F or T or S or A or -
11          $X_8$=G or S or A or C or R or T or V or -
12          $X_9$=P or D or E or A or F or -
13          $X_{10}$=A or E or D or S or T or Q or R or L or N or G or -
14          $X_{11}$=G or S or H or N or P or D or M or F
15          $X_{12}$=P or A or E or -
16          $X_{13}$=W or H or A or Q or E or R or K or L or V or P or -
17          $X_{14}$=F or Q or L or T or R or G or S or E or H or Y or N or M or K or D or A or -
18          $X_{15}$=N or A or C or Q or V or G or R or D
19          $X_{16}$=Y or C or F or L or S or W or E or P or R or D or -
20          $X_{17}$=L or A or F or H or I or S or T or M or G or V
21          $X_{18}$=N or R or H or P or G or D or A or T or Y or E or I or W or L or F or V or S
22          $X_{19}$=R or E or A or Q or K or S or T or C or G or N or V
23          $X_{20}$=F or Y or D or S or V or W or L or M or R
24          $X_{21}$=G or A or S or T or R or K or Q or H or D
25          $X_{22}$=C or P or D or G or R or T or A or -
26          $X_{23}$=P or E or D or H or S or N or L or F or Q or I or V or Y or A

| | |
|---|---|
| 65 | $X_{62}$=F or Y or - |
| 66 | $X_{63}$=Y or - |
| 67 | $X_{64}$=W or L or - |
| 68 | $X_{65}$=H or - |
| 69 | $X_{66}$=R or A or - |
| 70 | $X_{67}$=F or - |
| 71 | $X_{68}$=F or L or - |
| 72 | $X_{69}$=S or P or - |
| 73 | $X_{70}$=H or Q or - |
| 74 | $X_{71}$=Q or M or - |
| 75 | $X_{72}$=P or - |
| 76 | $X_{73}$=D or K or - |
| 77 | $X_{74}$=L or - |
| 78 | $X_{75}$=N or P or A or D or S or L or H or - |
| 79 | $X_{76}$=F or W or P or S or A or G or C or M or L or V or T or E or - |
| 80 | $X_{77}$=D or R or A or G or T or N or Q or S or E or M or K or - |
| 81 | $X_{78}$=N or R or H or A or E or C or S or Q or T or Y or - |
| 82 | $X_{79}$=D or T or R or E or A or P or Q or - |
| 83 | $X_{80}$=E or T or I or D or W or G or P or H or R or V or L or Q or N or Y or F or A or M |
| 84 | $X_{81}$=V or L or A or M or S or T or P |
| 85 | $X_{82}$=R or G or E or H or V or I or D or T or L or Q |
| 86 | $X_{83}$=A or N or E or R or W or Q or D or V or H or S or K |
| 87 | $X_{84}$=F or Y or W or L or A or R or G or M or Q |
| 88 | $X_{85}$=F or I or V or L or M or A |
| 89 | $X_{86}$=V or F or I or R or L or T or M or P or A |
| 90 | $X_{87}$=D or H or A or E or T or S or R or G |
| 91 | $X_{88}$=N or D or T or V or L or A or S or C or Q |
| 92 | $X_{89}$=A or V or I or M or L |
| 93 | $X_{90}$=L or R or V or A or E or S or G or Q or K |
| 94 | $X_{91}$=M or G or Y or H or F or R or W or T or - |
| 95 | $X_{92}$=W or F or L or Y or - |
| 96 | $X_{93}$=L or V or I or A or H or - |
| 97 | $X_{94}$=R or E or D or A or G or H or L or T or Q or S or K or I or M |
| 98 | $X_{95}$=D or H or E or A or N or M or Q or V or S or I |
| 99 | $X_{96}$=Y or F or L or R or M or C or A or V |
| 100 | $X_{97}$=H or Q or R or G or L or K or D |
| 101 | $X_{98}$=I or L or F or V |
| 102 | D |
| 103 | G |
| 104 | F |
| 105 | R |
| 106 | I |
| 107 | D |
| 108 | A |
| 109 | $X_{99}$=A or - |

Position  Amino acid
1         $X_1$=V or -
2         $X_2$=Y or -
3         A
4         D
5         V
6         V
7         $X_3$=F or I
8         N
9         H
10        $X_4$=F or L or T
11        $X_5$=G or A
12        $X_6$=P or A
13        $X_7$=T or D or A or E or S
14        $X_8$=G or S
15        $X_9$=Q or -
16        $X_{10}$=A or -
17        $X_{11}$=G or -
18        $X_{12}$=T or -
19        $X_{13}$=N or C or S
20        $X_{14}$=Y or W or F or V
21        $X_{15}$=L or I or A
22        $X_{16}$=E or A or R or H or G or D
23        $X_{17}$=A or K or Q or E or R
24        $X_{18}$=F or Y or I
25        $X_{19}$=S or G or T or A or V
26        $X_{20}$=P or R or G or C or -
27        $X_{21}$=H or P or S or E or D or G
28        $X_{22}$=Y or F
29        $X_{23}$=V or F or Y
30        $X_{24}$=S or A or T or Q
31        $X_{25}$=K or E or A or D or R
32        $X_{26}$=K or R or Q or L
33        $X_{27}$=H or Y or L or -
34        $X_{28}$=A or Q or G or K or E
35        $X_{29}$=T or S or N or D
36        $X_{30}$=E or P or D or G
37        $X_{31}$=W or S
38        $X_{32}$=G or V
39        $X_{33}$=E or R or P or D or Q or L or A

Figure 8A

| | |
|---|---|
| 40 | $X_{34}$=S or A or G or N |
| 41 | $X_{35}$=L or I or V or S |
| 42 | $X_{36}$=N or T |
| 43 | $X_{37}$=F or L or Y or C |
| 44 | $X_{38}$=D or C |
| 45 | $X_{39}$=G or D or S |
| 46 | $X_{40}$=E or P or R or K or L or N |
| 47 | $X_{41}$=S or H or G or R or D or T |
| 48 | $X_{42}$=A or S or C |
| 49 | $X_{43}$=G or A or T or D or R or Q |
| 50 | $X_{44}$=P or G or D or E or T or H |
| 51 | $X_{45}$=N or - |
| 52 | $X_{46}$=A or - |
| 53 | $X_{47}$=M or - |
| 54 | $X_{48}$=V or M |
| 55 | $X_{49}$=R or G |
| 56 | $X_{50}$=E or A or N or D or W or K |
| 57 | $X_{51}$=F or Y or W or L |
| 58 | $X_{52}$=V or F or L |
| 59 | $X_{53}$=T or V or I or F or L |
| 60 | $X_{54}$=T or A or E or D or H or S |
| 61 | $X_{55}$=N or S |
| 62 | $X_{56}$=A or V |
| 63 | $X_{57}$=A or S or L or R or E or V |
| 64 | $X_{58}$=H or Y or G or M or T |
| 65 | W |
| 66 | $X_{59}$=I or V or L or A |
| 67 | $X_{60}$=R or E or H or A or D or K |
| 68 | $X_{61}$=S or H |
| 69 | $X_{62}$=Y or F |
| 70 | $X_{63}$=H or K |
| 71 | $X_{64}$=L or V or F |
| 72 | D |
| 73 | G |
| 74 | P |
| 75 | R |
| 76 | I |
| 77 | D |
| 78 | A |

Figure 8B

GLYCOSYL HYDROLASES

CROSS REFERENCE TO RELATED APPLICATIONS

This application is a continuation of PCT application number PCT/EP02/14210 filed Dec. 13, 2002, which claims benefit of German application number 101 63 748.9 filed Dec. 21, 2001, the complete disclosures of which are hereby incorporated by reference in their entirety.

FIELD OF THE INVENTION

The present invention relates to new glycosyl hydrolases having amylolytic activity and to the nucleic acids coding for these glycosyl hydrolases, to a PCR-based method for identifying and isolating new glycosyl hydrolases from metagenomic DNA, and to various possible industrial applications thereof. Among these, washing and cleaning compositions with such enzymes, and corresponding methods and possible uses are of particular interest.

BACKGROUND OF THE INVENTION

Glycosyl hydrolases represent a very diverse group of enzymes which hydrolyze glycosidic linkages between two or more carbohydrates, or between a carbohydrate and a non-carbohydrate function.

Glycosyl hydrolases of particular industrial and technical interest are the α-amylases (E.C. 3. 2. 1. 1) which hydrolyze α-1,4-glycosidic linkages, which are located in the interior of polymers, of starch and starch-like polymers, such as, for example, amylose, amylopectin or glycogen, to form dextrins and β-1,6-branched oligosaccharides. They are among the most important of all the enzymes utilized in industry. There are two reasons for this: firstly they are usually, like many substrate-degrading enzymes, released by microorganisms into the surrounding medium so that they can be obtained on the industrial scale with comparatively little effort by fermentation and purification from the culture medium. Secondly, amylases are required for a wide range of applications.

The principal industrial use of α-amylase is in the production of glucose syrup. Other uses are, for example, that as active components in washing and cleaning compositions, for the treatment of raw materials in textile manufacture, for the production of adhesives or for the production of sugar-containing food products or food ingredients.

One example of an amylase which is employed particularly intensively in industry is the α-amylase from *Bacillus licheniformis*, which is supplied by Novozymes A/S, Bagsvaerd, Denmark, under the proprietary name Termamyl®. The amylase obtained from *B. subtilis* or *B. amyloliquefaciens* and disclosed in U.S. Pat. No. 1,227,374 is marketed by the same company under the name BAN®.

This amylase molecule, and its near relations, have been further developed in numerous inventions which were based on the object of optimizing, with the aid of various molecular biological modifications, their enzymatic properties for specific applications. Such optimizations may relate for example to the substrate specificities, the stability of the enzyme under various reaction conditions or the enzymatic activity itself. Examples of such optimizations which may be mentioned are the following property rights: EP 0410498 B1 for the sizing of textiles and WO 96/02633 A1 for the liquefaction of starch.

Since developments which consist merely of optimizations of only a few known starting enzymes are possibly restricted in the results which can be achieved, an intensive search is taking place in parallel thereto for comparable enzymes from other natural sources. Those which have been identified are starch-cleaving enzymes for example from *Pimelobacter, Pseudomonas* and *Thermus* for the manufacture of food products, cosmetics and drugs (EP 0 636 693 A2), ones of the same type from *Rhizobium, Arthrobacter, Brevibacterium* and *Micrococcus* (EP 0 628 630 A2), from *Pyrococcus* (WO 94/19454 A2) and Sulfolobus for the liquefaction of starch at high temperatures, or strongly acidic reaction conditions (EP 0 727 485 A1 and WO 96/02633 A1). Amylases for use at alkaline pH values have been found in *Bacillus* sp. (WO 95/26397 A1 and WO 97/00324 A1). Because of their low sensitivity to washing compositions, other amylases from various *Bacilli* (EP 0 670 367 A1) are suitable for use in washing or cleaning compositions.

Further optimizations of enzymes isolated from natural sources for the respective area of application can be carried out for example by molecular biological methods (for example as in U.S. Pat. No. 5,171,673 or WO 99/20768 A1) or by chemical modifications (DE 4013142 A1). The patent application WO 99/43793 A1, for example, describes a further development of the known Novamyl® α-amylase. Similarities in sequence between Novamyl® and known cyclodextrin glucanotransferases (CGTases) are utilized therein to construct, with the aid of molecular biology techniques, a multitude of related molecules. These comprise α-amylases with additional CGTase-specific consensus sequences (boxes) and functions or, conversely, CGTases with additional regions and functions typical of α-amylases, or chimeras of the two molecules. The point of this development is to optimize Novamyl® for these applications.

The new enzymes derived from the optimization of known glycosyl hydrolases and, in particular, amylases are, by their nature, limited in their properties because they represent local optima in the "fitness landscape" of glycosyl hydrolases. In order to find further, possibly even better, local optima it is necessary to start from other original enzymes which either themselves represent such a local optimum, or can be optimized with reasonable effort in the direction thereof. However, the finding of new glycosyl-transferases which may be such original enzymes requires, by the route of classical microbiological screening, the isolation of defined strains. However, more than 95% of all occurring microorganisms cannot be cultivated, so that the new glycosyl hydrolases occurring in these microorganisms, including the amylases, have not to date been accessible to characterization.

α-Amylases are typically monomeric enzymes with a molecular weight of about 55 kDa. The central domain has an α/β barrel structure (TIM barrel) which, according to the current state of knowledge, represents the most widespread protein-folding motif. The linear protein strand consists of in each case 8 α-helices and 8 β-pleated sheet segments (β sheets) which occur in alternating sequence and fold three-dimensionally in such a way that the β-pleated sheets are disposed in the form of a circle in parallel orientation and are surrounded by the α-helices on the outside.

The enzymatic activity is probably derived from amino acid residues which are located at the C-terminal end of the individual helices and β-pleated sheets.

For the example of the amylase known as Termamyl from *Bacillus licheniformis*, the amino acid residues are the aspartate 231 (general base catalyst) and glutamate 261 (general acid catalyst). The residue Asp 328 which was originally regarded as general acid catalyst is, according to recent investigations, attributed with an essential influence on the electrostatic conditions in the active site. Further residues such as, for example, His 210 are thought to be involved in the binding of the substrate or further factors such as, for example, $Ca^{2+}$ ions.

Besides the actual amylases, further enzymes are included in the amylase superfamily, for example α-1,6-glucosidases, cyclodextrin glucanotransferases (CGTases), isoamylases, neopullulanases, glycogen debranching enzyme, dextran glucosidases and glycosyltransferases.

The substrate binding specificity, which differs widely in some cases, is brought about by protein loops which are inserted between particular structural elements and form relatively small independent domains.

Thus, a B domain exists and is disposed between β-pleated sheets 3 and helix 3. It comprises in the case of α-amylases, and α-1,6-glucosidases and cyclodextrin glucanotransferases (CGTases) closely related thereto, approximately 40 amino acids, but may also, as, for example, in the case of glucan-debranching enzymes, comprise 270 amino acids (Jespersen, H. M.; E. A. MacGregor, B. Henrissat, M. Sierks and B. Svensson: "Starch- and Glycogen-Debranching and Branching Enzymes", *J. of Protein Chemistry*, volume 12, pp. 791-805, 1993).

Further domains are disposed at the C terminus, such as the C domain in all enzymes and one or more further D or E domains (for example in CGTases). These are likewise attributed with involvement in substrate binding.

Despite this generally similar structure, the sequence homology of the linear protein strand varies widely, making it extremely difficult to define characteristic sequence segments as probes which could be used to search in an efficient manner for new amylases.

Structural elements responsible for the folding may also be formed without homology in the primary structure. Thus, the amylases from *Bacillus licheniformis* and *Bacillus amyloliquefaciens* are more than 80% identical. By contrast, the homology over all amylases of bacterial, animal and vegetable origin is less than 10% (Nakajima et al., *Appl. Microbiol. Biotechnol.*, volume 23, pp. 355-360 (1986)).

Further TIM barrel proteins are, despite an identical protein-folding structure, no longer homologous in any way.

Thus, proteins having little similarity in terms of homology may nevertheless display an identical or closely related enzymic activity as long as there is a similar protein-folding pattern and the appropriate topological disposition, which is necessary for the catalytic reaction, of the amino acid residues involved.

It can be stated in summary that there are great problems in the finding of new glycosyl hydrolases both due to the impossibility of cultivating many microorganisms which produce glycosyl hydrolases of potential interest, and due to the often only small sequence homology within the family of glycosyl hydrolases.

SUMMARY OF THE INVENTION

It has surprisingly been found that new glycosyl hydrolases can be characterized by screening DNA from environmental samples, so-called metagenomic DNA, and be provided in an industrially utilizable manner.

Mutually independent aspects of the present invention are therefore the new glycosyl hydrolases which are detailed in the sequence listing hereinafter under the sequence identification numbers (SEQ. ID.) 1, 2 and 3, glycosyl hydrolases which are substantially homologous thereto, and glycosyl hydrolases which can be obtained from those described by sequences 1 to 3 by conservative amino acid exchanges. Further aspects of the invention are nucleic acids (DNA or RNA) which code for one of the aforementioned glycosyl hydrolases.

An expression in the form "at least X %" hereinafter means "X % to 100% including the extreme values of X and 100 and all integral and non-integral percentages in between".

A protein means for the purposes of the present application a polymer which is composed of the natural amino acids, has a substantially linear structure, and assumes in most cases a three-dimensional structure to exercise its function. In the present application, the 19 proteinogenic naturally occurring L-amino acids are designated by the internationally used 1- and 3-letter codes.

An enzyme means for the purposes of the present application a protein which exercises a particular biochemical function. Glycosyl hydrolases means proteins which hydrolase glycosidic linkages. Preferred and industrially important glycosyl hydrolases are amylolytic proteins or enzymes having an amylolytic function, that is to say those which hydrolyze α-1,4-glycosidic linkages of polysaccharides, especially those linkages located in the interior of the polysaccharides. They are also referred to as α-1,4-amylases (E.C.3.2.1.1) or for short: α-amylases.

Numerous proteins are produced as so-called preproteins, i.e. together with a signal peptide. The latter then means the N-terminal part of the protein whose function is usually to ensure exportation of the produced protein from the producing cell into the periplasm or the surrounding medium and/or correct folding thereof. Subsequently, the signal peptide is under natural conditions cleaved off the remaining protein by a signal peptidase, so that this protein exercises its actual catalytic activity without the initially present N-terminal amino acids.

For industrial applications, the mature peptides, i.e. the enzymes processed after production thereof, are preferred because of their enzymatic activity to the preproteins.

Proproteins are inactive precursors of proteins. The precursors thereof having a signal sequence are referred to as preproproteins.

Nucleic acids mean for the purposes of the present application the molecules which are naturally composed of nucleotides and serve as information carriers and which code for the linear amino acid sequence in proteins or enzymes. They may be in the form of a single strand, of a single strand complementary to the single strand, or of a double strand. For molecular biological operations, preference is given to the nucleic acid DNA, as the naturally more durable information carrier. In contrast, an RNA is produced to implement the invention in a natural environment such as, for example, in an expressing cell, which is why RNA molecules essential to the invention likewise represent embodiments of the present invention.

In the case of DNA, the sequences of the two complementary strands in all three possible reading frames in each case must be taken into account. Account must also be taken of the fact that different codon triplets may code for the same amino acids, so that a particular amino acid sequence can be derived from a plurality of different nucleotide sequences which may exhibit only little identity (degeneracy of the genetic code). In addition, different organisms exhibit differences in the usage of these codons. For these reasons, both amino acid sequences and nucleotide sequences must be included in consideration of the scope of protection, and indicated nucleotide sequences are in each case to be regarded only as an example of coding for a particular amino acid sequence.

The information unit corresponding to a protein is also referred to as gene for the purposes of the present invention.

A skilled person is able by methods generally known nowadays, such as, for example, chemical synthesis or polymerase chain reaction (PCR) in conjunction with standard methods of molecular biology and/or protein chemistry, to prepare on the basis of known DNA and/or amino acid sequences the corresponding nucleic acids as far as the complete genes. Such methods are disclosed for example in the "Lexikon der Biochemie", Spektrum Akademischer Verlag, Berlin, 1999, volume 1, pp. 267-271 and volume 2, pp. 227-229.

Alterations in the nucleotide sequence like those which can be brought about for example by methods of molecular biology known per se are referred to as mutations. Depending on the nature of the alteration, known examples are deletion, insertion or substitution mutations or those in which different genes or parts of genes are fused together (shuffling); these are gene mutations. The relevant organisms are referred to as mutants. The proteins derived from mutated nucleic acids are referred to as variants. Thus, for example, deletion, insertion, substitution mutations or fusions lead to deletion-, insertion-, substitution-mutated or fusion genes and, at the protein level, to corresponding deletion, insertion or substitution variants or fusion proteins.

Fragments mean all proteins or peptides which are smaller than natural proteins or those which correspond to completely translated genes and can for example also be obtained synthetically. They can be assigned to the relevant complete proteins on the basis of their amino acid sequences. They may, for example, adopt identical structures or exercise proteolytic activities or part activities such as, for example, complexation of a substrate. Fragments and deletion variants of starting proteins are in principle similar; whereas fragments tend to represent relatively small pieces, deletion mutants tend to lack only short regions and thus only individual part functions.

The fragments correspond at the nucleic acid level to the partial sequences.

Chimeric or hybrid proteins mean for the purposes of the present application proteins which are composed of elements which naturally originate from different polypeptide chains from the same organism or from different organisms. This procedure is also called shuffling or fusion mutagenesis. The point of such a fusion may be, for example, to bring about or to modify a particular enzymatic function with the aid of the protein portion which is fused on. It is in this connection immaterial for the purposes of the present invention whether such a chimeric protein consists of a single polypeptide chain or a plurality of subunits on which different functions may be distributed. To implement the latter alternative it is possible for example for a single chimeric polypeptide chain to be broken down into a plurality thereof by a specific proteolytic cleavage post-translationally or only after a purification step.

Proteins obtained by insertion mutation mean variants which have been obtained by methods known per se through introduction of a nucleic acid fragment or protein fragment into the starting sequences. Because of their similarity in principle, they are to be assigned to the chimeric proteins. They differ from the latter only in the ratio of the size of the unaltered protein portion to the size of the complete protein. The proportion of foreign protein in such insertion-mutated proteins is less than in chimeric proteins.

Inversion mutagenesis, i.e. a partial inversion of sequence, can be regarded as a special form both of deletion and of insertion. The same applies to a regrouping, differing from the original amino acid sequence, of various parts of the molecule. It can be regarded as deletion variant, as insertion variant and as shuffling variant of the original protein.

Derivatives mean for the purposes of the present application proteins whose pure amino acid chain has been chemically modified. Such derivatizations may, for example, take place biologically in connection with protein biosynthesis by the host organism. Methods of molecular biology can be employed for this purpose. However, they can also be carried out chemically, for example by chemical transformation of a side chain of an amino acid or by covalent bonding of another compound to the protein. Such a compound may also be, for example, other proteins which are linked for example via bifunctional chemical compounds to proteins of the invention. Such modifications may, for example, influence the substrate specificity or the strength of binding to the substrate or bring about a temporary blocking of the enzymatic activity if the substance which is coupled on is an inhibitor. This may be worthwhile for example for the period of storage. Derivatization likewise means covalent bonding to a macromolecular support.

Proteins may also be included in groups of immunologically related proteins via the reaction with an antiserum or a particular antibody. Those belonging to a group are distinguished by having the same antigenic determinant recognized by an antibody.

For the purposes of the present invention, all enzymes, proteins, fragments and derivatives are, unless they need to be explicitly referred to as such, included under the generic term of proteins.

Vectors mean for the purposes of the present invention elements which consist of nucleic acids and which comprise as characterizing nucleic acid region a gene of interest. They are able to establish the latter as a stable genetic element which replicates independently of the remaining genome in a species or a cell line over a plurality of generations or cell divisions. Vectors are, especially when used in bacteria, specific plasmids, that is to say circular genetic elements. In genetic engineering a distinction is made on the one hand between vectors which are used for storage and thus to a certain extent also for the genetic engineering operation, called cloning vectors, and on the other hand those which perform the function of establishing the gene of interest in the host cell, i.e. making expression of the relevant protein possible. These vectors are referred to as expression vectors.

The enzymatic activity of an enzyme under consideration can be deduced from the amino acid or nucleotide sequence by comparison with known enzymes which are deposited for example in generally accessible databases. This activity can be qualitatively or quantitatively modified by other regions of the protein which are not involved in the actual reaction. This might affect for example the enzyme stability, the activity, the reaction conditions or the substrate specificity.

Such a comparison takes place by correlating similar sequences in the nucleotide or amino acid sequence of the proteins under consideration with one another. This is called homologization. A tabular correlation of the relevant positions is referred to as alignment. In the analysis of nucleotide sequences in turn account must be taken of both complementary strands and all three possible reading frames in each case; likewise the degeneracy of the genetic code and the organism-specific codon usage. Alignments are now produced by computer programs, such as, for example, by the FASTA or BLAST algorithms; this procedure is described for example by D. J. Lipman and W. R. Pearson (1985) in *Science*, volume 227, pp. 1435-1441.

A compilation of all the positions which agree in the compared sequences is referred to as a consensus sequence.

Such a comparison also permits a statement to be made about the similarity or homology of the compared sequences with one another. This is expressed in percent identity, i.e. the proportion of identical nucleotides or amino acid residues at the same positions. A broader definition of homology includes the conserved amino acid exchanges in this value. The term then used is percent similarity. Such statements can be made about complete proteins or genes or only about individual regions.

Production of an alignment is the first step in defining a sequence space. This hypothetical space includes all sequences which are to be derived by permutation in individual positions and which result by taking account of all the variations occurring in the relevant individual positions of the alignment. Every hypothetically possible protein molecule forms a point in this sequence space. For example, two amino acid sequences which, while being substantially identical, have two different amino acids only at two different positions in each case thus form the basis for a sequence space of four different amino acid sequences. A very large sequence space is obtained if further homologous sequences are found for each individual sequence in a space. Sequences of very low homology can also be recognized as belonging to a sequence space via such high homologies existing pairwise in each case.

Homologous regions of different proteins are those having the same functions which can be recognized by agreements in the primary amino acid sequence. This ranges as far as complete identities in very small regions, called boxes, which include only a few amino acids and usually exercise functions which are essential for the overall activity. Functions of the homologous regions mean very small partial functions of the function exercised by the complete protein, such as, for example, the formation of individual hydrogen bonds for complexation of a substrate or transition complex.

For the purposes of the present application, a distinction must be made between screening (hybridization screening or DNA screening) and activity assay. "Screening" of transformants generally means a detection reaction suitable for recognizing clones in which the desired transformation event has taken place. It usually aims, as, for example, in the familiar blue-white selection, at detection of a biochemical activity which the transformants have acquired or which is no longer present after recombination has taken place. This type of biochemical detection reaction is referred to for the purposes of the present application also as activity assay.

However, screening also designates the searching of a gene library with particular nucleic acids and the identification, possible thereby, of sufficiently similar nucleic acid sequences. This takes place for example via Southern or Northern blot hybridizations as are sufficiently well known from the prior art. This term includes for example also PCR-based methods of the invention for identifying and/or obtaining new genes from a collection of organisms or nucleic acids, which are characterized in that PCR primers having a variable 3' region and a 5' region with high homology to corresponding regions from known genes are used.

The performance of an enzyme means its activity in the industrial sector considered in each case. This is based on the actual enzymatic activity but also depends on further factors relevant to the particular process. These include, for example, stability, substrate binding, interaction with the material carrying the substrate or interactions with other ingredients, in particular synergies. Thus, for example, when investigating whether an enzyme is suitable for use in washing or cleaning compositions, its contribution to the washing or cleaning performance of a composition formulated with further constituents will be considered. For various industrial applications it is possible for an enzyme to be developed further and optimized by techniques of molecular biology which are known per se, especially those mentioned above.

ORI: original of replication; lacI: gene for lac repressor; lacZ-alpha: gene for alpha peptide of beta-galactosidase; ampicillinR: beta-lactamase.

Figure 2:
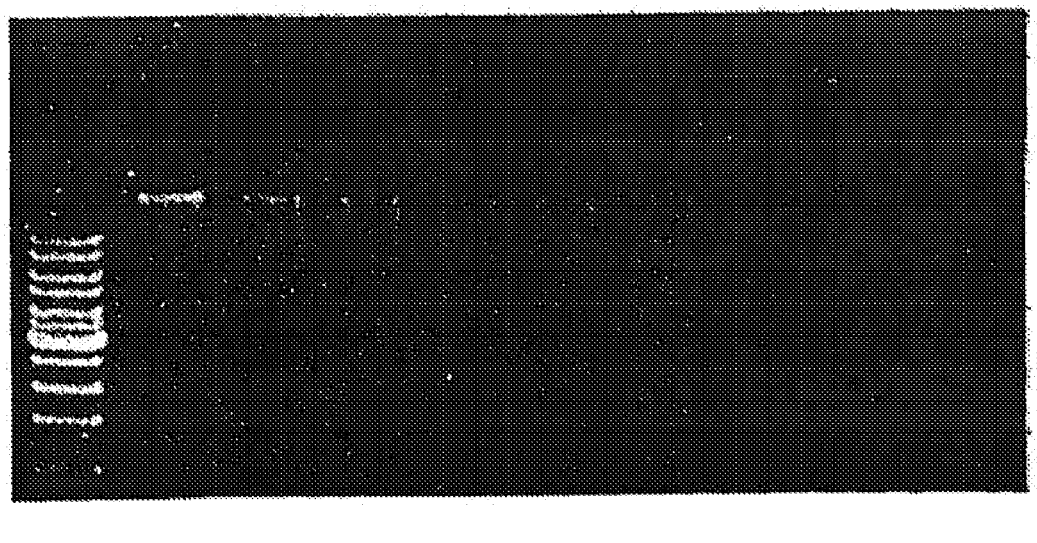

FIG. 2: Analysis of Sau3AI restriction kinetics of metagenomic DNA from soil to establish the optimal restriction time at a specified enzyme concentration. From a complete mixture of 20 µl with 0.3 U of Sau3A1 per µg of DNA, 2 µl portions were transferred after 0, 1, 2, 3, 4, 5, 6, 8 and 10 min to 1× stop buffer and fractionated on a 0.7% agarose gel (lanes 1-9 from left to right). Markers (M): 1 kb DNA ladder (in kb from top to bottom: 10; 8; 6; 5; 4; 3.5; 3; 2.5; 2; 1.5; 1. Lane 7 representative of restriction for 5 min here shows optimal partial digestion in the size range 8-12 kb.

Figure 3:
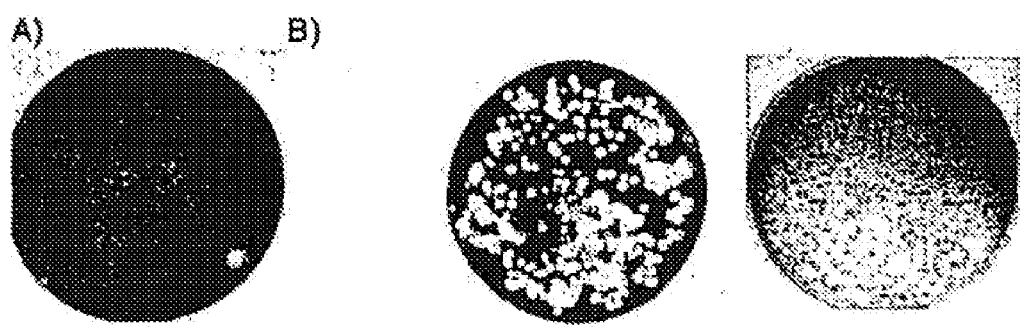

FIG. 3: Activity assay to detect amylase in a metagenomic expression gene library. Lugol-stained LB agar plates with 1% soluble starch. Amylase-expressing recombinant *E. coli* clones exhibit a zone of starch degradation around the colonies, which appears pale after lugol staining.

A) Example of a "parent plate" (primary plating) of a zone-forming clone from the complete plating of a plasmid expression gene library after transformation of *E. coli*.

B) Isolated colonies after replating (secondary plating) from a starch zone region of a parent plate. Individual colonies with and without zone are evident. The plasmids from colonies with zone were analyzed and their insert DNA was sequenced.

Left: lugol-stained plate with pale zones of degradation

Figure 4:
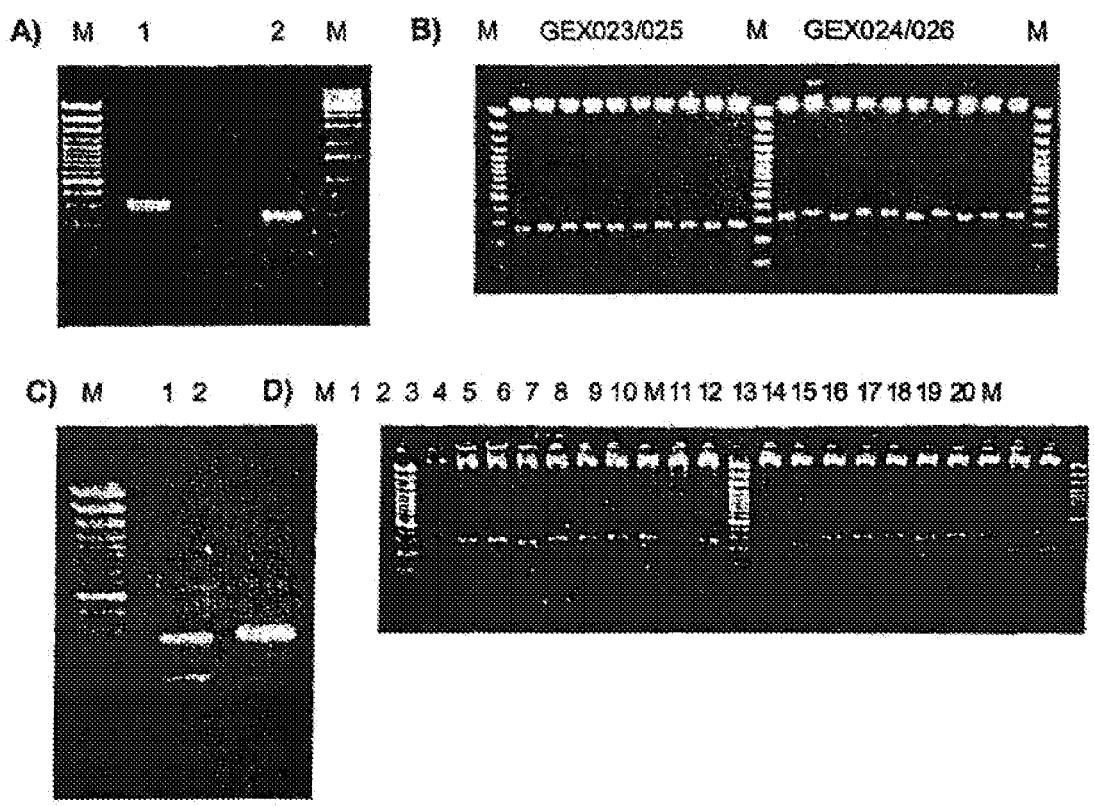

Right: clarification zones of active clones on cloudy starch without Lugol stain FIG. 4: Size analysis of the PCR reaction products with primers GEX023/025, GEX024/026 and GEX036/038 on soil metagenomic DNA.

Example of the size analysis of the PCR reaction products from soil S196 (A) and soil S131 (C). The PCR was carried out with the amylase-specific primers GEX024/026 (A, lane 1), GEX023/025 (A, lane 2) and GEX036/038 (C, lane 1), and the reaction products were fractionated (1/10 of the reaction volume) in a 2% agarose gel. A PCR with GEX024/026 on genomic DNA from *Streptomyces* sp. strain B124 (C, lane 2) took place in parallel as positive control. See text (above) for PCR conditions.

Markers (M): 100 bp DNA ladder (in bp from top to bottom: 3000, 2000, 1500, 1200, 1031, 900, 800, 700, 600, 500, 400, 300, 200, 100).

A 300 bp band is amplified with the primer pair GEX024/026, and a 280 bp fragment with the primer pair GEX023/025, whereas 2 products 300 and 150 bp in size are amplified with GEX036/038 only after reamplification of the original PCR mixture. All the PCR products were cloned, and the DNA of up to 18 clones was fractionated after excision of the inserts by EcoRI restriction on a 2% agarose gel (B). The clones for the PCR product GEX023/025 show insert DNA sizes of about 280 bp throughout (B, left), the fragment sizes for the clones from the PCR of GEX024/026 vary between 300 and 350 bp (B, right). The clones from the PCR of GEX036/038 show fragments around 300 bp and 150 bp (D).

FIG. 5: Consensus sequence—A-[SEQ ID NO:305] and amino acid exchanges of 50 glycosyl hydrolases from soil microorganisms. The consensus sequence is based on an alignment with Clustal X Version 1.64b (standard settings). Amino acid positions 1-8 and 116-123 are in part specified by the PCR primer sequences (GEX024/026).

FIG. 6: Consensus sequence—D-[SEQ ID NO: 306] (subsequence space to A) and amino acid exchanges of 42 amylases from soil microorganisms. The consensus sequence is based on an alignment with Clustal X Version 1.64b (standard settings). Amino acid positions 1-8 and 114-121 are in part specified by the PCR primer sequences (GEX024/026).

Figure 7B:
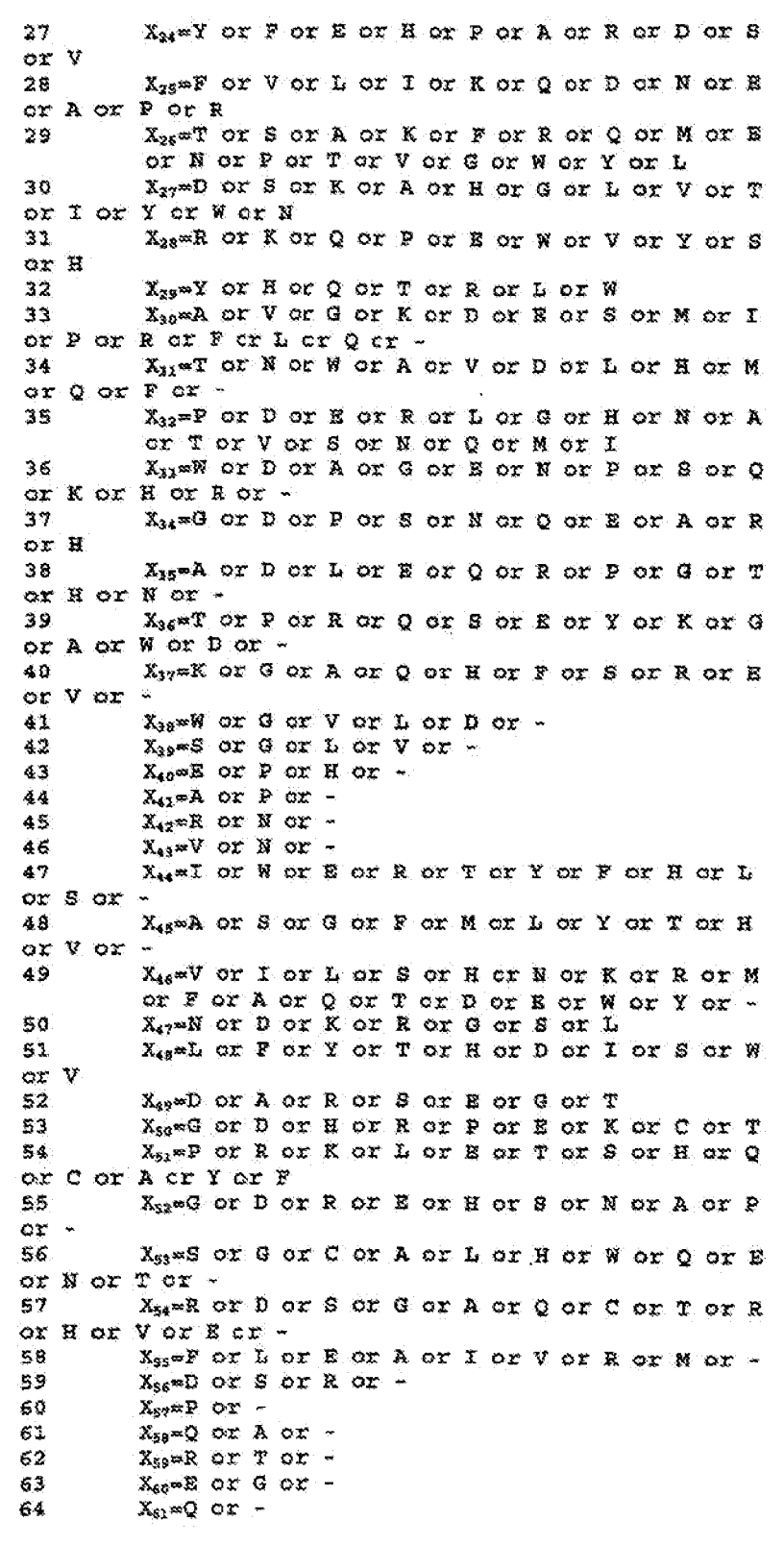

FIG. 7: Consensus sequence—B-[SEQ ID NO: 307] and amino acid exchanges of 99 glycosyl hydrolases from soil microorganisms. The consensus sequence is based on an alignment with Clustal X Version 1.64b (standard settings). Amino acid positions 1-12 and 102-109 are in part specified by the PCR primer sequences (GEX023/210/211/036 and GEX25/038).

FIG. 8: Consensus sequence—C-[SEQ ID NO:308] (subsequence space to B) and amino acid exchanges of 10 amylases from soil microorganisms. The consensus sequence is based on an alignment with Clustal X Version 1.64b (standard settings). Amino acid positions 1-12 and 72-78 are in part specified by the PCR primer sequences (GEX023/210/211 and GEX25).

Figure 9:
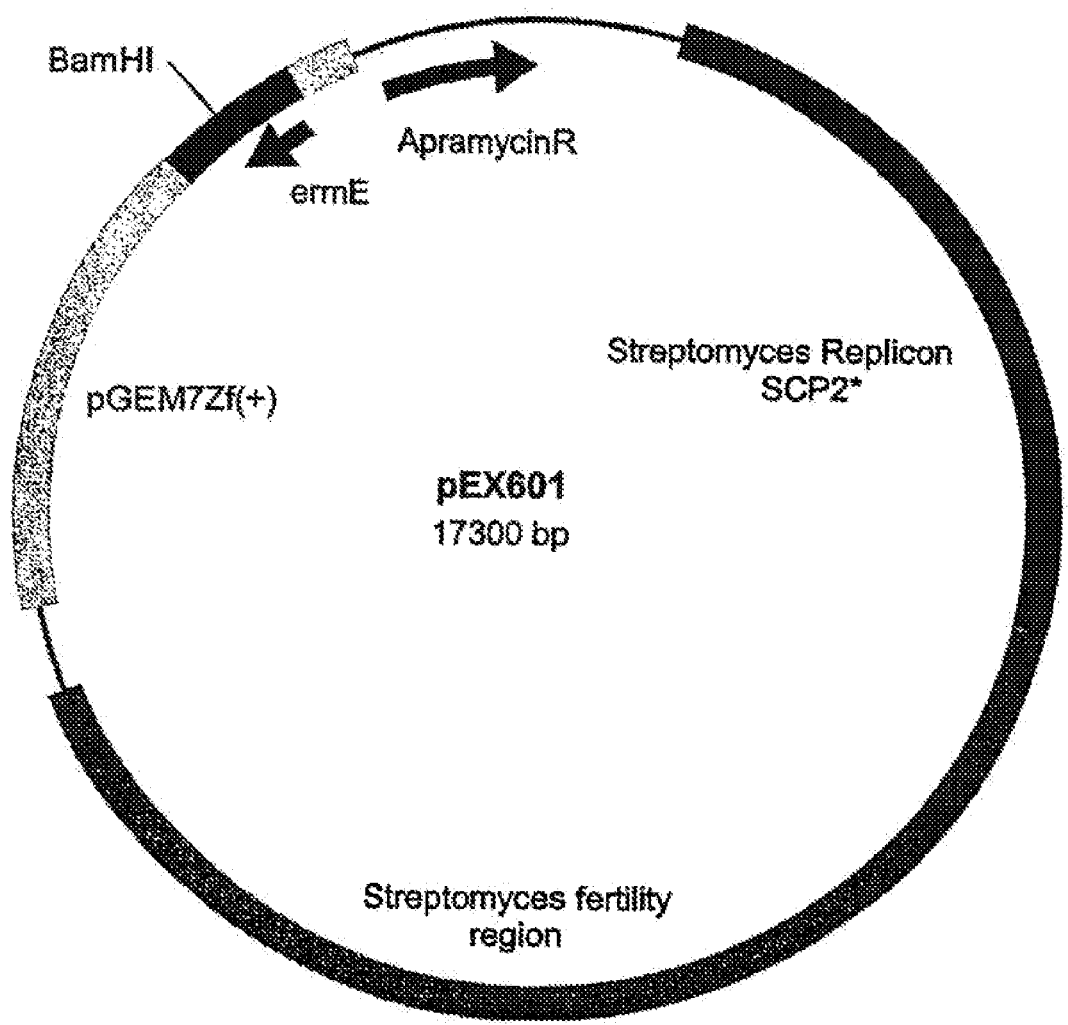

FIG. 9: Diagrammatic representation of the plasmid shuttle vector pEX601 used for the expression of the metagenomic amylases in Streptomyces lividans TK24.

The vector was produced by inserting the ermE/MCS/terminator cassette (BglII/EcoRI) from pWHM680pro into the BamHI/EcoRI-digested vector pWHM601. The BamHI recognition sequence present in the multicloning site was used to clone the amylase genes. Both pWHM601 and pWHM680pro originate from the laboratory of Dr C. R. Hutchinson (University of Wisconsin, pers. communication).

Expression of inserted genes takes place starting from the constitutive ermE promoter.

The indicated sizes of the vector and of the elements contained therein are estimates. SCP2* replicon origin of replication in streptomyces; ermE, ermE up promoter of *S. erythrea*; apramycinR apramycin resistance gene.

Expression of the amylase genes in *Streptomyces lividans* can also be achieved with other suitable shuttle vectors such as, for example, pAX5a (Faβ S. H., Engels, J. W. 1996; Influence of Specific Signal Peptide Mutations on the Expression and Secretion of the alpha-Amylase Inhibitor Tendamistat in *Streptomyces lividans*. J. Biol. Chem. 271, Number 25, 15244-15252).

DETAILED DESCRIPTION OF ILLUSTRATIVE EMBODIMENTS

A first aspect of the present invention is a glycosyl hydrolase whose amino acid sequence agrees at least 75%, at least 80%, preferably at least 85%, in particular at least 90%, particularly preferably at least 95% and very particularly preferably 100% with the amino acid sequence indicated in SEQ ID NO:1.

A further aspect of the present invention is a glycosyl hydrolase whose amino acid sequence agrees at least 50%, at least 60%, preferably at least 70%, in particular at least 80%, particularly preferably at least 90% and very particularly preferably 100% with the amino acid sequence indicated in SEQ ID NO: 2.

A further aspect of the present invention is a glycosyl hydrolase whose amino acid sequence agrees at least 60%, at least 70%, preferably at least 80%, in particular at least 90%, particularly preferably at least 95% and very particularly preferably 100% with the amino acid sequence indicated in SEQ ID NO: 3.

A further aspect of the present invention is a nucleic acid coding for a glycosyl hydrolase whose amino acid sequence is at least 70%, preferably at least 80%, in particular at least 90%, particularly preferably at least 95% and very particularly preferably 100% identical to one of the amino acid sequences indicated in Seq. 1 to 3, or whose amino acid sequence comprises a part which is at least 70%, preferably at least 80%, in particular at least 90%, particularly preferably at least 95% and very particularly preferably 100% identical to one of the amino acid sequences indicated in SEQ ID NOs: 1 to 3.

A further aspect of the present invention is a nucleic acid which codes for a glycosyl hydrolase and whose nucleotide sequence agrees at least 75%, at least 80%, preferably at least 85%, in particular at least 90%, particularly preferably at least 95% and very particularly preferably 100% with the nucleotide sequence indicated in SEQ ID NO: 4.

A further aspect of the present invention is a nucleic acid which codes for a glycosyl hydrolase and whose nucleotide sequence agrees at least 50%, at least 60%, preferably at least 70%, in particular at least 80%, particularly preferably at least 90% and very particularly preferably 100% with the nucleotide sequence indicated in SEQ ID NO:5.

A further aspect of the present invention is a nucleic acid which codes for a glycosyl hydrolase and whose nucleotide sequence agrees at least 60%, at least 70%, preferably at least 80%, in particular at least 90%, particularly preferably at least 95% and very particularly preferably 100% with the nucleotide sequence indicated in SEQ ID NO:6.

A further aspect of the present invention is a glycosyl hydrolase which is obtainable by one or more conservative amino acid exchanges from one of the abovementioned glycosyl hydrolases.

A further aspect of the present invention is a method for identifying and isolating new glycosyl hydrolases, which is characterized in that
 a) metagenomic DNA is obtained from various habitats,
 b) the metagenomic DNA is subcloned into a suitable, in particular bacterial, cloning system, and
 c) the gene library produced in this way is subjected to a screening for new glycosyl hydrolases.

In an important embodiment of the method of the invention, the biodiversity of the metagenomic DNA is determined by PCR typing using glycosyl hydrolase-specific PCR primers and subsequent sequencing, generating a multitude of gene fragments (PCR fragments) which cover one or more sequence spaces.

The glycosyl hydrolases of the invention have been provided by means of the method of the invention.

A habitat which is preferred according to the invention for obtaining metagenomic DNA is earth (soil). The soil samples are processed in a manner known to the skilled worker, for example dried and mechanically reduced in size. The sample is then chemically digested, and the DNA present in the sample extracted, for example as described in the publication by Zhou, J., Bruns, M. A., Tiedje, J. M. (1996): "DNA recovery from soils of diverse composition", *Appl. Environ. Microbiol.*, volume 62, pp. 316-322.

The screening in step c) is preferably carried out by selection for glycosyl hydrolase activity, for example by selection of clones which form a clear zone on starch-containing agar plates.

Cloning systems suitable for carrying out step b) are known to the skilled worker, for example *Escherichia coli* and *Streptomyces lividans*, but also *Bacillus*; in addition yeasts and fungi, e.g. *Saccharomyces, Candida, Pichia, Aspergillus* and others.

The screening in step c) can, however, also be carried out by colony hybridization using probes based on the above-mentioned PCR fragments. The probes may in this case be derived from a single gene fragment or else from a plurality, in the extreme case from an undifferentiated pool, of PCR fragments.

A minimum homology, which depends on the hybridization conditions, is necessary for a positive reaction. Screening a gene library with a probe which is derived from a single, previously known enzyme gene greatly restricts the breadth of diversity of the positive clones to be found. In order to be able to find the genes which are actually present in the gene library, including those less closely related, it is worthwhile to use a multitude of probes whose composition does not need to be characterized in detail but which encompass a part which is as large as possible of the sequence space.

Selection of suitable probes for embracing a sequence space which is as large as possible takes place as described in DE-A-101 31 441.8-41 or PCT/EP02/06842, which is incorporated herein by reference.

This is followed where appropriate by analysis of the sequence of individual clones found, checking of the open reading frame (ORF) for completeness, and determination of sequence homology.

Individual, overexpressed clones can be biochemically characterized and investigated for their stability in respect of, for example, pH, temperature and formulation components typical of washing and cleaning compositions.

Glycosyl hydrolase-specific PCR primers which can be employed in the method of the invention are those which bind to highly conserved regions of the nucleic acids coding for glycosyl hydrolases. The primer binding sites should additionally flank a region which codes for a protein segment having as few as possible loops of different lengths.

Suitable glycosyl hydrolase-specific PCR primers are especially those which bind to nucleic acid regions which code for those regions of the glycosy hydrolases which are grouped in direct vicinity around the catalytically active residues. Thus, for example, for the regions at the C-terminal end of β-pleated sheet 3, of β-pleated sheet 4 and of β-pleated sheet 7.

Glycosyl hydrolase-specific PCR primers which can be employed particularly preferably in the method of the invention are those listed in Table 1, with very particular preference for the primer pairs GEX 24/26 and GEX 23/25.

A number of PCR fragments covering a sequence space of glycosyl hydrolases has been provided with the aid of the method of the invention.

50 DNA sequences have been provided by means of the primer pair GEX 24/26 and are listed in the sequence listing under SEQ ID NOs:57 to 106. The amino acid sequences corresponding to these DNA sequences are listed in the sequence listing under SEQ ID NOs:7 to 56.

99 DNA sequences have been provided by means of the primer pairs GEX 23/25, GEX 36/38 and 210-211/25 and are listed in the sequence listing under SEQ ID NOs:206 to 304. Since the sequences produced with the three primer combinations cover essentially the same DNA segment, they are treated together below and, where appropriate, referred to as GEX23/25 for simplicity. The amino acid sequences corresponding to these DNA sequences are listed in the sequence listing under SEQ ID NOs:107 to 205.

Production of sequence alignments of the PCR fragments resulted in consensus sequences which represent this sequence space or part-spaces thereof.

Further aspects of the present invention are therefore glycosyl hydrolases which are to be regarded as representatives of the sequence spaces represented in consensus sequences A and B or of the sequence spaces represented in consensus sequences D [SEQ ID NO: 306] and C [SEQ ID NO:308].

Consensus sequences A [SEQ ID NO:305], D [SEQ ID NO:306], B [SEQ ID NO:307] and C [SEQ ID NO:308] are depicted in FIGS. 5 to 8 and in the sequence listing under SEQ ID NOs:305 to 308.

There is only very little variance in the consensus sequences shown, in positions 1-8 and 116-123 (A) [SEQ ID NO:305], 1-8, 114-121 (D) [SEQ ID NO:306], 1-12, 102-109 (B) [SEQ ID NO:307] and 1-12, 72-78 (C) [SEQ ID NO:308]. This emerges from the PCR-based method which is described hereinafter and in the examples and which was employed to identify this sequence: these partial sequences correspond to the DNA regions onto which the primers employed for the amplification have bound. Depending on the stringency of the conditions under which this binding takes place, it is also possible for different nucleotide sequences to be bound and amplified; thus, with the comparatively low selectivity at these positions, the DNA obtained as product does not agree completely with the template. For this reason, protection is sought in particular for the inner partial region of the consensus sequences which corresponds to the position between the sequence segments indicated above.

Comparison of the 149 amino acid sequences derived from the PCR fragments with the entries in the enzyme database GenBank (National Center for Biotechnology Information NCBI, National Institutes of Health, Bethesda, Md., USA) confirms that they are all partial sequences of glycosyl hydrolases.

The result of this comparison is shown in Table 2. Also indicated therein in each case are the database entries most similar to the partial sequences found, and the degree of homology between these two. Comparison with the sequences deposited in the database shows that the most similar proteins have levels of homology of 95.1% (primer pair 23/25) identity, and 91% (primer pair 24/26).

These amino acid sequences 107 to 205 define a sequence space which represents a part-space of the sequence space described by the consensus sequences with SEQ ID NOs: 307 and 308. It is included in the preferred scope of protection. Thus, every point in this sequence space represents a partial sequence of the invention.

In other words, all glycosyl hydrolases whose amino acid sequences can be homologized in a partial region with the consensus sequences with SEQ ID NO:307 and 308, and have in this region only amino acids which are located at the appropriate position in one of these two sequences, are claimed. In this sense, they can be traced back in any position of this part to one of these sequences.

Further aspects of the present invention are therefore glycosyl hydrolases whose amino acid sequences comprise a part which is 96% and increasingly preferably 97%, 98%, 99%, 99.25%, 99.5%, 99.75% or particularly preferably 100% identical to one of these consensus sequences with SEQ ID NO:307 (B) and 308 (C), or can be traced back in any homologous position directly to one of these sequences. This applies, as described above, in particular over the partial region corresponding to positions 13 to 101 of consensus sequence B [SEQ ID NO:307], or 13 to 71 of consensus sequence C [SEQ ID NO:308].

Further aspects of the present invention are therefore glycosyl hydrolases whose amino acid sequences comprise a part which is 92% and increasingly preferably 93%, 94%, 95%, 96%, 97%, 98%, 99% or particularly preferably 100% identical to one of these consensus sequences with SEQ ID NO:305 (A) and 306 (D), or can be traced back in any homologous position directly to one of these sequences. This applies, as described above, in particular over the partial region corresponding to positions 9 to 115 of consensus sequence A [SEQ ID NO:305] or 9 to 113 of consensus sequence D [SEQ ID NO:306].

A further specific aspect of the invention is a glycosyl hydrolase whose amino acid sequence comprises a part which is at least 92%, in particular at least 94%, preferentially at least 96%, preferably at least 99%, particularly preferably 100% identical to one of the amino acid sequences indicated under SEQ ID NOs:7 to 56, in particular over the partial region corresponding to positions 9 to 113 according to the consensus sequence of SEQ ID NO:306.

A further specific aspect of the invention is a glycosyl hydrolase whose amino acid sequence comprises a part which is at least 92%, in particular at least 94%, preferentially at least 96%, preferably at least 99%, particularly preferably 100% identical to one of the amino acid sequences indicated under SEQ ID NO:7 to 56, in particular over the partial region corresponding to positions 9 to 115 according to the consensus sequence of SEQ ID NO:305.

A further specific aspect of the invention is a glycosyl hydrolase whose amino acid sequence comprises a part which is 96%, in particular at least 97%, preferentially at least 98%, preferably at least 99%, particularly preferably 100% identical to one of the amino acid sequences indicated under SEQ ID NOs:107 to 205, in particular over the partial region corresponding to positions 13 to 71 according to the consensus sequence of SEQ ID NO:308.

A further specific aspect of the invention is a glycosyl hydrolase whose amino acid sequence comprises a part which is 96%, in particular at least 97%, preferentially at least 98%, preferably at least 99%, particularly preferably 100% identical to one of the amino acid sequences indicated under SEQ ID NOs:107 to 205, in particular over the partial region corresponding to positions 13 to 101 according to the consensus sequence of SEQ ID NO:307.

A further specific aspect of the invention is a glycosyl hydrolase which is obtainable by one or more conservative amino acid exchanges from a glycosyl hydrolase of the invention.

A further specific aspect of the invention is a glycosyl hydrolase which can be obtained by derivatization, fragmentation, deletion mutation or insertion mutation of a glycosyl hydrolase.

A further specific aspect of the invention is a nucleic acid coding for a glycosyl hydrolase whose amino acid sequence comprises a part which is at least 96%, in particular at least 97%, preferentially at least 98%, preferably at least 99%, particularly preferably 100% identical to the consensus sequence of SEQ ID NO:308, in particular over the partial region corresponding to positions 13 to 71.

A further specific aspect of the invention is a nucleic acid coding for a glycosyl hydrolase whose amino acid sequence comprises a part which is at least 96%, in particular at least 97%, preferentially at least 98%, preferably at least 99%, particularly preferably 100% identical to the consensus sequence of SEQ ID NO:307, in particular over the partial region corresponding to positions 13 to 101.

A further specific aspect of the invention is a nucleic acid coding for a glycosyl hydrolase whose amino acid sequence comprises a part which is at least 92%, in particular at least 94%, preferentially at least 96%, preferably at least 99%, particularly preferably 100% identical to the consensus sequence of SEQ ID NO:305, in particular over the partial region corresponding to positions 9 to 115.

A further specific aspect of the invention is a nucleic acid coding for a glycosyl hydrolase whose amino acid sequence comprises a part which is at least 92%, in particular at least 94%, preferentially at least 96%, preferably at least 99%, particularly preferably 100% identical to the consensus sequence of SEQ ID NO:306, in particular over the partial region corresponding to positions 9 to 113.

A further specific aspect of the invention is a nucleic acid coding for a glycosyl hydrolase whose amino acid sequence comprises a part which is at least 92%, in particular at least 94%, preferentially at least 96%, preferably at least 99%, particularly preferably 100% identical to one of the amino acid sequences indicated under SEQ ID NO:7 to 56, in particular over the partial region corresponding to positions 9 to 113 according to the consensus sequence of SEQ ID NO:306.

A further specific aspect of the invention is a nucleic acid coding for a glycosyl hydrolase whose amino acid sequence comprises a part which is at least 92%, in particular at least 94%, preferentially at least 96%, preferably at least 99%, particularly preferably 100% identical to one of the amino acid sequences indicated under SEQ ID NO:7 to 56, in particular over the partial region corresponding to positions 9 to 115 according to the consensus sequence of SEQ ID NO:305.

A further specific aspect of the invention is a nucleic acid coding for a glycosyl hydrolase whose amino acid sequence comprises a part which is 96%, in particular at least 97%, preferentially at least 98%, preferably at least 99%, particularly preferably 100% identical to one of the amino acid sequences indicated under SEQ ID NO:107 to 205, in particular over the partial region corresponding to positions 13 to 71 according to the consensus sequence of SEQ ID NO:308.

A further specific aspect of the invention is a nucleic acid coding for a glycosyl hydrolase whose amino acid sequence comprises a part which is 96%, in particular at least 97%, preferentially at least 98%, preferably at least 99%, particularly preferably 100% identical to one of the amino acid sequences indicated under SEQ ID NO:107 to 205, in particular over the partial region corresponding to positions 13 to 101 according to the consensus sequence of SEQ ID NO:307.

A further specific aspect of the invention is a nucleic acid coding for a glycosyl hydrolase of the invention.

A further specific aspect of the invention is a nucleic acid which codes for a glycosyl hydrolase and whose sequence is at least 80%, preferably at least 90%, particularly preferably 100% identical to one of the nucleotide sequence indicated under SEQ ID NO:57 to 106, or 206 to 304, preferably in the positions which are not specified by the PCR primer sequences.

A further specific aspect of the invention is an oligonucleotide, in particular a PCR primer, having one of the sequences indicated in SEQ ID NOs:309 to 316.

Further aspects of the invention are described in claims 20 and 21.

Nucleic acids which code for the variants possible according to the consensus sequence can be produced by generally known methods. For example, the "Lexikon der Biochemie", Spektrum Akademischer Verlag, Berlin, 1999, presents in volume 1, pp. 267-271, methods for de novo synthesis of DNA and in volume 2, pp. 227-229, the polymerase chain reaction (PCR). The sequences can be specified by the generally known coding system for amino acids, where appropriate in a codon usage characteristic of particular genera.

It is possible to employ for this purpose all conventional and expedient methods as disclosed for example in the manual of Fritsch, Sambrook and Maniatis "Molecular cloning: a laboratory manual", *Cold Spring Harbor Laboratory Press*, New York, 1989. It is also possible to use a PCR to introduce individual base exchanges into DNA.

The glycosyl hydrolases of the invention can be further optimized for example by chemical modification, directed evolution or sequence shuffling of the enzymes or enzyme fragments to give novel proteins or fusion proteins (hybrids, chimeric proteins). Methods known for this are, for example, the methods of directed evolution of enzymes like "In vivo homologous recombination" (Zhang, Y. M., Buchholz, F., Muyrers, J. P. P., Stewart, A. F. (1998): "A new logic for DNA engineering using recombination in *Escherichia coli*", *Nat. Genetics*, volume 20, pp. 123-128), "Staggered extension process StEP" (Zhao, H., Giver, L., Shao, Z., Affholter, J. A., Arnold, F. H. (1998): "Molecular evolution by staggered extension process (STEP) in vitro recombination", *Nat. Biotechnol.*, volume 16, pp. 258-261), "Random priming recombination" (Shao, Z., Zhao, H., Giver, L., Arnold, F. H. (1998): "Random-priming in vitro recombination: an effective tool for directional evolution", *Nucleic Acids Res.*, volume 26, pp. 681-683), "DNA shuffling" (Stemmer, W. P. C. (1994): "Rapid evolution of a protein in vitro by DNA shuffling", *Nature*, volume 370, pp. 389-391) and "Molecular breeding" (Ness, J. E., Welch, M., Giver, L., Bueno, M., Cherry, J. R., Borchert, T. V., Stemmer, W. P. C., Minshull, J. (1999): "DNA shuffling of subgenomic sequences of subtilisin", *Nat. Biotechnol.*, volume 17, pp. 893-896).

The glycosyl hydrolases of the invention can be protected in particular during storage by stabilizers for example from denaturation, decomposition or inactivation, for example through physical effects, oxidation or proteolysis. In many cases, complementary or mutually enhancing combinations of stabilizers are also used.

One group of stabilizers are reversible protease inhibitors such as, for example, benzamidine hydrochloride and leupeptin, borax, boric acids, boronic acids, salts or esters thereof, peptide aldehydes or purely peptide inhibitors such as ovomucoid or specific subtilisin inhibitors. Further familiar enzyme stabilizers are amino alcohols such as mono-, di-, triethanol- and -propanolamine, aliphatic carboxylic acids up to $C_{12}$, dicarboxylic acids, lower aliphatic alcohols, but especially polyols such as, for example, glycerol, ethylene glycol, propylene glycol or sorbitol. Calcium salts are likewise used, such as, for example, calcium acetate or calcium formate, magnesium salts, a wide variety of polymers such as, for example, lignin, cellulose ethers, polyamides or water-soluble vinyl copolymers, in order to stabilize the enzyme preparation in particular against physical effects or pH variations. Reducing agents and antioxidants such as, for example, sodium sulfite or reducing sugars increase the stability of the proteins to oxidative decomposition.

Numerous possible applications established in industry for glycosyl hydrolases are listed in manuals such as, for example, the book "Industrial enzymes and their applications" by H. Uhlig, published by Wiley, New York, 1998. The following compilation is not to be understood as a definitive list, but represents a selection of the possible industrial uses. Should it emerge that individual proteins lying outside the range of similarity are suitable, because of their enzymatic, in particular amylolytic, properties for the additional applications not expressly claimed herein, these are hereby included in the scope of protection of the present invention.

One embodiment of this aspect of the invention are washing and cleaning compositions which are characterized in that they comprise a glycosyl hydrolase of the invention or a derivative thereof.

One important area of use of glycosyl hydrolases and, in particular, amylases is that as active component in washing or cleaning compositions for cleaning textiles or solid surfaces, such as, for example, crockery, floors or utensils. In these applications, the amylolytic activity serves to break down by hydrolysis, or detach from the substrate, carbohydrate-containing contaminations and especially those based on starch. In such cases, they can be used alone, in suitable media or else in washing or cleaning compositions. The conditions to be chosen for this, such as, for example, temperature, pH, ionic strength, redox conditions or mechanical effects, should be optimized for the particular cleaning problem, i.e. in relation to the soiling and the substrate. Thus, usual temperatures for washing and cleaning compositions are in ranges from 10° C. for manual compositions via 40° C. and 60° C. up to 95° for machine compositions or for industrial applications. The ingredients of the relevant compositions are preferably also matched to one another. Since the temperature can usually be adjusted continuously in modern washing and dishwashing machines, all intermediate temperatures are also included. The other conditions can likewise be designed very specifically for the particular cleaning purpose via the other components of the compositions listed below.

Preferred compositions of the invention are distinguished by the washing or cleaning performance of this composition being improved by adding an amylolytic enzyme of the invention, compared with the formulation without this enzyme, under any of the conditions definable in this way. To this extent, the amylolytic proteins incorporated into compositions of the invention are preferably those able to improve the washing and/or cleaning performance of a washing or cleaning composition.

Further preferred compositions are distinguished by the amylolytic enzymes and the other components acting synergistically to remove the contaminations. This takes place for example by the hydrolysis products of the amylolytic proteins being solubilized by other components of the compositions, such as, for example, surfactants. A protein of the invention can be used both in compositions for large-scale consumers or industrial users and in products for the private consumer, and all presentations which are expedient and/or established in the art also represent embodiments of the present invention.

The washing or cleaning compositions of the invention mean all conceivable types of cleaning compositions, both concentrates and compositions to be used undiluted; for use on the commercial scale, in the washing machine or in hand washing or cleaning. They include, for example, washing compositions for textiles, carpets, or natural fibers, for which the term washing composition is used according to the present invention. They also include, for example, dishwashing compositions for dishwashing machines or manual dishwashing compositions or cleaners for hard surfaces such as metal, glass, porcelain, ceramic, tiles, stone, painted surfaces, plastics, wood or leather; the term cleaning composition is used according to the present invention for these. Every type of washing or cleaning composition represents an embodiment of the present invention as long as a protein of the invention has been added thereto.

Embodiments of the present invention include all presentations established in the art and/or all expedient presentations of the compositions of the invention. These include, for example, compositions which are solid, in powder form, liquid, in gel form or pasty, where appropriate also composed of a plurality of phases, compressed or uncompressed; the following also belong thereto, for example: extrudates, granules, tablets or pouches, packaged both in large containers and in portions.

The glycosyl hydrolases, in particular amylases, are combined in compositions of the invention for example with one or more of the following ingredients: nonionic, anionic and/or cationic surfactants, bleaches, bleach activators, bleach catalysts, builders and/or cobuilders, solvents, thickeners, sequestrants, electrolytes, optical brighteners, antiredeposition agents, corrosion inhibitors, especially silver protectants, soil-release agents, color transfer inhibitors, foam inhibitors, abrasives, dyes, fragrances, antimicrobial agents, UV stabilizers, enzymes such as, for example, proteases, (where appropriate other) amylases, lipases, cellulases, hemicellulases or oxidases, stabilizers, especially enzyme stabilizers, and other components known in the art.

Preferred compositions are characterized in that they comprise from 0.000001 percent by weight to 5% by weight, and increasingly preferably 0.00001 to 4% by weight, 0.0001 to 3% by weight, 0.001 to 2% by weight or 0.01 to 1% by weight, of the amylolytic protein or derivative.

The nonionic surfactants used are preferably alkoxylated, advantageously ethoxylated, in particular primary alcohols having preferably from 8 to 18 carbon atoms and, on average, from 1 to 12 mol of ethylene oxide (EO) per mole of alcohol, in which the alcohol radical can be linear or, preferably, methyl-branched in the 2-position or can comprise linear and methyl-branched radicals in a mixture as are customarily present in oxo alcohol radicals. Particular preference is, however, given to alcohol ethoxylates containing linear radicals of alcohols of native origin having from 12 to 18 carbon atoms, for example from coconut, palm, tallow fatty or oleyl alcohol, and, on average, from 2 to 8 EO per mole of alcohol. Preferred ethoxylated alcohols include, for example, $C_{12-14}$-alcohols having 3 EO or 4 EO, $C_{9-11}$-alcohol having 7 EO, $C_{13-15}$-alcohols having 3 EO, 5 EO, 7 EO or 8 EO, $C_{12-18}$-alcohols having 3 EO, 5 EO or 7 EO, and mixtures of these, such as mixtures of $C_{12-14}$-alcohol having 3 EO and $C_{12-18}$-alcohol having 5 EO. The degrees of ethoxylation given are statistical averages which may be an integer or a fraction for a specific product. Preferred alcohol ethoxylates have a narrowed homolog distribution (narrow range ethoxylates, NRE). In addition to these nonionic surfactants, fatty alcohols having more than 12 EO can also be used. Examples thereof are tallow fatty alcohol having 14 EO, 25 EO, 30 EO or 40 EO.

A further class of preferably used nonionic surfactants which are used either as the sole nonionic surfactant or in combination with other nonionic surfactants are alkoxylated, preferably ethoxylated or ethoxylated and propoxylated, fatty acid alkyl esters, preferably having from 1 to 4 carbon atoms in the alkyl chain, in particular fatty acid methyl esters.

A further class of nonionic surfactants which can advantageously be used are the alkyl polyglycosides (APG). Alkyl polyglycosides which may be used satisfy the general formula $RO(G)_z$, in which R is a linear or branched, in particular methyl-branched in the 2-position, saturated or unsaturated, aliphatic radical having from 8 to 22, preferably from 12 to 18 carbon atoms, and G is the symbol which stands for a glycose unit having 5 or 6 carbon atoms, preferably for glucose. The degree of glycosylation z is here between 1.0 and 4.0, preferably between 1.0 and 2.0 and in particular between 1.1 and 1.4. Preference is given to using linear alkyl polyglucosides, i.e. alkyl polyglycosides in which the polyglycosyl radical is a glucose radical, and the alkyl radical is an n-alkyl radical.

Nonionic surfactants of the amine oxide type, for example N-cocoalkyl-N,N-dimethylamine oxide and N-tallow alkyl-N,N-dihydroxyethylamine oxide, and of the fatty acid alkanolamides may also be suitable. The proportion of these nonionic surfactants is preferably no more than that of the ethoxylated fatty alcohols, in particular no more than half thereof.

Further suitable surfactants are polyhydroxy fatty acid amides of the formula (II):

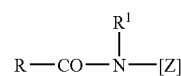

(II)

in which RCO is an aliphatic acyl radical having from 6 to 22 carbon atoms, $R^1$ is hydrogen, an alkyl or hydroxyalkyl radical having from 1 to 4 carbon atoms and [Z] is a linear or branched polyhydroxyalkyl radical having from 3 to 10 carbon atoms and from 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the formula (III):

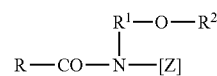

(III)

in which R is a linear or branched alkyl or alkenyl radical having from 7 to 12 carbon atoms, $R^1$ is a linear, branched or cyclic alkyl radical or an aryl radical having from 2 to 8 carbon atoms, and $R^2$ is a linear, branched or cyclic alkyl radical or an aryl radical or an oxyalkyl radical having from 1 to 8 carbon atoms, where $C_{1-4}$-alkyl or phenyl radicals are preferred, and [Z] is a linear polyhydroxyalkyl radical whose alkyl chain is substituted with at least two hydroxyl groups, or alkoxylated, preferably ethoxylated or propoxylated, derivatives of this radical.

[Z] is preferably obtained by reductive amination of a reducing sugar, for example glucose, fructose, maltose, lactose, galactose, mannose or xylose. The N-alkoxy- or N-aryloxy-substituted compounds may be converted, for example, by reaction with fatty acid methyl esters in the presence of an alkoxide as catalyst, into the desired polyhydroxy fatty acid amides.

The anionic surfactants used are, for example, those of the sulfonate and sulfate type. Suitable surfactants of the sulfonate type are preferably $C_{9-13}$-alkylbenzenesulfonates, olefinsulfonates, i.e. mixtures of alkene- and hydroxyalkanesulfonates, and disulfonates, as obtained, for example, from $C_{12-18}$-monoolefins having a terminal or internal double bond by sulfonation with gaseous sulfur trioxide and subsequent alkaline or acidic hydrolysis of the sulfonation products. Also suitable are alkanesulfonates which are obtained from $C_{12-18}$-alkanes, for example, by sulfochlorination or sulfoxidation with subsequent hydrolysis or neutralization. Likewise suitable are also the esters of α-sulfo fatty acids (estersulfonates), for example the α-sulfonated methyl esters of hydrogenated coconut, palm kernel or tallow fatty acids.

Further suitable anionic surfactants are sulfated fatty acid glycerol esters. Fatty acid glycerol esters mean the mono-, di- and triesters, and mixtures thereof, as are obtained during the preparation by esterification of a monoglycerol with from 1 to 3 mol of fatty acid or during the transesterification of triglycerides with from 0.3 to 2 mol of glycerol. Preferred sulfated fatty acid glycerol esters are here the sulfation products of saturated fatty acids having from 6 to 22 carbon atoms, for example of caproic acid, caprylic acid, capric acid, myristic acid, lauric acid, palmitic acid, stearic acid or behenic acid.

Preferred alk(en)yl sulfates are the alkali metal, and in particular the sodium, salts of sulfuric monoesters of $C_{12}$-$C_{18}$-fatty alcohols, for example of coconut fatty alcohol, tallow fatty alcohol, lauryl, myristyl, cetyl or stearyl alcohol or of $C_{10}$-$C_{20}$-oxo alcohols and those monoesters of secondary alcohols of these chain lengths. Further preferred are alk(en)yl sulfates of said chain length which comprise a synthetic, petrochemical-based straight-chain alkyl radical and have analogous degradation behavior to the equivalent compounds based on fatty chemical raw materials. From a washing performance viewpoint, preference is given to $C_{12-C16}$-alkyl sulfates and $C_{12}$-$C_{15}$-alkyl sulfates, and $C_{14}$-$C_{15}$-alkyl sulfates. 2,3-Alkyl sulfates are also suitable anionic surfactants.

The sulfuric monoesters of straight-chain or branched $C_{7-21}$-alcohols ethoxylated with from 1 to 6 mol of ethylene oxide, such as 2-methyl-branched $C_{9-11}$-alcohols having, on average, 3.5 mol of ethylene oxide (EO) or $C_{12-18}$-fatty alcohols having from 1 to 4 EO, are also suitable. Owing to their high foaming behavior, they are used in cleaning compositions only in relatively small amounts, for example in amounts up to 5% by weight, usually from 1 to 5% by weight.

Further suitable anionic surfactants are also the salts of alkylsulfosuccinic acid, which are also referred to as sulfosuccinates or as sulfosuccinic esters and which are monoesters and/or diesters of sulfosuccinic acid with alcohols, preferably fatty alcohols and, in particular, ethoxylated fatty alcohols. Preferred sulfosuccinates contain $C_{8-18}$-fatty alcohol radicals or mixtures thereof. Particularly preferred sulfosuccinates contain a fatty alcohol radical derived from ethoxylated fatty alcohols, which are themselves nonionic surfactants (see above for description). In this connection, sulfosuccinates whose fatty alcohol radicals are derived from ethoxylated fatty alcohols having a narrowed homolog distribution are, in turn, particularly preferred. Likewise, it is also possible to use alk(en)ylsuccinic acid having preferably from 8 to 18 carbon atoms in the alk(en)yl chain or salts thereof.

Further suitable anionic surfactants are, in particular, soaps. Saturated fatty acid soaps such as the salts of lauric acid, myristic acid, palmitic acid, stearic acid, hydrogenated erucic acid and behenic acid, and, in particular, soap mixtures derived from natural fatty acids, for example coconut, palm kernel or tallow fatty acids, are suitable.

The anionic surfactants including soaps may be present in the form of their sodium, potassium or ammonium salts, and as soluble salts of organic bases such as mono-, di- or triethanolamine. The anionic surfactants are preferably in the form of their sodium or potassium salts, in particular in the form of the sodium salts.

The surfactants may be present in the cleaning compositions or washing compositions of the invention in an overall amount of from preferably 5% by weight to 50% by weight, in particular from 8% by weight to 30% by weight, based on the finished agent.

Compositions of the invention may contain bleaches. Of the compounds which serve as bleaches and produce $H_2O_2$ in water, sodium percarbonate, sodium perborate tetrahydrate and sodium perborate monohydrate are of particular importance. Other bleaches which can be used are, for example, peroxopyrophosphates, citrate perhydrates and $H_2O_2$-producing peracidic salts or peracids, such as persulfates or persulfuric acid. Also useful is the urea peroxohydrate percarbamide which can be described by the formula $H_2N$—$CO$—$NH_2 \cdot H_2O_2$. In particular when used for cleaning hard surfaces, for example for machine dishwashing, the agents, if desired, may also contain bleaches from the group of organic bleaches, although the use thereof is possible in principle also in agents for washing textiles. Typical organic bleaches are diacyl peroxides such as, for example, dibenzoyl peroxide. Further typical organic bleaches are the peroxy acids, specific examples being alkyl peroxy acids and aryl peroxy acids. Preferred representatives are peroxy benzoic acid and its ring-substituted derivatives, such as alkylperoxybenzoic acids, but also peroxy-a-naphthoic acid and magnesium monoperphthalate, the aliphatic or substituted aliphatic peroxy acids such as peroxylauric acid, peroxystearic acid, ε-phthalimidoperoxycaproic acid (phthalimidoperoxyhexanoic acid, PAP), o-carboxy-benzamidoperoxycaproic acid, N-nonenylamidoperadipic acid and N-nonenylamidopersuccinates, and aliphatic and araliphatic peroxydicarboxylic acids such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyldi(6-aminopercaproic acid) may be used.

The bleach content of the agents may be from 1 to 40% by weight and, in particular, from 10 to 20% by weight, using advantageously perborate monohydrate or percarbonate. A synergistic use of amylase with percarbonate or of amylase with percarboxylic acid is disclosed by the applications WO 99/63036 and WO 99/63037.

In order to achieve improved bleaching action in cases of washing at temperatures of 60° C. and below, and in particular in the case of laundry pretreatment, the compositions may also include bleach activators. Bleach activators which can be used are compounds which, under perhydrolysis conditions, give aliphatic peroxo-carboxylic acids having preferably from 1 to 10 carbon atoms, in particular from 2 to 4 carbon atoms, and/or substituted or unsubstituted perbenzoic acid. Substances which carry O- and/or N-acyl groups of said number of carbon atoms and/or substituted or unsubstituted benzoyl groups are suitable. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycoluriles, in particular 1,3,4,6-tetraacetyl-glycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), acylated hydroxycarboxylic acids such as triethyl O-acetylcitrate (TEOC), carboxylic anhydrides, in particular phthalic anhydride, isatoic anhydride and/or succinic anhydride, carboxamides such as N-methyldiacetamide, glycolide, acylated polyhydric alcohols, in particular triacetin, ethylene glycol diacetate, isopropenyl acetate, 2,5-diacetoxy-2,5-dihydrofuran and the enol esters disclosed in German patent applications DE 196 16 693 and DE 196 16 767, and acetylated sorbitol and mannitol, or mixtures thereof described in European patent application EP 0 525 239 (SORMAN), acylated sugar derivatives, in particular pentaacetylglucose (PAG), pentaacetyl-fructose, tetraacetylxylose and octaacetyllactose, and acetylated, optionally N-alkylated glucamine or gluconolactone, triazole or triazole derivatives and/or particulate caprolactams and/or caprolactam derivatives, preferably N-acylated lactams, for example N-benzoylcaprolactam and N-acetylcaprolactam, which are disclosed in international patent applications WO 94/27970, WO 94/28102, WO 94/28103, WO 95/00626, WO 95/14759 and WO 95/17498. The hydrophilically substituted acyl acetals disclosed in German patent application DE 196 16 769 and the acyl lactams described in German patent application DE 196 16 770 and in international patent application WO 95/14075 are likewise used with preference. It is also possible to use the combinations of conventional bleach activators disclosed in German patent application DE 44 43 177. Nitrile derivatives such as cyanopyridines, nitrile quats, e.g. N-alkylammonium acetonitriles, and/or cyanamide derivatives may also be used. Preferred bleach activators are sodium 4-(octanoyloxy)benzenesulfonate, n-nonanoyl- or isononan-oyloxybenzenesulfonate (n- or iso-NOBS), undecenoyloxy-benzenesulfonate (UDOBS), sodium dodecanoyloxybenzenesulfonate (DOBS), decanoyloxybenzoic acid (DOBA, OBC 10) and/or dodecanoyloxybenzenesulfonate (OBS 12), and N-methylmorpholinium acetonitrile (MMA). Such bleach activators may be present in the customary quantitative range from 0.01 to 20% by weight, preferably in amounts from 0.1 to 15% by weight, in particular 1% by weight to 10% by weight, based on the total composition.

In addition to the conventional bleach activators or instead of them, it is also possible for "bleach catalysts" to be present. These substances are bleach-enhancing transition metal salts or transition metal complexes such as, for example, Mn, Fe, Co, Ru or Mo salen complexes or carbonyl complexes. Mn, Fe, Co, Ru, Mo, Ti, V and Cu complexes containing N-containing tripod ligands, and Co, Fe, Cu and Ru amine complexes are also suitable as bleach catalysts, preference being given to using those compounds described in DE 197 09 284 A1. Acetonitrile derivatives, according to WO 99/63038, and bleach-activating transition metal complex compounds, according to WO 99/63041, are capable of developing a bleach-activating action in combination with amylases.

Compositions of the invention usually contain one or more builders, in particular zeolites, silicates, carbonates, organic cobuilders and, where no ecological reasons oppose their use, also phosphates. The latter are the preferred builders for use in particular in cleaning compositions for machine dishwashing.

Compounds which may be mentioned here are crystalline, layered sodium silicates of the general formula $NaMSi_xO_{2x+1}.yH_2O$, where M is sodium or hydrogen, x is a number from 1.6 to 4, preferably from 1.9 to 4.0, and y is a number from 0 to 20, and preferred values for x are 2, 3 or 4. Crystalline phyllosilicates of this kind are described, for example, in European patent application EP 0 164 514. Preferred crystalline phyllosilicates of the formula indicated are those where M is sodium and x adopts the values 2 or 3. In particular, both β- and δ-sodium disilicates $Na_2Si_2O_5.yH_2O$ are preferred. Compounds of this kind are sold, for example, under the name SKS® (Clariant). Thus, SKS-60® is primarily a δ-sodium disilicate having the formula $Na_2Si_2O_5.yH_2O$, and SKS-7® is primarily the β-sodium disilicate. Reacting the δ-sodium disilicate with acids (for example citric acid or carbonic acid) gives kanemite, $NaHSi_2O_5.yH_2O$, sold under the names SKS-9® and, respectively, SKS-10® (Clariant). It may also be advantageous to use chemical modifications of said phyllosilicates. The alkalinity of the phyllosilicates, for example, can thus be suitably influenced. Phyllosilicates doped with phosphate or with carbonate have, compared to the δ-sodium disilicate, altered crystal morphologies, dissolve more rapidly and display an increased calcium binding ability, compared to δ-sodium disilicate. Thus, phyllosilicates of the general empirical formula $xNa_2O.ySiO_2.zP_2O_5$ where the x-to-y ratio corresponds to a number from 0.35 to 0.6, the x-to-z ratio to a number from 1.75 to 1200 and the y-to-z ratio to a number from 4 to 2800 are described in patent application DE 196 01 063. The solubility of the phyllosilicates may also be increased by using particularly finely granulated phyllosilicates. It is also possible to use compounds of the crystalline phyllosilicates with other ingredients. Compounds which may be mentioned here are in particular those with cellulose derivatives which have advantageous disintegrating action and are used in particular in washing composition tablets, and those with polycarboxylates, for example citric acid, or polymeric polycarboxylates, for example copolymers of acrylic acid.

It is also possible to use amorphous sodium silicates having an $Na_2O:SiO_2$ modulus of from 1:2 to 1:3.3, preferably from 1:2 to 1:2.8, and in particular from 1:2 to 1:2.6, which have delayed dissolution and secondary washing composition properties. The dissolution delay relative to conventional amorphous sodium silicates can have been induced by various means, for example by surface treatment, compounding, compaction/compression or by overdrying. Within the scope of this invention, the term "amorphous" also means "X-ray amorphous". This means that in X-ray diffraction experiments the silicates do not give the sharp X-ray reflections typical of crystalline substances, but instead, at best, one or more maxima of the scattered X-ray radiation, which have a width of several degree units of the diffraction angle. However, even particularly good builder properties will very likely result if, in electron diffraction experiments, the silicate particles give poorly defined or even sharp diffraction maxima. This is to be interpreted to the effect that the products have microcrystalline regions with a size from 10 to a few hundred nm, preference being given to values up to at most 50 nm and in particular up to at most 20 nm. Particular preference is given to compressed/ compacted amorphous silicates, compounded amorphous silicates and overdried X-ray amorphous silicates.

A finely crystalline, synthetic zeolite containing bonded water, which may be used where appropriate, is preferably zeolite A and/or P. As zeolite P, zeolite MAP® (commercial product from Crosfield) is particularly preferred. However, zeolite X and mixtures of A, X and/or P are also suitable. A product which is commercially available and can be used with preference within the scope of the present invention is, for example, also a cocrystal of zeolite X and zeolite A (approx. 80% by weight zeolite X), which is sold by CONDEA Augusta S.p.A. under the trade name VEGOBOND AX® and can be described by the formula:

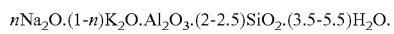

$n\text{Na}_2\text{O}\cdot(1-n)\text{K}_2\text{O}\cdot\text{Al}_2\text{O}_3\cdot(2-2.5)\text{SiO}_2\cdot(3.5-5.5)\text{H}_2\text{O}$.

Suitable zeolites have an average particle size of less than 10 µm (volume distribution; measurement method: Coulter counter) and preferably contain from 18 to 22% by weight, in particular from 20 to 22% by weight, of bonded water.

Use of the generally known phosphates as builder substances is of course also possible, provided such a use should not be avoided for ecological reasons. Among the multiplicity of commercially available phosphates, the alkali metal phosphates are the most important in the washing and cleaning compositions industry, with pentasodium or pentapotassium triphosphate (sodium or potassium tripolyphosphate) being particularly preferred.

In this connection, alkali metal phosphates is the collective term for the alkali metal (in particular sodium and potassium) salts of the various phosphoric acids, it being possible to differentiate between metaphosphoric acids $(\text{HPO}_3)_n$ and orthophosphoric acid $\text{H}_3\text{PO}_4$ as well as higher molecular weight representatives. The phosphates combine several advantages: they act as alkali carriers, prevent lime deposits on machine parts and lime incrustations in fabrics and, moreover, contribute to the cleaning performance.

Sodium dihydrogenphosphate, $\text{NaH}_2\text{PO}_4$, exists as dihydrate (density 1.91 gcm$^{-3}$, melting point 60° C.) and as monohydrate (density 2.04 gcm$^{-3}$). Both salts are white powders which are very readily soluble in water and which lose their water of crystallization upon heating and at 200° C. convert to the weakly acidic diphosphate (disodium hydrogendiphosphate, $\text{Na}_2\text{H}_2\text{P}_2\text{O}_7$), at a higher temperature to sodium trimetaphosphate ($\text{Na}_3\text{P}_3\text{O}_9$) and Maddrell's salt (see below). $\text{NaH}_2\text{PO}_4$ is acidic; it forms when phosphoric acid is adjusted to a pH of 4.5 using sodium hydroxide solution and the slurry is sprayed. Potassium dihydrogenphosphate (primary or monobasic potassium phosphate, potassium biphosphate, KDP), $\text{KH}_2\text{PO}_4$, is a white salt of density 2.33 gcm$^{-3}$, has a melting point of 253° C. [decomposition with the formation of potassium polyphosphate $(\text{KPO}_3)_x$] and is readily soluble in water.

Disodium hydrogenphosphate (secondary sodium phosphate), $\text{Na}_2\text{HPO}_4$, is a colorless crystalline salt which is very readily soluble in water. It exists in anhydrous form and with 2 mol (density 2.066 gcm$^{-3}$, loss of water at 95° C.), 7 mol (density 1.68 gcm$^{-3}$, melting point 48° C. with loss of 5 $\text{H}_2\text{O}$), and 12 mol (density 1.52 gcm$^{-3}$, melting point 35° C. with loss of 5 $\text{H}_2\text{O}$) of water, becomes anhydrous at 100° C. and upon more vigorous heating converts to the diphosphate $\text{Na}_4\text{P}_2\text{O}_7$. Disodium hydrogenphosphate is prepared by neutralizing phosphoric acid with sodium carbonate solution using phenolphthalein as indicator. Dipotassium hydrogenphosphate (secondary or dibasic potassium phosphate), $\text{K}_2\text{HPO}_4$, is an amorphous, white salt which is readily soluble in water.

Trisodium phosphate, tertiary sodium phosphate, $\text{Na}_3\text{PO}_4$, are colorless crystals which, in the form of the dodecahydrate, have a density of 1.62 gcm$^{-3}$ and a melting point of 73-76° C. (decomposition), in the form of the decahydrate (corresponding to 19-20% $\text{P}_2\text{O}_5$) have a melting point of 100° C. and in anhydrous form (corresponding to 39-40% $\text{P}_2\text{O}_5$) have a density of 2.536 gcm$^{-3}$. Trisodium phosphate is readily soluble in water with an alkaline reaction and is prepared by evaporating a solution of exactly 1 mol of disodium phosphate and 1 mol of NaOH. Tripotassium phosphate (tertiary or tribasic potassium phosphate), $\text{K}_3\text{PO}_4$, is a white, deliquescent granular powder of density 2.56 gcm$^{-3}$, has a melting point of 1340° C. and is readily soluble in water with an alkaline reaction. It is produced, for example, during the heating of Thomas slag with carbon and potassium sulfate. Despite the higher price, the more readily soluble, and therefore highly effective, potassium phosphates are often preferred over corresponding sodium compounds in the cleaning compositions industry.

Tetrasodium diphosphate (sodium pyrophosphate), $\text{Na}_4\text{P}_2\text{O}_7$, exists in anhydrous form (density 2.534 gcm$^{-3}$, melting point 988°, also 880° quoted) and as decahydrate (density 1.815-1.836 gcm$^{-3}$, melting point 94° with loss of water). Both substances are colorless crystals which dissolve in water with an alkaline reaction. $\text{Na}_4\text{P}_2\text{O}_7$ is formed during the heating of disodium phosphate to >200° C. or by reacting phosphoric acid with sodium carbonate in a stoichiometric ratio and dewatering the solution by spraying. The decahydrate complexes heavy metal salts and hardness constituents and thus reduces the water hardness. Potassium diphosphate (potassium pyrophosphate), $\text{K}_4\text{P}_2\text{O}_7$, exists in the form of the trihydrate and is a colorless, hygroscopic powder of density 2.33 gcm$^{-3}$, which is soluble in water, the pH of the 1% strength solution at 25° C. being 10.4.

Condensation of $\text{NaH}_2\text{PO}_4$ and $\text{KH}_2\text{PO}_4$ results in higher molecular weight sodium phosphates and potassium phosphates, respectively, amongst which cyclic representatives, the sodium and potassium metaphosphates, respectively, and chain-like types, the sodium and potassium polyphosphates, respectively, can be differentiated. Particularly for the latter, a multiplicity of names are in use: melt or thermal phosphates, Graham's salt, Kurrol's and Maddrell's salt. All higher sodium and potassium phosphates are together referred to as condensed phosphates.

The industrially important pentasodium triphosphate, $\text{Na}_5\text{P}_3\text{O}_{10}$ (sodium tripolyphosphate), is a nonhygroscopic, white, water-soluble salt which is anhydrous or crystallizes with 6 $\text{H}_2\text{O}$ and is of the general formula NaO—[P(O)(ONa)—O]$_n$—Na where n=3. In 100 g of water, about 17 g of the salt which is free of water of crystallization dissolve at room temperature, approx. 20 g dissolve at 60°, and about 32 g dissolve at 100°; if the solution is heated at 100° for two hours, about 8% of orthophosphate and 15% of diphosphate form due to hydrolysis. In the preparation of pentasodium triphosphate, phosphoric acid is reacted with sodium carbonate solution or sodium hydroxide solution in a stoichiometric ratio, and the solution is dewatered by spraying. Similarly to Graham's salt and sodium diphosphate, pentasodium triphosphate dissolves many insoluble metal compounds (including lime soaps, etc.). Pentapotassium triphosphate, $\text{K}_5\text{P}_3\text{O}_{10}$ (potassium tripolyphosphate), is available commercially, for example, in the form of a 50% strength by weight solution (>23% $\text{P}_2\text{O}_5$, 25% $\text{K}_2\text{O}$). The potassium polyphosphates are used widely in the washing compositions and cleaning compositions industry. In addition, sodium potassium tripolyphosphates also exist which can likewise be used within the scope of the present invention. These form, for example, when sodium trimetaphosphate is hydrolyzed with KOH:

$$(NaPO_3)_3 + 2KOH \rightarrow Na_3K_2P_3O_{10} + H_2O$$

According to the invention, these can be used in exactly the same way as sodium tripolyphosphate, potassium tripolyphosphate or mixtures of these two; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate can also be used according to the invention.

Organic cobuilders which can be used in the washing compositions and cleaning compositions of the invention are, in particular, polycarboxylates or polycarboxylic acids, polymeric polycarboxylates, polyaspartic acid, polyacetals, optionally oxidized dextrins, further organic cobuilders (see below), and phosphonates. These classes of substance are described below.

Useable organic builder substances are, for example, the polycarboxylic acids usable in the form of their sodium salts, the term polycarboxylic acids meaning those carboxylic acids which carry more than one acid function. Examples of these are citric acid, adipic acid, succinic acid, glutaric acid, malic acid, tartaric acid, maleic acid, fumaric acid, sugar acids, aminocarboxylic acids, nitrilotriacetic acid (NTA), as long as such a use is not to be avoided for ecological reasons, and mixtures thereof. Preferred salts are the salts of the polycarboxylic acids such as citric acid, adipic acid, succinic acid, glutaric acid, tartaric acid, sugar acids, and mixtures thereof.

It is also possible to use the acids per se. In addition to their builder action, the acids typically also have the property of an acidifying component and thus also serve to establish a lower and milder pH of washing or cleaning compositions, if the pH resulting from the mixture of the remaining components is not desired. Particular mention should be made here of system-compatible and environmentally safe acids such as citric acid, acetic acid, tartaric acid, malic acid, lactic acid, glycolic acid, succinic acid, glutaric acid, adipic acid, gluconic acid and any mixtures thereof. However, mineral acids, in particular sulfuric acid, or bases, in particular ammonium or alkali metal hydroxides, may also serve as pH regulators. The agents of the invention contain such regulators in amounts of preferably not more than 20% by weight, in particular from 1.2% by weight to 17% by weight.

Suitable builders are also polymeric polycarboxylates; these are, for example, the alkali metal salts of polyacrylic acid or of polymethacrylic acid, for example those having a relative molecular mass of from 500 to 70000 g/mol.

The molar masses given for polymeric polycarboxylates are, for the purposes of this specification, weight-average molar masses, $M_w$, of the respective acid form, always determined by means of gel permeation chromatography (GPC), using a UV detector. The measurement was made against an external polyacrylic acid standard which, owing to its structural similarity to the polymers studied, provides realistic molecular weight values. These figures differ considerably from the molecular weight values obtained using polystyrenesulfonic acids as the standard. The molar masses measured against polystyrenesulfonic acids are usually considerably higher than the molar masses given in this specification.

Suitable polymers are, in particular, polyacrylates which preferably have a molecular mass of from 2000 to 20,000 g/mol. Owing to their superior solubility, preference in this group may be given in turn to the short-chain polyacrylates which have molar masses of from 2000 to 10,000 g/mol, and particularly preferably from 3000 to 5000 g/mol.

Also suitable are copolymeric polycarboxylates, in particular those of acrylic acid with methacrylic acid and of acrylic acid or methacrylic acid with maleic acid. Copolymers which have proven to be particularly suitable are those of acrylic acid with maleic acid which contain from 50 to 90% by weight of acrylic acid and from 50 to 10% by weight of maleic acid. Their relative molecular mass, based on free acids, is generally from 2000 to 70000 g/mol, preferably from 20000 to 50000 g/mol and in particular from 30000 to 40000 g/mol. The (co)polymeric polycarboxylates may be used either as powders or as aqueous solution. The (co) polymeric polycarboxylates may be from 0.5 to 20% by weight, in particular 1 to 10% by weight of the content of the compositions.

To improve the solubility in water, the polymers may also contain allylsulfonic acids such as, for example, allyloxybenzenesulfonic acid and methallylsulfonic acid as monomers.

Particular preference is also given to biodegradable polymers of more than two different monomer units, for example those which contain, as monomers, salts of acrylic acid and of maleic acid, and vinyl alcohol or vinyl alcohol derivatives, or those which contain, as monomers, salts of acrylic acid and of 2-alkylallylsulfonic acid, and sugar derivatives.

Further preferred copolymers are those which preferably have, as monomers, acrolein and acrylic acid/acrylic acid salts or acrolein and vinyl acetate.

Further preferred builder substances which may be mentioned are also polymeric aminodicarboxylic acids, their salts or their precursor substances. Particular preference is given to polyaspartic acids or salts and derivatives thereof.

Further suitable builder substances are polyacetals which can be obtained by reacting dialdehydes with polyolcarboxylic acids having from 5 to 7 carbon atoms and at least 3 hydroxyl groups. Preferred polyacetals are obtained from dialdehydes such as glyoxal, glutaraldehyde, terephthalaldehyde and mixtures thereof and from polyolcarboxylic acids such as gluconic acid and/or glucoheptonic acid.

Further suitable organic builder substances are dextrins, for example oligomers or polymers of carbohydrates, which can be obtained by partial hydrolysis of starches. The hydrolysis can be carried out by customary processes, for example acid-catalyzed or enzyme-catalyzed processes. The hydrolysis products preferably have average molar masses in the range from 400 to 500,000 g/mol. Preference is given here to a polysaccharide having a dextrose equivalent (DE) in the range from 0.5 to 40, in particular from 2 to 30, where DE is a common measure of the reducing action of a polysaccharide compared with dextrose which has a DE of 100. It is possible to use both maltodextrins having a DE between 3 and 20 and dried glucose syrups having a DE between 20 and 37, and also "yellow dextrins" and "white dextrins" with higher molar masses in the range from 2000 to 30,000 g/mol.

The oxidized derivatives of such dextrins are their reaction products with oxidizing agents which are able to oxidize at least one alcohol function of the saccharide ring to the carboxylic acid function. Particularly preferred organic builders for compositions of the invention are oxidized starches and derivatives thereof of the applications EP 472 042, WO 97/25399 and EP 755 944, respectively.

Oxydisuccinates and other derivatives of disuccinates, preferably ethylenediamine disuccinate, are also further suitable cobuilders. Here, ethylenediamine N,N'-disuccinate (EDDS) is preferably used in the form of its sodium or magnesium salts. In this connection, further preference is also given to glycerol disuccinates and glycerol trisuccinates. Suitable use amounts in zeolite-containing and/or silicate-containing formulations are between 3 and 15% by weight.

Further organic cobuilders which can be used are, for example, acetylated hydroxycarboxylic acids or salts thereof, which may also be present, where appropriate, in lactone form and which contain at least 4 carbon atoms and at least one hydroxy group and at most two acid groups.

A further class of substance having cobuilder properties is the phosphonates. These are, in particular, hydroxyalkane- and aminoalkanephosphonates. Among the hydroxyalkanephosphonates, 1-hydroxyethane 1,1-diphosphonate (HEDP) is of particular importance as a cobuilder. It is preferably used as sodium salt, the disodium salt being neutral and the tetrasodium salt being alkaline (pH 9). Suitable aminoalkanephosphonates are preferably ethylenediaminetetramethylenephosphonate (EDTMP), diethylenetriamine-pentamethylenephosphonate (DTPMP) and higher homologs thereof. They are preferably used in the form of the neutral sodium salts, for example as the hexasodium salt of EDTMP or as the hepta- and octasodium salt of DTPMP. Here, preference is given to using HEDP as builder from the class of phosphonates. In addition, the aminoalkanephosphonates have a marked heavy metal-binding capacity. Accordingly, particularly if the agents also contain bleaches, it may be preferable to use aminoalkanephosphonates, in particular DTPMP, or mixtures of said phosphonates.

In addition, all compounds which are able to form complexes with alkaline earth metal ions can be used as cobuilders.

The agents of the invention may contain builder substances, where appropriate in amounts of up to 90% by weight, and preferably contain them in amounts of up to 75% by weight. Washing compositions of the invention have builder contents of, in particular, from 5% by weight to 50% by weight. In inventive compositions for cleaning hard surfaces, in particular for machine cleaning of dishes, the builder substance content is in particular from 5% by weight to 88% by weight, with preferably no water-insoluble builder materials being used in such compositions. A preferred embodiment of inventive compositions for, in particular, machine cleaning of dishes contains from 20% by weight to 40% by weight water-soluble organic builders, in particular alkali metal citrate, from 5% by weight to 15% by weight alkali metal carbonate and from 20% by weight to 40% by weight alkali metal disilicate.

Solvents which may be used in the liquid to gelatinous compositions of washing compositions and cleaning compositions are, for example, from the group of monohydric or polyhydric alcohols, alkanolamines or glycol ethers, as long as they are miscible with water in the given concentration range. Preferably, the solvents are selected from ethanol, n- or i-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol t-butyl ether, and mixtures of these solvents.

Solvents may be used in the liquid to gelatinous washing compositions and cleaning compositions of the invention in amounts of between 0.1 and 20% by weight, but preferably below 15% by weight, and in particular below 10% by weight.

To adjust the viscosity, one or more thickeners or thickening systems may be added to the compositions of the invention. These high molecular weight substances which are also called swell(ing) agents usually soak up the liquids and swell in the process, converting ultimately into viscous, true or colloidal solutions.

Suitable thickeners are inorganic or polymeric organic compounds. Inorganic thickeners include, for example, polysilicic acids, clay minerals, such as montmorillonites, zeolites, silicas and bentonites. The organic thickeners are from the groups of natural polymers, modified natural polymers and completely synthetic polymers. Such natural polymers are, for example, agar-agar, carrageen, tragacanth, gum arabic, alginates, pectins, polyoses, guar flour, carob seed flour, starch, dextrins, gelatin and casein. Modified natural substances which are used as thickeners are primarily from the group of modified starches and celluloses. Examples which may be mentioned here are carboxymethylcellulose and other cellulose ethers, hydroxyethylcellulose and hydroxypropylcellulose, and carob flour ether. Completely synthetic thickeners are polymers such as polyacrylic and polymethacrylic compounds, vinyl polymers, polycarboxylic acids, polyethers, polyimines, polyamides and polyurethanes.

The thickeners may be present in an amount up to 5% by weight, preferably from 0.05 to 2% by weight, and particularly preferably from 0.1 to 1.5% by weight, based on the finished composition.

The washing and cleaning composition of the invention may, where appropriate, comprise, as further customary ingredients, sequestering agents, electrolytes and further excipients.

Textile washing compositions of the invention may contain, as optical brighteners, derivatives of diaminostilbenedisulfonic acid or alkali metal salts thereof. Suitable are, for example, salts of 4,4'-bis(2-anilino-4-morpholino-1,3,5-triazinyl-6-amino)-stilbene-2,2'-disulfonic acid or similarly constructed compounds which carry a diethanolarnino group, a methylamino group, an anilino group or a 2-methoxyethylamino group instead of the morpholino group. In addition, brighteners of the substituted diphenylstyryl type may be present, for example the alkali metal salts of 4,4'-bis(2-sulfostyryl)diphenyl, 4,4'-bis(4-chloro-3-sulfostyryl)diphenyl, or 4-(4-chlorostyryl)-4'-(2-sulfostyryl) diphenyl. Mixtures of the abovementioned optical brighteners may also be used.

Antiredeposition agents have the function of keeping the soil detached from the textile fiber in suspension in the liquor. Suitable for this purpose are water-soluble colloids, usually organic in nature, for example starch, size, gelatin, salts of ethercarboxylic acids or ethersulfonic acids of starch or of cellulose, or salts of acidic sulfuric esters of cellulose or of starch. Water-soluble polyamides containing acidic groups are also suitable for this purpose. Furthermore, starch derivatives other than those mentioned above may be used, for example aldehyde starches. Preference is given to cellulose ethers such as carboxymethylcellulose (Na salt), methylcellulose, hydroxyalkylcellulose and mixed ethers such as methyl-hydroxyethylcellulose, methylhydroxypropylcellulose, methylcarboxymethylcellulose, and mixtures thereof, for example in amounts of from 0.1 to 5% by weight, based on the compositions.

In order to protect against silver corrosion, silver corrosion inhibitors may be used in dishwashing cleaning compositions of the invention. Such inhibitors are known in the prior art, for example benzotriazoles, iron(III) chloride or $CoSO_4$. As disclosed by, for example, European patent EP 0 736 084 B1, silver corrosion inhibitors which are particularly suitable for being used together with enzymes are manganese, titanium, zirconium, hafnium, vanadium, cobalt, or cerium salts and/or complexes in which the specified metals are present in any of the oxidation states II, III, IV, V or VI. Examples of such compounds are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$, and mixtures thereof.

Soil-release active ingredients or soil repellents are usually polymers which, when used in a washing composition, impart soil-repellent properties to the laundry fiber and/or assist the ability of the other washing composition ingredients to detach soil. A comparable effect can also be observed with their use in cleaning compositions for hard surfaces.

Soil-release active ingredients which are particularly effective and have been known for a long time are copolyesters having dicarboxylic acid, alkylene glycol and polyalkylene glycol units. Examples thereof are copolymers or mixed polymers of polyethylene terephthalate and polyoxyethylene glycol (DT 16 17 141, and, respectively, DT 22 00 911). German laid-open specification DT 22 53 063 discloses acidic agents containing, inter alia, a copolymer of a dibasic carboxylic acid and an alkylene or cycloalkylene polyglycol. German documents DE 28 57 292 and DE 33 24 258 and European patent EP 0 253 567 describe polymers of ethylene terephthalate and polyethylene oxide terephthalate and the use thereof in washing compositions. European patent EP 066 944 relates to compositions containing a copolyester of ethylene glycol, polyethylene glycol, aromatic dicarboxylic acid and sulfonated aromatic dicarboxylic acid in particular molar ratios. European patent EP 0 185 427 discloses methyl or ethyl group end-capped polyesters having ethylene and/or propylene terephthalate and polyethylene oxide terephthalate units, and washing compositions containing such a soil-release polymer. European patent EP 0 241 984 discloses a polyester which contains, in addition to oxyethylene groups and terephthalic acid units, also substituted ethylene units and glycerol units. European patent EP 0 241 985 discloses polyesters which contain, in addition to oxyethylene groups and terephthalic acid units, 1,2-propylene, 1,2-butylene and/or 3-methoxy-1,2-propylene groups, and glcerol units and which are end-group-capped with $C_1$- to $C_4$-alkyl groups. European patent application EP 0 272 033 discloses polyesters having polypropylene terephthalate and polyoxyethylene terephthalate units, which are at least partially end-group-capped by $C_{1-4}$-alkyl or acyl radicals. European patent EP 0 274 907 describes sulfoethyl end-group-capped terephthalate-containing soil-release polyesters. According to European patent application EP 0 357 280, sulfonation of unsaturated end groups produces soil-release polyesters having terephthalate, alkylene glycol and poly-$C_{2-4}$-glycol units. International patent application WO 95/32232 relates to acidic, aromatic polyesters capable of detaching soil. International patent application WO 97/31085 discloses nonpolymeric soil-repellent active ingredients for materials made of cotton, which have a plurality of functional units: a first unit which may be cationic, for example, is able to adsorb to the cotton surface by means of electrostatic interaction, and a second unit which is hydrophobic is responsible for the active ingredient remaining at the water/cotton interface.

The color transfer inhibitors suitable for use in laundry washing compositions of the invention include, in particular, polyvinylpyrrolidones, polyvinylimidazoles, polymeric N-oxides such as poly(vinylpyridine N-oxide) and copolymers of vinylpyrrolidone with vinylimidazole.

For use in machine cleaning processes, it may be of advantage to add foam inhibitors to the agents. Examples of suitable foam inhibitors are soaps of natural or synthetic origin having a high proportion of $C_{18}$-$C_{24}$ fatty acids. Examples of suitable nonsurfactant-type foam inhibitors are organopolysiloxanes and their mixtures with microfine, optionally silanized silica and also paraffins, waxes, microcrystalline waxes, and mixtures thereof with silanized silica or bis-stearyl-ethylenediamide. With advantages, use is also made of mixtures of different foam inhibitors, for example mixtures of silicones, paraffins or waxes. The foam inhibitors, in particular those containing silicone and/or paraffin, are preferably bound to a granular, water-soluble or dispersible support substance. Particular preference is given here to mixtures of paraffins and bis-stearylethylenediamides.

A cleaning composition of the invention for hard surfaces may, in addition, contain ingredients with abrasive action, in particular from the group comprising quartz flours, wood flours, polymer flours, chalks and glass microbeads, and mixtures thereof. Abrasives are present in the cleaning compositions of the invention preferably at not more than 20% by weight, in particular from 5% by weight to 15% by weight.

Dyes and fragrances are added to washing compositions and cleaning compositions in order to improve the esthetic appeal of the products and to provide the consumer, in addition to washing and cleaning performance, with a visually and sensorially "typical and unmistakable" product. As perfume oils and/or fragrances it is possible to use individual odorant compounds, for example the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate and benzyl salicylate. The ethers include, for example, benzyl ethyl ether; the aldehydes include, for example, the linear alkanals having 8-18 carbon atoms, citral, citronellal, citronellyloxyacetaldehyde, cyclamenaldehyde, hydroxycitronellal, lilial and bourgeonal; the ketones include, for example, the ionones, a-isomethylionone and methyl cedryl ketone; the alcohols include anethol, citronellol, eugenol, geraniol, linalool, phenylethyl alcohol, and terpineol; the hydrocarbons include primarily the terpenes such as limonene and pinene. Preference, however, is given to the use of mixtures of different odorants which together produce an appealing fragrance note. Such perfume oils may also contain natural odorant mixtures, as are obtainable from plant sources, for example pine oil, citrus oil, jasmine oil, patchouli oil, rose oil or ylang-ylang oil. Likewise suitable are muscatel, sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orangepeel oil and sandalwood oil. The dye content of washing compositions and cleaning compositions is usually less than 0.01% by weight, while fragrances may make up up to 2% by weight of the overall formulation.

The fragrances may be incorporated directly into the washing compositions and cleaning compositions; however, it may also be advantageous to apply the fragrances to carriers which enhance the adhesion of the perfume to the material to be cleaned and, by means of slower fragrance release, ensure long-lasting fragrance, in particular of treated textiles. Materials which have become established as such carriers are, for example, cyclodextrins, it being possible, in addition, for the cyclodextrin-perfume complexes also to be coated with further auxiliaries. Another preferred carrier for fragances is the described zeolite X which can also absorb fragrances instead of or in a mixture with surfactants. Preference is therefore given to washing compositions and cleaning compositions which contain the described zeolite X and fragrances which, preferably, are at least partially absorbed on the zeolite.

Preferred dyes whose selection is by no means difficult for the skilled worker have high storage stability and insensitivity to the other ingredients of the compositions and to light, and also have no pronounced affinity for textile fibers, so as not to stain them.

To control microorganisms, washing compositions or cleaning compositions may contain antimicrobial agents. Depending on antimicrobial spectrum and mechanism of action, a distinction is made here between bacteriostatics and bactericides, fungistatics and fungicides, etc. Examples of important substances from these groups are benzalkonium chlorides, alkylarylsulfonates, halophenols and phenylmercury acetate. The terms antimicrobial action and' antimicrobial agent have, within the teaching of the invention, the meaning common in the art, which is described, for example, by K. H. Wallhäufler in "Praxis der Sterilisation, Desinfektion—Konservierung: Keimidentifizierung—Betriebshygiene" (5th Edition—Stuttgart; New York: Thieme, 1995), it being possible to use all of the substances having antimicrobial action described there. Suitable antimicrobial agents are preferably selected from the groups of alcohols, amines, aldehydes, antimicrobial acids or their salts, carboxylic esters, acid amides, phenols, phenol derivatives, diphenyls, diphenylalkanes, urea derivatives, oxygen acetals, nitrogen acetals and also oxygen and nitrogen formals, benzamidines, isothioazolines, phthalimide derivatives, pyridine derivatives, antimicrobial surfactant compounds, guanidines, antimicrobial amphoteric compounds, quinolines, 1,2-dibromo-2,4-dicyanobutane, iodo-2-propyl-butyl carbamate, iodine, iodophors, peroxo compounds, halogen compounds, and any mixtures of the above.

The antimicrobial agent may be selected from ethanol, n-propanol, isopropanol, 1,3-butanediol, phenoxyethanol, 1,2-propylene glycol, glycerol, undecylenic acid, benzoic acid, salicylic acid, dihydracetic acid, o-phenylphenol, N-methylmorpholinoacetonitrile (MMA), 2-benzyl-4-chlorophenol, 2,2'-methylenebis(6-bromo-4-chlorophenol), 4,4'-dichloro-2'-hydroxydiphenyl ether (dichlosan), 2,4,4'-trichloro-2'-hydroxydiphenyl ether (trichlosan), chlorohexidine, N-(4-chlorophenyl)-N-(3,4-dichlorophenyl)urea, N,N'-(1,10-decanediyldi-1-pyridinyl-4-ylidene)-bis(1-octanamine) dihydrochloride, N,N'-bis(4-chlorophenyl)-3,12-diimino-2,4,11,13-tetraazatetradecanediimideamide, glucoprotamines, antimicrobial surface-active quaternary compounds, guanidines including the bi- and polyguanidines, such as, for example, 1,6-bis(2-ethylhexylbiguanidohexane) dihydrochloride, 1,6-di-($N_1,N_1$'-phenyl-diguanido-$N_5,N_5$')hexane tetrahydrochloride, 1,6-di-($N_1,N_1$'-phenyl-$N_1,N_1$'-methyldiguanido-$N_5,N_5$')hexane dihydrochloride, 1,6-di-($N_1,N_1$'-o-chlorophenyldiguanido-$N_5,N_5$')hexane dihydrochloride, 1,6-di-($N_1,N_1$'-2,6-dichlorophenyldiguanido-$N_5,N_5$') ')hexane dihydrochloride, 1,6-di-[$N_1,N_1$'-beta-(p-methoxyphenyl)diguanido-$N_5,N_5$'] hexane dihydrochloride, 1,6-di-($N_1,N_1$'-alpha-methyl-beta-phenyldiguanido-$N_5,N_5$ ')hexane dihydro-chloride, 1,6-di-($N_1,N_1$'-p-nitrophenyldiguanido-$N_5,N_5$')hexane dihydrochloride, omega:omega-di-($N_1,N_1$'-phenyl-diguanido-$N_5,N_5$')-di-n-propyl ether dihydrochloride, omega:omega'-di-($N_1,N_1$'-p-chlorophenyldiguanido-$N_5$, $N_5$')-di-n-propyl ether tetrahydrochloride, 1,6-di-($N_1,N_1$ '-2,4-dichlorophenyldiguanido-$N_5,N_5$')hexane tetrahydrochloride, 1,6-di-($N_1,N_1$'-p-methylphenyl-diguanido-$N_5,N_5$') hexane dihydrochloride, 1,6-di-($N_1,N_1$'-2,4,5-trichlorophenyldiguanido-$N_5,N_5$')hexane tetrahydrochloride, 1,6-di-[$N_1,N_1$'-alpha-(p-chlorophenyl)ethyldiguanido-$N_5,N_5$']hexane dihydrochloride, omega:omega-di-($N_1,N_1$'-p-chlorophenyldiguanido-$N_5,N_5$')m-xylene dihydrochloride, 1,12-di-($N_1,N_1$'-p-chlorophenyldiguanido-$N_5,N_5$')dodecane dihydrochloride, 1,10-di-($N_1,N_1$'-phenyldiguanido-$N_5,N_5$')decane tetrahydrochloride, 1,12-di-$N_1,N_1$'-phenyldiguanido-$N_5,N_5$')dodecane tetrahydrochloride, 1,6-di-($N_1,N_1$'-o-chlorophenyl-diguanido-$N_5,N_5$')hexane dihydrochloride, 1,6-di-($N_1,N_1$'-o-chlorophenyldiguanido-$N_5,N_5$')hexane tetrahydrochloride, ethylenebis(1-tolylbiguanide), ethylenebis(p-tolylbiguanide), ethylenebis(3,5-dimethylphenylbiguanide), ethylene-bis(p-tert-amylphenylbiguanide), ethylenebis(nonylphenylbiguanide), ethylenebis(phenylbiguanide), ethylenebis(N-butylphenylbiguanide), ethylene-bis(2,5-diethoxyphenylbiguanide), ethylene-bis(2,4-dimethylphenylbiguanide), ethylenebis(o-diphenylbiguanide), ethylenebis(mixed amyl naphthylbiguanide), N-butylethylenebis(phenylbiguanide), trimethylenebis(o-tolylbiguanide), N-butyl-trimethylbis (phenylbiguanide) and the corresponding salts such as acetates, gluconates, hydrochlorides, hydrobromides, citrates, bisulfites, fluorides, polymaleates, N-cocoalkylsarcosinates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates, and any mixtures thereof. Also suitable are halogenated xylene and cresol derivatives, such as p-chlorometacresol or p-chlorometaxylene, and natural antimicrobial agents of plant origin (for example from spices or herbs), animal origin and microbial origin. Preference may be given to using antimicrobial surface-active quaternary compounds, a natural antimicrobial agent of plant origin and/or a natural antimicrobial agent of animal origin, most preferably at least one natural antimicrobial agent of plant origin from the group comprising caffeine, theobromine and theophylline and essential oils such as eugenol, thymol and geraniol, and/or at least one natural antimicrobial agent of animal origin from the group comprising enzymes such as milk protein, lysozyme and lactoperoxidase, and/or at least one antimicrobial surface-active quaternary compound having an ammonium, sulfonium, phosphonium, iodonium or arsonium group, peroxo compounds and chlorine compounds. It is also possible to use substances of microbial origin, the "bacteriocines".

The quaternary ammonium compounds (QACs) which are suitable as antimicrobial agents have the general formula $(R^1)(R^2)(R^3)(R^4)$ $N^+X^-$ where $R^1$ to $R^4$ are identical or different $C_1$-$C_{22}$-alkyl radicals, $C_7$-$C_{28}$-aralkyl radicals or heterocyclic radicals, where two, or in the case of an aromatic incorporation such as in pyridine, even three radicals, together with the nitrogen atom, form the heterocycle, for example a pyridinium or imidazolinium compound, and X⁻ are halide ions, sulfate ions, hydroxide ions or similar anions. For optimal antimicrobial action, at least one of the radicals preferably has a chain length of from 8 to 18, in particular 12 to 16, carbon atoms.

QACs can be prepared by reacting tertiary amines with alkylating agents such as, for example, methyl chloride, benzyl chloride, dimethyl sulfate, dodecyl bromide, or else ethylene oxide. The alkylation of tertiary amines having one long alkyl radical and two methyl groups proceeds particularly readily, and the quaternization of tertiary amines having two long radicals and one methyl group can also be carried out with the aid of methyl chloride under mild conditions. Aminies which have three long alkyl radicals or hydroxy-substituted alkyl radicals have low reactivity and are preferably quaternized using dimethyl sulfate.

Examples of suitable QACs are benzalkonium chloride (N-alkyl-N,N-dimethylbenzylammonium chloride, CAS NO:8001-54-5), benzalkone B (m,p-dichlorobenzyldimethyl-C12-alkylammonium chloride, CAS NO:58390-78-6), benzoxonium chloride (benzyldodecylbis(2-hydroxyethyl) ammonium chloride), cetrimonium bromide (N-hexadecyl-N,N-trimethylammonium bromide, CAS NO:57-09-0), benzetonium chloride (N,N-dimethyl-N-[2-[2-[p-(1,1,3,3-tetramethylbutyl)phenoxy]ethoxy]ethyl]benzylammonium chloride, CAS NO:121-54-0), dialkyldimethylammonium chlorides such as di-n-decyldimethylammonium chloride (CAS NO:7173-51-5-5), didecyldimethylammonium bromide (CAS NO:2390-68-3), dioctyldimethylammonium chloride, 1-cetylpyridinium chloride (CAS NO:123-03-5) and thiazoline iodide (CAS NO: 15764-48-1), and mixtures thereof. Particularly preferred QACs are the benzalkonium chlorides having $C_8$-$C_{18}$-alkyl radials, in particular $C_{12}$-$C_{14}$-alkylbenzyldimethylammonium chloride.

Benzalkonium halides and/or substituted benzalkonium halides are commercially available, for example, as Barquat® ex Lonza, Marquat® ex Mason, Variquat® ex Witco/Sherex and Hyamine® ex Lonza, and Bardac® ex Lonza. Further commercially available antimicrobial agents are N-(3-chloroallyl)hexaminium chloride such as Dowicide® and Dowicil® ex Dow, benzethonium chloride such as Hyamine® 1622 ex Rohm & Haas, methylbenzethonium chloride such as Hyamine® 10X ex Rohm & Haas, cetylpyridinium chloride such as cepacol chloride ex Merrell Labs.

The antimicrobial agents are used in amounts of from 0.0001% by weight to 1% by weight, preferably from 0.001% by weight to 0.8% by weight, particularly preferably from 0.005% by weight to 0.3% by weight, and in particular from 0.01 to 0.2% by weight.

The compositions may contain UV absorbers which attach to the treated textiles and improve the light stability of the fibers and/or the light stability of other formulation constituents. UV absorbers mean organic substances (light protection filters) which are able to absorb ultraviolet radiation and to emit the absorbed energy again in the form of radiation of longer wavelength, for example heat.

Compounds which have these desired properties are, for example, the compounds which are active via radiationless deactivation and derivatives of benzophenone having substituents in position(s) 2 and/or 4. Furthermore, also suitable are substituted benzotriazoles, acrylates which are phenyl-substituted in position 3 (cinnamic acid derivatives, with or without cyano groups in position 2), salicylates, organic Ni complexes and natural substances such as umbelliferone and the endogenous urocanic acid. Of particular importance are biphenyl and especially stilbene derivatives, as described, for example, in EP 0728749 A and commercially available as Tinosorb® FD or Tinosorb® FR ex Ciba. UV-B absorbers which may be mentioned are: 3-benzylidenecamphor or 3-benzylidenenorcamphor and derivatives thereof, for example 3-(4-methylbenzylidene)camphor, as described in EP 0693471 B1; 4-aminobenzoic acid derivatives, preferably 2-ethylhexyl 4-(dimethylamino)benzoate, 2-octyl 4-(dimethylamino)benzoate and amyl 4-(dimethylamino) benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylenes); esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives such as, for example, 2,4,6-trianilino-(p-carbo-2'-ethyl-1'-hexyloxy)-1,3,5-triazine and octyltriazone, as described in EP 0818450 A1, or dioctylbutamidotriazones (Uvasorb® HEB); propane-1,3-diones such as, for example, 1-(4-tert-butylphenyl)-3-(4'-methoxyphenyl)propane-1,3-dione; ketotricyclo(5.2.1.0)decane derivatives, as described in EP 0694521 B1. Further suitable are 2-phenylbenzimidazole-5-sulfonic acid and its alkali metal, alkaline earth metal, ammonium, alkylammonium, alkanolammonium and glucammonium salts; sulfonic acid derivatives of benzophenones, preferably 2-hydroxy-4-methoxybenzophenone-5-sulfonic acid and its salts; sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters may of course also be used in mixtures. In addition to said soluble substances, insoluble light protection pigments, namely finely dispersed, preferably nanoized, metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are already used in the form of the pigments for skin-care and skin-protective emulsions and decorative cosmetics. The particles here should have an average diameter of less than 100 nm, preferably between 5 and 50 nm, and in particular between 15 and 30 nm. They can have a spherical shape, but it is also possible to use particles which have an ellipsoidal shape or a shape deviating in some other way from the spherical form. The pigments may also be surface-treated, i.e. hydrophilicized or hydrophobicized. Typical examples are coated titanium dioxides such as, for example, titanium dioxide T 805 (Degussa) or Eusolex® T2000 (Merck); suitable hydrophobic coating agents are here preferably silicones and, particularly preferably, trialkoxyoctylsilanes or simethicones. Preference is given to using micronized zinc oxide. Further suitable UV light protection filters can be found in the review by P. Finkel in *SÖFW-Journal*, volume 122 (1996), p. 543.

The UV absorbers are usually used in amounts of from 0.01% by weight to 5% by weight, preferably from 0.03% by weight to 1% by weight.

Enzymes such as proteases, amylases, lipases or cellulases have been used for decades as active components in washing compositions and cleaning compositions. Their particular contribution to the washing and, respectively, cleaning performance of the composition in question is, in the case of protease, the ability to break down proteinaceous soilings, in the case of amylase, the breaking-down of starch-containing soilings, and, in the case of lipase, fat-cleaving activity. Cellulases are preferably used in washing compositions, in particular due to their contribution to the secondary washing performance of a washing composition and due to their fiber action on textiles. The particular hydrolysis products are attacked, dissolved, emulsified or suspended by the other washing or cleaning composition components or are, due to their greater solubility, washed away with the wash liquor, advantageously resulting in synergistic effects between the enzymes and the other components.

Compositions of the invention may, in addition to the proteins essential to the invention, comprise other amylolytic enzymes, in particular α-amylases. These may also include enzymes established for use in washing and cleaning compositions. Examples of commercially available amylases are BAN®, Termamyl®, Purastar®, Amylase -LT®, Maxamyl®, Duramyl® and/or Purafect® OxAm. This is appropriate when the various enzymes are able to supplement one another. Such a supplementation may take place for example in respect of regulation, for example by mutual activation or by inactivation. It may result for example from at least one part, which is not homologous to the known α-amylases, of the enzyme essential to the invention having an effect on the amylolytic activities which are not essential to the invention. The joint use may, however, also be worthwhile because of different substrate specificities. Both are embodiments of the present invention.

Especially with chemically diverse soilings it may be advantageous to employ amylolytic enzymes in washing and cleaning compositions together with other enzymes having washing and/or cleaning activity. Thus, washing or cleaning compositions which, besides a protein of the invention, are characterized by further enzymes in addition represent preferred embodiments of the present invention.

Besides further amylases, these include for example proteases, but also lipases, cutinases, esterases, pullulanases, cellulases, hemicellulases and/or xylanases, and mixtures thereof. Particular preference is given to proteases, lipases, β-glucanases and/or cellulases. Further enzymes extend the cleaning performance of corresponding compositions by their respective enzymatic performance. These include, for example, oxidoreductases or peroxidases as components of enzymatic bleaching systems, for example laccases (WO 00/39306), β-glucanases (WO 99/06515 and WO 99/06516) or pectinolytic enzymes (WO 00/42145), which are employed in particular in specialty washing compositions.

Examples of commercially available enzymes for use in compositions of the invention are proteases such as Subtilisin BPN', Properase®, BLAP®, Optimase®, Opticlean®, Maxatase®, Maxacal®, Mazapem®, Alcalase®, Esperase®, Savinase®, Durazym®, Everlase®, and/or Purafect®G or Purafect® OxP and lipases such as Lipolase®, Lipomax®, Lumafast® and/or Lipozym®.

The protease activity in such compositions can be determined by the method described in *Tenside*, volume 7 (1970), pp. 125-132. They are accordingly indicated in PU (protease units). The protease activity of preferred compositions may be up to 1500000 protease units per gram of preparation.

Concerning the obtaining of the enzymes which can be used, those primarily suitable are obtained from microorganisms such as bacteria or fungi, for example from *Bacillus subtilis, B. licheniformis, Streptomyces griseus, Humicola lanuginosa, H. insolens, Pseudomonas pseudoalcaligenes* or *P. cepacia*, in particular the enzyme mixtures naturally produced by these strains, or mixtures with those from other strains. They are obtained in a known manner by fermentation processes from suitable microorganisms which are described for example in German laid-open specifications DE 19 40 488 and DE 2121 397, US patents U.S. Pat. No. 3,623,957 and U.S. Pat. No. 4,264,738, European patent application EP 006 638, and the international patent application WO 91/02792.

These enzymes which are additionally used where appropriate can also be, as described for example in European patent EP 0 564 476 or in the international patent application WO 94/23005, adsorbed onto carriers and/or embedded in enveloping substances in order to protect them from premature inactivation. They are present in washing compositions preferably in amounts of up to 10% by weight, in particular from 0.2% by weight to 2% by weight, particularly preferably employing enzymes stabilized against oxidative degradation, as disclosed for example in international patent applications WO 94/18314.

A protein of the invention can be protected, especially during storage, by stabilizers for example from denaturation, decomposition or inactivation, for example by physical effects, oxidation or proteolytic cleavage. Inhibition of proteolysis is particularly critical for proteins obtained from microorganisms because most microorganisms secrete various proteases as digestive enzymes into the surrounding media. These may cause considerable harm to the proteins of interest during the subsequent purification stages. Proteins essential to the invention may also be associated with proteases in washing and cleaning compositions, and therefore require special protection.

Compositions of the invention may also comprise stabilizers for this purpose. One group of stabilizers are reversible protease inhibitors which dissociate off on dilution of the composition in the wash liquor. Benzamidine hydrochloride and leupeptin are established for this purpose. Borax, boric acids, boronic acids or salts or esters thereof are frequently used, and among them especially derivatives having aromatic groups, for example ortho-, meta- or para-substituted phenylboronic acids, especially 4-formylphenylboronic acid, or the salts or esters of said compounds. Peptide aldehydes, i.e. oligopeptides with reduced C terminus, especially those composed of 2-50 monomers, are also employed for reversible inhibition of proteases in washing and cleaning compositions. Reversible protease inhibitors which are peptides include inter alia ovomucoid. Specific, reversible peptide inhibitors for the protease subtilisin are also suitable for use in protease-containing compositions, and corresponding fusion proteins composed of protease and inhibitor.

Further enzyme stabilizers are amino alcohols such as mono-, di-, triethanol-and -propanolamine and mixtures thereof, aliphatic carboxylic acids up to $C_{12}$, such as, for example, succinic acid, other dicarboxylic acids or salts of said acids. End-capped fatty amide alkoxylates are also suitable for this purpose. Certain organic acids employed as builders are able, as disclosed in WO 97/18287, additionally to stabilize a contained enzyme.

Lower aliphatic alcohols, but especially polyols such as, for example, glycerol, ethylene glycol, propylene glycol or sorbitol, are further frequently employed enzyme stabilizers.

Diglycerol phosphate also protects from denaturation by physical effects. Calcium and/or magnesium salts are likewise employed, such as, for example, calcium acetate or calcium formate.

Polyamide oligomers or polymeric compounds such as lignin, water-soluble vinyl copolymers or cellulose ethers, acrylic polymers and/or polyamides stabilize the enzyme preparation inter alia against physical effects or pH variations. Polyamine N-oxide-containing polymers act simultaneously as enzyme stabilizers and color transfer inhibitors. Other polymeric stabilizers are linear $C_8$-$C_{18}$ polyoxyalkylenes. Alkyl polyglycosides can also stabilize the enzymatic components of the composition of the invention and are preferably able additionally to enhance their performance. Crosslinked N-containing compounds preferably perform a dual function as soil release agents and as enzyme stabilizers. Hydrophobic, nonionic polymer has a stabilizing effect, preferably mixed with other stabilizers, on a cellulase which is present where appropriate and preferably also on the enzyme of the invention.

Reducing agents and antioxidants increase the stability of the enzymes against oxidative decomposition; sulfur-containing reducing agents for example are commonly used for this purpose. Other examples are sodium sulfite and reducing sugars.

Combinations of stabilizers in particular are employed, for example a combination of polyols, boric acid and/or borax, the combination of boric acid or borate, reducing salts and succinic acid or other dicarboxylic acids or the combination of boric acid or borate with polyols or polyamino compounds and with reducing salts. The effect of peptide aldehyde stabilizers is beneficially enhanced by combination with boric acid and/or boric acid derivatives and polyols, and even further by additional use of calcium ions.

Compositions having stabilized enzymic activities represent preferred embodiments of the present invention. Particular preferance is given to those with enzymes stabilized in a plurality of the ways described.

Compositions of the invention are characterized in that they consist of more than one phase, for example in order to release the contained active substances separately from one another in time or space. Possibilities in this connection are phases in different states of aggregation, but especially phases in the same states of aggregation.

Compositions of the invention which are composed of more than one solid component can be produced in a simple manner by mixing various solid components, especially powders, granules or extrudates with various ingredients and/or different release characteristics, with one another in overall loose form. Solid compositions of the invention which are composed of one or more phases can be produced in a known manner, for example by spray drying or granulation, in which cases the enzymes and possibly other thermally sensitive ingredients such as, for example, bleaches, are, where appropriate, added separately later. Compositions of the invention with increased bulk density, in particular in the range from 650 g/l to 950 g/l, are produced preferably in the process disclosed in European patent EP 0 486 592 and having an extrusion step. A further preferred production with the aid of a granulation process is described in European patent EP 0 642 576.

Proteins can be employed for solid compositions for example in dried, granulated, encapsulated or encapsulated and additionally dried form. They can be added separately, i.e. as independent phase, or with other components together in the same phase, with or without compaction. If microencapsulated enzymes are to be processed in solid form, the water can be removed from the aqueous solutions resulting from the processing by methods known in the art, such as spray drying, centrifugation or by resolubilization. The particles obtained in this way normally have a particle size between 50 and 200 μm.

The encapsulated form is appropriate for protecting the enzymes from other constituents such as, for example, bleaches, or for making controlled release possible. Depending on the size of these capsules, a distinction is made between milli-, micro- and nanocapsules, with microcapsules being particularly preferred for enzymes. Capsules of this type are disclosed for example in the patent applications WO 97/24177 and DE 199 18 267. A further possible encapsulation method is to encapsulate the enzymes suitable for use in washing or cleaning compositions in starch, or a starch derivative, starting from a mixture of the enzyme solution with a solution or suspension of starch or the starch derivative. Such an encapsulation method is described in the German application DE 199 56 382.

It is also possible for at least two solid phases to be present connected together. Thus, one possibility is to provide a solid composition of the invention in the compression or compaction to tablets. Such tablets may be single phase or multiphase. This presentation thus also makes it possible to introduce a solid composition of the invention with two phases. Compositions of the invention in tablet form, which may be single phase or multiphase, single color or multicolor, and/or may consist of one more layers, are produced by preferably mixing all the constituents—where appropriate each of one layer—together in a mixture and compressing the mixture using conventional tablet presses, for example eccentric presses or rotary presses, with compressive forces in the range from about 50 to 100 $kN/cm^2$, preferably at 60 to 70 $kN/cm^2$. It may be advantageous, especially in the case of multilayer tablets, for at least one layer to be precompressed. This is preferably carried out with compressive forces between 5 and 20 $kN/cm^2$, in particular at 10 to 15 $kN/cm^2$. A tablet produced in this way preferably has a weight of from 10 g to 50 g, in particular from 15 g to 40 g. The three-dimensional shape of the tablets is as desired and may be circular, oval or angular, with intermediate shapes also being possible.

It is particularly advantageous in multiphase compositions for at least one of the phases to comprise an amylase-sensitive material, in particular starch, or be at least partially surrounded or coated thereby. In this way, this phase is mechanically stabilized and/or protected from external influences and, at the same time, attacked by an amylase which is active in the wash liquor, so that release of the ingredients is facilitated.

Likewise preferred compositions of the invention are characterized in that they are overall in liquid, gel or pasty form. The contained proteins, preferably a protein of the invention, are added to such compositions preferably starting from a protein isolation carried out in accordance with the state of the art and preparation in concentrated aqueous or nonaqueous solution, for example in liquid form, for example as solution, suspension or emulsion, but also in gel form or encapsulated or as dry powder. Washing or cleaning compositions of the invention of this type in the form of solutions in conventional solvents are usually produced by simply mixing the ingredients which can be put undiluted or as solution into an automatic mixer.

One embodiment of the present invention are such compositions which are liquid, in gel form or pasty and to which a protein which is essential to the invention and/or one of the other contained proteins and/or one of the other contained ingredients has been added encapsulated, preferably in the form of microcapsules. Particular preference is given among these to those with capsules made of amylase-sensitive material. Such a joint use of amylase-sensitive materials and the amylolytic enzyme which is essential to the invention in a washing or cleaning composition may show synergistic effects, for example in such a way that the starch-cleaving enzyme assists the cleavage of the microcapsules and thus controls the process of release of the encapsulated ingredients, so that release thereof takes place not during storage and/or not at the start of the cleaning process but only at a particular time. Complex washing and cleaning composition systems with a wide variety of ingredients and a wide variety of capsule types may be based on this mechanism and represent particularly preferred embodiments of the present invention.

There is a comparable effect when the ingredients of the washing or cleaning composition are distributed to at least two different phases, for example two or more solid phases which are connected together of a washing or cleaning composition in tablet form, or different granules within the same composition in powder form. Two-phase or multiphase cleaners for use both in machine dishwashers and in washing compositions are state of the art. The activity of an amylolytic enzyme in a phase which has been activated earlier is a precondition for activation of a later phase if the latter is surrounded by an amylase-sensitive envelope or coating, or the amylase-sensitive material represents an integral constituent of the solid phase, and on partial or complete hydrolysis thereof the relevant phase disintegrates. The use of the enzyme which is essential to the invention for this purpose thus represents a preferred embodiment of the present invention.

The ingredients of washing and cleaning compositions are suitably capable of mutual assistance in their performance. The synergistic use of amylase and color transfer inhibitors to enhance the cleaning performance is disclosed for example in the application WO 99/63035. It is also known that polymers which can simultaneously be employed as cobuilders, such as alkyl polyglycosides, are able to stabilize and enhance the activity and stability of contained enzymes, for example from the application WO 98/45396. It is thus preferred for a protein or derivative of the invention, preferably having amylolytic activity, to be modified, in particular stabilized and/or enhanced in its contribution to the washing or cleaning performance of the composition, by one of the other constituents listed above. Correspondingly adjusted formulations for compositions of the invention thus represent particularly preferred embodiments of the present invention.

In accordance with the previous statements, methods of the invention for cleaning textiles or hard surfaces can be improved by using in at least one of the method steps a protein or derivative of the invention, preferably having amylolytic activity. The methods are then according to the invention and thus embodiments of the present invention.

Such methods are preferably characterized in that a composition as described above is employed in at least one of the method steps.

Such methods are particularly preferably characterized in that the protein or derivative of the invention, preferably having amylolytic activity, is employed in machines, for example in usual domestic dishwashers or domestic washing machines, preferentially from 0.01 mg to 400 mg, preferably from 0.02 mg to 200 mg, particularly preferably from 0.02 mg to 100 mg, of the enzyme of the invention in the method step characterized by this enzyme.

The concentrations resulting therefrom are beneficially from 0.0005 to 20 mg per 1, preferably 0.005 to 10 mg per 1, particularly preferably 0.005 to 8 mg of the amylolytic protein per 1 of wash liquor. The protein concentration can be determined with the aid of known methods, for example the BCA method (bicinchoninic acid; 2,2'-biquinolyl-4,4'-dicarboxylic acid) or the biuret method (A. G. Gornall, C. S. Bardawill and M. M. David, *J. Biol. Chem*. 177 (1948), pp. 751-766).

In accordance with previous statements, the use of a protein or derivative of the invention, preferably having amylolytic activity, alone or together with at least one other active substance which has cleaning activity or assists the cleaning effect for cleaning textiles or hard surfaces represents an embodiment of the present invention.

This preferably takes place by the use of a composition of the invention.

The composition of the invention or a protein or derivative of the invention, preferably having amylolytic activity, is preferably employed in the ranges of amounts indicated above, so that the concentrations indicated above of the amylolytic protein beneficially result in the wash liquor. This dosage can be undertaken by the manufacturer of the composition or by the final user, depending on the cleaning problem.

A further possibility for using a protein or derivative of the invention, preferably having amylolytic activity, represents the for activation of its own or other phases when it is provided alone or together with at least one other active substance which has cleaning activity or assists the cleaning effect in a washing or cleaning composition consisting of more than one phase.

A further possibility for using a protein or derivative of the invention, preferably having amylolytic activity, represents the for release of the ingredients from the capsules when it is provided alone or together with at least one other active substance which has cleaning activity or assists the cleaning effect in a washing or cleaning composition having encapsulated ingredients.

A further embodiment represents the use of a protein or derivative of the invention for the treatment of raw materials or intermediate products in textile manufacture, in particular for desizing cotton.

Raw materials and intermediate products of textile manufacture, for example for those based on cotton, are finished with starch during their manufacture and further processing in order to make better processing possible. This method, which is applied to yarns, to intermediate products and to textiles, is called sizing. Amylolytic proteins of the invention are suitable for removing the sizes, i.e. the starch-containing protective layer (desizing).

A further embodiment is represented by methods for liquefaction of starch, in particular for ethanol production, which are characterized in that the protein or derivative of the invention is employed therein.

For liquefaction of starch, starch swollen in water or buffer is incubated with amylolytic enzymes, whereby the polysaccharide is cleaved into smaller constituents, finally predominantly into maltose. Enzymes of the invention are preferably employed for such a process or a part step thereof if they can be fitted well into a corresponding production process because of their biochemical properties. This may be the case for example if they are to be introduced into a step in addition to other enzymes which require the same reaction conditions. Amylolytic proteins of the invention are particularly preferred when interest centers precisely on the products they themselves produce. Liquefaction of starch may also represent one step in a multistage process for obtaining ethanol or downstream products derived therefrom, for example acetic acid.

A further embodiment is represented by the use of a protein or derivative of the invention for producing linear and/or short-chain oligosaccharides.

Because of their enzymatic activity, amylolytic proteins of the invention produce from starch-like polymers, after a relatively short incubation time, predominantly relatively high molecular weight oligosaccharides such as, for example, maltohexose, maltoheptose or maltooctose. After a longer incubation time, the proportion of lower oligosaccharides such as, for example, maltose or maltotriose increases among the reaction products. If there is particular interest in certain reaction products, corresponding variants of proteins of the invention can be used and/or the reaction conditions can be designed appropriately. This is attractive especially when the interest is not in pure compounds but in mixtures of similar compounds, such as, for example, in the production of solutions, suspensions or gels merely with certain physical properties.

A further embodiment is represented by the use of a protein or derivative of the invention for hydrolyzing cyclodextrins.

Cyclodextrins are $\alpha$-1,4-glycosidically linked, cyclic oligosaccharides, of which the greatest economic importance is possessed by the $\alpha$-, $\beta$- or $\gamma$-cyclodextrins composed of 6, 7 or 8 glucose monomers (or cyclohexa-, -hepta- or -octamyloses). They are able to form inclusion compounds with hydrophobic guest molecules such as, for example, fragrances, flavorings or pharmaceutical active substances, from which the guest molecules can be released again as required. Such inclusion compounds are important, depending on the area of use of the ingredients, for example for producing foodstuffs, for pharmacy or for cosmetics, for example in corresponding products for the final consumer. The release of ingredients from cyclodextrins thus represents a possible use of proteins of the invention.

A further embodiment is represented by the use of a protein or derivative of the invention for releasing low molecular weight compounds from polysaccharide carriers or cyclodextrins.

Because of their enzymatic activity, amylolytic proteins of the invention are also able to release low molecular weight compounds from other $\alpha$-1,4-glycosidically linked polysaccharides. This may, as for the cyclodextrins, take place at the molecular level and in larger systems such as, for example, ingredients encapsulated in the form of microcapsules. For example, starch is a material established in the art for encapsulating compounds such as, for example, enzymes, which are to be introduced in defined amounts into reaction mixtures, during storage. The controlled release process from such capsules can be assisted by amylolytic enzymes of the invention.

A further embodiment is represented by the use of a protein or derivative of the invention for producing food products and/or food ingredients.

The use of a protein or derivative of the invention for producing animal feed and/or animal feed ingredients likewise represents an embodiment of this aspect of the invention.

Wherever starch or carbohydrates derived from starch play a role as ingredient of food products or animal feeds, an amylolytic activity can be used to produce these articles. It increases the proportion of mono- or oligomers compared with the polymeric sugar, which may benefit for example the taste, the digestability or the consistency of the food product. This may be necessary for the production of certain animal feeds, but also for example in the production of fruit juices, wine or other food products if the proportion of polymeric sugars is to be reduced and that of sweet and/or more readily soluble sugars is to be increased. The possible use for liquefaction of starch and/or ethanol production mentioned above can be regarded as industrial variant of this principle.

In addition, amylases also counteract the loss of taste, known as staling, of bakery products (antistaling effect). It is suitable for this purpose to add them to the dough before baking. Preferred embodiments of the present invention are therefore those in which proteins of the invention are used for manufacturing bakery products.

A further embodiment is represented by the use of a protein or derivative of the invention for breaking down starch-containing adhesive bonds.

Likewise, temporary bonding methods which are characterized in that a protein or derivative of the invention is employed therein represent an embodiment of this aspect of the invention.

Besides other natural products, starch has also been used for centuries as binder in paper manufacturing and the gluing of papers and boards. This relates for example to prints and books. Over a long period of time, such papers may with unfavorable effects such as, for example, moisture become wrinkled or break, which may lead to complete destruction thereof. In the restoration of such papers and boards it may be necessary to break down the adhesive layers and this can be considerably facilitated through use of an amylolytic protein of the invention.

Vegetable polymers such as starch or cellulose and water-soluble derivatives thereof are used inter alia as adhesives or pastes. For this purpose, they must first swell in water and, after application to the item for gluing, dry, whereby the latter is fixed on the substrate. The enzyme of the invention can be added to such an aqueous suspension in order to influence the adhesive properties of the resulting paste. However, instead of or in addition to this function, it can also be added to the paste in order to remain inactively on the item for gluing after drying for a long time, for example some years. Deliberate alteration of the environmental conditions, for example by humidification, can then be used at a later time to activate the enzyme and thus bring about breakdown of the paste. In this way, the glued item can more easily be detached again from the substrate. In this process, the enzyme of the invention acts, because of its amylolytic activity, as separating agent in a temporary bonding process or as so-called "switch" for detaching the glued item.

EXAMPLES

The following examples illustrate the invention without, however, restricting it thereto.

Example 1

Isolation of Metagenomic DNA from Microbial Habitats

Obtaining Soil Samples

The soil samples were obtained from various locations in Germany (inter alia) and initially processed mechanically while dry (screening through 4 mm and 1 mm sieves).

DNA Isolation from Soil

For DNA preparation, 5 g of soil were slurried by addition of 13.5 ml of extraction buffer (100 mM Tris-HCl, pH 8.0; 100 mM EDTA, pH 8.0; 100 mM sodium phosphate, pH 8.0;

1.5 M NaCl; 1% hexadecyltrimethylammonium bromide). The suspension was shock-frozen 3 times with addition of liquid nitrogen ($N_2$), ground in a mortar and boiled in a microwave. After being transferred into a 50 ml screw-cap vessel and adding 1.5 ml of lysozyme solution (50 mg/ml), the suspension was incubated at 37° C. for 30 min and inverted at intervals of 5 min. Addition of 200 µl of a proteinase K solution (10 mg/ml) was followed by incubation at 37° C. for 30 minutes with inversion as before. This was followed by treatment with SDS (by addition of 3 ml of a 10% solution) at 65° C. for two hours (inversion of the vessel every 20 min). After centrifugation (6000×g, 10 min) and slurrying with 4.5 ml of extraction buffer plus 1 ml of 10% SDS, the sediment was again extracted and incubated at 65° C. for 10 min and centrifuged as before. The combined supernatants from the two centrifugations were mixed with 1 volume of phenol/chloroform (1:1) and centrifuged as before. The DNA was precipitated from the upper aqueous phase by addition of 0.6 volume of isopropanol and incubation at room temperature for one hour and centrifugation at 16 000×g for 20 minutes. The DNA pellet was washed with 70% ethanol and dried in air and then dissolved in 200 µl of TE buffer (100 mM Tris-HCl pH 8.0; 1 mM EDTA pH 8.0).

The high molecular weight genomic DNA was finally separated from dissolved inhibitory humic acids by preparative gel electrophoresis (0.7% agarose) and subsequent extraction (QIAex II Gel Extraction Kit; from Qiagen, Hilden).

Example 2

Setting Up the Expression Gene Libraries and Screening for Amylolytic Activity

Figure 1:
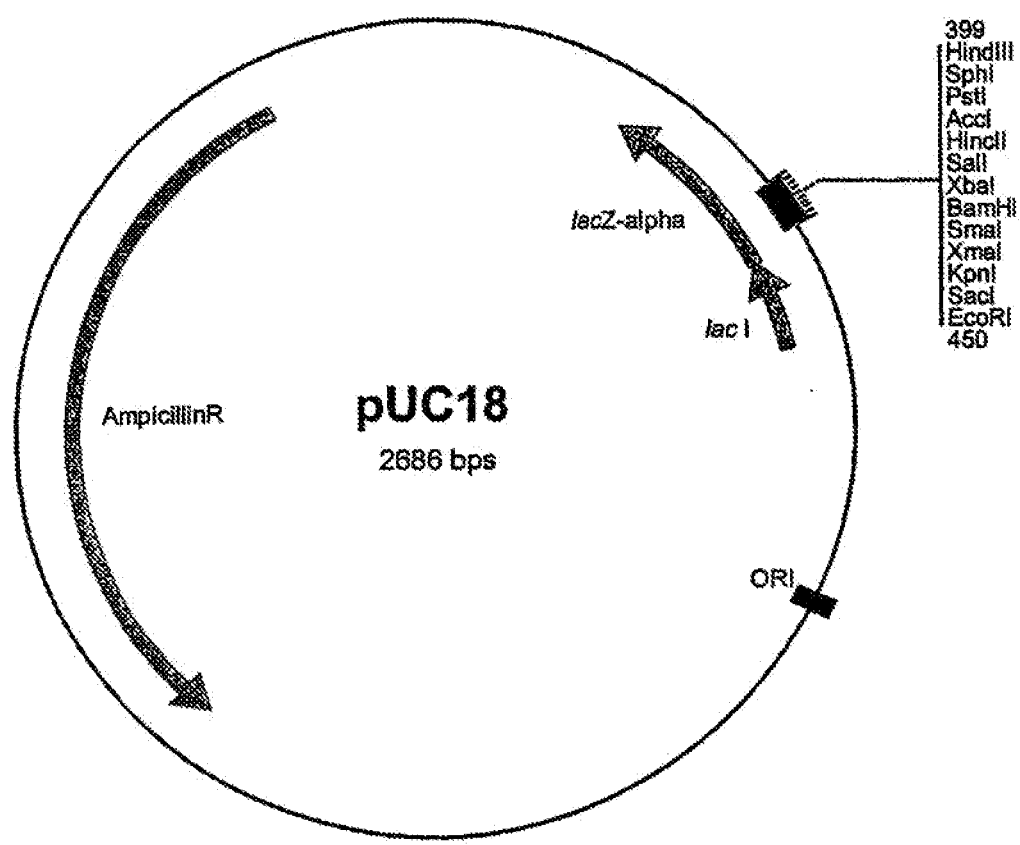
FIG. 1: Diagrammatic representation of the plasmid vector pUC18 (GenBank Acc. L08752) used for the expression gene libraries. The vector was linearized with BamHI for the uptake of Sau3AI-digested metagenomic DNA.

Expression cloning in the heterologous host organism *Escherischia coli* was chosen for the cloning and isolation of complete α-amylase genes from metagenome. Since heterologous recognition of the promoters of unknown donor organisms cannot be assumed in the host organism *E. coli*, use was made of an *E. coli* promoter which is inducible in a known manner with IPTG (isopropyl thiogalactoside), the β-galactosidase promoter of the lac operon (lac promoter) on the pUC18 plasmid vector (GenBank NCBI/NIH, Bethesda, Acc.-NO: L08752; FIG. 1). It is thus possible in host strains with a laciq genotype (for example JM109) to induce expression of the genes under the control of this promoter by adding IPTG.

The *E. coli* strains JM 109, DH 10B and DH 12S proved to be suitable systems for cloning the metagenome-derived α-amylases and activity-dependent detection thereof. This is because, although they have the periplasmic enzyme encoded by mals (Freundlieb, S., Boos, W. (1986): "Alpha-amylase of *Escherichia coli*, mapping and cloning of the structural gene, malS, and identification of its product as a periplasmic protein"; *J. Biol. Chem.* 261 (6), pp. 2946-2953), they showed negligible release of amylase under the experimental conditions.

Purified metagenomic DNA from soil was partially cleaved with restriction enzymes, preferably Sau3AI, and the fragment size range from preferably 8 to 12 kb was fractionated and isolated by gel electrophoresis. These DNA fragments were ligated into suitable vectors, preferably pUC18 plasmid vector linearized with the restriction enzyme BamHI (FIG. 1).

To establish the optimal restriction parameters for the preparative partial digestion of metagenomic DNA, firstly restriction kinetics were carried out using about 4 fg of DNA and restriction enzyme (Sau3AI) in concentrations of from 0.3 to 0.4 U per µg of DNA in 1× buffer where appropriate with bovine serum album (BSA) in accordance with the manufacturer's instructions, in a total volume of 20 µl. The mixtures were for this purpose initially equilibrated at 37° C. without enzyme. Then the respective reaction was started by adding restriction endonuclease. At fixed intervals between 0 and 10 min, in each case 2 µl of reaction mixture were added to 1× stop buffer (6X: 10 mM Tris, pH 7.0; 20% glycerol; 0.1% SDS) on ice and analyzed on a 0.7% agarose gel. In this way, the optimal restriction time for a partial digestion was established individually for each DNA preparation.

The preparative partial digestion took place with the absolutely identical procedure as for the restriction kinetics in 15 to 20 individual mixtures. After the reaction was stopped by adding 1× stop buffer, the mixture was fractionated by electrophoresis on a 0.7% agarose gel, the region of the gel with DNA 8-12 kb in size was cut out and it was isolated by electroelution in dialysis tubes at 4° C. for two hours. The DNA was precipitated with ¹⁄₁₀ volume of 3 M sodium acetate and 2.5 times the volume of ethanol, and taken up in a smaller volume and was, for further removal of smaller fragments, subjected to a second gel electrophoresis with subsequent electroelution and renewed concentration.

Ligation with the plasmid vector pUC18 took place in a total volume of 20 µl using 100 ng of BamHI-linearized pUC18 vector, which had been dephosphorylated with CIAP (alkaline phosphatase from calf thymus) in accordance with the manufacturer's instructions, and 800 ng of partially cleaved genomic DNA, and an appropriate amount of ligase (600 NEB units in this case) in 1× ligase buffer at 16° C. overnight.

Transformation of competent *E. coli* DH12S cells (Gibco Life Technologies, Karlsruhe) took place by electrotransformation. For this purpose, 1 µl of ligation mixture and 25 µl of cells were mixed, incubated in an electroporation cuvette on ice for 1 min and treated in the electroporator (BTX® ECM630, Genetronics Inc. San Diego, USA) in accordance with the manufacturer's instructions. After immediate transfer into 1 ml of SOC medium (2% Bacto tryptone; 0.5% yeast extract; 10 mM NaCl; 2.5 mM KCl; pH 7.0, adjusted with NaOH; autoclaved; supplemented with 10 mM $MgSO_4$ and $MgCl_2$, and 20 mM D(+)glucose), a recovery period of 1 h at 37° C. followed before plating.

To examine the quality of the gene library, the number of primary transformants generated in total, and the number of insert-harboring clones was determined by blue/white selection in a test plating. For this purpose, 1 and 10 µl portions of the ligation mixture were plated out on LB medium with ampicillin, IPTG, X-Gal (as described above) and incubated at 37° C. overnight. To confirm the actually cloned insert sizes, the plasmids were isolated from at least 10 white colonies of the test plating, and a suitable restriction digestion was carried out with subsequent size analysis by gel electrophoresis.

In the screening of the gene libraries, the ability of individual recombinant *E. coli* clones in metagenomic libraries to degrade starch was determined. For this purpose, LB agar with 1% soluble starch (from Merck, Darmstadt, Order NO: #1252) on which clones able to degrade starch can be identified by zones of degradation was used. Initial storage of the plates at 4° C. for two to four weeks until cloudy was necessary for this, storage degradation of the starch was visible as clearing around the active colonies on the plates. For use, IPTG (100 mM) was added to the plates to induce the promoter and ampicillin (100 µg/ml) was added to apply the selection pressure to the transformants.

Appropriate for the titer of the library generated in each case, a defined volume of the transformation mixture was plated out uniformly by means of glass beads with about 10000 colonies per plate (14 cm diameter) (primary plating). After incubation at 37° C. for 16 hours, the plates were incubated at 28° C. for a further 24-48 h for amylase expression and release. The incubation at 28° C. was usually indispensible for visible degradation of starch. It is possible that improved protein folding and a permeabilization of the outer cell membrane are involved in this (Stathopoulos, C., Georgiou, G., Earhart, C. F. (1996): "Characterization of *Escherichia coli* expressing an Lpp'OmpA(46-159)PhoA fusion protein localized in the outer membrane"; *Appl. Microbiol. Biotechnol.*, 45 (1-2), 112-119). Thus, release of the α-amylase produced in each case was associated therewith, and it was unnecessary additionally to carry out cell lysis to detect unexported cytoplasmic amylases. After isolation of the colonies from the zone regions of the primary plating by renewed (secondary) plating on the same starch plates it was possible to select amylase-producing single colonies on the basis of renewed zone formation. For photodocumentation purposes after securing the clones, staining of the starch plates with 50% lugol solution (from Merck) proved suitable for unambiguous visualization of starch-free regions (degradation zones).

The plasmid DNA of active clones obtained after minipreparation (kit from Qiagen, Hilden, Germany, used in accordance with the manufacturer's instructions) was examined for the size of the insert in a restriction analysis with EcoRI or SacI/HindIII and then sequenced. In this case, the insert-flanking M13 primers (M13 forward: 5'-GTAAAAC-GACGGCCAG-3' [SEQ ID NO:317]; M13 reverse: 5'-CAGGAAACAGCTATGAC-3' [SEQ ID NO:318]) were initially used in order finally to obtain the complete sequence by so-called primer walking as known in the art.

Example 3

Characterization of the Metagenomic Pool by PCR

To estimate the content of gene sequences for glycosyl hydrolases in metagenomic DNA from soil, a DNA amplification was carried out by the polymerase chain. reaction (PCR). This was carried out using HotStar Taq polymerase (from Qiagen, Hilden) and the glycosylhydrolase-specific primers (Table 1). For this purpose, 0.1 µl portions of the metagenomic DNA isolated by the above method were employed in the presence of 200 µM dNTPs (in each case dATP, dTTP, dCTP, dGTP), 20 pmol of each primer of a pair (forward-/reverse), 2.5 U HotStar Taq-polymerase (Qiagen, Hilden) and 1× PCR buffer in a total volume of 50 µl. Fragments of sizes 150 to 300 bp were amplified in the following cycles: 1 cycle at 95° C. for 15 min, 35 cycles at 95° C. for 30 s each, 30 s at 57° C. (GEX036/038)or 60° C. (other primer pairs) and 30 s at 72° C.; 1 cycle at 72° C. for 7 min.

Using the primer pairs GEX024/026 and GEX023/025, in each case unique PCR products were amplified (respectively 300 bp and 280 bp; FIG. 4). Amplification in these cases was frequently possible only after 1:10 dilution of the metagenomic DNA. This was presumably due to inhibitory components in the DNA preparations which became inactive by dilution below a critical threshold. With primer pair GEX036/038, PCR fragments (150 and 300 bp) were obtained only after reamplification using 4 µl of the original reaction.

All PCR fragments firstly underwent intermediate cloning using the TOPOTA kit (Invitrogen, Groningen NL) in accordance with the manufacturer's instructions into the pCR2.1-TOPO® vector for the sequencing. The ligation products were used for transformation into *E.coli*-TOP® 10F' (Invitrogen, Groningen NL). After blue/white selection of recombinant clones on LB medium with ampicillin (100 µg/ml), IPTG (100 mM) and X-Gal (40 mg/ml), the plasmid DNA of white clones was isolated after minipreparation and examined in a restriction analysis with EcoRI for the content of insert DNA. In this case, differences in the insert sizes are evident, especially in the clones from the PCR with GEX024/026 and 036/038 (FIG. 4), and reflect the molecular diversity of the amplified glycosyl hydrolase sequences in the metagenome.

Sequence analysis of plasmids with insert DNA took place routinely on an ABI PRISM® 310 (from Perkin Elmer, Weiterstadt) in accordance with the manufacturer's instructions using AmpliTaq-FS-Big Dye® Terminator kit (from Perkin Elmer, Weiterstadt) and employing 200-500 ng of plasmid DNA, 10 pmol of primers (TopoF: 5'-GCTCG-GATCCACTAGTAACG-3' [SEQ ID NO:319] and TopoR: 5'-CTCTAGATGCATGCTCGAG-3' [SEQ ID NO:320]), 4 µl of premix in a total volume of 20 µl.

The resulting DNA sequences were conceptionally transcribed into an amino acid sequence, compared via the BlastX, BlastN and BlastP algorithms (Altschul S F, Gish W, Miller W, Myers E W, Lipman D J (1990) Basic local alignment search tool. J Mol Biol 1990 Oct. 5; 215(3): 403-10) using the FASTA program (Pearson W R, Lipman D J. (1988) Improved tools for biological sequence comparison. Proc Natl Acad Sci USA Apr; 85(8): 2444-8) with the entries present in the sequence database GenBank (Rel 122.0) and identified in this way as partial sequences of α-amylases and other glycosyl hydrolases (see Table 2).

Parts of the constant primer regions which were unclear owing to a late onset of sequencing reading definition, or unexpectedly differed from the synthetically presented sequence, were corrected only at the amino acid sequence level and thus entered in the corresponding sequence lists. It is therefore possible for DNA sequences in these constant primer regions to differ from the conceptionally translated amino acid sequences.

The amino acid sequences are listed in the sequence listing under numbers SEQ ID NO:7 to 56 and SEQ ID NO:107 to 205 and included in the consensus sequences A [SEQ ID NO:305] to D [SEQ ID NO:306].

Example 4

Sequence Analysis of the Amylase Genes Found

A clone HA 11 which indicated amylase activity by zone formation in the expression screening described above was completely sequenced. Sequence analysis revealed the existence of two open reading frames, one of which, ORF1, was identifiable as amylase gene by homology comparisons. The derived protein sequence is shown in SEQ ID NO:1. The result of a Fasta3 search revealed an amylase from *Bacillus* sp. as the most similar enzyme with an AA homology of 72.3%. This amylase showed in the carboxy-terminal region of the protein sequence extensive homologies with an experimentally verified new type of starch-binding domain in the most similar known sequence (Sumitani, J.; Tottori, T., Kawaguchi, T. and Arai, M.; Biochem J 350, 477-484, (2000)).

A second reading frame, ORF 2, with a homology of 46%, based on the complete available gene sequence, to the most similar gene (bifunctional amylase-dextrinase) from Streptomyces coelicolor A3 (Redenbach, M; Kieser, H. M.; Depanaite, D.; Eichner, A, Cullum J; Kinashi, H. and Hopwood, D. A., Mol. Microbiol 21, 77-96 (1996)) was only incompletely present in the genomic clone. A stop codon at the 3' end was missing, so that the actual gene extends beyond the known cloned sequence.

The amylase gene from HA 11 was amplified from the isolated genomic clone by PCR and use of suitable primer oligonucleotides and was cloned in the E. coli-Streptomyces shuttle vector pEX601. After expression in the heterologous host Streptomyces lividans TK 24, the enzyme obtained in the culture supernatant underwent biochemical characterization.

The amylase domain of the bifunctional ORF 2 was separately cloned in analogy to the amylase and was expressed in S. lividans TK 24. Analysis of the supernatants revealed unambiguously an amylase activity measurable by the DNSA assay. The part, cloned and expressed in this way, of the bifunctional ORF 2 is called HA 13, and the protein sequence is indicated in SEQ ID NO:3.

Example 5

Biochemical Characterization of the Expressed Genes

In view of the diverse areas of application of aα-amylases, the enzymatic properties which may be the basis for application-based selection of enzymes were characterized. The enzymes can for this purpose be prepared by cloning and heterologous expression of the gene sequences in accordance with Example 4. The amylolytic activity was determined by means of a modified dinitrosalicylic acid assay (DNSA assay; Hofstetter, F. & E. Borel (1951); Helv. Chim. Acta, 34, 2133-2139)). This entails the hydrolysis of a complex starch substrate being determined on the basis of the increase in reducing ends of the polysaccharide, with the absorption at 540 nm of the unreacted DNSA reagent serving as measure of the hydrolytic activity.

To carry out the assay, 25 μl portions of substrate solution (1% soluble starch Merck analytical grade, in 180 mM Tris-maleate buffer, pH 8.6, or in 180 mM of the appropriate assay buffer) were introduced into the sample and blank wells of a 96-well plate for PCR thermocycler (0.2 ml "thin-wall plate" #3416, Molecular BioProducts MβP, San Diego, USA) and preincubated at 50° C., or the particular assay temperature, in a thermocycler block for 5 min. After addition of 20 μl of enzyme solution to each well, substrate conversion took place at 50° C. or the particular assay temperature for 15 min. After addition of 65 μl of DNSA reagent (8.8 g of dinitrosalicylic acid, 250 g of potassium sodium tartrate, 6.3 g of sodium disulfite, 334 ml of 4.5% (w/v) NaOH, 915 ml of $H_2O$) to the sample and blank wells, and addition of 20 μl of enzyme solution to the blank wells, the assay plate was immediately transferred into a thermoblock preheated to 100° C., and incubated at 100° C. for 20 min. The samples were measured by transferring 60 μl portions of the assay mixture into 200 μl of $H_2O$ which had been introduced into a 96-well measuring plate (PS-Microplate, 96 well #655101, Greiner) subsequently determining the absorption at 540 nm using a microtiter plate spectral photometer (Spectramax 190, Molecular Devices, Sunnivale USA) with $H_2O$ as reference. Three measurements were carried out in each case; evaluation took place by subtracting the average of the 3 blank wells from the average of the 3 sample wells.

Temperature Profile

The temperature profile was determined by carrying out the conversion by the procedure described above at various temperatures with 100 mM Tris-maleate, pH 8.6. The alpha-amylase HA11 (SEQ ID NO:1) was found to have maximum activity at 50.4° C. Temperatures above 60° led to losses of activity of this enzyme (see Table 3).

The maximum for the amylase domain HA13 was found to be 55.5° C. (see Table 4).

Temperature Stability of the Amylase Domain HA13

After preincubation in the temperature gradient from 50° C. to 69.7° C. for 15 min, substrate conversion and the DNSA assay took place as described above at 50° C. in Tris-HCl, pH 8.6. Table 5 shows that the stability declines markedly above 60° C.

Stability to pH Variations

To determine the activity of the α-amylase amylases under various pH conditions, the starch substrate solution was made up in the pH range from 4 to 12 using the buffer suitable for the particular pH. The buffer concentration was adjusted in each case to 180 mM so that a concentration of 100 mM resulted after dilution under assay conditions. The amylolytic activity at the respective pH values was determined as indicated above at 50° C. The respective buffers and the relative activity values for the two amylases (HA 11 and HA 13) are to be found in Table 6. It is evident that both amylases exhibit the maximum in the range pH 5 to 6.5, and that amylase HA 13 is distinguished by a broad maximum and still has considerable remaining activity even at 12.

Stability to Surfactants:

The surfactant stability was determined by adjusting a final concentration of SDS between 0 and 1%. The substrate conversion took place with 100 mM Tris-HCl pH 8.6 at 50° C. for 15 min (Table 7=HA11; Tab. 8=HA13).

Effect of Bleaches

The effect of bleaches was determined from the action of up to 0.7% $H_2O_2$ in 100 mM glycine-NaOH pH 9.5. Preincubation in the presence of $H_2O_2$ at room temperature under appropriate conditions was followed by further incubation at 50° C. for 15 min. The substrate conversion was then measured in the DNSA assay. (Table 9: HA 11; Table 10: HA13)

Effect of Complexing Agents:

The effect of complexing agents was investigated by adjusting a concentration of 2 mM $CaCl_2$ or 1 mM EDTA in 100 mM Tris-HCl pH 8.6 at 50° C. for 15 min. (Table 11=HA11; Table 12=HA13)

Example 6

Investigation of the Washing Performance

The washing performance of prepared amylase sample was determined in miniwash tests using standardized test soilings. These consisted of starch immobilized on fabric, and a color indicator (EMPA 162, starch on blended polyester/cotton fabric and CF PCS 26, cornstarch on cotton).

For this purpose, 19.6 $cm^2$ fabric samples were incubated in 20 ml of wash liquor with and without added bleach. The amount of enzyme employed in each case was that able to generate from soluble starch, at 37° C. and pH 6.5, per minute an amount of reducing sugars equivalent to 12 μmol of glucose. The fabric samples were incubated at 40° C. and 80 rpm for 90 minutes. They were then rinsed with H₂O, dried and the color (L value) was determined using a Minolta surface photometer. The lightening as the measure of the detachment of starch and thus the washing performance was then determined by forming the difference from the untreated fabric sample. The results are shown in Table 13.

It is evident from this that the washing performance of HA 11 (SEQ ID NO: 1) on use of the same enzymic activity was greatest in each case. Termamyl® was weaker, but in each case better than BAN®. These enzymes showed a decrease in the presence of a bleach-containing formulation. HA13 (SEQ ID NO:3) by contrast proved to be relatively insensitive to bleach, so that the washing performance in the bleach-free formulation was below that of the other enzymes but was comparable with Termamyl in the bleach-containing one.

TABLE 1

PCR primers for amplification of partial sequences of metagenomic DNA sequences coding for glycosyl hydrolases.

| Name | Sequence (5'-3') | | Orientation |
|---|---|---|---|
| GEX 023 | GGTCTACGCCGACGTCGTSWWCAACCA | [SEQ ID NO:309] | forward |
| GEX 024 | CGTCGACGGCTTCCGSATCGACRC | [SEQ ID NO:310] | forward |
| GEX 025 | GGCGTCGATGCGGAASCCGTC | [SEQ ID NO:311] | reverse |
| GEX 026 | GCTCGGTGTCGTGGTTGTCSACGWA | [SEQ ID NO:312] | reverse |
| GEX 036 | GTACGCCGACGCCGTNWTHAAYCA | [SEQ ID NO:313] | forward |
| GEX 038 | GGCGGCGTCGATCCKRAANCCRTC | [SEQ ID NO:314] | reverse |
| GEX 210 | CGACGTGGTGTTCAACCAYYTNGGNCC | [SEQ ID NO:315] | forward |
| GEX 211 | GCCGACGTGGTGTTCAAYCAYYTNGG | [SEQ ID NO:316] | forward |

Symbols for degenerate base positions (mixtures of different nucleotides): R = AG; Y = CT; M = AC; K = GT; W = AT; S = CG; B = CGT; D = AGT; H = ACT; V = ACG; N = ACGT

TABLE 2

List of the 149 single sequences with the identities to their closest relations in GenBank (NCBI; Release 121.0); determined using the FASTA program on Feb. 2, 2001.

| Primer | SEQ ID No. in Seq. listing | Closest database hit | Gene/product | Identity (%) | Organism |
|---|---|---|---|---|---|
| 23/25 | 107 | AB003697 | oligo-1,6-glucosidase | 74.5 | Bacillus flavocaldarius |
| 23/25 | 108 | AB015615 | isoamylase | 65 | Bacillus flavocaldarius |
| 23/25 | 109 | AB015615 | isoamylase | 61.7 | Orysa sativum |
| 23/25 | 110 | AB015615 | isoamylase | 66.2 | Orysa sativum |
| 23/25 | 111 | AB015615 | isoamylase | 64.2 | Orysa sativum |
| 23/25 | 112 | AB015615 | isoamylase | 68.8 | Orysa sativum |
| 23/25 | 113 | AB031392 | glycogen debranching enzyme | 77.8 | Arthrobacter sp. |
| 23/25 | 114 | AB031392 | glycogen debranching enzyme | 63 | Arthrobacter sp. |
| 23/25 | 115 | AB031392 | glycogen debranching enzyme | 80.2 | Arthrobacter sp. |
| 23/25 | 116 | AB031392 | glycogen debranching enzyme | 77.8 | Arthrobacter sp. |
| 23/25 | 117 | AB031392 | glycogen debranching enzyme | 79 | Arthrobacter sp. |
| 23/25 | 118 | AB031392 | glycogen debranching enzyme | 77.8 | Arthrobacter sp. |
| 23/25 | 119 | AB031392 | glycogen debranching enzyme | 81.5 | Arthrobacter sp. |
| 23/25 | 120 | AB031392 | glycogen debranching enzyme | 76.5 | Arthrobacter sp. |
| 23/25 | 121 | AB031392 | glycogen debranching enzyme | 86.4 | Arthrobacter sp. |

TABLE 2-continued

List of the 149 single sequences with the identities to their closest relations in
GenBank (NCBI; Release 121.0); determined using the FASTA program on Feb. 2, 2001.

| Primer | SEQ ID No. as in Seq. listing | Closest database hit | Gene/product | Identity (%) | Organism |
|---|---|---|---|---|---|
| 23/25 | 122 | AB031392 | glycogen debranching enzyme | 86.8 | *Arthrobacter* sp. |
| 23/25 | 123 | AB031392 | glycogen debranching enzyme | 80.2 | *Arthrobacter* sp. |
| 23/25 | 124 | AE001888 | glycogen operon protein GlgX | 76.5 | *Deinococcus radiodurans* |
| 23/25 | 125 | AE001888 | glycogen operon protein GlgX | 37.8 | *Deinococcus radiodurans* |
| 23/25 | 126 | AE001888 | glycogen operon protein GlgX | 72.8 | *Deinococcus radiodurans* |
| 23/25 | 127 | AE001888 | glycogen operon protein GlgX | 77.8 | *Deinococcus radiodurans* |
| 23/25 | 128 | AE001888 | glycogen operon protein GlgX | 69.1 | *Deinococcus radiodurans* |
| 23/25 | 129 | AE001888 | glycogen operon protein GlgX | 76.5 | *Deinococcus radiodurans* |
| 23/25 | 130 | AE001888 | glycogen operon protein GlgX | 76.5 | *Deinococcus radiodurans* |
| 23/25 | 131 | AE001888 | glycogen operon protein GlgX | 71.6 | *Deinococcus radiodurans* |
| 23/25 | 132 | AE001888 | glycogen operon protein GlgX | 77.8 | *Deinococcus radioduransv* |
| 23/25 | 133 | AE001888 | glycogen operon protein GlgX | 77.8 | *Deinococcus radiodurans* |
| 23/25 | 134 | AE001905 | maltooligosyltrehalose trehalohydrolase | 45.6 | *Deinococcus radiodurans* |
| 23/25 | 135 | AE001905 | maltooligosyltrehalose trehalohydrolase | 50.7 | *Deinococcus radiodurans* |
| 23/25 | 136 | AE004643 | probable glycosyl hydrolase | 38.9 | *Pseudomonas aeruginosa* |
| 23/25 | 137 | AE004643 | probable glycosyl hydrolase | 53.8 | *Pseudomonas aeruginosa* |
| 23/25 | 138 | AF002109 | putative isoamylase | 71.2 | *Arabidopsis thaliana* |
| 23/25 | 139 | AF002109 | putative isoamylase | 62 | *Arabidopsis thaliana* |
| 23/25 | 140 | AF002109 | putative isoamylase | 60.8 | *Arabidopsis thaliana* |
| 23/25 | 141 | AF002109 | putative isoamylase | 62 | *Arabidopsis thaliana* |
| 23/25 | 142 | AF002109 | putative isoamylase | 64.6 | *Arabidopsis thaliana* |
| 23/25 | 143 | AF002109 | putative isoamylase | 65.4 | *Arabidopsis thaliana* |
| 23/25 | 144 | AF002109 | putative isoamylase | 60.8 | *Arabidopsis thaliana* |
| 23/25 | 145 | AF002109 | putative isoamylase | 62 | *Arabidopsis thaliana* |
| 23/25 | 146 | AF142590 | isoamylase 1 | 66.7 | *Triticum aestivum* |
| 23/25 | 147 | AF142590 | isoamylase 1 | 53.2 | *Triticum aestivum* |
| 23/25 | 148 | AF201335 | maltooligosyl trehalose trehalohydrolase | 47.1 | *Sulfolobus shibatae batae* |
| 23/25 | 149 | AJ001206 | putative glycogen debranching enzyme | 82.7 | *Streptomyces coelicolor* |
| 23/25 | 150 | AJ133789 | cyclomaltodextrinase | 91 | *Alicyclobacillus acidocaldarius* |
| 23/25 | 151 | AJ133789 | cyclomaltodextrinase | 93.3 | *Alicyclobacillus acidocaldarius* |
| 23/25 | 152 | AJ133789 | cyclomaltodextrinase | 92.1 | *Alicyclobacillus acidocaldarius* |
| 23/25 | 153 | AJ291603 | glycogen debranching enzyme | 70.4 | *Rhizobium tropici* |
| 23/25 | 154 | AJ291603 | glycogen debranching enzyme | 44.4 | *Rhizobium tropici* |
| 23/25 | 155 | AJ291603 | glycogen debranching enzyme | 41.9 | *Rhizobium tropici* |
| 23/25 | 156 | AL157916 | putative glycosyl hydrolase | 60 | *Streptomyces coelicolor* |
| 23/25 | 157 | AL355752 | secreted alpha-amylase/dextrinase | 93.5 | *Streptomyces coelicolor* |

TABLE 2-continued

List of the 149 single sequences with the identities to their closest relations in GenBank (NCBI; Release 121.0); determined using the FASTA program on Feb. 2, 2001.

| Primer | SEQ ID No. as in Seq. listing | Closest database hit | Gene/product | Identity (%) | Organism |
|---|---|---|---|---|---|
| 23/25 | 158 | AL356932 | glycogen debranching enzyme | 79 | Streptomyces coelicolor |
| 23/25 | 159 | AL356932 | putative glycogen debranching enzyme | 95.1 | Streptomyces coelicolor |
| 23/25 | 160 | AL512975 | glycogen operon protein GlgX | 71.6 | Sulfolobus solfataricus |
| 23/25 | 161 | AL512975 | glycogen operon protein GlgX | 75.3 | Sulfolobus solfataricus |
| 23/25 | 162 | AL512975 | alpha-amylase | 52.9 | Sulfolobus solfataricus |
| 23/25 | 163 | AL512975 | glycogen operon protein GlgX | 68.8 | Sulfolobus solfataricus |
| 23/25 | 164 | AL512975 | alpha-amylase | 50 | Sulfolobus solfataricus |
| 23/25 | 165 | AL512975 | glycogen operon protein GlgX | 75.3 | Sulfolobus solfataricus |
| 23/25 | 166 | AL512975 | glycogen operon protein GlgX | 70.4 | Sulfolobus solfataricus |
| 23/25 | 167 | AL512975 | glycogen operon protein GlgX | 70.4 | Sulfolobus solfataricus |
| 23/25 | 168 | AL512975 | glycogen operon protein GlgX | 72.8 | Sulfolobus solfataricus |
| 23/25 | 169 | AL512975 | alpha-amylase | 62.7 | Sulfolobus solfataricus |
| 23/25 | 170 | AL512975 | alpha-amylase | 50 | Sulfolobus solfataricus |
| 23/25 | 171 | AL512975 | alpha-amylase | 50 | Sulfolobus solfataricus |
| 23/25 | 172 | AL512975 | glycogen operon protein GlgX | 69.1 | Sulfolobus solfataricus |
| 23/25 | 173 | AL512975 | glycogen operon protein GlgX | 75.3 | Sulfolobus solfataricus |
| 23/25 | 174 | AL512975 | glycogen operon protein GlgX | 56.8 | Sulfolobus solfataricus |
| 23/25 | 175 | AL589708 | glycogen debranching enzyme | 74.1 | Streptomyces coelicolor |
| 23/25 | 176 | AX063741 | putative ORF | 72 | Corynebacterium glutamicum |
| 23/25 | 177 | D63343 | maltooligosyl trehalose trehalohydrolase | 62.9 | Arthrobacter sp. |
| 23/25 | 178 | D63343 | maltooligosyl trehalose trehalohydrolase | 62.7 | Arthrobacter sp. |
| 23/25 | 179 | D78001 | maltooligosyl trehalose trehalohydrolase | 50.7 | Rhizobium sp |
| 23/25 | 180 | D83245 | glycogen debranching enzyme | 56.8 | Sulfolobus acidocaldarius |
| 23/25 | 181 | D83245 | glycogen debranching enzyme | 74.1 | Sulfolobus acidocaldarius |
| 23/25 | 182 | D83245 | glycogen debranching enzyme | 61.7 | Sulfolobus acidocaldarius |
| 23/25 | 183 | D83245 | glycogen debranching enzyme | 74.1 | Sulfolobus acidocaldarius |
| 23/25 | 184 | D83245 | glycogen debranching enzyme | 80.2 | Sulfolobus acidocaldarius |
| 23/25 | 185 | D83245 | glycogen debranching enzyme | 69.1 | Sulfolobus acidocaldarius |
| 23/25 | 186 | D83245 | glycogen debranching enzyme | 70.4 | Sulfolobus acidocaldarius |
| 23/25 | 187 | D83245 | glycogen debranching enzyme | 71.6 | Sulfolobus acidocaldarius |
| 23/25 | 188 | D90900 | glycogen operon protein GlgX | 64.2 | Synechocystis sp |
| 23/25 | 189 | D90908 | glycogen operon protein GlgX | 64.2 | Synechocystis sp |
| 23/25 | 190 | D90900 | glycogen operon protein GlgX | 55.6 | Synechocystis sp |
| 210-211/25 | 191 | D90908 | glycogen operon protein GlgX | 91.1 | Synechocystis sp |
| 210-211/25 | 192 | D90908 | glycogen operon protein GlgX | 88.6 | Synechocystis sp |

TABLE 2-continued

List of the 149 single sequences with the identities to their closest relations in GenBank (NCBI; Release 121.0); determined using the FASTA program on Feb. 2, 2001.

| Primer | SEQ ID No. as in Seq. listing | Closest database hit | Gene/product | Identity (%) | Organism |
|---|---|---|---|---|---|
| 210-211/25 | 193 | D90908 | glycogen operon protein GlgX | 56.8 | Synechocystis sp |
| 210-211/25 | 194 | U18997 | glgX | 69.6 | E. coli |
| 210-211/25 | 195 | Y08256 | glycogen operon protein GlgX | 71.6 | Sulfolobus solfataricus |
| 210-211/25 | 196 | Y08256 | glycogen operon protein GlgX | 72.8 | Sulfolobus solfataricus |
| 210-211/25 | 197 | Y08256 | glycogen operon protein GlgX | 58 | Sulfolobus solfataricus |
| 210-211/25 | 198 | Y08256 | alpha-amylase precursor | 51.5 | Sulfolobus solfataricus |
| 210-211/25 | 199 | Y08256 | alpha-amylase precursor | 59.7 | Sulfolobus solfataricus |
| 210-211/25 | 200 | Y08256 | alpha-amytase precursor | 52.9 | Sulfolobus solfataricus |
| 36/38 | 201 | Y08256 | alpha-amylase precursor | 44.8 | Sulfolobus solfataricus |
| 36/38 | 202 | Y08256 | glycogen operon protein GlgX | 70.4 | Sulfolobus solfataricus |
| 36/38 | 203 | Z74020 | glgX | 36.4 | Mycobacterium tuberculosis |
| 36/38 | 204 | Z74020 | glgX | 74.1 | Mycobacterium tuberculosis |
| 36/38 | 205 | Z74020 | glgX | 77.8 | Mycobacterium tuberculosis |
| 24/26 | 7 | A20154 | alpha-amylase | 42 | Bacillus amyloliquefaciens |
| 24/26 | 8 | AE006357 | alpha-amylase | 44.3 | Lactococcus lactis |
| 24/26 | 9 | AF153911 | beta-agarase | 60 | Pseudomonas sp. |
| 24/26 | 10 | AF153911 | beta-agarase | 58 | Pseudomonas sp. |
| 24/26 | 11 | AF153911 | beta-agarase | 59 | Pseudomonas sp. |
| 24/26 | 12 | AF153911 | beta-agarase | 60 | Pseudomonas sp. |
| 24/26 | 13 | AF153911 | beta-agarase | 58 | Pseudomonas sp. |
| 24/26 | 14 | AF208003 | alpha-amylase | 45.4 | Diabrotica virgifera |
| 24/26 | 15 | AL352956 | secreted alpha-amylase | 74 | Streptomyces coelicolor |
| 24/26 | 16 | AL352956 | secreted alpha-amylase | 89 | Streptomyces coelicolor |
| 24/26 | 17 | AL352956 | secreted alpha-amylase | 81 | Streptomyces coelicolor |
| 24/26 | 18 | AL352956 | secreted alpha-amylase | 88 | Streptomyces coelicolor |
| 24/26 | 19 | AL352956 | secreted alpha-amylase | 80 | Streptomyces coelicolor |
| 24/26 | 20 | AL352956 | secreted alpha-amylase | 80 | Streptomyces coelicolor |
| 24/26 | 21 | AL352956 | secreted alpha-amylase | 80 | Streptomyces coelicolor |
| 24/26 | 22 | AL352956 | secreted alpha-amylase | 82 | Streptomyces coelicolor |
| 24/26 | 23 | AX036894 | unnamed protein product | 54.2 | Bacillus stearothermophilus |
| 24/26 | 24 | J01542 | alpha-amylase protein precursor | 42.9 | Bacillus amyloliquefaciens |
| 24/26 | 25 | L01642 | alpha-amylase | 56.6 | E. coli |
| 24/26 | 26 | L01642 | alpha-amylase | 52.8 | E. coli |
| 24/26 | 27 | M13255 | amyS | 52.3 | B. stearothermophilus |
| 24/26 | 28 | M13255 | amyS | 57 | B. stearothermophilus |
| 24/26 | 29 | M13255 | amyS | 50.5 | B. stearothermophilus |
| 24/26 | 30 | M13255 | amyS | 52.3 | B. stearothermophilus |
| 24/26 | 31 | M13255 | amyS | 50.5 | B. stearothermophilus |
| 24/26 | 32 | M18244 | alpha-amylase | 55.4 | Streptomyces limosus |
| 24/26 | 33 | M25263 | alpha-amylase | 65 | Streptomyces venezuelae |

TABLE 2-continued

List of the 149 single sequences with the identities to their closest relations in GenBank (NCBI; Release 121.0); determined using the FASTA program on Feb. 2, 2001.

| Primer | SEQ ID No. as in Seq. listing | Closest database hit | Gene/product | Identity (%) | Organism |
|---|---|---|---|---|---|
| 24/26 | 34 | M25263 | alpha-amylase | 91 | Streptomyces venezuelae |
| 24/26 | 35 | U51129 | amylase | 85 | Streptomyces albus |
| 24/26 | 36 | U51129 | amylase | 85 | Streptomyces albus |
| 24/26 | 37 | U75445 | alpha-amylase | 56.1 | Bacillus sp. MK 716 |
| 24/26 | 38 | U75445 | alpha-amylase | 54.2 | Bacillus sp. MK 717 |
| 24/26 | 39 | U75445 | alpha-amylase | 55.9 | Bacillus sp. MK 718 |
| 24/26 | 40 | X15752 | cyclomaltodextrin glucanotransferase | 33.9 | Bacillus licheniformis |
| 24/26 | 41 | X57568 | alpha-amylase | 64 | Streptomyces griseus |
| 24/26 | 42 | X57568 | alpha-amylase | 56.4 | Streptomyces griseus |
| 24/26 | 43 | X57568 | alpha-amylase | 75 | Streptomyces griseus |
| 24/26 | 44 | X57568 | alpha-amylase | 45.2 | Streptomyces griseus |
| 24/26 | 45 | X57568 | alpha-amylase | 47.1 | Streptomyces griseus |
| 24/26 | 46 | X59279 | putative alpha-glucanotransferase/ hydrolase | 35.1 | Anabaena variabilis |
| 24/26 | 47 | X70255 | alpha-amylase | 43.1 | Streptomyces lividans |
| 24/26 | 48 | X70255 | alpha-amylase | 44 | Streptomyces lividans |
| 24/26 | 49 | Y13332 | alpha-amylase | 58.4 | Streptomyces sp. |
| 24/26 | 50 | Y13332 | alpha-amylase | 94 | Streptomyces sp. |
| 24/26 | 51 | Y13332 | alpha-amylase | 89 | Streptomyces sp. |
| 24/26 | 52 | Y13332 | alpha-amylase | 93 | Streptomyces sp. |
| 24/26 | 53 | Y13332 | alpha-amylase | 86 | Streptomyces sp. |
| 24/26 | 54 | Y13332 | alpha-amylase | 91 | Streptomyces sp. |
| 24/26 | 55 | Y13332 | alpha-amylase | 92 | Streptomyces sp. |
| 24/26 | 56 | Y13332 | alpha-amylase | 92 | Streptomyces sp. |

TABLE 3

Temperature profile of the α-amylase from HA11

| Temperature [° C.] | Activity relative to that at 45° C. [%] |
|---|---|
| 45 | 100 |
| 46.4 | 123 |
| 50.4 | 146 |
| 55.8 | 121 |
| 61 | 38 |
| 64.7 | 28 |

TABLE 4

Ha13 amylase
The temperature profile (in analogy to HA11) and the temperature stability after preincubation for 15 min was determined. The remaining activity at 50° C. in 100 mM Tris HCl pH 8.6 was then determined.
Substrate conversion in the temperature gradients from 50° C. to 69.7° C. in the DNSS assay (Tris-HCl pH 8.6).

| Temperature | Percent activity remaining |
|---|---|
| 50° C. | 100 |
| 51.4° C. | 110 |
| 55.5° C. | 139 |
| 60.8° C. | 118 |
| 66° C. | 98 |
| 69.7° C. | 41 |

TABLE 5

Temperature stability of the amylase domain from HA13
Substrate conversion in the DNSA assay after preincubation
in the temperature gradient from 50° C. to 69.7° C. for
15 min, then substrate conversion at 50° C. in Tris-HCl pH 8.6.

| Temperature | Percent activity remaining |
|---|---|
| 50° C. | 100 |
| 51.4° C. | 97 |
| 55.5° C. | 82 |
| 60.8° C. | 38 |
| 66° C. | 2 |
| 69.7° C. | 2 |

TABLE 6 pH stability of the amylases HA11 and HA13
Substrate conversion in the respective buffer system in
the DNSA assay at 50° C. for 15 min.

| | | Percent activity remaining | |
|---|---|---|---|
| pH | Buffer | HA 11 | HA 13 |
| 4.0 | Glycine-HCl | 60 | 90 |
| 4.5 | Glycine-HCl | 59 | 96 |
| 5.0 | Na-Acetate | 110 | 107 |
| 6.5 | Na-Acetate | 104 | 106 |
| 6.5 | Tris-Maleate | 100 | 100 |
| 8.6 | Tris-HCl | 64 | 99 |
| 10 | Glycine-NaOH | 41 | 83 |
| 12 | Glycine-NaOH | 6 | 74 |

TABLE 7

Effect of surfactants on the activity of amylase HA 11
Substrate conversion in the DNSA assay with 100 mM
with Tris-HCl pH 8.6 at 50° C. for 15 min.

| Surfactants added | Percent activity remaining |
|---|---|
| +0.05% SDS | 100 |
| +0.10% SDS | 86 |
| +0.50% SDS | 66 |
| +1.00% SDS | 49 |

TABLE 8

Effect of surfactants on the activity of amylase HA 13
Substrate conversion in the DNSA assay with 100 mM
with Tris-HCl pH 8.6 at 50° C. for 15 min.

| Surfactants added | Percent activity remaining |
|---|---|
| without SDS | 100 |
| +0.05% SDS | 90 |
| +0.10% SDS | 74 |
| +0.50% SDS | 71 |
| +1.00% SDS | 67 |

TABLE 9

Effect of bleaches on HA11 amylase
Substrate conversion in the DNSA assay with 100 mM
glycine-NaOH pH 9.5.
Preincubation at room temperature under appropriate conditions
is followed by further incubation at 50° C. for 15 min.

| Bleach | Percent activity remaining |
|---|---|
| without $H_2O_2$ | 100 |
| +0.05% $H_2O_2$ | 99 |
| +0.10% $H_2O_2$ | 87 |
| +0.20% $H_2O_2$ | 4 |
| +0.35% $H_2O_2$ | 1 |
| +0.70% $H_2O_2$ | 1 |

TABLE 10

Effect of bleaches on HA13 amylase
Substrate conversion in the DNSA assay with 100 mM
glycine-NaOH pH 9.5.
Preincubation at room temperature under appropriate conditions
is followed by further incubation at 50° C. for 15 min.

| Bleach | Percent activity remaining |
|---|---|
| without $H_2O_2$ | 100 |
| +0.05% $H_2O_2$ | 81 |
| +0.10% $H_2O_2$ | 85 |
| +0.20% $H_2O_2$ | 80 |
| +0.35% $H_2O_2$ | 68 |
| +0.70% $H_2O_2$ | 60 |

TABLE 11

Calcium dependence of the HA11 amylase
Substrate conversion in the DNSA assay with 100 mM
Tris-HCl pH 8.6 at 50° C. for 15 min.

| Addition | Percent activity remaining |
|---|---|
| 2 mM CaCl2 | 100 |
| 1 mM EDTA | 44 |

TABLE 12

Calcium dependence of the HA13 amylase domain
Substrate conversion in the DNSA assay with 100 mM
Tris-HCl pH 8.6 at 50° C. for 15 min.

| Addition | Percent activity remaining |
|---|---|
| 2 mM CaCl2 | 100 |
| 1 mM EDTA | 104 |

TABLE 13

Investigation of the washing performance

| | with bleach | | without bleach | |
|---|---|---|---|---|
| | CFT | PCS 26 | CFT | PCS 26 |
| without enzyme | 3.8 | 0.4 | 3.7 | 0.2 |
| HA11 (S213) | 7.7 | 3 | 9.4 | 4.5 |
| HA13 (S213Pb) | 5.7 | 2 | 5.9 | 1.8 |

TABLE 13-continued

| | Investigation of the washing performance | | | |
|---|---|---|---|---|
| | with bleach | | without bleach | |
| | CFT PCS 26 | CFT PCS 26 | CFT PCS 26 | CFT PCS 26 |
| BAN | 4.2 | 0.7 | 7.3 | 2.9 |
| Termamyl | 5.6 | 1.7 | 8.1 | 3.5 |

What is claimed:

1. An isolated protein comprising a polypeptide having at least 95% homology with SEQ ID NO:3, wherein the polypeptide has α-amylase activity.

2. An isolated protein comprising a polypeptide having at least 95% homology with an amino acid sequence encoded by the nucleotide sequence of SEQ ID NO:6, wherein the polypeptide has α-amylase.

3. A washing or cleaning composition comprising:
an isolated protein comprising a polypeptide having at least 95% homology with SEQ ID NO:3, wherein the polypeptide has α-amylase activity.

4. The isolated protein of claim 1, wherein the polypeptide has the amino acid sequence of SEQ ID NO:3.

5. The isolated protein of claim 2, wherein the polypeptide has the amino acid sequence encoded by the nucleotide sequence of SEQ ID NO:6.

6. The washing or cleaning composition of claim 3 comprising an isolated protein comprising a polypeptide having the amino acid sequence of SEQ ID NO:3.

* * * * *

SEQUENCE LISTING

<160> NUMBER OF SEQ ID NOS: 320

<210> SEQ ID NO 1
<211> LENGTH: 700
<212> TYPE: PRT
<213> ORGANISM: glycosyl hydrolases

<400> SEQUENCE: 1

```
Met Thr Gly Leu Pro Asp Ser Gly Thr Leu Arg Arg Pro Gly Pro Arg
1               5                   10                  15

Lys Arg Leu Arg Thr Leu Ile Ala Val Thr Ala Ala Val Leu Ala
            20                  25                  30

Gly Leu Ala Ala Ile Gly Pro Gly Ala Pro Ala Gly Pro Ala Glu Ala
        35                  40                  45

Ala Ala Pro Gly Pro Lys Asp Ala Thr Ala Val Leu Phe Ser Tyr Thr
    50                  55                  60

Trp Asn Ala Ile Ala Arg Glu Cys Thr Glu Asn Leu Gly Pro Ala Gly
65                  70                  75                  80

Tyr Gly Tyr Val Gln Thr Ser Pro Pro Gln Glu His Val Gln Gly Pro
                85                  90                  95

Gln Trp Trp Ile His Tyr Gln Pro Val Ser Tyr Arg Val Glu Ser Arg
            100                 105                 110

Leu Gly Thr Arg Ala Glu Phe Lys Ala Met Val Asp Thr Cys His Ala
        115                 120                 125

Ala Gly Val Lys Val Ile Ala Asp Ala Val Ile Asn His Met Ser Gly
    130                 135                 140

Tyr Ser Ala Gly Gly Val Gly Trp Ala Gly Ser Ser Phe Gln His Tyr
145                 150                 155                 160

Ser Tyr Pro Gly Ile Tyr Gln Ser Gln Asp Phe His Ser Cys Arg Arg
                165                 170                 175

Asp Ile Ala Asn Tyr Gln Asp Arg Trp Glu Val Gln Glu Cys Asn Leu
            180                 185                 190

Val Asn Leu Ala Asp Leu Asn Thr Gly Ser Ala Tyr Val Gln Gly Arg
        195                 200                 205

Ile Ala Ala Tyr Leu Asn Asp Leu Val Ser Leu Gly Val Asp Gly Phe
    210                 215                 220

Arg Ile Asp Ala Val Lys His Ile Ser Ala Ala Asp Met Asn Gly Ile
225                 230                 235                 240

Leu Ser Arg Val Asn Asp Arg Ala Arg Leu Tyr Leu Val Gln Glu Val
                245                 250                 255
```

-continued

```
Ile Arg Ala Asn Glu Pro Val Gln Pro Glu Glu Tyr Leu Gly Leu Gly
            260                 265                 270

Asp Ile His Glu Phe Ala Tyr Ala Arg Lys Leu Lys Glu Ala Phe Gly
            275                 280                 285

Gly Arg Thr Leu Asn Trp Leu Ile Ser Gly Ala Gly Ile Gly Pro Ser
            290                 295                 300

Trp Ala Gly Phe Leu Gln Asn Ala Asp Ala Ala Val Phe Val Asp Asn
305                 310                 315                 320

His Asp Thr Glu Arg Asn Gly Glu Thr Leu Ser Tyr Arg Asp Gly Ala
                325                 330                 335

Ala Tyr Asp Leu Ala Gln Val Phe Thr Leu Ala Trp Asn Tyr Gly Ser
            340                 345                 350

Pro Ser Ile His Ser Gly Tyr Gln Phe Ser Asn Lys Asp Ala Gly Pro
            355                 360                 365

Ala Leu Ala Gly Asn Gly Arg Val Val Asp Pro Val Cys Gly Gln Asn
        370                 375                 380

Gly Trp Thr Cys Lys His Ala Gln Thr Asn Ile Glu Asn Met Val Gly
385                 390                 395                 400

Phe Arg Thr Ala Thr Tyr Gly Thr Ala Ile Thr Asn Lys Trp Asp Asn
                405                 410                 415

Gly Ser Ser Ala Ile Ala Phe Gly Arg Gly Asp Lys Gly Phe Val Ala
            420                 425                 430

Ile Asn Arg Gly Thr Ala Ala Val Asp Arg Thr Trp Gln Thr Ser Leu
        435                 440                 445

Pro Ala Gly Arg Tyr Cys Asn Val Ile Val Gly Leu Pro Thr Ala Ser
    450                 455                 460

Gly Cys Ser Ala Gly Gly Val Ile Thr Val Asp Ser Ser Gly Arg Phe
465                 470                 475                 480

Ala Ala Ser Val Ala Ala Asp Thr Ala Leu Ala Leu His Val Gly Ala
                485                 490                 495

Lys Ala Gly Gly Thr Gly Thr Thr Pro Pro Thr Gly Ser Thr Met
            500                 505                 510

Thr Val Tyr Phe Ala Thr Thr Lys Gly Trp Thr Asn His Tyr Val His
            515                 520                 525

His Arg Val Gly Ser Gly Ala Trp Thr Ala Leu Pro Gly Ala Ala Met
        530                 535                 540

Ala Ala Ala Cys Thr Gly Trp Val Ser Arg Thr Ile Asp Leu Gly Ser
545                 550                 555                 560

Ala Thr Gly Ile Thr Ala Ala Phe Thr Asn Gly Ala Gly Ala Trp Asp
                565                 570                 575

Asn Asn Gly Gly Arg Asp Tyr Ala Leu Thr Gly Ser Val Ala Ala Val
            580                 585                 590

Lys Asp Gly Val Val Thr Ala Thr Asn Pro Cys Ala Ala Gln Pro Thr
        595                 600                 605

Ser Thr Thr Val Tyr Tyr Ala Thr Gly Trp Ser Thr Ala Asn Ile His
    610                 615                 620

Tyr Arg Val Gly Ser Gly Ala Trp Thr Ala Val Pro Gly Val Ala Met
625                 630                 635                 640

Ala Asn Ala Cys Ala Gly Trp Lys Ser Lys Thr Ile Glu Leu Gly Ala
                645                 650                 655

Ala Ser Gly Ile Thr Ala Ala Phe Asn Asn Gly Ala Gly Thr Trp Asp
            660                 665                 670

Asn Asn Gly Gly Lys Asp Tyr Ala Ile Gly Ala Gly Ala Met Lys Val
```

```
              675                 680                 685
Gln Asn Gly Thr Val Thr Ala Gly Asn Pro Cys Ser
    690                 695                 700

<210> SEQ ID NO 2
<211> LENGTH: 2013
<212> TYPE: PRT
<213> ORGANISM: Glycosyl hydrolases

<400> SEQUENCE: 2

Met Thr His Arg Ala Arg Ala Arg Ser Trp Leu Ala Leu Gly Val Thr
1               5                   10                  15

Gly Ala Val Ala Ala Ser Val Leu Ala Val Val Pro Ile Gly Ala Ala
            20                  25                  30

Ala Glu Glu Gly Asp Thr Phe Ala Leu Val Gly Ser Leu Gln Ser Glu
        35                  40                  45

Leu Gly Cys Ser Glu Asp Trp Gln Pro Ser Cys Glu Ala Thr Glu Leu
    50                  55                  60

Leu Pro Thr Asp Thr Ala Gly Leu Tyr Ala Ala Glu Phe Thr Val Pro
65                  70                  75                  80

Ala Gly Ser Tyr Glu Tyr Lys Val Ala Ala Asn Asp Ser Trp Asp Ala
                85                  90                  95

Ser Trp Gly Leu Asp Gly Gly Asp Asn Ile Pro Leu Thr Val Gly
            100                 105                 110

Gly Asp Thr Asp Val Arg Val Phe Asp Asp Thr Gln Lys Arg Val
        115                 120                 125

Gly Leu Glu Leu Leu Ser Thr Arg Gly Ala Tyr Asp Glu Gln Ala Asp
    130                 135                 140

Ala Ala Leu Ala Leu Pro Pro Val Arg Gln Pro Gly Ser Ala Glu Asn
145                 150                 155                 160

Phe Tyr Phe Val Met Thr Asp Arg Phe Ala Asn Gly Asp Glu Ser Asn
                165                 170                 175

Asp Thr Ala Gly Ile Glu Gly Asp Arg Leu Ala His Gly Phe Asp Pro
            180                 185                 190

Thr Asp Lys Gly Phe Tyr His Gly Gly Asp Ile Gln Gly Ile Arg Asp
        195                 200                 205

His Leu Asp Tyr Ile Glu Gly Leu Gly Thr Thr Ala Ile Trp Phe Thr
    210                 215                 220

Pro Ser Phe Lys Asn Lys Pro Val Gln Gly Glu Gly Ala Asn Ala Ser
225                 230                 235                 240

Ala Gly Tyr His Gly Tyr Trp Ile Thr Asp Phe Thr Gln Ile Asp Pro
                245                 250                 255

His Leu Gly Thr Asn Ala Glu Leu Glu Ala Leu Ile Asp Glu Ala His
            260                 265                 270

Glu Arg Gly Ile Lys Val Tyr Phe Asp Ile Ile Thr Asn His Thr Ala
        275                 280                 285

Asp Val Ile Ser Tyr Glu Glu Gly Gln Tyr Ser Tyr Ile Asp Lys Ala
    290                 295                 300

Thr Ser Pro Tyr Arg Asp Ala Asp Gly Asn Val Phe Asp Pro Ser Thr
305                 310                 315                 320

Ile Ala Gly Ser Ala Asp Phe Pro Ala Leu Asp Pro Ala Thr Ser Phe
                325                 330                 335

Pro Tyr Thr Pro Thr Val Ala Pro Glu Glu Ala Asp Val Lys Val Pro
            340                 345                 350
```

```
Ala Trp Leu Asn Asp Pro Thr Leu Tyr His Asn Arg Gly Asp Ser Thr
    355                 360                 365

Trp Ser Gly Glu Ser Val Thr Phe Gly Asp Phe Val Gly Leu Asp Asp
    370                 375                 380

Leu Met Thr Glu His Pro Thr Val Val Asp Gly Phe Ile Glu Val Tyr
385                 390                 395                 400

Gln Asp Trp Val Asp Leu Gly Ile Asp Gly Phe Arg Ile Asp Thr Ala
                405                 410                 415

Lys His Val Asn Phe Glu Phe Trp Glu Glu Trp Ser Thr Glu Val Leu
                420                 425                 430

Asp Tyr Ala His Ala Gln Gly Lys Pro Asp Phe Phe Met Phe Gly Glu
            435                 440                 445

Val Tyr Asp Ala Asp Pro Val Lys Leu Ser Pro Tyr Val Arg Lys Thr
    450                 455                 460

Asp Met Asn Ser Val Leu Asp Phe Thr Phe Gln Ser Gln Ala Val Ser
465                 470                 475                 480

Phe Ala Ala Gly Asn Ser Ala Lys Asn Leu Gln Ser Leu Phe Ala Gly
                485                 490                 495

Asp Asp Tyr Tyr Thr Thr Pro Asp Ser Ser Ala Thr Ala Leu Pro Thr
            500                 505                 510

Phe Leu Gly Asn His Asp Met Gly Arg Ile Gly Tyr Phe Leu Ala Asn
    515                 520                 525

Ser Gly Ala Thr Ala Val Gln Arg Asn Glu Leu Ala His Glu Leu Met
530                 535                 540

Tyr Leu Thr Arg Gly Gln Pro Val Val Tyr Tyr Gly Asp Glu Gln Gly
545                 550                 555                 560

Phe Ala Gly Thr Gly Gly Asp Lys Asp Ala Arg Gln Thr Leu Phe Ala
                565                 570                 575

Ser Gln Val Asp Glu Tyr Val Asn Gln Pro Leu Val Thr Gly Glu Asn
            580                 585                 590

Ala Gly Ser Val Asp Arg Tyr Gly Thr Asp Ala Pro Leu Tyr Glu His
    595                 600                 605

Ile Ala Gly Leu Ala Glu Leu Arg Lys Ala His Pro Ala Leu Glu Gln
    610                 615                 620

Gly Ala Gln Ile Glu Arg Phe Val Ala Asp Gly Ala Ser Val Tyr Ala
625                 630                 635                 640

Phe Ser Arg Val Asp Arg Asp Glu Lys Val Glu Tyr Leu Val Ala Val
                645                 650                 655

Asn Asn Ala Asn Glu Ala Lys Ala Val Glu Val Ser Thr Leu Thr Ala
            660                 665                 670

Asp Gly Ala Phe Glu Val Leu Tyr Gly Asp Gly Gln Ala Leu Thr Ala
    675                 680                 685

Asn Ala Asp Gly Val Ala Ser Val Thr Ala Pro Ala Leu Gly Ala Val
    690                 695                 700

Val Trp Lys Ala Asp Arg Glu Val Thr Ala Pro Glu Ala Ser Ala
705                 710                 715                 720

Ile Ala Val Asp Val Pro Val Ala Gly Ala Gly Val Thr Gly Ile Ala
                725                 730                 735

Pro Val Ser Ala Asp Val Ala Asp Ala Thr Trp Gln Glu Thr Ser Phe
            740                 745                 750

Ala Trp Arg Val Ala Gly Ser Asp Glu Trp Thr Pro Leu Gly Thr Ala
    755                 760                 765

Glu Asp Thr Thr Pro Arg Val Tyr His Asp Thr Ala Gly Leu Ala Lys
```

-continued

```
            770              775              780
Gly Thr Leu Val Glu Tyr Arg Ala Val Ser Thr Asp Ala Ala Gly Asn
785              790                   795                   800

Arg Ala Ala Ala Ser Thr Tyr Ala Ser Val Gly Asn Ala Val Asn Leu
                805              810                  815

Ala Val Val Glu Glu Pro Glu Thr Asp Ile Glu Leu Val Thr Val Pro
            820              825                  830

Gly Ser His Asn Ser Glu Met Gly Cys Pro Gly Asp Trp Gln Pro Gly
                835              840                  845

Cys Glu Ala Ala Lys Leu Thr Lys Arg Ala Asp Gly Ile Tyr Ala Gly
850              855                  860

Thr Phe Gln Ile Pro Ala Gly Thr Tyr Glu Tyr Lys Val Ala Ile Asn
865              870                  875                  880

Gly Ser Trp Ala Leu Asn Tyr Gly Ala Asn Gly Val Gln Asp Gly Ala
                885              890                  895

Asn Ala Thr Tyr Thr Thr Ser Gly Gly Ala Val Thr Phe Tyr Trp Asp
                900              905                  910

Pro Arg Ser Lys Val Phe Ser Thr Ala Glu Gly Pro Ile Val Thr
                915              920                  925

Leu Pro Gly Ser Met Gln Ser Glu Leu Gly Cys Pro Gly Asp Trp Gln
930              935                  940

Pro Asp Cys Met Val Thr Phe Ala Gln Asp Gly Asp Lys Asp Gly Val
945              950                  955                  960

Tyr Glu Phe Ser Thr Asn Gly Leu Pro Ala Gly Ser Tyr Glu Leu Lys
                965              970                  975

Val Ala His Gly Leu Ser Trp Asp Glu Asn Tyr Gly Val Asp Gly Val
                980              985                  990

Arg Asn Gly Gly Asn Ile Ser Phe  Val Val Gly Lys Ala  Gly Glu Phe
                995              1000             1005

Val Thr  Phe Arg Tyr Thr Leu  Glu Thr His Val Leu  Glu Val Val
    1010             1015                 1020

Val Ala Asp Pro Pro Leu Ala  Gly Thr Gly Gln Gln  Arg Ala Tyr
    1025             1030                 1035

Trp Leu  Asp Ala Glu Thr Leu  Ala Trp Pro Ala Ser  Leu Leu Gly
    1040             1045                 1050

Gly Ala  Asn Ala Ala Asp Arg  Ala Tyr Thr Leu Glu  Phe Ala Ala
    1055             1060                 1065

Asp Gly  Gly Leu Gly Thr Ala  Asp Gly Ala Val Thr  Gly Ala Asp
    1070             1075                 1080

Arg Thr  Val Glu Leu Ala His  Glu Pro Ala Gly Ile  Gly Ala Glu
    1085             1090                 1095

Leu Thr  Ala Arg Phe Pro His  Leu Ala Ser Tyr Val  Ala Leu Arg
    1100             1105                 1110

Pro Val  Gly Leu Asp Arg Ala  Ala Ile Ala Glu Leu  Val Thr Gly
    1115             1120                 1125

Glu Leu  Gln Val Ala Gln Arg  Ala Gly Asp Glu Leu  Thr Ala Met
    1130             1135                 1140

Thr Gly  Val Gln Leu Pro Gly  Val Leu Asp Asp Leu  Tyr Ala Gln
    1145             1150                 1155

Gly Val  Ala Ser Ala Ser Leu  Gly Ala Thr Val Asp  Gly Asp Ala
    1160             1165                 1170

Ala Ser  Leu Ser Val Trp Ala  Pro Thr Ala Lys Ser  Val Ser Ala
    1175             1180                 1185
```

-continued

Gln Val Trp Ala Ala Gly Ala Thr Gly Asp Pro Glu Val Leu Pro
    1190                1195                1200

Ala Glu Phe Asp Ala Glu Ser Gly Ala Trp Ser Val Asp Glu Gly
    1205                1210                1215

Ile Glu Ala Gly Asp Glu Tyr Arg Trp Leu Val Glu Val Tyr Ala
    1220                1225                1230

Pro Thr Thr Gly Lys Val Glu Arg Asn Ser Val Thr Asp Pro Tyr
    1235                1240                1245

Ser Val Ala Leu Thr Val Asn Ser Ala Arg Thr Val Val Val Asp
    1250                1255                1260

Leu Asp Asp Pro Ala Leu Ala Pro Glu Leu Trp Ala Glu Thr Pro
    1265                1270                1275

Ala Pro Val Val Glu Arg Gln Val Asp Arg Ala Ile Tyr Glu Leu
    1280                1285                1290

His Val Arg Asp Phe Ser Ile Thr Asp Glu Thr Val Pro Glu Ala
    1295                1300                1305

Glu Arg Gly Thr Tyr Arg Ala Phe Thr Arg Asn Ser Ala Gly Ser
    1310                1315                1320

Ala Gln Leu Arg Glu Leu Ala Ala Gly Ile Asn Thr Val His
    1325                1330                1335

Leu Leu Pro Thr Phe Asp Ile Ala Thr Ile Glu Glu Arg Arg Asp
    1340                1345                1350

Gln Gln Ala Thr Pro Asp Cys Asp Leu Glu Ser Tyr Gly Pro Ala
    1355                1360                1365

Ser Glu Glu Gln Gln Ala Cys Ile Glu Ala Ile Arg Asp Leu Asp
    1370                1375                1380

Gly Phe Asn Trp Gly Tyr Asp Pro Tyr His Phe Gln Ala Pro Glu
    1385                1390                1395

Gly Ser Tyr Ala Val Asp Pro Asp Gly Gly Ala Arg Val Ala Glu
    1400                1405                1410

Phe Arg Glu Met Val Gly Ala Leu His Ala Ala Gly Met Gln Val
    1415                1420                1425

Val Leu Asp Glu Val Tyr Asn His Thr Ala Glu Ser Gly Gln Gly
    1430                1435                1440

Gln Lys Ser Val Leu Asp Lys Val Val Pro Gly Tyr Tyr His Arg
    1445                1450                1455

Leu Asn Ala Thr Gly Gly Val Glu Thr Ser Thr Cys Cys Gln Asn
    1460                1465                1470

Val Ala Thr Glu His Ala Val Ala Glu Lys Leu Met Val Asp Ser
    1475                1480                1485

Thr Val Leu Trp Val Lys Glu Tyr Lys Val Asp Gly Phe Arg Phe
    1490                1495                1500

Asp Leu Met Gly His His Ser Lys Ala Asn Leu Leu Ala Val Arg
    1505                1510                1515

Ala Ala Leu Asp Glu Leu Thr Leu Ala Glu Asp Gly Val Asp Gly
    1520                1525                1530

Ser Lys Val Phe Leu Tyr Gly Glu Gly Trp Asn Phe Gly Glu Val
    1535                1540                1545

Ala Asn Asn Ala Arg Phe Glu Gln Ala Ser Gln Gly Gln Leu Gly
    1550                1555                1560

Gly Thr Gly Ile Ala Thr Phe Asn Asp Arg Leu Arg Asp Gly Val
    1565                1570                1575

-continued

His Gly Gly Ser Pro Val Ala Gly Asp Ser Lys Tyr Glu Gln Gly
1580            1585                1590

Phe Gly Thr Gly Leu Ala Gly Glu Pro Asn Gly Leu Pro Gln Arg
1595            1600                1605

Asp Gly Ile Arg Asn Leu Gly Gln Gln Thr Asp Leu Val Lys Ile
1610            1615                1620

Gly Leu Ala Gly Asn Leu Arg Asp Phe Arg Phe Thr Gly Tyr Asp
1625            1630                1635

Gly Val Leu Lys Ser Gly Ala Glu Val Asp Tyr Asn Gly Ser Pro
1640            1645                1650

Ala Gly Tyr Ala Asp His Pro Glu Glu Val Ile Asn Tyr Val Asp
1655            1660                1665

Ala His Asp Asn Glu Thr Leu Phe Asp Leu Gly Val Leu Lys Leu
1670            1675                1680

Pro Gln Glu Thr Ser Met Ala Asp Arg Ile Arg Met Asn Thr Leu
1685            1690                1695

Ser Leu Ala Thr Val Thr Phe Ser Gln Ser Pro Ser Phe Trp His
1700            1705                1710

Ala Gly Thr Glu Leu Leu Arg Ser Lys Ser Leu Asp Arg Asn Ser
1715            1720                1725

Tyr Asn Ser Gly Asp Trp Phe Asn Arg Ile Asp Trp Thr Gly Gln
1730            1735                1740

Glu Ser Thr Phe Gly Ser Gly Leu Pro Met Lys Ser Asp Asn Glu
1745            1750                1755

Asp His Trp Pro Thr Met Ala Thr Leu Leu Ala Asp Pro Ala Leu
1760            1765                1770

Lys Pro Ala Pro Ala Asp Ile Ala Ala Glu Ala Ala Ala Leu
1775            1780                1785

Asp Leu Leu Arg Val Arg Asp Ser Val Asp Leu Leu Lys Leu Gly
1790            1795                1800

Ser Ala Glu Leu Ile Thr Gln Lys Val Ser Phe Pro Asn Ser Gly
1805            1810                1815

Ala Asp Ala Thr Asp Gly Leu Ile Val Met Leu Ile Asp Asp Leu
1820            1825                1830

Val Gly Asp Asp Val Asp Pro Glu Leu Glu Gly Ala Leu Val Val
1835            1840                1845

Phe Asn Ala Ser Ala Glu Pro Ile Thr Glu Ala Val Asp Gly Leu
1850            1855                1860

Ala Gly Arg Glu Phe Ala Leu Ala Pro Ala Leu Ala Asn Gly Thr
1865            1870                1875

Asp Ala Val Val Lys Gln Thr Ala Trp Glu Ala Ala Thr Gly Thr
1880            1885                1890

Leu Thr Ile Pro Ala Arg Thr Ala Ala Val Phe Val Asp Asp Gln
1895            1900                1905

Ala Lys Pro Gly Gly Gly Lys Pro Asp Lys Pro Gly Lys Pro Glu
1910            1915                1920

Lys Pro Gly Lys Pro Asp Lys Pro Gly Lys Pro Asp Lys Pro Glu
1925            1930                1935

Lys Pro Gly Lys Pro Glu Lys Pro Gly Lys Pro Glu Lys Pro Gly
1940            1945                1950

Lys Pro Glu Gln Pro Gly Lys Pro Val Val Arg Leu Asp Ala Ala
1955            1960                1965

Ser Val Gln Thr Gly Ser Thr Leu Ala Val Ser Gly Lys Gly Phe

```
                    1970                1975                1980
Ala  Lys  Gly  Glu  Leu  Val  Gln  Val  Trp  Leu  Glu  Ser  Thr  Pro  Thr
     1985                1990                1995

Leu  Met  Glu  Ala  Gln  Pro  Ala  Ser  Ala  Asp  Gly  Thr  Val  Glu  Phe
     2000                2005                2010

<210> SEQ ID NO 3
<211> LENGTH: 952
<212> TYPE: PRT
<213> ORGANISM: Glycosyl hydrolases

<400> SEQUENCE: 3

Met  Thr  His  Arg  Ala  Arg  Ala  Arg  Ser  Trp  Leu  Ala  Leu  Gly  Val  Thr
1                  5                   10                  15

Gly  Ala  Val  Ala  Ala  Ser  Val  Leu  Ala  Val  Val  Pro  Ile  Gly  Ala  Ala
                20                  25                  30

Ala  Glu  Glu  Gly  Asp  Thr  Phe  Ala  Leu  Val  Gly  Ser  Leu  Gln  Ser  Glu
            35                  40                  45

Leu  Gly  Cys  Ser  Glu  Asp  Trp  Gln  Pro  Ser  Cys  Glu  Ala  Thr  Glu  Leu
     50                  55                  60

Leu  Pro  Thr  Asp  Thr  Ala  Gly  Leu  Tyr  Ala  Ala  Glu  Phe  Thr  Val  Pro
65                  70                  75                  80

Ala  Gly  Ser  Tyr  Glu  Tyr  Lys  Val  Ala  Ala  Asn  Asp  Ser  Trp  Asp  Ala
                85                  90                  95

Ser  Trp  Gly  Leu  Asp  Gly  Gly  Asp  Asn  Ile  Pro  Leu  Thr  Val  Gly
            100                 105                 110

Gly  Asp  Thr  Asp  Val  Arg  Val  Val  Phe  Asp  Asp  Thr  Gln  Lys  Arg  Val
            115                 120                 125

Gly  Leu  Glu  Leu  Leu  Ser  Thr  Arg  Gly  Ala  Tyr  Asp  Glu  Gln  Ala  Asp
     130                 135                 140

Ala  Ala  Leu  Ala  Leu  Pro  Pro  Val  Arg  Gln  Pro  Gly  Ser  Ala  Glu  Asn
145                 150                 155                 160

Phe  Tyr  Phe  Val  Met  Thr  Asp  Arg  Phe  Ala  Asn  Gly  Asp  Glu  Ser  Asn
                165                 170                 175

Asp  Thr  Ala  Gly  Ile  Glu  Gly  Asp  Arg  Leu  Ala  His  Gly  Phe  Asp  Pro
            180                 185                 190

Thr  Asp  Lys  Gly  Phe  Tyr  His  Gly  Gly  Asp  Ile  Gln  Gly  Ile  Arg  Asp
            195                 200                 205

His  Leu  Asp  Tyr  Ile  Glu  Gly  Leu  Gly  Thr  Thr  Ala  Ile  Trp  Phe  Thr
     210                 215                 220

Pro  Ser  Phe  Lys  Asn  Lys  Pro  Val  Gln  Gly  Glu  Gly  Ala  Asn  Ala  Ser
225                 230                 235                 240

Ala  Gly  Tyr  His  Gly  Tyr  Trp  Ile  Thr  Asp  Phe  Thr  Gln  Ile  Asp  Pro
                245                 250                 255

His  Leu  Gly  Thr  Asn  Ala  Glu  Leu  Glu  Ala  Leu  Ile  Asp  Glu  Ala  His
            260                 265                 270

Glu  Arg  Gly  Ile  Lys  Val  Tyr  Phe  Asp  Ile  Ile  Thr  Asn  His  Thr  Ala
            275                 280                 285

Asp  Val  Ile  Ser  Tyr  Glu  Glu  Gly  Gln  Tyr  Ser  Tyr  Ile  Asp  Lys  Ala
     290                 295                 300

Thr  Ser  Pro  Tyr  Arg  Asp  Ala  Asp  Gly  Asn  Val  Phe  Asp  Pro  Ser  Thr
305                 310                 315                 320

Ile  Ala  Gly  Ser  Ala  Asp  Phe  Pro  Ala  Leu  Asp  Pro  Ala  Thr  Ser  Phe
                325                 330                 335
```

-continued

```
Pro Tyr Thr Pro Thr Val Ala Pro Glu Glu Ala Asp Val Lys Val Pro
            340                 345                 350

Ala Trp Leu Asn Asp Pro Thr Leu Tyr His Asn Arg Gly Asp Ser Thr
            355                 360                 365

Trp Ser Gly Glu Ser Val Thr Phe Gly Asp Phe Val Gly Leu Asp Asp
            370                 375                 380

Leu Met Thr Glu His Pro Thr Val Val Asp Gly Phe Ile Glu Val Tyr
385                 390                 395                 400

Gln Asp Trp Val Asp Leu Gly Ile Asp Gly Phe Arg Ile Asp Thr Ala
                405                 410                 415

Lys His Val Asn Phe Glu Phe Trp Glu Glu Trp Ser Thr Glu Val Leu
            420                 425                 430

Asp Tyr Ala His Ala Gln Gly Lys Pro Asp Phe Phe Met Phe Gly Glu
            435                 440                 445

Val Tyr Asp Ala Asp Pro Val Lys Leu Ser Pro Tyr Val Arg Lys Thr
    450                 455                 460

Asp Met Asn Ser Val Leu Asp Phe Thr Phe Gln Ser Gln Ala Val Ser
465                 470                 475                 480

Phe Ala Ala Gly Asn Ser Ala Lys Asn Leu Gln Ser Leu Phe Ala Gly
                485                 490                 495

Asp Asp Tyr Tyr Thr Thr Pro Asp Ser Ser Ala Thr Ala Leu Pro Thr
            500                 505                 510

Phe Leu Gly Asn His Asp Met Gly Arg Ile Gly Tyr Phe Leu Ala Asn
            515                 520                 525

Ser Gly Ala Thr Ala Val Gln Arg Asn Glu Leu Ala His Glu Leu Met
            530                 535                 540

Tyr Leu Thr Arg Gly Gln Pro Val Val Tyr Tyr Gly Asp Glu Gln Gly
545                 550                 555                 560

Phe Ala Gly Thr Gly Gly Asp Lys Asp Ala Arg Gln Thr Leu Phe Ala
                565                 570                 575

Ser Gln Val Asp Glu Tyr Val Asn Gln Pro Leu Val Thr Gly Glu Asn
            580                 585                 590

Ala Gly Ser Val Asp Arg Tyr Gly Thr Asp Ala Pro Leu Tyr Glu His
            595                 600                 605

Ile Ala Gly Leu Ala Glu Leu Arg Lys Ala His Pro Ala Leu Glu Gln
610                 615                 620

Gly Ala Gln Ile Glu Arg Phe Val Ala Asp Gly Ala Ser Val Tyr Ala
625                 630                 635                 640

Phe Ser Arg Val Asp Arg Asp Glu Lys Val Glu Tyr Leu Val Ala Val
                645                 650                 655

Asn Asn Ala Asn Glu Ala Lys Ala Val Glu Val Ser Thr Leu Thr Ala
            660                 665                 670

Asp Gly Ala Phe Glu Val Leu Tyr Gly Asp Gly Gln Ala Leu Thr Ala
            675                 680                 685

Asn Ala Asp Gly Val Ala Ser Val Thr Ala Pro Ala Leu Gly Ala Val
            690                 695                 700

Val Trp Lys Ala Asp Arg Glu Val Thr Ala Pro Glu Ala Ala Ser Ala
705                 710                 715                 720

Ile Ala Val Asp Val Pro Val Ala Gly Ala Val Thr Gly Ile Ala
                725                 730                 735

Pro Val Ser Ala Asp Val Ala Asp Ala Thr Trp Gln Glu Thr Ser Phe
            740                 745                 750

Ala Trp Arg Val Ala Gly Ser Asp Glu Trp Thr Pro Leu Gly Thr Ala
```

-continued

```
            755                 760                 765
Glu Asp Thr Thr Pro Arg Val Tyr His Asp Thr Ala Gly Leu Ala Lys
        770                 775                 780

Gly Thr Leu Val Glu Tyr Arg Ala Val Ser Thr Asp Ala Ala Gly Asn
785                 790                 795                 800

Arg Ala Ala Ala Ser Thr Tyr Ala Ser Val Gly Asn Ala Val Asn Leu
                805                 810                 815

Ala Val Val Glu Glu Pro Glu Thr Asp Ile Glu Leu Val Thr Val Pro
                820                 825                 830

Gly Ser His Asn Ser Glu Met Gly Cys Pro Gly Asp Trp Gln Pro Gly
                835                 840                 845

Cys Glu Ala Ala Lys Leu Thr Lys Arg Ala Asp Gly Ile Tyr Ala Gly
        850                 855                 860

Thr Phe Gln Ile Pro Ala Gly Thr Tyr Glu Tyr Lys Val Ala Ile Asn
865                 870                 875                 880

Gly Ser Trp Ala Leu Asn Tyr Gly Ala Asn Gly Val Gln Asp Gly Ala
                885                 890                 895

Asn Ala Thr Tyr Thr Thr Ser Gly Gly Ala Val Thr Phe Tyr Trp Asp
                900                 905                 910

Pro Arg Ser Lys Val Phe Ser Ser Thr Ala Glu Gly Pro Ile Val Thr
            915                 920                 925

Leu Pro Gly Ser Met Gln Ser Glu Leu Gly Cys Pro Gly Asp Trp Gln
        930                 935                 940

Pro Asp Cys Met Val Thr Phe Ala
945                 950
```

<210> SEQ ID NO 4
<211> LENGTH: 2103
<212> TYPE: DNA
<213> ORGANISM: Glycosyl hydrolases

<400> SEQUENCE: 4

```
atgacaggcc ttcccgactc cgggacgctt cgacgccccg gcccgcgcaa gcgtttgcga    60
acgctgatcg cggtcaccgc cgccgcggtc ctcgccggcc tcgccgccat cgtcccggc    120
gcgcccgccg gccccgccga ggcggccgcc cccggcccga aggacgccac cgcggtgctc    180
ttctcgtaca cctggaacgc catcgcccgc gagtgcaccg agaacctcgg acccgccggc    240
tacggctacg tgcagacctc gccgccgcag gagcacgtgc agggccccca gtggtggatc    300
cactaccagc ccgtcagcta ccgcgtcgag tcgcgcctcg gcacgcgcgc cgagttcaag    360
gccatggtcg acacgtgcca cgcggccggc gtgaaggtca tcgccgacgc cgtcatcaac    420
cacatgagcg ggtacagcgc gggcggcgtc ggctgggccg gtcgtcgtt ccagcactac    480
tcgtaccccg gcatctacca gtcgcaggac ttccactcgt gccgacgcga catcgcgaac    540
taccaggacc ggtgggaggt gcaggagtgc aacctcgtga acctcgccga cctgaacacc    600
ggctcggcct acgtgcaggg ccgcatcgcc gcgtacctca cgacctcgt ctcgctcggc    660
gtcgacggat ccggatcga cgccgtcaag cacatctcgg cggccgacat gaacggcatc    720
ctctcgcgcg tcaacgaccg ggcgcgtctc tacctcgttc aggaggtcat ccgcgccaac    780
gagcccgtgc agcccgagga gtacctgggc ctcggcgaca tccacgagtt cgcgtatgcg    840
cgcaagctca aggaggcgtt cggcggccgc accctgaact ggctcatcag cggcgcgggc    900
atcggcccga ctgggccgg cttcctgcag aacgcggatg ccgcggtgtt cgtcgacaac    960
cacgacaccg agcgcaacgg cgagacgctg agctaccgcg acggcgcggc gtacgacctc   1020
```

```
gcgcaggtgt tcacgctcgc gtggaactac ggttcgccgt cgatccactc cgggtaccag    1080
ttctcgaaca aggacgccgg accggcgctc gcgggcaacg gacgcgtggt cgatcccgtg    1140
tgcgggcaga acggctggac ctgcaagcac gcccagacga acatcgagaa catggtcggc    1200
ttccgcacgg ccacctacgg caccgccatc acgaacaagt gggacaacgg ttcgtcggcg    1260
atcgcgttcg gtcgcggtga caagggcttc gtcgccatca accgcggcac cgcggcggtc    1320
gaccgcacct ggcagacgtc cctgccggcc gggcgctact gcaacgtgat cgtcgggctg    1380
ccgacggcga gcggatgcag cgccggaggc gtcatcacgg tcgactcgag cggccggttc    1440
gcggcatccg tcgccgccga caccgcgctc gccctccacg tcggcgcgaa ggccggcggc    1500
accggcacga ccccgccgcc gaccggatcg acgatgaccg tgtacttcgc gaccacgaag    1560
ggctggacga accactacgt gcaccaccgc gtcggctcgg gcgcatggac cgccctgccc    1620
ggcgcagcga tggcggcggc ctgcaccggt tgggtgtcca ggaccatcga cctcggatcg    1680
gcgacgggca tcaccgcggc cttcaccaac ggcgcggggcg cgtgggacaa caacggcggg    1740
cgcgactacg cgctcaccgg atccgtcgcc gccgtgaagg acgggtcgt caccgcgacg    1800 aacccgtgcg ccgcgcagcc cacctcgacc acggtgtact acgcgaccgg atggagcacc    1860
gcgaacatcc actaccgcgt cgggtcgggc gcctggacgg cggtgccggg cgtcgcgatg    1920
gcgaacgcct gcgcgggctg gaagtcgaag accatcgagc tcggcgcggc atccggcatc    1980
accgcggcct tcaacaacgg cgccggcacg tgggacaaca acggcgggaa ggactacgcg    2040
atcggggcgg cgcgatgaa ggtgcagaac ggcaccgtca ccgccggcaa cccgtgtagc    2100
tga                                                                 2103

<210> SEQ ID NO 5
<211> LENGTH: 6040
<212> TYPE: DNA
<213> ORGANISM: Glycosyl hydrolases

<400> SEQUENCE: 5
atgacgcatc gagcgcgcgc tcgcagctgg ttggcattgg gggtgacggg cgccgtcgcg      60
gcatccgtgc tcgccgtcgt tcccatcggg gctgcagccg aggagggcga cacgttcgct     120
ctcgtcggtt cgctgcagag cgaactgggc tgttccgagg actggcagcc gagctgcgag     180
gccaccgagc tgctgcccac cgacaccgcg ggcctctacg ccgccgagtt caccgtcccg     240
gcgggctcgt acgagtacaa ggtcgcggcg aacgactcgt gggacgcctc gtggggtctc     300
gacgggggcg gcgacaacat cccgctcacg gtcggcggcg acaccgacgt gcgcgtcgtg     360
ttcgacgaca cccagaagcg cgtcggcctc gagctgctga gcacccgtgg cgcgtacgac     420
gagcaggcgg atgccgcgct cgcgctgccg cccgtccgcc agccgggcag cgccgagaac     480
ttctacttcg tcatgaccga ccgcttcgcc aacggcgacg agtcgaacga caccgccggc     540
atcgagggag accgcctcgc gcacggcttc gaccccaccg acaagggctt ctaccacggc     600
ggcgacatcc agggcatccg cgatcacctc gactacatcg agggcctcgg cacgaccgcg     660
atctggttca cgccgagctt caagaacaag cccgtgcagg gcgagggtgc gaacgccagc     720
gccggctacc acggctactg gatcaccgac ttcacgcaga tcgaccccgca cctcggcacg     780 aacgccgagc tcgaggcgct catcgacgag gcgcacgagc gcggcatcaa ggtctacttc     840
gacatcatca cgaaccacac ggccgacgtg atctcgtacg aggagggcca gtactcgtac     900
atcgacaagg ccacgagccc gtaccgcgac gccgacggca acgtgttcga cccgagcacc     960
```

-continued

```
atcgcgggca gcgccgactt cccggcgctc gatccggcca cgagcttccc gtacacgccg    1020
accgtcgcgc ccgaggaggc cgacgtcaag gtccccgcgt ggctcaacga cccgacgctg    1080
taccacaacc gcggcgactc gacctggtcg ggcgaatcgg tgacgttcgg cgacttcgtc    1140
ggcctcgacg acctgatgac cgagcacccg accgtcgtcg acggcttcat cgaggtgtac    1200
caggactggg tcgacctcgg catcgacggc ttccggatcg acaccgccaa gcacgtgaac    1260
ttcgagttct gggaggagtg gtcgaccgag gtcctcgact acgccacgc ccagggcaag    1320 cccgacttct tcatgttcgg cgaggtctac gacgccgacc cggtgaagct ctcgccgtac    1380
gtgcgcaaga ccgacatgaa ctcggtcctc gacttcacct tccagtcgca ggccgtgtcg    1440
ttcgccgccg gcaactcggc gaagaacctg cagtcgctgt tcgccggtga cgactactac    1500
acgacgcccg actcgtcggc gacggccctg ccgaccttcc tcggcaacca cgacatgggt    1560
cgcatcggct acttcctcgc caactcgggc gccaccgcgg tgcagcgcaa cgagctcgcg    1620
cacgagctca tgtacctcac gcgcggccag ccggtcgtct actacggcga cgagcagggc    1680
ttcgcaggca cgggcggcga caaggacgcc cgccagacgc tcttcgcgag ccaggtcgac    1740
gagtacgtca accagccgct cgtcaccggc gagaacgccg gcagcgtcga ccgctacggc    1800
accgacgcgc cgctctacga gcacatcgcc ggactcgccg agctgcgcaa ggcgcacccg    1860
gcgctcgagc agggcgcgca gatcgagcgc ttcgtcgccg acggcgccag cgtgtacgcg    1920
ttcagccgcg tcgaccgcga cgagaaggtc gagtacctgg tcgccgtgaa caacgcgaac    1980
gaggccaagg ccgtggaggt ctccacccte accgccgacg cgcgcgttcga ggtgctgtac    2040 ggcgacgggc aggccctgac cgcgaacgcc gacggcgtgg catccgtcac cgcgccggcg    2100
ctcggcgccg tggtgtggaa ggccgaccgc gaggtgaccg cccccgaggc ggcatccgcc    2160
atcgccgtcg acgtgcccgt cgccggggcc ggcgtcacgg gcatcgcacc cgtctcggcc    2220
gacgtcgccg acgccacctg gcaggagacg agcttcgcct ggcgcgtggc cggttccgac    2280
gagtggacgc cgctcggcac cgccgaggac accaccccgc gcgtctacca cgacaccgcg    2340
ggcctcgcga agggcacgct ggtcgagtac cgggccgtgt cgacggatgc cgcgggcaac    2400
cgcgccgccg catcgaccta cgcctcggtg ggcaacgccg tgaacctcgc ggtcgtcgag    2460
gagcccgaga ccgacatcga gctggtcacc gtccccggca gccacaactc ggagatgggc    2520
tgcccgggcg actggcagcc cggctgcgag gccgcgaagc tcaccaagcg cgccgacggc    2580
atctacgccg gcacgttcca gatcccggcc ggcacgtacg agtacaaggt cgcgatcaac    2640
ggcagctggg cgctgaacta cggcgccaac ggcgtgcagg acgcgcgcaa cgccacctac    2700
acgacgagtg gcggcgcggt caccttctac tgggacccgc gcagcaaggt gttctcgtcg    2760
accgccgagg ggccgatcgt cacgctgccc ggcagcatgc agtccgaact cggctgcccc    2820
ggcgactggc agcccgactg catggtcacc ttcgcgcagg acggcgacaa ggacggcgtc    2880
tacgagttct cgacgaacgg cctgccggcc ggctcctacg aactgaaggt cgcgcacggc    2940
ctgtcgtggg atgagaacta cggcgtcgac ggtgtccgca acggcggcaa catctcgttc    3000
gtcgtcggca aggccggcga gttcgtcacc ttcgcgctaca cgctcgagac ccacgtgctc    3060
gaggtcgtcg tggccgaccc gccgctcgcg ggcaccggac agcagcgcgc gtactggctc    3120
gacgccgaga cgctcgcctg gcccgcctcg ctcctcggcg gagcgaacgc ggcggaccgc    3180
gcctacacgc tcgagttcgc cgccgacggc ggactcggca ccgccgacgg cgccgtgacc    3240
ggcgccgacc ggacggtcga gctcgcccac gagcccgcgg catcggcgc ggagctcacc    3300 gcgcggttcc cgcacctggc gagctacgtg gcgctccggc ctgtcggcct cgaccgcgcg    3360
```

```
gcgatcgccg aactcgtcac gggcgagctc caggtggcgc agcgcgccgg cgacgagctc    3420
accgcgatga ccggcgtgca gctgccgggc gtgctcgacg acctctacgc ccagggcgtg    3480
gcatccgcct cgctcggcgc cacggtcgac ggcgacgccg cgagcctctc cgtctgggcg    3540
ccgaccgcga agtcggtgtc ggcccaggtc tgggccgccg gagcgacggg cgaccccgag    3600
gtgctgccgg ccgagttcga cgccgagtcc ggcgcgtggt cggtcgacga gggcatcgag    3660
gcgggcgacg agtaccgctg gctcgtcgag gtgtacgccc cgaccaccgg caaggtggag    3720
cgcaactcgg tgaccgaccc gtactcggtc gcgctcaccg tgaactccgc ccgcaccgtc    3780
gtcgtcgacc tcgacgaccc ggcgctcgca cccgagctgt gggccgagac gcccgcaccg    3840
gtcgtcgagc ggcaggtcga ccgggcgatc tacgagctgc acgtgcgcga cttctcgatc    3900
accgatgaga cggtgcccga ggccgagcgc ggcacctacc gggcgttcac ccgcaacagt    3960
gcgggcagtg cgcagctgcg cgagctgccg cggccggca tcaacacggt gcacctgctg    4020
cccacgttcg acatcgcgac catcgaggag cgccgcgacc agcaggcgac ccccgactgc    4080
gacctcgagt cgtacggtcc ggcgtcggag gagcagcagg cctgcatcga ggcgatccgc    4140
gacctcgacg gcttcaactg ggctacgac ccgtaccact ccaggcgcc cgagggctcc    4200 tacgcggtcg accccgacgg cggcgcgcgc gtcgcggagt ccgcgagat ggtcggcgcc    4260 ctgcacgccg cgggcatgca ggtcgtgctc gacgaggtgt acaaccacac cgccgagtcg    4320 ggccaggcc agaagtcggt gctcgacaag gtcgtgcccg gctactacca ccgcctgaac    4380
gcgaccggcg gcgtcgagac ctcgacgtgc tgccagaacg tcgcgaccga gcacgccgtc    4440
gccgagaagc tcatggtcga ctcgaccgtc tctgggtga aggagtacaa ggtcgacggg    4500
ttccgcttcg acctgatggg ccaccactcc aaggcgaacc tcctggccgt gcgcgcggcg    4560
ctcgacgagc tcacgctcgc cgaggacggc gtcgacggct cgaaggtctt cctctacggc    4620
gagggctgga acttcggcga ggtcgcgaac aacgcgcggt tcgaacaggc ctcgcagggc    4680
cagctcggcg gcacgggcat cgcgacgttc aacgaccggc tgcgtgacgg cgtgcacggc    4740
ggcagcccgg tcgcgggcga ctcgaagtac gagcagggct tcggcaccgg cctcgcgggc    4800
gagccgaacg gcctgcccca gcgcgacggc atccggaacc tcggccagca gaccgacctc    4860
gtgaagatcg gcctcgcggg caacctgcgc gacttccggt tcaccgggta cgacggggtg    4920
ctgaagtcgg gcgccgaggt cgactacaac gggtcgccgg ccggctacgc cgaccacccc    4980
gaggaggtca tcaactacgt cgacgcgcac gacaacgaga cgctgttcga cctcggcgtg    5040
ctgaagctgc cgcaggagac gtcgatggcc gaccgcatcc gcatgaacac gctgtcgctc    5100
gcgaccgtga cgttctcgca gagcccgtcg ttctggcacg ccggcaccga gctgctccgc    5160
tcgaagtcgc tcgaccgcaa tagctacaac tcgggcgact ggttcaaccg gatcgactgg    5220
accggccagg agtcgacctt cgggtcgggc ctgccgatga agtccgacaa cgaggaccac    5280
tggccgacga tggcgacgct gctcgccgac ccggcgctga agcccgctcc ggcggacatc    5340
gccgccgccg aggccgccgc gctcgacctg ctgcgcgtgc gcgacagcgt cgacctgctc    5400
aagctgggct cggccgagct catcacgcag aaggtgtcgt tcccgaacag cggtgcggat    5460
gccacggacg ggctcatcgt gatgctcatc gacgacctcg tgggcgacga cgtcgacccc    5520
gagctcgagg gtgcgctggt cgtgttcaac gcttccgccg agccgatcac cgaggcggtg    5580
gacggactcg ccggtcgcga gttcgccctc gccccggcgc tcgcgaacgg gaccgacgcg    5640
gtcgtcaagc agaccgcgtg ggaggccgcg accggcacgc tcacgatccc ggcccgcacg    5700
```

```
gcggcggtgt tcgtcgacga ccaggccaag cccggcggcg gcaagcccga caagccgggc    5760
aagcccgaga agcccggcaa gccggacaag cccggcaagc cggacaagcc cgagaagccg    5820
ggcaagccgg agaagcccgg caagccggag aagcccggca agccggagca gcccggcaag    5880
cccgtcgtcc gcctggacgc ggcgtcggtg cagaccggct cgaccctggc cgtgtccggg    5940
aagggcttcg cgaagggcga gctcgtgcag gtgtggctgg agtcgacgcc gacgctcatg    6000
gaggcgcagc ccgcctccgc ggacggcacg gtcgagttcg                         6040

<210> SEQ ID NO 6
<211> LENGTH: 2859
<212> TYPE: DNA
<213> ORGANISM: Glycosyl hydrolases

<400> SEQUENCE: 6
atgacgcatc gagcgcgcgc tcgcagctgg ttggcattgg gggtgacggg cgccgtcgcg     60
gcatccgtgc tcgccgtcgt tcccatcggg gctgcagccg aggagggcga cacgttcgct    120
ctcgtcggtt cgctgcagag cgaactgggc tgttccgagg actggcagcc gagctgcgag    180
gccaccgagc tgctgcccac cgacaccgcg ggcctctacg ccgccgagtt caccgtcccg    240
gcgggctcgt acgagtacaa ggtcgcggcg aacgactcgt gggacgcctc gtggggtctc    300 gacggggggcg cgacaacat cccgctcacg gtcggcggcg acaccgacgt gcgcgtcgtg    360
ttcgacgaca cccagaagcg cgtcggcctc gagctgctga gcacccgtgg cgcgtacgac    420
gagcaggcga tgccgcgct cgcgctgccg cccgtccgcc agccgggcag cgccgagaac    480
ttctacttcg tcatgaccga ccgcttcgcc aacggcgacg agtcgaacga caccgccggc    540
atcgagggag accgcctcgc gcacggcttc gaccccaccg acaagggctt ctaccacggc    600
ggcgacatcc agggcatccg cgatcacctc gactacatcg agggcctcgg cacgaccgcg    660
atctggttca cgccgagctt caagaacaag cccgtgcagg gcgagggtgc gaacgccagc    720
gccggctacc acggctactg gatcaccgac ttcacgcaga tcgacccgca cctcggcacg    780
aacgccgagc tcgaggcgct catcgacgag gcgcacgagc gcggcatcaa ggtctacttc    840
gacatcatca cgaaccacac gggccgacgtg atctcgtacg aggagggcca gtactcgtac    900
atcgacaagg ccacgagccc gtaccgcgac gccgacggca cgtgttcga cccgagcacc    960 atcgcgggca gcgccgactt cccggcgctc gatccggcca cgagcttccc gtacacgccg    1020
accgtcgcgc ccgaggaggc cgacgtcaag gtccccgcgt ggctcaacga cccgacgctg    1080
taccacaacc gcgcgactc gacctggtcg ggcgaatcgg tgacgttcgg cgacttcgtc    1140
ggcctcgacg acctgatgac cgagcacccg accgtcgtcg acggcttcat cgaggtgtac    1200
caggactggg tcgacctcgg catcgacggc ttccggatcg acaccgccaa gcacgtgaac    1260
ttcgagttct gggaggagtg gtcgaccgag gtcctcgact acgcccacgc ccagggcaag    1320
cccgacttct tcatgttcgg cgaggtctac gacgccgacc cggtgaagct ctcgccgtac    1380
gtgcgcaaga ccgacatgaa ctcggtcctc gacttcacct tccagtcgca ggccgtgtcg    1440
ttcgccgccg gcaactcggc gaagaacctg cagtcgctgt cgccggtga cgactactac    1500 acgacgcccg actcgtcggc gacggccctg ccgaccttcc tcggcaacca cgacatgggt    1560
cgcatcggct acttcctcgc caactcgggc gccaccgcgg tgcagcgcaa cgagctcgcg    1620
cacgagctca tgtacctcac gcgcggccag ccggtcgtct actacggcga cgagcagggc    1680
ttcgcaggca cggcggcga caaggacgcc gccagacgcc tcttcgcgag ccaggtcgac    1740
gagtacgtca accagccgct cgtcaccggc gagaacgccg gcagcgtcga ccgctacggc    1800
```

```
accgacgcgc cgctctacga gcacatcgcc ggactcgccg agctgcgcaa ggcgcacccg    1860
gcgctcgagc agggcgcgca gatcgagcgc ttcgtcgccg acggcgccag cgtgtacgcg    1920
ttcagccgcg tcgaccgcga cgagaaggtc gagtacctgg tcgccgtgaa caacgcgaac    1980
gaggccaagg ccgtggaggt ctccaccctc accgccgacg gcgcgttcga ggtgctgtac    2040
ggcgacgggc aggccctgac cgcgaacgcc gacggcgtgg catccgtcac cgcgccggcg    2100
ctcggcgccg tggtgtggaa ggccgaccgc gaggtgaccg cccccgaggc ggcatccgcc    2160
atcgccgtcg acgtgcccgt cgccggggcc ggcgtcacgg gcatcgcacc cgtctcggcc    2220
gacgtcgccg acgccacctg gcaggagacg agcttcgcct ggcgcgtggc cggttccgac    2280
gagtggacgc cgctcggcac cgccgaggac accaccccgc gcgtctacca cgacaccgcg    2340
ggcctcgcga agggcacgct ggtcgagtac cgggccgtgt cgacggatgc cgcgggcaac    2400
cgcgccgccg catcgaccta cgcctcggtg gcaacgccg tgaacctcgc ggtcgtcgag    2460
gagcccgaga ccgacatcga gctggtcacc gtccccggca gccacaactc ggagatgggc    2520
tgcccgggcg actggcagcc cggctgcgag gccgcgaagc tcaccaagcg cgccgacggc    2580
atctacgccg gcacgttcca gatcccggcc ggcacgtacg agtacaaggt cgcgatcaac    2640
ggcagctggg cgctgaacta cggcgccaac ggcgtgcagg acggcgcgaa cgccacctac    2700
acgacgagtg gcggcgcggt caccttctac tgggacccgc gcagcaaggt gttctcgtcg    2760
accgccgagg ggccgatcgt cacgctgccc ggcagcatgc agtccgaact cggctgcccc    2820
ggcgactggc agcccgactg catggtcacc ttcgcgtga                         2859

<210> SEQ ID NO 7
<211> LENGTH: 99
<212> TYPE: PRT
<213> ORGANISM: Bacillus amyloliquefaciens

<400> SEQUENCE: 7

Val Asp Gly Phe Arg Ile Asp Ala Ala Lys His Ile Pro Pro Ala Asp
1               5                   10                  15

Leu Ala Ala Ile Lys Asp Leu Leu Thr Gly Ser Pro Tyr Leu His Gln
            20                  25                  30

Glu Val Ile Gln Gly Asp Asn Glu Val Ile Gln Pro Gly Gln Tyr Thr
        35                  40                  45

Gly Ile Gly Asp Val His Glu Phe Val Tyr Gly Arg Lys Leu Lys Glu
    50                  55                  60

Gln Phe Asn Gly Gln Ile Lys Trp Leu Gly Ser Phe Gly Gln Ser Trp
65                  70                  75                  80

Gly Leu Ser Val Pro Gly Asp Lys Ala Val Val Phe Val Asp Asn His
                85                  90                  95

Asp Thr Glu

<210> SEQ ID NO 8
<211> LENGTH: 100
<212> TYPE: PRT
<213> ORGANISM: Lactococcus lactis

<400> SEQUENCE: 8

Val Asp Gly Phe Arg Ile Asp Thr Ala Lys His Ile Ala Ala Ser Asp
1               5                   10                  15

Leu Ala Ala Ile Arg Ala Arg Val Asn Gly Gly Asp Val Tyr Trp Lys
            20                  25                  30
```

```
Gln Glu Val Ile His Gly Ala Gly Glu Ala Val Gln Pro Gly Glu Tyr
            35                  40                  45

Thr Gly Val Gly Asp Val Gln Glu Phe Arg Tyr Ala Tyr Asp Leu Lys
        50                  55                  60

Arg Val Phe Gln Asn Glu Arg Leu Ala Tyr Leu Glu Asn Tyr Gly Glu
 65                  70                  75                  80

Gly Trp Gly Tyr Leu Pro Ser Gly Gly Ala Ala Val Phe Val Asp Asn
                85                  90                  95

His Asp Thr Glu
            100

<210> SEQ ID NO 9
<211> LENGTH: 99
<212> TYPE: PRT
<213> ORGANISM: Pseudomonas sp.

<400> SEQUENCE: 9

Val Asp Gly Phe Arg Ile Asp Thr Ser Lys His Met Pro Ala Ala Asp
 1               5                  10                  15

Ile Ala Ala Ile Lys Ser Lys Leu Ser Arg Pro Ala Tyr Ile Val Gln
            20                  25                  30

Glu Val Ile Phe Gly Ala Gly Glu Pro Ile Gly Pro Gly Glu Tyr Thr
            35                  40                  45

Gly Asn Gly Asp Val His Glu Phe Arg Tyr Gly Lys Asp Leu Ala Arg
        50                  55                  60

Val Phe Arg Ser Glu Arg Leu Ala Tyr Leu Lys Asn Phe Gly Glu Gly
 65                  70                  75                  80

Trp Gly His Leu Pro Ser Gly Val Ser Val Tyr Val Asp Asn His
                85                  90                  95

Asp Thr Glu

<210> SEQ ID NO 10
<211> LENGTH: 100
<212> TYPE: PRT
<213> ORGANISM: Pseudomonas sp.

<400> SEQUENCE: 10

Val Asp Gly Phe Arg Ile Asp Ala Val Lys Arg Met Pro Ala Ala Asp
 1               5                  10                  15

Leu Ala Asn Ile Lys Ser Arg Leu Ser Asn Pro Asp Ala Tyr Trp Lys
            20                  25                  30

Gln Glu Val Ile His Gly Ala Gly Glu Ala Val Gln Pro Gly Glu Tyr
            35                  40                  45

Thr Gly Asn Gly Asp Val Gln Glu Phe Arg Tyr Ala Tyr Asp Leu Lys
        50                  55                  60

Arg Val Phe His Asn Glu Asn Leu Ala Tyr Leu Lys Asn Tyr Gly Glu
 65                  70                  75                  80

Gly Trp Gly Tyr Leu Lys Asn Ser Ser Ala Gly Val Phe Val Asp Asn
                85                  90                  95

His Asp Thr Glu
            100

<210> SEQ ID NO 11
<211> LENGTH: 116
<212> TYPE: PRT
<213> ORGANISM: Pseudomonas sp.

<400> SEQUENCE: 11
```

Val Asp Gly Phe Arg Ile Asp Ala Thr Lys Ala Ile Lys Asn Phe Asp
1               5                   10                  15

Thr Leu Lys Leu Leu Thr Asp Ala Ala Tyr Ser Lys Ile Glu Asp Arg
            20                  25                  30

Lys Pro Phe Ile Thr Ile Gly Glu His Val Pro Glu Asp Pro Glu Val
            35                  40                  45

Thr Gly Arg Asp Arg Gly Arg Pro Met Asp Ala Ala Trp His Asp Tyr
        50                  55                  60

Phe Gly His Val Ala Arg Ala Val Ala Glu Val Gln Lys Asp Asp
65                  70                  75                  80

Leu His Pro His Asp Ile Lys Arg Phe Leu Glu Arg Leu Asp Pro Lys
                85                  90                  95

Thr Asn Gly Tyr Gly Ser Ala Tyr Arg Thr Val Thr Phe Val Asp Asn
                100                 105                 110

His Asp Thr Glu
        115

<210> SEQ ID NO 12
<211> LENGTH: 101
<212> TYPE: PRT
<213> ORGANISM: Pseudomonas sp.
<220> FEATURE:
<221> NAME/KEY: misc_feature
<222> LOCATION: (62)..(62)
<223> OTHER INFORMATION: Xaa can be any naturally occurring amino acid

<400> SEQUENCE: 12

Val Asp Gly Phe Arg Ile Asp Ala Ala Lys His Ile Pro Asn Glu Asp
1               5                   10                  15

Leu Arg Ala Ile Phe Gly Arg Leu Arg Glu Thr Val Ser Gly Ala Arg
            20                  25                  30

Pro Tyr Val Phe His Glu Val Phe Pro Gly Glu Pro Pro Arg Pro Gln
            35                  40                  45

Asp Tyr Phe Ser Thr Gly Asp Val Leu Asp Phe Thr Tyr Xaa Asp Lys
        50                  55                  60

Ile Lys Thr Ala Phe Gln Gly Asp Ile Ala Trp Leu Ser Ser Phe Gly
65                  70                  75                  80

Pro Ser Trp Gly Leu Leu Pro Ala Ala Asp Ser Val Ser Tyr Val Asp
                85                  90                  95

Asn His Asp Thr Glu
                100

<210> SEQ ID NO 13
<211> LENGTH: 96
<212> TYPE: PRT
<213> ORGANISM: Pseudomonas sp.

<400> SEQUENCE: 13

Val Asp Gly Phe Arg Ile Asp Ala Ala Lys His Met Tyr His Gly Asp
1               5                   10                  15

Ile Gln Gly Ile Leu Ser Arg Ala Gly Asn Pro Tyr Val Phe Leu Glu
            20                  25                  30

Val Ile Gly Ser Ala Gly Glu Ala Val Gln Pro Ser Gln Tyr Thr Tyr
            35                  40                  45

Leu Gly Gln Val Thr Glu Phe Gly Tyr Ser Ser His Ile Gly His Arg
        50                  55                  60

Phe Lys Tyr Gly Gln Ile Lys Asp Leu Asn Asn Ile Ala Asp Gly Lys

```
                 65                  70                  75                  80
Leu Pro Ser Thr Ser Ala Ile Val Tyr Val Asp Asn His Asp Thr Glu
                 85                  90                  95

<210> SEQ ID NO 14
<211> LENGTH: 99
<212> TYPE: PRT
<213> ORGANISM: Diabrotica virgifera

<400> SEQUENCE: 14

Val Asp Gly Phe Arg Ile Asp Ala Ala Lys His Ile Pro Pro Ala Asp
1               5                   10                  15

Leu Ala Ala Ile Lys Asp Leu Leu Thr Gly Ser Pro Tyr Leu His Gln
                20                  25                  30

Glu Val Ile Gln Gly Asp Asn Glu Val Ile Gln Pro Gly Gln Tyr Thr
            35                  40                  45

Gly Ile Gly Asp Val His Glu Phe Val Tyr Gly Arg Lys Leu Lys Glu
        50                  55                  60

Gln Phe Asn Gly Gln Ile Lys Trp Leu Gly Ser Phe Gly Gln Ser Trp
65                  70                  75                  80

Gly Leu Ser Val Pro Gly Asp Lys Ala Val Tyr Val Asp Asn His
                85                  90                  95

Asp Thr Glu

<210> SEQ ID NO 15
<211> LENGTH: 102
<212> TYPE: PRT
<213> ORGANISM: Streptomyces coelicolor

<400> SEQUENCE: 15

Val Asp Gly Phe Arg Ile Asp Ala Ile Lys His Met Asp Thr Arg Phe
1               5                   10                  15

Val Asn Ala Trp Leu Asp Ala Val Arg Gly Pro Arg Phe Ala Val Ser
                20                  25                  30

Glu Ala Trp Phe Ala Lys Leu Asp Gln Leu Thr Ala Tyr Ala Lys Glu
            35                  40                  45

Leu Gly Asp Arg Thr Arg Leu Phe Asp Val Pro Leu His Tyr Leu Phe
        50                  55                  60

Tyr Gly Met Ser Asn Gly Asn Gly Ala Trp Asp Met Arg Asn Leu Lys
65                  70                  75                  80

Phe Ala Gly Phe Thr Glu Ala Asn Gly Lys Leu Ser Val Pro Tyr Val
                85                  90                  95

Asp Asn His Asp Thr Glu
            100

<210> SEQ ID NO 16
<211> LENGTH: 96
<212> TYPE: PRT
<213> ORGANISM: Streptomyces coelicolor

<400> SEQUENCE: 16

Val Asp Gly Phe Arg Ile Asp Thr Val Lys His Ile Ala His Gly Asp
1               5                   10                  15

Leu Ala Gly Ile Leu Ser Arg Ala Gly Asn Pro Tyr Asn Phe Met Glu
                20                  25                  30

Val Ile Gly Ala Ala Gly Glu Pro Ile Gln Pro Ser Glu Tyr Thr Tyr
            35                  40                  45
```

```
Leu Gly Gln Val Thr Glu Phe Gly Tyr Ser Ser His Leu Gly His Arg
            50                  55                  60

Phe Lys Phe Gly Gln Ile Lys Asp Leu Arg Asn Ile Gly Asp Gly Lys
 65                  70                  75                  80

Leu Pro Ser Asp Lys Ala Ile Val Tyr Val Asp Asn His Asp Thr Glu
                85                  90                  95

<210> SEQ ID NO 17
<211> LENGTH: 99
<212> TYPE: PRT
<213> ORGANISM: Streptomyces coelicolor

<400> SEQUENCE: 17

Val Asp Gly Phe Arg Ile Asp Ala Ala Lys His Ile Ser Pro Asp Asp
 1               5                  10                  15

Ile Ala Ala Ile Lys Ser Arg Leu Lys Gly Ser Pro Tyr Ile His Gln
                20                  25                  30

Glu Val Ile Tyr Gly Asp Asn Glu Ala Val Gln Pro Ser Trp Tyr Thr
            35                  40                  45

Gly Asn Gly Asp Val Asp Glu Phe Val Tyr Gly Arg Lys Leu Lys Glu
        50                  55                  60

Gln Phe Thr Gly Gln Ile Lys Trp Leu Gln Ser Phe Gly Gln Ser Trp
 65                  70                  75                  80

Gly Leu Ser Val Gly Ser Asp Lys Ala Met Val Phe Val Asp Asn His
                85                  90                  95

Asp Thr Glu

<210> SEQ ID NO 18
<211> LENGTH: 96
<212> TYPE: PRT
<213> ORGANISM: Streptomyces coelicolor

<400> SEQUENCE: 18

Val Asp Gly Phe Arg Ile Asp Thr Ala Lys His Met Tyr His Gly Asp
 1               5                  10                  15

Ile Gln Gly Ile Leu Ser Arg Ala Gly Asn Pro Tyr Val Phe Leu Glu
                20                  25                  30

Val Ile Gly Ser Ala Gly Glu Ala Val Gln Pro Ser Gln Tyr Thr Tyr
            35                  40                  45

Leu Gly Gln Val Thr Glu Phe Gly Tyr Ser Ser His Ile Gly His Arg
        50                  55                  60

Phe Lys Tyr Gly Gln Ile Lys Asp Leu Asn Asn Ile Ala Asp Gly Lys
 65                  70                  75                  80

Leu Pro Ser Thr Ser Ala Ile Val Tyr Val Asp Asn His Asp Thr Glu
                85                  90                  95

<210> SEQ ID NO 19
<211> LENGTH: 117
<212> TYPE: PRT
<213> ORGANISM: Streptomyces coelicolor

<400> SEQUENCE: 19

Val Asp Gly Phe Arg Ile Asp Ala Ala Arg His Val Asn Thr Ala Phe
 1               5                  10                  15

Trp His Ala Phe Asn Thr Ala Ile Arg Asp Arg Ala Arg Ala Leu Gly
                20                  25                  30

Arg Pro Asp Phe Ile Gln Phe Gly Glu Val Tyr Asn Asp Thr Pro Glu
            35                  40                  45
```

```
Ala Pro Ala Val Leu Ser Glu Phe Ser Thr Gly Met Pro Met Asp Thr
         50                  55                  60

Thr Leu Asp Phe Gly Phe Phe Asn Ala Ala Arg His Phe Val Ser Gln
 65                  70                  75                  80

Gln Arg Pro Ala Ala Glu Leu Ala Ala Phe Phe Arg Thr Asp Asp Leu
                 85                  90                  95

Tyr Thr Asp His Asp Ser Asn Ile His Ala Thr Leu Thr Tyr Val Asp
             100                 105                 110

Asn His Asp Thr Glu
        115

<210> SEQ ID NO 20
<211> LENGTH: 100
<212> TYPE: PRT
<213> ORGANISM: Streptomyces coelicolor

<400> SEQUENCE: 20

Val Asp Gly Phe Arg Ile Asp Thr Ala Lys His Met Pro Ala Ala Asp
 1               5                  10                  15

Leu Ala Asn Ile Lys Ser Arg Leu Gly Asp Pro Asn Val Tyr Trp Lys
             20                  25                  30

Gln Glu Ala Ile Tyr Gly Ala Gly Glu Ala Val Ser Pro Asp Glu Tyr
         35                  40                  45

Ala Gly Thr Gly Asp Val Gln Glu Phe Arg Tyr Ala Arg Gly Leu Lys
     50                  55                  60

Gln Val Phe Asn Asn Glu Asn Leu Ala Tyr Leu Lys Asn Tyr Gly Glu
 65                  70                  75                  80

Gly Trp Gly Phe Met Pro Ser Ser Lys Ala Ala Val Tyr Val Asp Asn
                 85                  90                  95

His Asp Thr Glu
        100

<210> SEQ ID NO 21
<211> LENGTH: 108
<212> TYPE: PRT
<213> ORGANISM: Streptomyces coelicolor

<400> SEQUENCE: 21

Val Asp Gly Phe Arg Ile Asp Thr Ile Arg His Met Pro Gln Ala Phe
 1               5                  10                  15

Trp His Ala Phe Ala Arg Arg Ile Arg Ala Glu His Pro Gly Phe Phe
             20                  25                  30

Met Phe Gly Glu Ala Phe Asp Thr Lys Ala Ala Asn Ile Ala Pro Phe
         35                  40                  45

Thr Trp Ala Glu Asn Ala Asn Val Ser Val Leu Asp Phe Pro Leu Lys
     50                  55                  60

Glu Gly Leu Ile Glu Val Phe Gly Arg Lys Arg Ala Gly Phe Glu Ile
 65                  70                  75                  80

Leu Leu Pro Arg Leu Tyr Leu Thr Asp Gly Pro Tyr Ala Asn Pro Tyr
                 85                  90                  95

Glu Leu Met Thr Tyr Val Asp Asn His Asp Thr Glu
            100                 105

<210> SEQ ID NO 22
<211> LENGTH: 117
<212> TYPE: PRT
<213> ORGANISM: Streptomyces coelicolr
```

-continued

```
<400> SEQUENCE: 22

Val Asp Gly Phe Arg Ile Asp Ala Ala Arg His Val Asn Thr Ala Phe
1               5                   10                  15

Trp His Ala Phe Asn Thr Ala Ile Arg Asp Arg Ala Arg Ala Leu Gly
            20                  25                  30

Arg Pro Asp Phe Ile Gln Phe Gly Glu Val Tyr Asn Asp Thr Pro Glu
        35                  40                  45

Ala Pro Ala Val Leu Ser Glu Phe Ser Thr Gly Met Pro Met Asp Thr
    50                  55                  60

Thr Leu Asp Phe Gly Phe Asn Ala Ala Arg His Phe Val Ser Gln
65                  70                  75                  80

Gln Arg Pro Ala Ala Glu Leu Ala Ala Phe Phe Arg Thr Asp Asp Leu
                85                  90                  95

Tyr Thr Asp His Asp Ser Asn Ile His Ala Thr Leu Thr Phe Val Asp
            100                 105                 110

Asn His Asp Thr Glu
            115

<210> SEQ ID NO 23
<211> LENGTH: 96
<212> TYPE: PRT
<213> ORGANISM: Bacillus stearothermophilus

<400> SEQUENCE: 23

Val Asp Gly Phe Arg Ile Asp Ala Val Lys His Ile Ala His Gly Asp
1               5                   10                  15

Leu Ala Gly Ile Leu Ser Arg Ala Gly Asn Pro Tyr Asn Phe Met Glu
            20                  25                  30

Val Ile Gly Ala Ala Gly Glu Pro Ile Gln Pro Ser Glu Tyr Thr Tyr
        35                  40                  45

Leu Gly Gln Val Thr Glu Phe Gly Tyr Ser Ser His Leu Gly His Arg
    50                  55                  60

Phe Lys Phe Gly Gln Ile Lys Asp Leu Arg Asn Ile Gly Asp Gly Lys
65                  70                  75                  80

Leu Pro Ser Asp Lys Ala Ile Val Phe Val Asp Asn His Asp Thr Glu
                85                  90                  95

<210> SEQ ID NO 24
<211> LENGTH: 96
<212> TYPE: PRT
<213> ORGANISM: Bacillus amyloliquefaciens

<400> SEQUENCE: 24

Val Asp Gly Phe Arg Ile Asp Thr Val Lys His Ile Ala His Gly Asp
1               5                   10                  15

Leu Ala Gly Ile Leu Ser Arg Ala Gly Asn Pro Tyr Asn Phe Met Glu
            20                  25                  30

Val Ile Gly Ala Ala Gly Glu Pro Ile Gln Pro Ser Glu Tyr Thr Tyr
        35                  40                  45

Leu Gly Gln Val Thr Glu Phe Gly Tyr Ser Ser His Leu Gly His Arg
    50                  55                  60

Phe Lys Phe Gly Gln Ile Lys Asp Leu Arg Asn Ile Gly Asp Gly Lys
65                  70                  75                  80

Leu Pro Ser Asp Lys Ala Met Val Tyr Val Asp Asn His Asp Thr Glu
                85                  90                  95
```

```
<210> SEQ ID NO 25
<211> LENGTH: 100
<212> TYPE: PRT
<213> ORGANISM: E.coli

<400> SEQUENCE: 25

Val Asp Gly Phe Arg Ile Asp Ala Ala Lys His Ile Ala Thr Glu Asp
1               5                   10                  15

Leu Ala Ala Val Lys Ala Lys Leu Ser Lys Pro Asp Val Tyr Trp Lys
            20                  25                  30

Gln Glu Thr Ile Tyr Ser Ala Gly Glu Ala Val Gln Pro Gln Glu Tyr
        35                  40                  45

Leu Gly Asn Gly Asp Val Gln Glu Phe Arg Tyr Ala Arg Asp Leu Lys
    50                  55                  60

Arg Val Phe Gln Ser Glu Arg Leu Ala Tyr Leu Lys Asn Tyr Gly Glu
65                  70                  75                  80

Gly Trp Gly Tyr Leu Pro Gly Asp Arg Ala Ser Val Tyr Val Asp Asn
                85                  90                  95

His Asp Thr Glu
            100

<210> SEQ ID NO 26
<211> LENGTH: 100
<212> TYPE: PRT
<213> ORGANISM: E.coli

<400> SEQUENCE: 26

Val Asp Gly Phe Arg Ile Asp Ala Ala Lys His Met Ala Ala Gly Asp
1               5                   10                  15

Leu Ala Asn Ile Lys Ser Arg Leu Thr Asn Pro Asn Val Tyr Trp Lys
            20                  25                  30

His Glu Ala Ile Tyr Gly Ala Gly Glu Ala Val Ser Pro Ala Glu Tyr
        35                  40                  45

Leu Gly Ser Gly Asp Val Gln Glu Phe Arg Tyr Ala Arg Asp Leu Lys
    50                  55                  60

Arg Val Phe Asn Asn Glu Asn Leu Ala Tyr Leu Lys Asn Phe Gly Glu
65                  70                  75                  80

Ser Trp Gly Tyr Leu Pro Ser Asp Gln Ala Ala Val Tyr Val Asp Asn
                85                  90                  95

His Asp Thr Glu
            100

<210> SEQ ID NO 27
<211> LENGTH: 100
<212> TYPE: PRT
<213> ORGANISM: B.stearothermophilus

<400> SEQUENCE: 27

Val Asp Gly Phe Arg Ile Asp Ala Ala Lys His Met Ala Ala Ser Asp
1               5                   10                  15

Leu Ala Asp Ile Lys Ser Arg Leu Ser Asn Pro Ser Val Tyr Trp Lys
            20                  25                  30

Gln Glu Ala Ile Phe Gly Ala Gly Glu Ala Val Ser Pro Ser Glu Tyr
        35                  40                  45

Leu Gly Asn Gly Asp Val Gln Glu Phe Arg Tyr Ala Arg Asp Leu Lys
    50                  55                  60

Arg Val Phe Asn Asn Glu Asn Leu Ala Tyr Leu Lys Asn Tyr Gly Glu
```

```
                65                  70                  75                  80
Gly Trp Gly Tyr Met Ser Ser Gly Ser Ser Ala Val Tyr Val Asp Asn
                    85                  90                  95

His Asp Thr Glu
            100

<210> SEQ ID NO 28
<211> LENGTH: 100
<212> TYPE: PRT
<213> ORGANISM: B.stearothermophilus

<400> SEQUENCE: 28

Val Asp Gly Phe Arg Ile Asp Thr Ala Lys His Met Ala Ala Gly Asp
1               5                  10                  15

Leu Ala Asn Ile Lys Ser Arg Leu Thr Asn Pro Asn Val Tyr Trp Lys
                20                  25                  30

His Glu Ala Ile Tyr Gly Ala Gly Glu Ala Val Ser Pro Ala Glu Tyr
            35                  40                  45

Leu Gly Ser Gly Asp Val Gln Glu Phe Arg Tyr Ala Arg Asp Leu Lys
        50                  55                  60

Arg Val Phe Asn Asn Glu Asn Leu Ala Tyr Leu Lys Asn Phe Gly Glu
65                  70                  75                  80

Ser Trp Gly Tyr Leu Pro Ser Asp Gln Ala Ala Val Tyr Val Asp Asn
                    85                  90                  95

His Asp Thr Glu
            100

<210> SEQ ID NO 29
<211> LENGTH: 100
<212> TYPE: PRT
<213> ORGANISM: B.stearothermophilus

<400> SEQUENCE: 29

Val Asp Gly Phe Arg Ile Asp Thr Ala Lys His Met Pro Ala Ala Asp
1               5                  10                  15

Leu Ala Asn Ile Lys Ser Arg Leu Thr Asn Pro Ser Ala Tyr Trp Lys
                20                  25                  30

Gln Glu Val Ile Tyr Gly Ala Asp Glu Ala Val Gln Pro Gly Glu Tyr
            35                  40                  45

Thr Gly Thr Gly Asp Val Gln Glu Phe Arg Tyr Ala Tyr Asp Leu Lys
        50                  55                  60

Arg Val Phe Asn Asn Glu Asn Leu Ala Tyr Leu Lys Asn Tyr Gly Glu
65                  70                  75                  80

Gly Trp Gly Tyr Leu Lys Ser Ser Ala Gly Val Tyr Val Asp Asn
                    85                  90                  95

His Asp Thr Glu
            100

<210> SEQ ID NO 30
<211> LENGTH: 100
<212> TYPE: PRT
<213> ORGANISM: B.stearothermophilus

<400> SEQUENCE: 30

Val Asp Gly Phe Arg Ile Asp Ala Ala Lys His Met Pro Ala Ala Asp
1               5                  10                  15

Leu Ala Asn Ile Lys Ser Arg Leu Thr Asp Pro Gly Ala Tyr Trp Lys
                20                  25                  30
```

```
Gln Glu Ala Ile His Gly Ala Gly Glu Ala Val Ser Pro Ser Glu Tyr
        35                  40                  45

Leu Gly Ser Gly Asp Val Gln Glu Phe Arg Tyr Ala Arg Asp Leu Lys
    50                  55                  60

Arg Val Leu Gln Asn Glu Lys Leu Ala Tyr Leu Lys Asn Phe Gly Glu
65                  70                  75                  80

Ala Trp Gly His Met Pro Ser Gly Arg Ala Gly Val Phe Val Asp Asn
                85                  90                  95

His Asp Thr Glu
            100

<210> SEQ ID NO 31
<211> LENGTH: 107
<212> TYPE: PRT
<213> ORGANISM: B.stearothermophilus

<400> SEQUENCE: 31

Val Asp Gly Phe Arg Ile Asp Ala Val Lys His Ile Arg Asn Thr Tyr
1               5                   10                  15

Phe Ala His Trp Leu Gly Lys Leu Arg Ala Glu Asn Pro Gly Arg Glu
                20                  25                  30

Leu Phe Ala Val Gly Glu Tyr Trp Ser Asp Lys Val Gln Leu Leu His
            35                  40                  45

Asp Tyr Leu Thr Ala Ser Gly Ser Ala Met Ser Leu Phe Asp Val Pro
    50                  55                  60

Leu His Tyr Lys Phe Tyr Gln Ala Ser Arg Asn Gly Gly Gly Phe Asp
65                  70                  75                  80

Met Gly Ser Ile Leu Gln Arg Thr Leu Met Lys Glu Gln Pro Ala Arg
                85                  90                  95

Ala Val Thr Tyr Val Asp Asn His Asp Thr Glu
            100                 105

<210> SEQ ID NO 32
<211> LENGTH: 100
<212> TYPE: PRT
<213> ORGANISM: Streptomyces limosus

<400> SEQUENCE: 32

Val Asp Gly Phe Arg Ile Asp Ala Ala Lys His Ile Pro Ala Ala Asp
1               5                   10                  15

Leu Ala Asn Ile Lys Ser Arg Leu Thr Asn Pro Ser Val Tyr Trp Lys
                20                  25                  30

Gln Glu Val Ile Tyr Gly Ala Gly Glu Ala Val Gln Pro Thr Glu Tyr
        35                  40                  45

Thr Gly Asn Gly Asp Val Gln Glu Phe Arg Tyr Ala Tyr Asp Leu Lys
    50                  55                  60

Arg Val Phe Asn Asn Glu Asn Leu Ala Tyr Leu Lys Asn Tyr Gly Glu
65                  70                  75                  80

Gly Trp Gly Tyr Met Ser Ser Ser Val Ala Gly Val Phe Val Asp Asn
                85                  90                  95

His Asp Thr Glu
            100

<210> SEQ ID NO 33
<211> LENGTH: 107
<212> TYPE: PRT
<213> ORGANISM: Streptomyces venezuelae
```

-continued

```
<400> SEQUENCE: 33

Val Asp Gly Phe Arg Ile Asp Ala Val Lys His Ile Pro Ala Ser Phe
1               5                   10                  15

Phe Glu Asp Trp Phe Asn His Leu Arg Thr His Phe Gly Gly Glu Glu
                20                  25                  30

Leu Phe Gly Val Gly Glu Tyr Trp Ser Gly Asn Leu Asp Glu Leu Asn
            35                  40                  45

Lys Tyr Leu Ala Asp Thr Ala Gly Val Met Lys Leu Phe Asp Val Pro
    50                  55                  60

Leu His Phe Asn Leu Met Asn Ala Ser Arg Gly Gly Arg Asp Tyr Asp
65                  70                  75                  80

Leu Ser Lys Val Phe Asp Gly Thr Leu Val Arg Gly Asn Pro Gln Met
                85                  90                  95

Ala Val Thr Tyr Val Asp Asn His Asp Thr Glu
            100                 105

<210> SEQ ID NO 34
<211> LENGTH: 107
<212> TYPE: PRT
<213> ORGANISM: Streptomyces venezuelae

<400> SEQUENCE: 34

Val Asp Gly Phe Arg Ile Asp Ala Val Lys His Ile Pro Ala Ser Phe
1               5                   10                  15

Tyr Lys Asp Trp Phe Cys His Leu Arg Glu Lys Phe Pro Asp Arg Glu
                20                  25                  30

Leu Phe Gly Val Ala Glu Tyr Trp Ser Gly Ser Leu Asp Glu Leu Lys
            35                  40                  45

Gly Tyr Leu Ala Ala Thr Asp Gly Val Val Arg Leu Phe Asp Val Pro
    50                  55                  60

Leu His Tyr Arg Leu Met Glu Ala Ser Arg Arg Gly Arg Asp Phe Asp
65                  70                  75                  80

Leu Ser Lys Ile Phe Asp Gly Thr Leu Val Gln Asp Asn Pro Leu Met
                85                  90                  95

Ala Val Thr Phe Val Asp Asn His Asp Thr Glu
            100                 105

<210> SEQ ID NO 35
<211> LENGTH: 100
<212> TYPE: PRT
<213> ORGANISM: Streptomyces albus

<400> SEQUENCE: 35

Val Asp Gly Phe Arg Ile Asp Ala Ala Lys His Ile Pro Ala Ala Asp
1               5                   10                  15

Leu Ala Asn Ile Lys Ser Arg Leu Ser Asn Pro Gly Val Tyr Trp Lys
                20                  25                  30

His Glu Val Ile Tyr Gly Ala Gly Glu Ala Val Gln Pro Thr Glu Tyr
            35                  40                  45

Thr Gly Ser Gly Asp Val Gln Glu Phe Arg Tyr Ala Tyr Asp Leu Lys
    50                  55                  60

Arg Val Phe Thr Asn Glu Asn Leu Ala Tyr Leu Lys Asn Tyr Gly Glu
65                  70                  75                  80

Gly Trp Gly Tyr Leu Asn Ser Gly Val Ser Gly Val Phe Val Asp Asn
                85                  90                  95
```

-continued

```
His Asp Thr Glu
            100

<210> SEQ ID NO 36
<211> LENGTH: 100
<212> TYPE: PRT
<213> ORGANISM: Streptomyces albus

<400> SEQUENCE: 36

Val Asp Gly Phe Arg Ile Asp Ala Ala Lys His Ile Pro Ala Ala Asp
1               5                   10                  15

Leu Ala Asn Ile Lys Ser Arg Leu Thr Asn Pro Ser Val Tyr Trp Lys
            20                  25                  30

Gln Glu Val Ile Tyr Gly Ala Gly Glu Ala Val Gln Pro Thr Glu Tyr
        35                  40                  45

Thr Gly Asn Gly Asp Val Gln Glu Phe Arg Tyr Ala Tyr Asp Leu Lys
    50                  55                  60

Arg Val Phe Asn Asn Glu Asn Leu Ala Tyr Leu Lys Asn Tyr Gly Glu
65                  70                  75                  80

Gly Trp Gly Tyr Met Ser Ser Ser Val Ala Gly Val Tyr Val Asp Asn
                85                  90                  95

His Asp Thr Glu
            100

<210> SEQ ID NO 37
<211> LENGTH: 100
<212> TYPE: PRT
<213> ORGANISM: Bacillus sp. MK716

<400> SEQUENCE: 37

Val Asp Gly Phe Arg Ile Asp Thr Thr Lys His Met Pro Ala Ala Asp
1               5                   10                  15

Leu Ala Asn Ile Lys Ser Arg Leu Thr Asp Pro Gly Val Tyr Trp Lys
            20                  25                  30

Gln Glu Val Ile Phe Gly Ala Gly Glu Ala Val Gln Pro Thr Glu Tyr
        35                  40                  45

Ile Gly Asn Gly Asp Val Gln Glu Phe Arg Tyr Ala Tyr Asp Leu Lys
    50                  55                  60

Arg Val Phe Asn Asn Glu Asn Leu Ala Tyr Leu Lys Asn Tyr Gly Glu
65                  70                  75                  80

Gly Trp Gly Tyr Leu Lys Ser Ser Ser Ala Gly Val Tyr Val Asp Asn
                85                  90                  95

His Asp Thr Glu
            100

<210> SEQ ID NO 38
<211> LENGTH: 100
<212> TYPE: PRT
<213> ORGANISM: Bacillus sp. MK717
<220> FEATURE:
<221> NAME/KEY: misc_feature
<222> LOCATION: (9)..(9)
<223> OTHER INFORMATION: Xaa can be any naturally occurring amino acid

<400> SEQUENCE: 38

Val Asp Gly Phe Arg Ile Asp Ala Xaa Lys His Ile Pro Ala Ala Asp
1               5                   10                  15

Leu Ala Asn Ile Lys Ser Arg Leu Thr Asn Pro Ser Val Tyr Trp Lys
            20                  25                  30
```

```
Gln Glu Val Ile Tyr Gly Ala Gly Glu Ala Val Arg Pro Thr Glu Tyr
        35                  40                  45

Thr Gly Asn Gly Asp Val Gln Glu Phe Arg Tyr Ala Tyr Asp Leu Lys
    50                  55                  60

Arg Val Phe Asn Asn Glu Asn Leu Ala Tyr Leu Lys Asn Tyr Gly Glu
65                  70                  75                  80

Gly Trp Gly Tyr Met Ser Ser Val Ala Gly Val Tyr Val Asp Asn
                85                  90                  95

His Asp Thr Glu
            100

<210> SEQ ID NO 39
<211> LENGTH: 100
<212> TYPE: PRT
<213> ORGANISM: Bacillus sp. MK718

<400> SEQUENCE: 39

Val Asp Gly Phe Arg Ile Asp Ala Ala Lys His Met Pro Ala Ala Asp
1               5                   10                  15

Leu Ala Asn Ile Lys Ser Arg Leu Gly Asp Pro Asn Val Tyr Trp Lys
                20                  25                  30

Gln Glu Ala Ile Tyr Gly Ala Gly Glu Ala Val Ser Pro Asp Glu Tyr
            35                  40                  45

Ala Gly Thr Gly Asp Val Gln Glu Phe Arg Tyr Ala Arg Gly Leu Lys
        50                  55                  60

Gln Val Phe Asn Asn Glu Asn Leu Ala Tyr Leu Lys Asn Tyr Gly Glu
65                  70                  75                  80

Gly Trp Gly Phe Met Pro Ser Ser Lys Ala Ala Val Phe Val Asp Asn
                85                  90                  95

His Asp Thr Glu
            100

<210> SEQ ID NO 40
<211> LENGTH: 100
<212> TYPE: PRT
<213> ORGANISM: Bacillus licheniformis

<400> SEQUENCE: 40

Val Asp Gly Phe Arg Ile Asp Ala Ala Lys His Ile Pro Ala Ala Asp
1               5                   10                  15

Leu Ala Asn Ile Lys Ser Arg Leu Thr Asn Pro Ser Val Tyr Trp Lys
                20                  25                  30

Gln Glu Val Ile Tyr Gly Ala Gly Glu Ala Val Gln Pro Thr Glu Tyr
            35                  40                  45

Thr Gly Asn Gly Asp Val Gln Glu Phe Arg Tyr Ala Tyr Asp Leu Lys
        50                  55                  60

Arg Val Phe Asn Asn Glu Asn Pro Ala Tyr Leu Lys Asn Tyr Gly Glu
65                  70                  75                  80

Gly Trp Gly Tyr Met Ser Ser Ser Val Ala Gly Val Tyr Val Asp Asn
                85                  90                  95

His Asp Thr Glu
            100

<210> SEQ ID NO 41
<211> LENGTH: 111
<212> TYPE: PRT
<213> ORGANISM: Streptomyces griseus
```

```
<400> SEQUENCE: 41

Val Asp Gly Phe Arg Ile Asp Ala Thr Lys His Ile Thr Ser Thr Phe
1               5                   10                  15

Phe Asn Glu Trp Leu Tyr His Val Arg Gln Ala Thr Gly Lys Pro Asn
            20                  25                  30

Ala Phe Ala Val Ser Glu Tyr Trp Glu Arg Asp Ile Asn Ala Leu Asn
        35                  40                  45

Asn Tyr Val Asn Ser Val Asn Ser Thr Ala Ser Asp Lys Met Ser Ala
50                  55                  60

Phe Asp Val Pro Leu His Ala Lys Phe Glu Gln Ala Ala Asn Ala Asn
65                  70                  75                  80

Gly Met Phe Asp Met Gly Ser Leu Leu Thr Asn Thr Leu Val Ala Trp
                85                  90                  95

Gln Pro Ala Arg Ala Ala Thr Tyr Val Asp Asn His Asp Thr Glu
            100                 105                 110

<210> SEQ ID NO 42
<211> LENGTH: 107
<212> TYPE: PRT
<213> ORGANISM: Streptomyces griseus

<400> SEQUENCE: 42

Val Asp Gly Phe Arg Ile Asp Ala Leu Lys His Leu Pro Ala Ser Phe
1               5                   10                  15

Ile Lys Asp Trp Leu Asn Ala Leu Arg Thr His Phe Ser Gly Arg Glu
            20                  25                  30

Leu Phe Ala Val Gly Glu Tyr Trp Ser Ala Asp Val Asn Glu Leu His
        35                  40                  45

Gly Tyr Leu Ser Lys Val Glu Gly Ala Thr Arg Leu Phe Asp Val Pro
50                  55                  60

Leu His Phe Arg Phe Leu Glu Ala Ser Lys Gln Gly Glu Ser Phe Asp
65                  70                  75                  80

Leu Thr Thr Ile Phe Ala Gly Ser Leu Val Ala Glu Asn Pro Leu Ser
                85                  90                  95

Ala Val Thr Tyr Val Asp Asn His Asp Thr Glu
            100                 105

<210> SEQ ID NO 43
<211> LENGTH: 107
<212> TYPE: PRT
<213> ORGANISM: Streptomyces griseus

<400> SEQUENCE: 43

Val Asp Gly Phe Arg Ile Asp Thr Ile Lys His Ile Pro Ala Ser Phe
1               5                   10                  15

Tyr Arg Glu Trp Phe Asp His Val Arg Gly Ala Phe Pro Ala Arg Glu
            20                  25                  30

Leu Phe Gly Val Gly Glu Tyr Trp Ser Gly Asp Val Asn Glu Leu Asp
        35                  40                  45

Gly Tyr Leu Ala Ala Thr Gly Gly Val Met Arg Leu Phe Asp Val Pro
50                  55                  60

Leu His Phe Arg Leu His Glu Ala Ser Lys Lys Gly Arg Asp Phe Asp
65                  70                  75                  80

Leu Ser Lys Leu Phe Asp Gly Thr Leu Val Gln Arg Asn Pro Leu Met
                85                  90                  95

Ala Val Thr Tyr Val Asp Asn His Asp Thr Glu
```

```
            100                 105

<210> SEQ ID NO 44
<211> LENGTH: 107
<212> TYPE: PRT
<213> ORGANISM: Streptomyces griseus

<400> SEQUENCE: 44

Val Asp Gly Phe Arg Ile Asp Thr Ile Lys His Ile Pro Ala Ser Phe
1               5                   10                  15

Phe Lys Asp Trp Leu Thr His Val Arg Ser Thr Phe Lys His Arg Glu
            20                  25                  30

Leu Phe Ala Val Gly Glu Tyr Trp Ser Gly Ser Leu Asp Glu Leu Lys
        35                  40                  45

Gly Tyr Leu Ala Ala Val Asp Gly Ala Met Arg Leu Phe Asp Val Pro
    50                  55                  60

Leu His Phe Asn Phe Arg Asp Ala Ala Gln Gln Gly Lys Ser Phe Asp
65                  70                  75                  80

Leu Ser Lys Ile Phe Asp Gly Ser Leu Val Gln Asp Asn Pro Leu Met
                85                  90                  95

Ala Val Thr Tyr Val Asp Asn His Asp Thr Glu
            100                 105

<210> SEQ ID NO 45
<211> LENGTH: 101
<212> TYPE: PRT
<213> ORGANISM: Streptomyces griseus

<400> SEQUENCE: 45

Val Asp Gly Phe Arg Ile Asp Ala Ala Glu His Ile Asp Ala Ala Asp
1               5                   10                  15

Leu Ser Ala Val Val Ala Gly Leu His Thr Thr Thr Ser Gly Ala Ala
            20                  25                  30

Pro Tyr Ile Thr Gln Glu Ile Tyr Pro Gly Thr Pro Pro Ala Gln Asp
        35                  40                  45

Glu Tyr Tyr Gly Thr Gly Asp Val Leu Asp Phe Thr Phe Ala Ala Gln
    50                  55                  60

Val Lys Ser Gln Phe Gln Gly Asp Ile Ala Asn Leu Ser Ser Phe Gly
65                  70                  75                  80

Ser Ser Trp Gly Leu Thr Thr Glu Ala Asn Ser Asn Thr Tyr Val Asp
                85                  90                  95

Asn His Asp Thr Glu
            100

<210> SEQ ID NO 46
<211> LENGTH: 101
<212> TYPE: PRT
<213> ORGANISM: Anabaena variabilis

<400> SEQUENCE: 46

Val Asp Gly Phe Arg Ile Asp Ala Ala Lys His Ile Asp Ala Ala Asp
1               5                   10                  15

Leu Ser Ala Val Val Ala Gly Leu His Thr Thr Thr Ser Gly Ala Ala
            20                  25                  30

Pro Tyr Ile Thr Gln Glu Ile Tyr Pro Gly Thr Pro Pro Ala Gln Asp
        35                  40                  45

Glu Tyr Tyr Gly Thr Gly Asp Val Leu Asp Phe Thr Phe Ala Ala Gln
    50                  55                  60
```

```
Val Lys Ser Gln Phe Gln Gly Asp Ile Ala Asn Leu Ser Ser Phe Gly
 65                  70                  75                  80

Ser Ser Trp Gly Leu Thr Thr Glu Ala Asn Ser Asn Thr Phe Val Asp
                 85                  90                  95

Asn His Asp Thr Glu
                100

<210> SEQ ID NO 47
<211> LENGTH: 100
<212> TYPE: PRT
<213> ORGANISM: Streptomyces lividans

<400> SEQUENCE: 47

Val Asp Gly Phe Arg Ile Asp Ala Ala Lys His Ile Pro Ala Ala Asp
 1               5                  10                  15

Leu Ala Asn Ile Lys Ser Arg Leu Thr Asn Pro Ser Val Tyr Trp Lys
                 20                  25                  30

Gln Glu Val Ile Tyr Gly Ala Gly Glu Ala Val Gln Pro Thr Glu Tyr
             35                  40                  45

Thr Gly Asp Gly Asp Val Gln Glu Phe Arg Tyr Ala Tyr Asp Leu Lys
     50                  55                  60

Arg Val Phe Asn Asn Glu Asn Leu Ala Tyr Leu Lys Asn Tyr Gly Glu
 65                  70                  75                  80

Gly Trp Gly Tyr Met Ser Ser Val Ala Gly Val Tyr Val Asp Asn
                 85                  90                  95

His Asp Thr Glu
                100

<210> SEQ ID NO 48
<211> LENGTH: 100
<212> TYPE: PRT
<213> ORGANISM: Streptomyces lividans

<400> SEQUENCE: 48

Val Asp Gly Phe Arg Ile Asp Ala Ala Lys His Met Pro Ala Gly Asp
 1               5                  10                  15

Leu Ala Asn Ile Lys Ser Arg Leu Ser Asn Pro Asn Val Tyr Trp Lys
                 20                  25                  30

His Glu Ala Ile Phe Gly Ala Gly Glu Ala Val Ser Pro Ser Glu Tyr
             35                  40                  45

Leu Gly Ser Gly Asp Val Gln Glu Phe Arg Tyr Gly Arg Ser Leu Lys
     50                  55                  60

Gln Val Phe Asn Asn Glu Asn Leu Ala Asn Leu Lys Asn Phe Gly Glu
 65                  70                  75                  80

Gly Trp Gly Phe Met Glu Ser Gly Lys Ser Ala Val Tyr Val Asp Asn
                 85                  90                  95

His Asp Thr Glu
                100

<210> SEQ ID NO 49
<211> LENGTH: 107
<212> TYPE: PRT
<213> ORGANISM: Streptomyces sp.

<400> SEQUENCE: 49

Val Asp Gly Phe Arg Ile Asp Ala Leu Lys His Leu Pro Ala Gly Phe
 1               5                  10                  15
```

```
Ile Lys Asp Trp Leu Ser Ala Met Arg Thr His Phe Ser Gly Arg Glu
            20                  25                  30

Leu Phe Ala Val Gly Glu Tyr Trp Ser Ala Asp Val Asn Glu Leu His
        35                  40                  45

Ser Tyr Leu Thr Lys Val Glu Gly Thr Gln Leu Phe Asp Val Pro
50                  55                  60

Leu His Phe Arg Phe Leu Glu Ala Ser Ser Gln Gly Glu Ser Phe Asp
65                  70                  75                  80

Leu Thr Lys Ile Phe Glu Gly Ser Leu Val Ala Glu Asn Pro Leu Val
                85                  90                  95

Ala Val Thr Phe Val Asp Asn His Asp Thr Glu
                100                 105

<210> SEQ ID NO 50
<211> LENGTH: 99
<212> TYPE: PRT
<213> ORGANISM: Streptomyces sp.

<400> SEQUENCE: 50

Val Asp Gly Phe Arg Ile Asp Thr Ser Lys His Met Pro Ala Ala Asp
1               5                   10                  15

Ile Ala Ile Lys Ala Lys Leu Asn Gly Ala Pro Tyr Leu Val Gln
            20                  25                  30

Glu Val Ile Tyr Gly Ala Gly Glu Pro Ile His Pro Asn Glu Tyr Thr
            35                  40                  45

Gly Asn Gly Asp Val His Glu Phe Arg Tyr Gly Lys Asp Leu Ser Arg
        50                  55                  60

Val Phe Arg His Glu Lys Leu Ala Tyr Leu Ala Asn Phe Gly Glu Gly
65                  70                  75                  80

Trp Gly His Ile Ser Ser Ala Lys Ala Val Ala Tyr Val Asp Asn His
                85                  90                  95

Asp Thr Glu

<210> SEQ ID NO 51
<211> LENGTH: 107
<212> TYPE: PRT
<213> ORGANISM: Streptomyces sp.

<400> SEQUENCE: 51

Val Asp Gly Phe Arg Ile Asp Ala Val Lys His Val Arg Ser Ser Phe
1               5                   10                  15

Phe Arg Asp Trp Met Asn His Leu Arg Val His Phe Gly Gly Arg Glu
            20                  25                  30

Leu Phe Ala Val Gly Glu His Trp Ser Ala His Ala Ala Asp Leu His
        35                  40                  45

Arg Tyr Ile Thr Ala Thr Glu Gly Val Met Ser Leu Phe Asp Val Ala
50                  55                  60

Leu His Tyr Arg Phe Arg Glu Ala Ser Leu Ser Gly Asn Ser Tyr Asp
65                  70                  75                  80

Met Arg Thr Ile Leu Asp Gly Thr Leu Val Gly Gln Gln Pro Ala Lys
                85                  90                  95

Ala Val Thr Tyr Val Asp Asn His Asp Thr Glu
                100                 105

<210> SEQ ID NO 52
<211> LENGTH: 107
<212> TYPE: PRT
```

<213> ORGANISM: Streptomyces

<400> SEQUENCE: 52

Val Asp Gly Phe Arg Ile Asp Thr Val Lys His Ile Arg Arg Tyr
1               5                   10                  15

Phe Cys Asp Trp Leu Asn His Leu Arg Thr His Phe Gly Gly Arg Glu
                20                  25                  30

Leu Phe Ala Val Gly Glu Tyr Trp Ser Gly Asp Val Asn Glu Leu His
            35                  40                  45

Arg Tyr Leu Asp Ala Thr Glu Asn Thr Leu Ser Val Phe Asp Val Pro
    50                  55                  60

Leu His Tyr Asn Phe Ala Ala Ser His Ala Gly Arg Asp Tyr Asp
65                  70                  75                  80

Leu Arg Arg Ile Phe Asp Asn Thr Leu Val Ala Gln Arg Pro Thr Lys
                85                  90                  95

Ala Val Thr Phe Val Asp Asn His Asp Thr Glu
            100                 105

<210> SEQ ID NO 53
<211> LENGTH: 100
<212> TYPE: PRT
<213> ORGANISM: Streptomyces sp.

<400> SEQUENCE: 53

Val Asp Gly Phe Arg Ile Asp Thr Ala Lys His Met Ala Ala Ser Asp
1               5                   10                  15

Leu Ala Asn Ile Lys Ser Arg Leu Ser Asn Pro Asn Ala Tyr Trp Lys
                20                  25                  30

Gln Glu Ala Ile Phe Gly Ala Gly Glu Ala Val Ser Pro Ser Glu Tyr
            35                  40                  45

Leu Gly Asn Gly Asp Val Gln Glu Phe Arg Tyr Ala Arg Asp Leu Lys
    50                  55                  60

Arg Val Phe Asn Asn Glu Asn Leu Ala Tyr Leu Lys Asn Tyr Gly Glu
65                  70                  75                  80

Gly Trp Gly Tyr Met Ser Ser Gly Ser Ser Ala Val Tyr Val Asp Asn
                85                  90                  95

His Asp Thr Glu
            100

<210> SEQ ID NO 54
<211> LENGTH: 109
<212> TYPE: PRT
<213> ORGANISM: Streptomyces

<400> SEQUENCE: 54

Val Asp Gly Phe Arg Ile Asp Ala Gly Lys His Ile His Pro Pro Phe
1               5                   10                  15

Leu Ser Arg Trp Phe Gln Glu Val Lys Gly Thr Ser Arg Phe Ala Val
                20                  25                  30

Thr Glu Phe Tyr Asp Gly Asn Pro Ala His Leu Ala Thr Val Ile Asp
            35                  40                  45

Leu Tyr Ala Arg Gln Ser His Leu Phe Asp Phe Ala Leu His Phe Leu
    50                  55                  60

Leu Gln Arg Met Ser Ala Gly Asn Gly Gly Phe Asp Met Arg Ser Leu
65                  70                  75                  80

Arg Phe Gly Ser Ser Asp Asp Gly Ser Arg Phe Leu Glu Gln His Pro
                85                  90                  95

```
Ala Phe Ala Val Thr Tyr Val Asp Asn His Asp Thr Glu
            100                 105
```

<210> SEQ ID NO 55
<211> LENGTH: 107
<212> TYPE: PRT
<213> ORGANISM: Streptomyces

<400> SEQUENCE: 55

```
Val Asp Gly Phe Arg Ile Asp Ala Val Lys His Val Pro Ala Ser Phe
1               5                   10                  15

Tyr Lys Trp Trp Leu Asp Glu Met Arg Gln Asn Tyr Pro Ser Arg Glu
            20                  25                  30

Leu Phe Ala Val Gly Glu Tyr Trp Ser Gly Asn Met Gly Glu Leu His
            35                  40                  45

Gly Tyr Leu Ala Ala Thr Asp Gly Ala Met Lys Leu Phe Asp Val Pro
        50                  55                  60

Leu His Tyr Lys Phe Met Glu Ala Ser Gln Lys Gly Arg Glu Phe Asp
65                  70                  75                  80

Leu Pro Thr Ile Phe Asp Gly Thr Leu Val Lys Glu Asn Pro Leu Met
                85                  90                  95

Ala Val Thr Phe Val Asp Asn His Asp Thr Glu
            100                 105
```

<210> SEQ ID NO 56
<211> LENGTH: 109
<212> TYPE: PRT
<213> ORGANISM: Streptomyces sp.

<400> SEQUENCE: 56

```
Val Asp Gly Phe Arg Ile Asp Ala Gly Lys His Ile His Pro Pro Phe
1               5                   10                  15

Leu Ser Arg Trp Phe Gln Glu Val Lys Gly Thr Ser Arg Phe Ala Val
            20                  25                  30

Thr Glu Phe Tyr Asp Gly Asn Pro Ala His Leu Ala Thr Val Ile Asp
            35                  40                  45

Leu Tyr Ala Arg Gln Ser His Leu Phe Asp Phe Ala Leu His Phe Leu
        50                  55                  60

Leu Gln Arg Met Ser Ala Gly Asn Gly Gly Ser Asp Met Arg Asn Leu
65                  70                  75                  80

Arg Phe Gly Ser Ser Asp Asp Gly Ser Arg Phe Leu Glu Gln His Pro
                85                  90                  95

Ala Phe Ala Val Thr Phe Val Asp Asn His Asp Thr Glu
            100                 105
```

<210> SEQ ID NO 57
<211> LENGTH: 302
<212> TYPE: DNA
<213> ORGANISM: Bacillus amyloliquefaciens

<400> SEQUENCE: 57

```
cgtcgacggc ttccggatcg acgccgccaa gcacatcgcg accgaggacc tcgccgccgt      60
caaggccaag ctgagcaagc cggacgtcta ctggaagcag agaccatct acagcgccgg      120 cgaagccgtt cagccgcagg agtacctggg caacggcgac gtccaggagt tccgctacgc      180
gcgcgacctc aagcgcgtct tccagagcga cggctggcc tacctgaaga actacgcga       240 gggctggggc tacctgcccg cgaccgggc gtccgtctac ggtgacaacc acgacaccga      300
```

```
gc                                                                        302

<210> SEQ ID NO 58
<211> LENGTH: 302
<212> TYPE: DNA
<213> ORGANISM: Lactococcus lactis

<400> SEQUENCE: 58
cgtcgacggc ttccggatcg acgcggccaa gcacatggcc gccggcgacc tcgccaacat         60
caagtcccgg ctcaccaatc cgaacgtgta ctggaagcac gaggcgatct acggcgccgg        120
cgaggccgtc tccccggccg agtacctcgg cagcggcgac gtacaggagt tccgctacgc        180
ccgcgacctc aagcgcgtct tcaacaacga gaacctcgcc tacctgaaga acttcggcga        240
gtcctggggc tacctgccct cggaccaggc cgccgtctac gtggacaacc acgacaccga        300
gc                                                                       302

<210> SEQ ID NO 59
<211> LENGTH: 302
<212> TYPE: DNA
<213> ORGANISM: Pseudomonas sp.

<400> SEQUENCE: 59
cgtcgacggc ttccgcatcg acgccgccaa gcacatggcc gcctctgacc tggccgacat         60
caagtcccgg ctgagcaacc cgagcgtcta ctggaagcag gaggccatct tcggcgcggg        120
ggaggcggtc tcgcccagcg aatacctggg caacggcgac gtccaggagt tccgctacgc        180
ccgtgacctg aagcgggtct tcaacaacga gaacctcgcc tacctgaaga actacggcga        240
aggttggggc tacatgtcct cgggcagctc ggccgtctac gtcgacaacc acgacaccga        300
gc                                                                       302

<210> SEQ ID NO 60
<211> LENGTH: 302
<212> TYPE: DNA
<213> ORGANISM: Pseudomonas sp.

<400> SEQUENCE: 60
gctcggtgtc gtggttgtcc acgtagacgg cggcctggtc cgagggcagg tagccccagg         60
actcgccgaa gttcttcagg taggcgaggt tctcgttgtt gaagacgcgc ttgaggtcgc        120
gggcgtagcg gaactcctgt acgtcgccgc tgccgaggta ctcggccggg gagacggcct        180
cgccggcgcc gtagatcgcc tcgtgcttcc agtacacgtt cggattggtg agccgggact        240
tgatgttggc gaggtcgccg gcggccatgt gcttggccgt gtcgatgcgg aagccgtcga        300
cg                                                                       302

<210> SEQ ID NO 61
<211> LENGTH: 302
<212> TYPE: DNA
<213> ORGANISM: Pseudomonas sp.

<400> SEQUENCE: 61
cgtcgacggc ttccggatcg acacggccaa gcacatgccc gccgccgacc tggcgaacat         60
caagtcccgg ctgaccaacc cgtccgccta ctggaagcag gaggtcatct acggcgcgga        120
cgaggccgtc cagcccggcg agtacaccgg caccggcgac gtccaggagt tccgctacgc        180
ctacgacctc aagcgggtct tcaacaacga gaacctcgcc tacctgaaga actacggtga        240
```

```
gggctggggc tacctcaaga gctccagcgc cggcgtctac gtcgacaacc acgacaccga    300
gc                                                                  302

<210> SEQ ID NO 62
<211> LENGTH: 302
<212> TYPE: DNA
<213> ORGANISM: Pseudomonas sp.

<400> SEQUENCE: 62
cgtcgacggc ttccgcatcg acgccgccaa gcacatgccg ccgccgacc tcgcgaacat     60 caagtcgcgg ctcaccgacc ccggcgcgta ctggaagcag gaggccatcc acggcgccgg   120
cgaggccgtc tcaccgagcg agtacctcgg cagcggcgac gtgcaggagt tccgctacgc   180 ccgcgaccte aagcgcgtcc tgcagaacga gaagctggcg tacctgaaga acttcggcga   240
ggcctggggc cacatgccct ccggccgggc cggcgtcttc gtcgacaacc acgacaccga   300
gc                                                                  302

<210> SEQ ID NO 63
<211> LENGTH: 323
<212> TYPE: DNA
<213> ORGANISM: Pseudomonas sp.

<400> SEQUENCE: 63
cgtcgacggc ttccggatcg acgcggtgaa gcacatccgc aacacctact cgcccactg     60 gctcggcaag ctccgcgccg agaatcccgg gcgcgagctg ttcgcggtgg gggagtattg   120
gtccgacaag gttcaactgc tgcacgacta cctgaccgcc agcgggagcg cgatgtcgct   180
cttcgacgtg ccgctgcact acaagttcta ccaggcgagt cgcaacggcg gcgggttcga   240
catggggtcg atcctccagc gcacgttgat gaaggagcag cccgcgcggg cggtcacgta   300
cgtcgacaac cacgacaccg agc                                           323

<210> SEQ ID NO 64
<211> LENGTH: 302
<212> TYPE: DNA
<213> ORGANISM: Diabrotica virgifera

<400> SEQUENCE: 64
cgtcgacggc ttccggatcg acgcggccaa gcacatcccg gcggccgacc tcgccaacat    60
caagtcgcgg ctgaccaatc cgtcggtgta ctggaagcag gaggtcatct acggcgccgg   120
ggaggcggtc cagccgaccg agtacaccgg caacggcgac gtccaggagt tccggtacgc   180
ctacgacctc aagcgggtct tcaacaacga gaacctcgcc tacctcaaga actacggcga   240
gggctggggc tatatgagca gctccgtcgc ggggtcttc gtcgacaacc acgacaccga    300
gc                                                                  302

<210> SEQ ID NO 65
<211> LENGTH: 323
<212> TYPE: DNA
<213> ORGANISM: Streptomyces coelicolor

<400> SEQUENCE: 65
cgtcgacggc ttccgcatcg acgccgtcaa gcatatcccc gcgagttttt ttgaagactg    60
gttcaaccac cttcgcaccc atttcggcgg cgaagagctg ttcggcgtcg gtgagtattg   120
gagcgggaac ctcgacgagt tgaataaata tcttgccgac accgcgggcg tgatgaagct   180
gttcgacgtg ccgctgcatt ttaatctgat gaacgcctcc aggggcggtc gcgactacga   240
```

```
tctcagcaaa gtcttcgacg gaacgctcgt gcggggcaac ccgcagatgg ccgtcacgta      300
cgtcgacaac cacgacaccg agc                                             323

<210> SEQ ID NO 66
<211> LENGTH: 323
<212> TYPE: DNA
<213> ORGANISM: Streptomyces coelicolor

<400> SEQUENCE: 66
cgtcgacggc ttccggatcg acgccgtcaa gcacatcccc gccagcttct acaaggactg      60
gttctgccac ctccgcgaga gttccccga ccgcgaactg ttcggcgtcg ccgagtactg      120
gagcggcagc ctcgacgagc tcaaagggta cctcgccgcg accgacggcg tcgtgcgcct      180
gttcgacgtc cccctccact accgcctgat ggaggcctcg cgccggggcc gcgacttcga      240
cctctccaag atcttcgacg gcacgctcgt ccaggacaac ccgctcatgg ccgtcacgtt      300
cgtcgacaac cacgacaccg agc                                             323

<210> SEQ ID NO 67
<211> LENGTH: 302
<212> TYPE: DNA
<213> ORGANISM: Streptomyces coelicolor

<400> SEQUENCE: 67
cgtcgacggc ttccgcatcg acgcggccaa gcacatcccg gcggccgacc tcgcgaacat      60
caagtcccgg ctgagcaatc cgggcgtgta ttggaagcac gaggtcatct acggcgccgg      120
ggaggccgtc cagccgaccg agtacaccgg cagcggcgac gtgcaggagt ccgctacgc      180 ctacgacctc aagcgcgtct tcaccaacga gaacctggcc tacctgaaga actacggcga      240
gggctggggg tacctgaaca gcggcgtctc cggtgtcttc gtcgacaacc acgacaccga      300
gc                                                                    302

<210> SEQ ID NO 68
<211> LENGTH: 302
<212> TYPE: DNA
<213> ORGANISM: Streptomyces coelicolor

<400> SEQUENCE: 68
cgtcgacggc ttccggatcg acgcggccaa gcacatcccg gcggccgacc tcgccaacat      60
caagtcgcgg ctgaccaatc cgtcggtgta ctggaagcag gaggtcatct acggcgccgg      120
ggaggcggtc cagccgaccg agtacaccgg caacggcgac gtccaggagt ccggtacgc      180 ctacgacctc aagcgggtct tcaacaacga gaacctcgcc tacctcaaga actacggcga      240
gggctggggc tatatgagca gctccgtcgc gggggtctac gtcgacaacc acgacaccga      300
gc                                                                    302

<210> SEQ ID NO 69
<211> LENGTH: 302
<212> TYPE: DNA
<213> ORGANISM: Streptomyces coelicolor

<400> SEQUENCE: 69
gctcggtgtc gtggttgtcc tcgtagacgc ccgcggagga gctcttgagg tagccccagc      60
cctcgccgta gttcttcagg taggcgaggt tctcgttgtt gaagacccgc ttgaggtcgt      120
aggcgtaccg gaattcctgg acgtcgccgt tgccgatgta ctcggtgggc tggacggcct      180
```

```
cgcccgcgcc gaagatgacc tcctgcttcc agtacacgcc ggggtcggtg agccgggact    240
tgatgttcgc caggtcggcg gccggcatgt gcttggtggt gtcgatgcgg aagccgtcga    300
cg                                                                   302
```

<210> SEQ ID NO 70
<211> LENGTH: 302
<212> TYPE: DNA
<213> ORGANISM: Streptomyces coelicolor
<220> FEATURE:
<221> NAME/KEY: misc_feature
<222> LOCATION: (27)..(28)
<223> OTHER INFORMATION: n is a, c, g, or t

<400> SEQUENCE: 70

```
cgtcgacggc ttccggatcg acgcgannaa gcacatcccg gcggccgacc tcgccaacat    60
caagtcgcgg ctgaccaatc cgtcggtgta ctggaagcag gaggtcatct acggcgctgg    120
ggaggcggtc cggccgaccg agtacaccgg caacggcgac gtccaggagt tccggtacgc    180
ctacgacctc aagcgggtct caacaacga gaacctcgcc tacctcaaga actacggcga    240
gggctggggc tatatgagca gctccgtcgc gggggtctac gtcgacaacc acgacaccga    300
gc                                                                   302
```

<210> SEQ ID NO 71
<211> LENGTH: 302
<212> TYPE: DNA
<213> ORGANISM: Streptomyces coelicolor

<400> SEQUENCE: 71

```
cgtcgacggc ttccgcatcg acgccgccaa gcacatgccc gccgccgacc tggcgaacat    60
caagtcacgg ctgggcgacc cgaacgtcta ctggaagcag gaggcgatat acggcgcggg    120
cgaggcggtc tcgccggacg agtacgccgg caccggggac gtccaggaat tccggtacgc    180
ccgcggcctc aagcaggtct caacaacga gaacctcgcc tatctgaaga actacggcga    240
gggctggggc ttcatgccct cgtcgaaggc agcggtcttc gtcgacaacc acgacaccga    300
gc                                                                   302
```

<210> SEQ ID NO 72
<211> LENGTH: 302
<212> TYPE: DNA
<213> ORGANISM: Streptomyces coelicolor

<400> SEQUENCE: 72

```
gctcggtgtc gtggttgtcc acgtagaccc ccgcgacgga gctgctcata tagccccagc    60
cctcgccgta gttcttgagg taggcggggt tctcgttgtt gaagacccgc ttgaggtcgt    120
aggcgtaccg gaactcctgg acgtcgccgt tgccggtgta ctcggtcggc tggaccgcct    180
ccccggcgcc gtagatgacc tcctgcttcc agtacaccga cggattggtc agccgcgact    240
tgatgttggc gaggtcggcc gccgggatgt gcttggccgc gtcgatccgg aagccgtcga    300
cg                                                                   302
```

<210> SEQ ID NO 73
<211> LENGTH: 335
<212> TYPE: DNA
<213> ORGANISM: Bacillus stearothermophilus

<400> SEQUENCE: 73

```
cgtcgacggc ttccgcatcg acgccaccaa gcacattaca tcgactttt tcaacgaatg     60
```

```
gctgtatcac gtgcgccagg ccaccggcaa accgaatgcc tttgccgtga gcgagtactg    120
ggagcgcgac atcaacgcgc tcaataacta cgtcaattcg gtgaacagta cggccagcga    180
caagatgtcg gccttcgacg tgcccctgca cgcgaaattc gaacaggcgg ccaatgccaa    240
tggcatgttc gacatgggct ccctgctgac caacaccctg gtggcatggc agccggcacg    300
ggccgcgacc tacgtggaca accacgacac cgagc                               335

<210> SEQ ID NO 74
<211> LENGTH: 323
<212> TYPE: DNA
<213> ORGANISM: Bacillus amyloliquefaciens

<400> SEQUENCE: 74
cgtcgacggc ttccgcatcg acgcgctcaa gcacctgccg gccagcttca tcaaggattg    60
gctgaacgcg ctacgcacgc acttcagcgg acgcgagctg tttgcggtgg gcgagtactg    120
gagtgcagac gtgaacgagc tgcacggcta cttgagcaag gtggagggcg ctacgcggct    180
gttcgacgtg ccgctgcact ttcgtttcct cgaggccagc aagcagggg agagcttcga    240 tctgactacc atctttgcgg gctccctggt ggccgagaac ccgctctcgg ccgtcacgta    300
cgtggacaac cacgacaccg agc                                            323

<210> SEQ ID NO 75
<211> LENGTH: 323
<212> TYPE: DNA
<213> ORGANISM: E.coli

<400> SEQUENCE: 75
cgtcgacggc ttccgcatcg acacgatcaa gcatatcccg gccagcttct accgcgagtg    60
gttcgatcac gtccgcggcg cgttccccgc tcgcgaactg ttcggcgtcg gcgagtactg    120
gagcggcgac gtcaacgagc tcgacggcta cctcgccgcc accggcggcg tcatgcgcct    180
cttcgacgtc ccgcttcatt tccgcctgca cgaggcatcg aagaagggcc gcgacttcga    240
cctgtcgaag ctcttcgacg gcacgctcgt gcagcgcaac ccgctgatgg ccgtcacgta    300
cgtcgacaac cacgacaccg agc                                            323

<210> SEQ ID NO 76
<211> LENGTH: 323
<212> TYPE: DNA
<213> ORGANISM: E.coli

<400> SEQUENCE: 76
cgtcgacggc ttccggatcg acacgatcaa gcacatccca gccagctttt tcaaagactg    60
gcttacgcat gtgcgctcca cattcaaaca tcgagaacta tttgctgtcg gcgagtactg    120
gagcggcagc ctggatgaac tgaagggcta cctcgccgcg gtggatggcg cgatgcggct    180
gttcgacgtg ccgctgcatt tcaatttccg tgacgcggcg cagcagggaa aatcgttcga    240
cctgagcaag attttcgacg gctccctcgt acaggacaac ccgctgatgg ccgtcaccta    300
cgtggacaac cacgacaccg agc                                            323

<210> SEQ ID NO 77
<211> LENGTH: 305
<212> TYPE: DNA
<213> ORGANISM: B.stearothermophilus

<400> SEQUENCE: 77
```

```
cgtcgacggc ttccggatcg acgcggccga gcacatcgac gccgccgacc tgagcgctgt    60
cgtcgccgga ctgcacacca cgacctccgg cgcggcgccg tacatcaccc aggagatcta   120
ccccggcacc ccgcccgcgc aggacgagta ctacggcacc ggtgacgtcc tcgacttcac   180
cttcgccgcg caggtgaagt cccagttcca gggcgacatc gccaacctgt cgagcttcgg   240
cagcagctgg ggcctgacga ccgaggcgaa ctccaacacc tacgtcgaca accacgacac   300
cgagc                                                               305
```

<210> SEQ ID NO 78
<211> LENGTH: 305
<212> TYPE: DNA
<213> ORGANISM: B.stearothermophilus

<400> SEQUENCE: 78

```
cgtcgacggc ttccggatcg acgcggccaa gcacatcgac gccgccgacc tgagcgccgt    60
cgtcgccgga ctgcacacca cgacctccgg cgcggcgccg tacatcaccc aggagatcta   120
ccccggcacc ccgcccgcgc aggacgagta ctacggcacc ggtgacgtcc tcgacttcac   180
cttcgccgcg caggtgaagt cccagttcca gggcgacatc gccaacctgt cgagcttcgg   240
cagcagctgg ggcctgacga ccgaggcgaa ctccaacacc ttcgtcgaca accacgacac   300
cgagc                                                               305
```

<210> SEQ ID NO 79
<211> LENGTH: 302
<212> TYPE: DNA
<213> ORGANISM: B.stearothermophilus

<400> SEQUENCE: 79

```
cgtcgacggc ttccggatcg acgcggccaa gcacatcccg gcggccgacc tcgccaacat    60
caagtcgcgg ctgaccaatc cgtcggtgta ctggaagcag gaggtcatct acggcgccgg   120
ggaggcggtc cagccgaccg agtacaccgg cgacggcgac gtccaggagt tccggtacgc   180
ctacgacctc aagcgggtct tcaacaacga gaacctcgcc tacctcaaga actacggcga   240
gggctggggc tacatgagca gctccgtcgc gggggtctac gtcgacaacc acgacaccga   300
gc                                                                  302
```

<210> SEQ ID NO 80
<211> LENGTH: 302
<212> TYPE: DNA
<213> ORGANISM: B.stearothermophilus

<400> SEQUENCE: 80

```
cgtcgacggc ttccgcatcg acgccgccaa gcacatgccc gccggtgacc tcgccaacat    60
caagtcccgg ctgagcaatc cgaacgtcta ctggaagcac gaggcgatct tcggggccgg   120
tgaggccgtc tcgccctccg agtacctcgg cagcggtgac gtccaggagt tccgctacgg   180
ccgaagcctc aagcaggtct tcaacaacga gaacctcgcc aacctgaaga acttcggcga   240
gggatggggc ttcatggagt ccggcaagtc cgcggtctac gtcgacaacc acgacaccga   300
gc                                                                  302
```

<210> SEQ ID NO 81
<211> LENGTH: 323
<212> TYPE: DNA
<213> ORGANISM: B.stearothermophilus

<400> SEQUENCE: 81

```
cgtcgacggc ttccggatcg acgcgctcaa gcacctgccg gcggggttca tcaaagactg    60
gctgagcgcc atgcgcacac atttcagtgg ccgcgagctg ttcgcggtcg gtgagtactg   120
gagtgcagac gtcaacgagc tgcacagcta cctgaccaag gtagagggcg gcacccagct   180
gttcgacgta ccgctccact ttcgctttct ggaggccagc agccagggcg agagcttcga   240
cctgaccaag atcttcgagg gctcgctggt ggcggagaat ccgctggtcg cggtcacctt   300
cgtggacaac cacgacaccg agc                                           323

<210> SEQ ID NO 82
<211> LENGTH: 299
<212> TYPE: DNA
<213> ORGANISM: Streptomyces limosus

<400> SEQUENCE: 82
cgtcgacggc ttccggatcg acaccagcaa gcacatgccg gccgccgaca tcgccgcgat    60
caaggccaag ctcaacgggg cgccttacct cgtgcaggag gtcatctacg gcgcgggcga   120
gcccatccac ccgaatgagt acaccggcaa cggcgacgtc cacgagttcc gctacggcaa   180
ggacctcagc cgggtgttcc gccacgagaa gctcgcctac ctcgccaact tcggcgaagg   240
gtgggggcac atcagcagtg ccaaggccgt ggcctacgtc gacaaccacg acaccgagc    299

<210> SEQ ID NO 83
<211> LENGTH: 323
<212> TYPE: DNA
<213> ORGANISM: Streptomyces venezuelae

<400> SEQUENCE: 83
cgtcgacggc ttccgcatcg acgccgtgaa acacgtccgc tcgagcttct tccgtgactg    60
gatgaaccac ctgcgcgtcc acttcggcgg ccgggagctg ttcgccgtcg gcgagcactg   120
gtccgcccac gctgctgacc tccaccgcta catcaccgcc accgagggtg tgatgagtct   180
gttcgatgtg gccctgcact atcgcttccg cgaggcgagc ctctccggaa acagctacga   240
catgcggacg atcctcgacg ggacgctggt cggccagcaa ccggccaagg ccgtcaccta   300
cgtggacaac cacgacaccg agc                                           323

<210> SEQ ID NO 84
<211> LENGTH: 323
<212> TYPE: DNA
<213> ORGANISM: Streptomyces venezuelae

<400> SEQUENCE: 84
cgtcgacggc ttccggatcg acaccgtgaa gcacatccgc cggcggtact tctgcgactg    60
gctgaaccac cttcgtacgc acttcggcgg gcgcgagctg ttcgcggtgg gggagtactg   120
gtcgggcgac gtgaacgagc tgcaccgcta tctcgacgcg acggagaaca cgctgtccgt   180
cttcgacgtc ccgctacact acaacttctt cgccgcgagc catgcggggc gcgattacga   240
cctccgtcgg atcttcgaca acacgctcgt cgcgcagcgg ccgacgaagg cggtgacgtt   300
cgtcgacaac cacgacaccg agc                                           323

<210> SEQ ID NO 85
<211> LENGTH: 302
<212> TYPE: DNA
<213> ORGANISM: Streptomyces albus

<400> SEQUENCE: 85
```

```
cgtcgacggc ttccggatcg acaccgccaa gcacatggcc gcctccgacc tggccaacat    60
caagtcccgg ctgagcaacc cgaacgccta ctggaagcag gaggccatct tcggcgcggg   120
ggaggcggtc tcgcccagcg agtacctcgg caacggcgac gtccaggagt tccgctacgc   180
ccgcgacctg aagcgggtct tcaacaacga gaacctcgcc tacctgaaga actacggcga   240
gggctggggc tacatgtcct cgggcagctc ggccgtctac gtcgacaacc acgacaccga   300
gc                                                                  302

<210> SEQ ID NO 86
<211> LENGTH: 330
<212> TYPE: DNA
<213> ORGANISM: Streptomyces albus

<400> SEQUENCE: 86
tcgtcgacgg cttccgcatc gacgccggaa acacatcca tccgccattt ctctcgcgct    60
ggttccaaga agtgaagggg acctcccgct tgccgtgac cgagttttac gacggcaacc   120
cggcccacct cgccacggtc atcgatctct acgcccggca gagccacctt ttcgacttcg   180
cgttgcactt tctgctgcag cgcatgagcg ccggcaacgg cggattcgac atgcgcagtc   240
tgcggttcgg ttcgagtgac gatggctcgc ggtttctcga gcagcatccg gccttcgccg   300
tcacctacgt cgacaaccac gacaccgagc                                   330

<210> SEQ ID NO 87
<211> LENGTH: 323
<212> TYPE: DNA
<213> ORGANISM: Bacillus sp. MK716

<400> SEQUENCE: 87
cgtcgacggc ttccggatcg acgccgtcaa gcacgtcccg gcgagctttt acaagtggtg    60
gctggatgag atgcggcaga actatccgag ccgcgagctg ttcgccgtcg gcgaatactg   120
gagcggcaac atgggcgagc tgcacggtta tctcgccgcc accgacgggg cgatgaagct   180
ctttgacgtc ccgctgcact acaagttcat ggaggcgtca cagaaggggc gcgagttcga   240
cctgcccacg atcttcgacg gcacgctggt gaaggaaaac ccgctgatgg ccgtcacctt   300
cgtcgacaac cacgacaccg agc                                          323

<210> SEQ ID NO 88
<211> LENGTH: 329
<212> TYPE: DNA
<213> ORGANISM: Bacillus sp. MK717

<400> SEQUENCE: 88
cgtcgacggc ttccgcatcg acgccggaaa acacatccat ccgccatttc tctcgcgctg    60
gttccaagaa gtgaagggga cctcccgctt gccgtgacc gagttttacg acggcaaccc   120
ggcccacctc gccacggtca tcgatctcta cgcccggcag agccaccttt tcgacttcgc   180
gttgcacttt ctgctgcagc gcatgagcgc cggcaacggc ggatccgaca tgcgcaatct   240
gcggttcggt tcgagtgacg atggctcgcg gtttctcgag cagcatccgg ccttcgccgt   300
caccttcgtg gacaaccacg acaccgagc                                    329

<210> SEQ ID NO 89
<211> LENGTH: 299
<212> TYPE: DNA
<213> ORGANISM: Bacillus sp. MK718

<400> SEQUENCE: 89
```

-continued

```
cgtcgacggc ttccgcatcg acgcggccaa gcacatcccg ccggccgacc tggccgcgat    60
caaggacctc ctcaccggat cgccctacct ccaccaggag gtcatccagg gcgacaacga   120
ggtgatccag cccggccagt acacgggcat cggcgacgtg cacgagttcg tctacggtcg   180
caagctcaag gagcagttca cgggcagat caaatggctc ggttccttcg ggcagagctg   240
ggggctctcc gtccccggcg acaaggccgt ggtgttcgtc gacaaccacg acaccgagc   299
```

<210> SEQ ID NO 90
<211> LENGTH: 302
<212> TYPE: DNA
<213> ORGANISM: Bacillus licheniformis

<400> SEQUENCE: 90

```
cgtcgacggc ttccggatcg acaccgccaa gcacatcgcc gccagcgacc tggccgccat    60
cagggcccgg gtgaacggcg cgacgtcta ctggaagcaa gaggtcatcc acggcgccgg   120
cgaggcggtc cagcccggcg agtacacggg cgtcggcgac gtgcaggagt ccgctacgc   180
ctacgacctc aagcgtgtct tccagaacga gcgcctcgcc tacctggaga actacggtga   240
gggctggggc tacctcccga gcggcggcgc cgccgtcttc gtcgacaacc acgacaccga   300
gc                                                                 302
```

<210> SEQ ID NO 91
<211> LENGTH: 299
<212> TYPE: DNA
<213> ORGANISM: Streptomyces griseus

<400> SEQUENCE: 91

```
cgtcgacggc ttccggatcg acaccagcaa gcacatgccg ccgccgaca tcgcggcgat    60
caagagcaag ctctcccgcc cggcgtacat cgtgcaggag gtcatcttcg gcgcgggcga   120
gccgatcggc cccggtgagt acaccggcaa cggcgacgtg cacgagttcc gctacggcaa   180
ggacctcgcc cgggtcttcc gctccgagcg gctggcgtac ctgaagaact cggcgaggg   240
ctggggccac ctgcccagcg gcgtctcctc ggtctacgtc gacaaccacg acaccgagc   299
```

<210> SEQ ID NO 92
<211> LENGTH: 302
<212> TYPE: DNA
<213> ORGANISM: Streptomyces griseus

<400> SEQUENCE: 92

```
cgtcgacggc ttccgcatcg acgcggtcaa gcgcatgcct gccgccgacc tggcgaacat    60
caagtcccgg ctgagcaacc ccgacgcgta ctggaagcag gaggtcatcc acggcgcggg   120
cgaggccgtc cagcccggcg agtacacggg caacggcgac gtccaggagt ccgctacgc   180
ctacgacctc aagcgggtct tccacaacga gaacctcgcc tacctgaaga actacggcga   240
gggctggggc tacctgaaga actcctccgc cggcgtcttc gtggacaacc acgacaccga   300
gc                                                                 302
```

<210> SEQ ID NO 93
<211> LENGTH: 350
<212> TYPE: DNA
<213> ORGANISM: Streptomyces griseus

<400> SEQUENCE: 93

```
cgtcgacggc ttccggatcg acgccaccaa ggcgatcaag aacttcgaca cgctcaagct    60
```

```
gctgaccgat gccgcctaca gcaagatcga agaccgcaag ccgttcatca ccatcggcga    120
gcacgtgccg aagatccgg aagtgacagg ccgcgaccgc ggccggccga tggacgcggc     180
gtggcacgac tacttcggcc acgtcgcgcg ggccgtcgtc gcggaggtgc agaaggatga    240
tctgcatccg catgacatca agcgatttct tgagcggctc gatccgaaga ccaacggcta   300
cggcagcgcg tatcgcaccg tcaccttcgt cgacaaccac gacaccgagc              350

<210> SEQ ID NO 94
<211> LENGTH: 305
<212> TYPE: DNA
<213> ORGANISM: Streptomyces griseus
<220> FEATURE:
<221> NAME/KEY: misc_feature
<222> LOCATION: (186)..(186)
<223> OTHER INFORMATION: n is a, c, g, or t

<400> SEQUENCE: 94
cgtcgacggc ttccgcatcg acgccgccaa gcacatcccc aacgaggacc tgcgggcgat    60
cttcggccgg ctgcgcgaga ccgtctccgg tgcgcggccg tacgtcttcc acgaggtgtt   120
ccccggcgag ccgccccgcc cgcaggacta cttcagcacc ggcgacgtgc tggacttcac   180
ctacgncgac aagatcaaga ccgccttcca gggcgacatc gcctggctgt cgtcgttcgg   240
cccgagctgg ggcctgctgc cggcggccga ctcggtctcg tacgtggaca accacgacac   300
cgagc                                                                305

<210> SEQ ID NO 95
<211> LENGTH: 290
<212> TYPE: DNA
<213> ORGANISM: Streptomyces griseus

<400> SEQUENCE: 95
cgtcgacggc ttccgcatcg acgcggccaa gcacatgtat cacggcgata tccagggtat   60
cctcagccgc gcgggcaatc cctacgtgtt cctcgaggtc atcggctccg cgggcgaggc  120
cgtgcagccc agccagtata cgtatctcgg ccaggtgacc gagtttggct atagctcgca  180
catcggccat cgcttcaagt acggccagat caaagatctg aacaacatcg cggacggcaa  240
gctgcccagc accagcgcga tcgtgtacgt ggacaaccac gacaccgagc              290

<210> SEQ ID NO 96
<211> LENGTH: 299
<212> TYPE: DNA
<213> ORGANISM: Anabaena variabilis

<400> SEQUENCE: 96
cgtcgacggc ttccggatcg acgcggccaa gcacatcccg ccggccgacc tggccgcgat   60
caaggacctc ctcaccggat cgccctacct ccaccaggag gtcatccagg gcgacaacga  120
ggtgatccag cccggccagt acacgggcat cggcgacgtg cacgagttcg tctacggtcg  180
caagctcaag gagcagttca cgggcagat caaatggctc ggttccttcg gcagagctg   240 ggggctctcc gtccccggcg acaaggccgt ggtgtacgtg gacaaccacg acaccgagc   299

<210> SEQ ID NO 97
<211> LENGTH: 308
<212> TYPE: DNA
<213> ORGANISM: Streptomyces lividans

<400> SEQUENCE: 97
cgtcgacggc ttccggatcg acgccatcaa gcacatggac acgcgcttcg tgaacgcgtg   60
```

```
                                             -continued gctcgacgcc gtgcgcggcc cgcgtttcgc cgtgagcgag gcatggttcg cgaagctcga   120
ccagctcacg gcctacgcga aggagctcgg cgaccgcacg cgcctcttcg acgtgccgct   180
ccactacctg ttttacggga tgagcaacgg caacggggcg tgggacatgc ggaacctcaa   240
gttcgccggc ttcacggagg cgaacggcaa gctctccgtg ccctacgtgg acaaccacga   300
caccgagc                                                            308

<210> SEQ ID NO 98
<211> LENGTH: 290
<212> TYPE: DNA
<213> ORGANISM: Streptomyces lividans

<400> SEQUENCE: 98
cgtcgacggc ttccggatcg acacggtcaa gcacatcgcc catggcgacc tcgccggcat    60
cctgtcgcgc gccggcaatc cgtacaactt catggaggtg atcggcgcgg ccggcgagcc   120
catccagccg agcgagtaca cgtatctcgg ccaggtgacc gaattcggtt acagctcgca   180
cctcggccat cgcttcaagt tcggccagat caaggatctg cgcaacatcg gcgacggcaa   240
gctgcccagc gacaaggcca tcgtgtacgt ggacaaccac gacaccgagc               290

<210> SEQ ID NO 99
<211> LENGTH: 299
<212> TYPE: DNA
<213> ORGANISM: Streptomyces sp.

<400> SEQUENCE: 99
cgtcgacggc ttccggatcg acgccgccaa gcacatcagc ccggacgaca tcgccgcgat    60
caagtccagg ctcaagggct cgccgtacat ccaccaggag gtcatctacg gcgacaacga   120
agcggtccag ccgagctggt acaccggcaa cggcgacgtg gacgagttcg tctacggccg   180
caagctgaag gagcagttca ccggccagat caagtggctg cagagcttcg gccagagctg   240
gggcctgtcc gtgggcagcg acaaggccat ggtcttcgtg gacaaccacg acaccgagc    299

<210> SEQ ID NO 100
<211> LENGTH: 290
<212> TYPE: DNA
<213> ORGANISM: Streptomyces sp.

<400> SEQUENCE: 100
cgtcgacggc ttccgcatcg acacggccaa gcacatgtat cacggcgata tccagggtat    60
cctcagccgc gcgggcaatc cctacgtgtt cctcgaggtc atcggctccg cgggcgaggc   120
cgtgcagccc agccagtata cgtatctcgg ccaggtgacc gagtttggct atagctcgca   180
catcggccat cgcttcaagt acggccagat caaagatctg aacaacatcg cggacggcaa   240
gctgcccagc accagcgcga tcgtgtacgt ggacaaccac gacaccgagc               290

<210> SEQ ID NO 101
<211> LENGTH: 353
<212> TYPE: DNA
<213> ORGANISM: Streptomyces sp.

<400> SEQUENCE: 101
cgtcgacggc ttccgcatcg acgccgctcg gcacgtcaac accgccttct ggcacgcgtt    60
caacaccgcg atccgcgacc gcgcgcgcgc cctcggccga cccgacttca tccaattcgg   120
tgaggtgtac aacgacacac ccgaggctcc cgccgtgctg agcgagttct ccaccggcat   180
```

```
gccgatggac acgacgctcg acttcggctt tttcaacgcc gcccgccact tcgtctcgca    240
acagcgcccc gccgccgagc tcgccgcctt cttccgcacg gacgacctct acaccgacca    300
cgacagcaac atccacgcga cgctcaccta cgtcgacaac cacgacaccg agc           353

<210> SEQ ID NO 102
<211> LENGTH: 302
<212> TYPE: DNA
<213> ORGANISM: Streptomyces sp.

<400> SEQUENCE: 102
cgtcgacggc ttccggatcg acaccgccaa gcacatgccc gccgccgacc tggcgaacat    60
caagtcgcgg ctgggcgacc cgaacgtcta ctggaagcag gaggcgatat acggcgcggg    120
cgaggcggtc tcgccggacg agtacgccgg caccggggac gtccaggaat tccggtacgc    180
ccgcggcctc aagcaggtct tcaacaacga gaacctcgcc tatctgaaga actacggcga    240
gggctggggc ttcatgccct cgtcgaaggc agcggtctac gtcgacaacc acgacaccga    300
gc                                                                   302

<210> SEQ ID NO 103
<211> LENGTH: 326
<212> TYPE: DNA
<213> ORGANISM: Streptomyces sp.

<400> SEQUENCE: 103
cgtcgacggc ttccgcatcg acaccatccg ccacatgccg caggcgttct ggcacgcgtt    60
cgcgcgccgc atccgcgccg agcatcccgg tttcttcatg ttcggcgagg cgttcgacac    120
caaggccgcg aacatcgcgc cgttcacctg ggcggagaac gccaacgtca gcgtgctcga    180
ttttccgctg aaggaaggtc tgatcgaggt gttcggccgc aagcgcgccg gcttcgagat    240
cctgctgccg cggctgtacc tgaccgacgg cccgtacgcc aatccgtacg agctgatgac    300
ctacgtcgac aaccacgaca ccgagc                                         326

<210> SEQ ID NO 104
<211> LENGTH: 353
<212> TYPE: DNA
<213> ORGANISM: Streptomyces sp.

<400> SEQUENCE: 104
cgtcgacggc ttccggatcg acgccgcccg gcacgtcaac accgccttct ggcacgcgtt    60
caacaccgcg atccgcgacc gcgccgcgc cctcggccgc cccgacttca tccaatttgg    120
tgaggtgtac aacgacacgc ccgaggctcc cgccgtgctg agcgagtttt ccaccggcat    180
gccgatggat acgacgctcg acttcggctt tttcaacgcc gcccgccact tcgtctcgca    240
acagcgcccc gccgccgagc tcgccgcctt cttccgcacg gacgacctct acaccgacca    300
cgacagcaac atccacgcga cgctcacctt cgtcgacaac cacgacaccg agc           353

<210> SEQ ID NO 105
<211> LENGTH: 290
<212> TYPE: DNA
<213> ORGANISM: Streptomyces sp.

<400> SEQUENCE: 105
cgtcgacggc ttccgcatcg acgcggtcaa gcacatcgcc catggcgacc tcgccggcat    60
cctgtcgcgc gccggcaatc cgtacaactt catggaggtg atcggcgcgg ccggcgagcc    120
catccagccg agcgagtaca cgtatctcgg ccaggtgacc gaattcggtt acagctcgca    180
```

```
cctcggccat cgcttcaagt tcggccagat caaggatctg cgcaacatcg gcgacggcaa        240
gctgcccagc gacaaggcca tcgtgttcgt ggacaaccac gacaccgagc                   290
```

<210> SEQ ID NO 106
<211> LENGTH: 290
<212> TYPE: DNA
<213> ORGANISM: Streptomyces sp.

<400> SEQUENCE: 106

```
cgtcgacggc ttccggatcg acacggtcaa gcacatcgcc catggcgacc tcgccggcat        60
cctgtcgcgc gccggcaatc cgtacaactt catggaggtg atcggcgcgg ccggcgagcc        120
catccagccg agcgagtaca cgtatctcgg ccaggtgacc gaattcggtt acagctcgca        180
cctcggccat cgcttcaagt tcggccagat caaggatctg cgcaacatcg gcgacggcaa        240
gctgcccagc gacaaggcca tggtgtacgt cgacaaccac gacaccgagc                   290
```

<210> SEQ ID NO 107
<211> LENGTH: 78
<212> TYPE: PRT
<213> ORGANISM: Bacillus flavocaldarius

<400> SEQUENCE: 107

```
Val Tyr Ala Asp Val Val Phe Asn His Thr Gly Glu Gly Asp Ala Thr
1               5                   10                  15

Lys Pro Thr Trp Thr Phe Arg Gly Leu Asp Asp Arg Leu Tyr Leu His
            20                  25                  30

Asp Arg Asp Gly Thr Tyr Asn Asp Asp Ala Gly Cys Gly Asn Val Ala
        35                  40                  45

Asp Pro Gly Ala Glu Glu Val Arg Arg Leu Val Leu Glu Ala Leu Gln
    50                  55                  60

Arg Phe Thr Asp Leu Gly Ile Asp Gly Phe Arg Ile Asp Ala
65                  70                  75
```

<210> SEQ ID NO 108
<211> LENGTH: 81
<212> TYPE: PRT
<213> ORGANISM: Bacillus flavocaldarius

<400> SEQUENCE: 108

```
Val Tyr Ala Asp Val Val Phe Asn His Thr Ala Glu Gly Asn Arg Met
1               5                   10                  15

Gly Pro Thr Leu Ser Trp Arg Gly Ile Asp Asn Thr His Tyr Tyr Arg
            20                  25                  30

Leu Thr Glu Asp Lys Arg Tyr His Leu Asp Tyr Thr Gly Thr Gly Asn
        35                  40                  45

Ala Leu Asn Met Thr Ser Pro Arg Val Leu Gln Met Ile Met Asp Ser
    50                  55                  60

Leu Arg Tyr Trp Val Met Glu Met His Val Asp Gly Phe Arg Ile Asp
65                  70                  75                  80

Ala
```

<210> SEQ ID NO 109
<211> LENGTH: 82
<212> TYPE: PRT
<213> ORGANISM: Orysa sativum

<400> SEQUENCE: 109

Val Tyr Ala Asp Val Phe Asn His Thr Gly Glu Gly Asn His Asn
1               5                   10                  15

Gly Pro Thr Ile Ser Phe Arg Gly Gln Ala Asn Glu Ala Tyr Tyr His
                20                  25                  30

Leu Val Asp Glu Asp Arg Lys Tyr Tyr Met Asp Tyr Ser Gly Cys Gly
            35                  40                  45

Asn Thr Ile Asn Ala Asn His Pro Leu Val Thr Lys Leu Ile Ile Glu
        50                  55                  60

Ser Leu Glu Tyr Trp Val Thr Glu His His Val Asp Gly Phe Arg Ile
65                  70                  75                  80

Asp Ala

<210> SEQ ID NO 110
<211> LENGTH: 80
<212> TYPE: PRT
<213> ORGANISM: Orysa sativum

<400> SEQUENCE: 110

Val Tyr Ala Asp Val Phe Asn His Thr Ala Glu Gly Asn Glu Thr
1               5                   10                  15

Gly Pro Thr Phe Cys Phe Lys Gly Leu Glu Asn Glu Val Tyr Tyr Met
                20                  25                  30

Leu Asn Glu Asn Gly Thr Tyr Lys Asn Phe Ser Gly Cys Gly Asn Thr
            35                  40                  45

Val Asn Gly Asn His Pro Val Met Arg Glu Met Ile Phe His Cys Leu
        50                  55                  60

Arg His Trp Val His Asn Tyr His Ile Asp Gly Phe Arg Ile Asp Ala
65                  70                  75                  80

<210> SEQ ID NO 111
<211> LENGTH: 82
<212> TYPE: PRT
<213> ORGANISM: Orysa sativum

<400> SEQUENCE: 111

Val Tyr Ala Asp Val Phe Asn His Thr Cys Glu Gly Asn Glu Arg
1               5                   10                  15

Gly Pro Thr Leu Cys Tyr Arg Gly Leu Asp Ala Pro Val Trp Tyr Trp
                20                  25                  30

Val Asp Pro Ala Gln Pro Ser Arg His Leu Asp Phe Thr Gly Cys Gly
            35                  40                  45

Asn Ser Phe Asn Met Arg His Pro Gln Val Leu Lys Leu Ala Met Asp
        50                  55                  60

Ser Leu Arg Tyr Trp Val Thr Glu Met His Val Asp Gly Phe Arg Ile
65                  70                  75                  80

Asp Ala

<210> SEQ ID NO 112
<211> LENGTH: 80
<212> TYPE: PRT
<213> ORGANISM: Orysa sativum

<400> SEQUENCE: 112

Val Tyr Ala Asp Val Phe Asn His Thr Ala Glu Glu Gly Leu Gly
1               5                   10                  15

Gly Pro Thr Ser Ser Leu Arg Gly Ile Asp Asn Arg Asn Tyr Tyr Arg
                20                  25                  30

```
Gln Thr Pro Asp Gly Glu Tyr Ile Asp Val Thr Gly Cys Gly Asn Ser
            35                  40                  45

Val Asn Thr Ala Thr Glu Ala Ser Arg Arg Leu Ile Leu Asp Ser Leu
 50                  55                  60

Arg Tyr Trp Ala Asn Glu Val Gln Val Asp Gly Phe Arg Ile Asp Ala
 65                  70                  75                  80

<210> SEQ ID NO 113
<211> LENGTH: 82
<212> TYPE: PRT
<213> ORGANISM: Arthrobacter sp.

<400> SEQUENCE: 113

Val Tyr Ala Asp Val Val Phe Asn His Thr Ala Glu Gly Asn His Met
 1               5                  10                  15

Gly Pro Thr Leu Ser Phe Arg Gly Ile Asp Asn Val Ser Tyr Tyr Arg
            20                  25                  30

Val Asp Pro Ala Asn Pro Arg Leu Tyr Val Asp Tyr Thr Gly Cys Gly
            35                  40                  45

Asn Thr Leu Asn Met Gln Asn Pro Arg Val Leu Gln Leu Ile Met Asp
 50                  55                  60

Ser Leu Arg Tyr Trp Val Thr Glu Met His Val Asp Gly Phe Arg Ile
 65                  70                  75                  80

Asp Ala

<210> SEQ ID NO 114
<211> LENGTH: 82
<212> TYPE: PRT
<213> ORGANISM: Arthrobacter sp.

<400> SEQUENCE: 114

Val Tyr Ala Asp Val Ile Asn His Thr Ala Glu Gly Asn Glu Arg
 1               5                  10                  15

Gly Pro Thr Leu Ser Phe Arg Gly Ile Asp Asn Ala Ser Tyr Tyr Arg
            20                  25                  30

Leu Val Asp Gly Asp Trp Gln His Tyr Tyr Asp Thr Thr Gly Thr Gly
            35                  40                  45

Asn Ser Leu Leu Met Arg His Pro Tyr Val Leu Gln Leu Ile Met Asp
 50                  55                  60

Ser Leu Arg Tyr Trp Val Thr Glu Met His Val Asp Gly Phe Arg Ile
 65                  70                  75                  80

Asp Ala

<210> SEQ ID NO 115
<211> LENGTH: 81
<212> TYPE: PRT
<213> ORGANISM: Arthrobacter sp.

<400> SEQUENCE: 115

Val Tyr Ala Asp Val Val Tyr Asn His Thr Ala Glu Gly Asn Gln Met
 1               5                  10                  15

Gly Pro Thr Leu Ser Phe Arg Gly Ile Asp Asn Ala Ser Tyr Tyr Leu
            20                  25                  30

Leu Gly Asp Asp Pro Arg Tyr Tyr Phe Asp Thr Thr Gly Cys Gly Asn
            35                  40                  45

Ala Val Asn Leu Arg His Gln Arg Val Leu Gln Met Val Met Asp Ser
 50                  55                  60
```

```
Leu Arg Tyr Trp Val Gln Glu Cys His Val Asp Gly Phe Arg Ile Asp
 65                  70                  75                  80

Ala

<210> SEQ ID NO 116
<211> LENGTH: 82
<212> TYPE: PRT
<213> ORGANISM: Arthrobacter sp.

<400> SEQUENCE: 116

Val Tyr Ala Asp Val Val Phe Asn His Ser Ala Glu Gly Asn His Met
  1               5                  10                  15

Gly Pro Thr Leu Ser Phe Lys Gly Phe Asp Asn Pro Leu Tyr Tyr Arg
             20                  25                  30

Leu Val Ala Asp Glu Gln Glu His Tyr Phe Asp Tyr Thr Gly Thr Gly
         35                  40                  45

Asn Thr Met Asn Met Arg Ser Pro His Thr Leu Gln Leu Val Met Asp
     50                  55                  60

Ser Leu Arg Trp Trp Ala Thr Glu Met His Val Asp Gly Phe Arg Ile
 65                  70                  75                  80

Asp Ala

<210> SEQ ID NO 117
<211> LENGTH: 81
<212> TYPE: PRT
<213> ORGANISM: Arthrobacter sp.

<400> SEQUENCE: 117

Val Tyr Ala Asp Val Val Phe Asn His Thr Cys Glu Gly Asn Glu Glu
  1               5                  10                  15

Gly Pro Ile Leu Ser Phe Lys Gly Leu Glu Asn Arg Val Tyr Tyr Met
             20                  25                  30

Leu Ala Asn Gly Gly Ser Gln Tyr Met Asn Tyr Ser Gly Cys Gly Asn
         35                  40                  45

Thr Val Asn Gly Asn His Pro Ile Val Arg Glu Met Ile Phe His Cys
     50                  55                  60

Leu Arg His Trp Val His Asn Tyr His Ile Asp Gly Phe Arg Ile Asp
 65                  70                  75                  80

Ala

<210> SEQ ID NO 118
<211> LENGTH: 82
<212> TYPE: PRT
<213> ORGANISM: Arthrobacter sp.

<400> SEQUENCE: 118

Val Tyr Ala Asp Val Val Phe Asn His Thr Ala Glu Gly Asn His Thr
  1               5                  10                  15

Gly Pro Met Leu Ser Phe Lys Gly Ile Asp Asn Gln Ala Tyr Tyr Arg
             20                  25                  30

Leu Met Glu Asp Glu Pro Lys Tyr Tyr Arg Asp Tyr Thr Gly Thr Gly
         35                  40                  45

Ser Ser Leu Asn Val Arg His Pro His Ser Leu Gln Leu Ile Met Asp
     50                  55                  60

Ser Leu Arg Tyr Trp Val Thr Glu Met His Val Asp Gly Phe Arg Ile
 65                  70                  75                  80

Asp Ala
```

<210> SEQ ID NO 119
<211> LENGTH: 82
<212> TYPE: PRT
<213> ORGANISM: Arthrobacter sp.

<400> SEQUENCE: 119

Val Tyr Ala Asp Val Val Phe Asn His Thr Ala Glu Gly Asn His Leu
1               5                   10                  15

Gly Pro Ser Phe Asn Leu Lys Gly Ile Asp Asn Pro Thr Tyr Tyr Arg
            20                  25                  30

Leu Val Pro Asn Glu Pro Arg Tyr Tyr Phe Asp Tyr Thr Gly Thr Gly
        35                  40                  45

Asn Thr Leu Asn Val Arg His Pro Gln Val Leu Ala Leu Ile Met Asp
    50                  55                  60

Ser Leu Arg Tyr Trp Ala Ile Glu Met His Val Asp Gly Phe Arg Ile
65                  70                  75                  80

Asp Ala

<210> SEQ ID NO 120
<211> LENGTH: 82
<212> TYPE: PRT
<213> ORGANISM: Arthrobacter sp.

<400> SEQUENCE: 120

Val Tyr Ala Asp Val Val Tyr Asn His Ala Ala Glu Gly Asn His Leu
1               5                   10                  15

Gly Pro Met Leu Ser Phe Lys Gly Tyr Asp Asn Glu Ala Tyr Tyr Arg
            20                  25                  30

Leu Gly Pro Asp Asp Pro Arg Tyr Tyr Val Asp Tyr Thr Gly Cys Gly
        35                  40                  45

Asn Ser Leu Asn Met Arg Asn Pro His Val Leu Gln Leu Ile Met Asp
    50                  55                  60

Ser Leu Arg Tyr Trp Val Glu Glu Met His Val Asp Gly Phe Arg Ile
65                  70                  75                  80

Asp Ala

<210> SEQ ID NO 121
<211> LENGTH: 82
<212> TYPE: PRT
<213> ORGANISM: Arthrobacter sp.

<400> SEQUENCE: 121

Val Tyr Ala Asp Val Val Phe Asn His Thr Ser Glu Gly Asn His Asp
1               5                   10                  15

Gly Pro Thr Ile Ser Phe Lys Gly Phe Glu Asn Ser Val Tyr Tyr His
            20                  25                  30

Leu Thr Pro Arg Asp Arg Gln Tyr Tyr Met Asp Tyr Ser Gly Cys Gly
        35                  40                  45

Asn Thr Val Asn Cys Asn His Pro Leu Val Asp Lys Phe Ile Leu Asp
    50                  55                  60

Ser Leu Glu Phe Trp Val His Glu Met His Val Asp Gly Phe Arg Ile
65                  70                  75                  80

Asp Ala

<210> SEQ ID NO 122
<211> LENGTH: 81

-continued

```
<212> TYPE: PRT
<213> ORGANISM: Arthrobacter sp.

<400> SEQUENCE: 122

Val Tyr Ala Asp Val Val Phe Asn His Thr Ala Glu Gly Asn His Leu
1               5                   10                  15

Gly Pro Val Leu Ala Phe Lys Gly Ile Asp Asn Ala Ser Tyr Tyr Arg
                20                  25                  30

Leu Ala Asp Asp Ala Arg Tyr Tyr Met Asp Phe Thr Gly Cys Gly Asn
            35                  40                  45

Thr Leu Asn Met Arg Ser Pro Gln Val Leu Gln Leu Ile Met Asp Ser
        50                  55                  60

Leu Arg Tyr Trp His Leu Asp Met His Val Asp Gly Phe Arg Ile Asp
65                  70                  75                  80

Ala

<210> SEQ ID NO 123
<211> LENGTH: 82
<212> TYPE: PRT
<213> ORGANISM: Arthrobacter sp.

<400> SEQUENCE: 123

Val Tyr Ala Asp Val Val Phe Asn His Thr Thr Glu Gly Asp Glu His
1               5                   10                  15

Gly Pro Thr Leu Ser Phe Arg Gly Ile Asp Asn Pro Thr His Tyr Leu
                20                  25                  30

Leu Asn Pro Asp Asp Arg Ala Arg Tyr Ile Asp Tyr Thr Gly Cys Gly
            35                  40                  45

Asn Thr Ile Ser Gly Asn His Pro Ile Val Arg Arg Met Ile Leu Asp
        50                  55                  60

Ala Leu Arg Tyr Trp Val Glu His Met His Val Asp Gly Phe Arg Ile
65                  70                  75                  80

Asp Ala

<210> SEQ ID NO 124
<211> LENGTH: 82
<212> TYPE: PRT
<213> ORGANISM: Arthrobacter sp.

<400> SEQUENCE: 124

Val Tyr Ala Asp Val Val Phe Asn His Thr Ala Glu Gly Asn His Leu
1               5                   10                  15

Gly Pro Val Leu Ser Phe Lys Gly Leu Asp Asn Ala Ala Tyr Tyr Arg
                20                  25                  30

Leu Leu Ala Gly Asp Ala Arg Tyr Tyr Met Asp Tyr Thr Gly Thr Gly
            35                  40                  45

Asn Ser Leu Asn Met Arg His Pro His Val Leu Gln Leu Leu Met Asp
        50                  55                  60

Ser Leu Arg Tyr Trp Val Leu Glu Met His Val Asp Gly Phe Arg Ile
65                  70                  75                  80

Asp Ala

<210> SEQ ID NO 125
<211> LENGTH: 82
<212> TYPE: PRT
<213> ORGANISM: Deinococcus radiodurans

<400> SEQUENCE: 125
```

```
Val Tyr Ala Asp Val Asn Asn His Thr Ala Glu Gly Asn His Leu
1               5                   10                  15

Gly Pro Met Leu Ser Met Lys Gly Ile Asp Asn Ala Ala Tyr Tyr Arg
            20                  25                  30

Leu Thr Pro Glu Asp Lys Gln Phe Tyr Met Asp Tyr Thr Gly Thr Gly
            35                  40                  45

Asn Ser Leu Asn Met Arg His Pro His Val Leu Gln Leu Ile Met Asp
        50                  55                  60

Ser Leu Arg Tyr Trp Val Leu Asp Met His Val Asp Gly Phe Arg Ile
65                  70                  75                  80

Asp Ala
```

```
<210> SEQ ID NO 126
<211> LENGTH: 82
<212> TYPE: PRT
<213> ORGANISM: Deinococcus radiodurans

<400> SEQUENCE: 126

Val Tyr Ala Asp Val Val Tyr Asn His Thr Val Glu Gly Asp Gln Arg
1               5                   10                  15

Gly Pro Thr Leu Ser Leu Arg Gly Phe Asp Asn Ala Asn Tyr Tyr Arg
            20                  25                  30

Leu Ser Pro His Asp Arg Ser Leu Tyr Glu Asn Phe Ser Gly Thr Gly
            35                  40                  45

Asn Thr Val Ser Phe Asp His Pro Ala Val Arg Ser Leu Val Ile Glu
        50                  55                  60

Cys Leu Arg Tyr Trp Val Ser Asp Met Gly Leu Asp Gly Phe Arg Ile
65                  70                  75                  80

Asp Ala
```

```
<210> SEQ ID NO 127
<211> LENGTH: 80
<212> TYPE: PRT
<213> ORGANISM: Deinococcus radiodurans

<400> SEQUENCE: 127

Val Tyr Ala Asp Val Val Phe Asn His Thr Ser Glu Gly Asn Glu Ser
1               5                   10                  15

Gly Pro Thr Phe Gly Phe Lys Gly Leu Glu Asn Arg Val Tyr Tyr Met
            20                  25                  30

Leu Asn Ala Asp Gly Thr Tyr Arg Asn Tyr Thr Gly Cys Gly Asn Thr
            35                  40                  45

Val Asn Gly Asn His Pro Ile Val Arg Glu Met Ile Phe His Cys Leu
        50                  55                  60

Arg His Trp Val His Asn Tyr His Ile Asp Gly Phe Arg Ile Asp Ala
65                  70                  75                  80
```

```
<210> SEQ ID NO 128
<211> LENGTH: 80
<212> TYPE: PRT
<213> ORGANISM: Deinococcus radiodurans

<400> SEQUENCE: 128

Val Tyr Ala Asp Val Val Phe Asn His Thr Ala Glu Gly Asn Glu Thr
1               5                   10                  15

Gly Pro Thr Phe Cys Phe Lys Gly Leu Glu Asn Lys Val Tyr Tyr Met
            20                  25                  30
```

```
Leu Asn Asp Asn Gly Thr Tyr Lys Asn Phe Ser Gly Cys Gly Asn Thr
            35                  40                  45

Val Asn Gly Asn His Pro Val Met Arg Glu Met Ile Phe His Cys Leu
 50                  55                  60

Arg His Trp Val His Asn Tyr His Ile Asp Gly Phe Arg Ile Asp Ala
 65                  70                  75                  80

<210> SEQ ID NO 129
<211> LENGTH: 82
<212> TYPE: PRT
<213> ORGANISM: Deinococcus radiodurans

<400> SEQUENCE: 129

Val Tyr Ala Asp Val Val Phe Asn His Thr Ala Glu Gly Asn His Leu
 1               5                  10                  15

Gly Pro Val Leu Ser Leu Lys Gly Ile Asp Asn Ala Ala Tyr Tyr Arg
                20                  25                  30

Leu Val Ala Asp His Arg Arg Tyr Tyr Met Asp Tyr Thr Gly Thr Gly
            35                  40                  45

Asn Ser Leu Asn Met Arg His Pro His Val Leu Gln Leu Leu Met Asp
 50                  55                  60

Ser Leu Arg Tyr Trp Val Thr Glu Met His Val Asp Gly Phe Arg Ile
 65                  70                  75                  80

Asp Ala

<210> SEQ ID NO 130
<211> LENGTH: 82
<212> TYPE: PRT
<213> ORGANISM: Deinococcus radiodurans

<400> SEQUENCE: 130

Val Tyr Ala Asp Val Val Asn Asn His Thr Ala Glu Gly Asn His Leu
 1               5                  10                  15

Gly Pro Thr Leu Ser Phe Arg Gly Ile Asp Asn Thr Ser Tyr Tyr Arg
                20                  25                  30

Leu Leu His Asp Asn Pro Arg Tyr Tyr Met Asp Phe Thr Gly Cys Gly
            35                  40                  45

Asn Thr Leu Asn Met Gln Cys Pro Gln Val Leu Gln Leu Ile Met Asp
 50                  55                  60

Ser Leu Arg Tyr Trp Val Leu Glu Met His Val Asp Gly Phe Arg Ile
 65                  70                  75                  80

Asp Ala

<210> SEQ ID NO 131
<211> LENGTH: 79
<212> TYPE: PRT
<213> ORGANISM: Deinococcus radiodurans

<400> SEQUENCE: 131

Val Tyr Ala Asp Val Val Phe Asn His Thr Ser Glu Gly Asn Glu Thr
 1               5                  10                  15

Gly Pro Thr Phe Ser Phe Lys Gly Leu Glu Asn Arg Val Tyr Tyr Met
                20                  25                  30

Leu Asn Asp Asp Gly Thr Tyr Arg Asn Tyr Ser Gly Cys Gly Asn Thr
            35                  40                  45

Val Asn Gly Asn His Pro Ile Val Arg Glu Met Ile Phe His Cys Leu
 50                  55                  60
```

```
Arg His Trp Val His Asn Tyr His Val Asp Gly Phe Arg Thr Ala
 65                  70                  75
```

<210> SEQ ID NO 132
<211> LENGTH: 82
<212> TYPE: PRT
<213> ORGANISM: Deinococcus radiodurans

<400> SEQUENCE: 132

```
Val Tyr Ala Asp Val Val Phe Asn His Thr Ala Glu Gly Asn His Leu
  1               5                  10                  15

Gly Pro Thr Leu Ser Leu Arg Gly Ile Asp Asn Thr Ser Ser Tyr Arg
             20                  25                  30

Leu Gln Pro His Asp Pro Arg Phe Tyr Gln Asp Phe Thr Gly Cys Gly
         35                  40                  45

Asn Thr Leu Asn Met Arg Ser Pro Arg Met Leu Gln Leu Leu Met Asp
     50                  55                  60

Ser Leu Arg Tyr Trp Val Gln Glu Met His Val Asp Gly Phe Arg Ile
 65                  70                  75                  80

Asp Ala
```

<210> SEQ ID NO 133
<211> LENGTH: 70
<212> TYPE: PRT
<213> ORGANISM: Deinococcus radiodurans

<400> SEQUENCE: 133

```
Val Tyr Ala Asp Val Val Phe Asn His Leu Gly Pro Ala Gly Asn Tyr
  1               5                  10                  15

Leu Asn Arg Phe Gly Pro Tyr Phe Thr Asp Arg Tyr Ala Thr Pro Trp
             20                  25                  30

Gly Ala Ala Val Asn Leu Asp Gly Pro Gly Ser Asp Glu Val Arg Ala
         35                  40                  45

Phe Phe Val Asp Asn Ala Leu Met Trp Leu Arg Asp Tyr His Ile Asp
     50                  55                  60

Gly Phe Arg Ile Asp Ala
 65                  70
```

<210> SEQ ID NO 134
<211> LENGTH: 82
<212> TYPE: PRT
<213> ORGANISM: Deinococcus radiodurans

<400> SEQUENCE: 134

```
Val Tyr Ala Asp Val Val Ile Asn His Thr Ala Glu Gly Asn His Leu
  1               5                  10                  15

Gly Pro Thr Leu Ser Leu Arg Gly Val Asp Asn Ala Thr Tyr Tyr Arg
             20                  25                  30

Leu Met Pro Asp Asp Arg Arg His Tyr Leu Asp Phe Thr Gly Cys Gly
         35                  40                  45

Asn Thr Leu Asn Met Gln Ser Pro Gln Val Leu Gln Leu Ile Met Asp
     50                  55                  60

Ser Leu Arg Tyr Trp Val Leu Glu Met His Val Asp Gly Phe Arg Ile
 65                  70                  75                  80

Asp Ala
```

<210> SEQ ID NO 135

```
<211> LENGTH: 81
<212> TYPE: PRT
<213> ORGANISM: Deinococcus radiodurans

<400> SEQUENCE: 135
```

| Val | Tyr | Ala | Asp | Val | Ile | Asn | His | Thr | Ala | Glu | Gly | Asn | His | Leu |
|---|---|---|---|---|---|---|---|---|---|---|---|---|---|---|
| 1 | | | | 5 | | | | | 10 | | | | | 15 |

| Gly | Pro | Thr | Leu | Ser | Phe | Lys | Gly | Leu | Asp | Asn | Pro | Ser | Tyr | Tyr | Arg |
|---|---|---|---|---|---|---|---|---|---|---|---|---|---|---|---|
| | | | 20 | | | | | 25 | | | | | 30 | | |

| Leu | Ala | Asp | Asp | Pro | Arg | Tyr | Tyr | Thr | Asp | Thr | Thr | Gly | Thr | Gly | Asn |
|---|---|---|---|---|---|---|---|---|---|---|---|---|---|---|---|
| | | | 35 | | | | | 40 | | | | | 45 | | |

| Ser | Leu | Leu | Met | Arg | Ser | Pro | His | Val | Leu | Gln | Met | Ile | Met | Asp | Ser |
|---|---|---|---|---|---|---|---|---|---|---|---|---|---|---|---|
| | 50 | | | | | 55 | | | | | 60 | | | | |

| Leu | Arg | Tyr | Trp | Val | Thr | Glu | Met | His | Val | Asp | Gly | Phe | Arg | Ile | Asp |
|---|---|---|---|---|---|---|---|---|---|---|---|---|---|---|---|
| 65 | | | | | 70 | | | | | 75 | | | | | 80 |

Ala

```
<210> SEQ ID NO 136
<211> LENGTH: 81
<212> TYPE: PRT
<213> ORGANISM: Pseudomonas aeruginosa

<400> SEQUENCE: 136
```

| Val | Tyr | Ala | Asp | Val | Ile | Asn | His | Ser | Arg | Glu | Gly | Asn | His | Tyr |
|---|---|---|---|---|---|---|---|---|---|---|---|---|---|---|
| 1 | | | | 5 | | | | | 10 | | | | | 15 |

| Gly | Pro | Thr | Val | Ser | Phe | Lys | Gly | Leu | Asp | Asn | Asn | Ile | Tyr | Tyr | Met |
|---|---|---|---|---|---|---|---|---|---|---|---|---|---|---|---|
| | | | 20 | | | | | 25 | | | | | 30 | | |

| Leu | Glu | Ser | Ala | Pro | Glu | Phe | Tyr | Asn | Asp | Phe | Thr | Gly | Cys | Gly | Asn |
|---|---|---|---|---|---|---|---|---|---|---|---|---|---|---|---|
| | | | 35 | | | | | 40 | | | | | 45 | | |

| Thr | Leu | Asn | Cys | Asn | His | Pro | Val | Val | Arg | Lys | Phe | Ile | Leu | Asp | Cys |
|---|---|---|---|---|---|---|---|---|---|---|---|---|---|---|---|
| | 50 | | | | | 55 | | | | | 60 | | | | |

| Leu | Arg | Tyr | Trp | Val | Thr | Glu | Met | His | Val | Asp | Gly | Phe | Arg | Ile | Asp |
|---|---|---|---|---|---|---|---|---|---|---|---|---|---|---|---|
| 65 | | | | | 70 | | | | | 75 | | | | | 80 |

Ala

```
<210> SEQ ID NO 137
<211> LENGTH: 80
<212> TYPE: PRT
<213> ORGANISM: Pseudomonas aeruginosa

<400> SEQUENCE: 137
```

| Val | Tyr | Ala | Asp | Val | Ile | Asn | His | Ser | Ala | Glu | Leu | Asp | Lys | Asp |
|---|---|---|---|---|---|---|---|---|---|---|---|---|---|---|
| 1 | | | | 5 | | | | | 10 | | | | | 15 |

| Gly | Pro | Thr | Leu | Ser | Leu | Ser | Gly | Ile | Asp | Asn | Arg | Ser | Tyr | Tyr | Trp |
|---|---|---|---|---|---|---|---|---|---|---|---|---|---|---|---|
| | | | 20 | | | | | 25 | | | | | 30 | | |

| Leu | Met | Asp | Asn | Gly | Asp | Tyr | Gln | Asn | Trp | Thr | Gly | Cys | Gly | Asn | Thr |
|---|---|---|---|---|---|---|---|---|---|---|---|---|---|---|---|
| | | | 35 | | | | | 40 | | | | | 45 | | |

| Leu | Asn | Leu | Ser | Thr | Pro | Gly | Val | Val | Ala | Gln | Met | Met | Asp | Cys | Leu |
|---|---|---|---|---|---|---|---|---|---|---|---|---|---|---|---|
| | 50 | | | | | 55 | | | | | 60 | | | | |

| Arg | Tyr | Trp | Val | Glu | Ser | Phe | His | Ile | Asp | Gly | Phe | Arg | Ile | Asp | Ala |
|---|---|---|---|---|---|---|---|---|---|---|---|---|---|---|---|
| 65 | | | | | 70 | | | | | 75 | | | | | 80 |

```
<210> SEQ ID NO 138
<211> LENGTH: 82
<212> TYPE: PRT
<213> ORGANISM: Arabidopsis thaliana

<400> SEQUENCE: 138
```

```
Val Tyr Ala Asp Val Phe Asn His Thr Ala Glu Gly Asn His Met
1               5                   10                  15

Gly Pro Val Leu Ser Met Lys Gly Ile Asp Asn Ala Gly Tyr Tyr Arg
                20                  25                  30

Leu Val Asp Ser Asp Arg Arg Tyr Tyr Asp Thr Thr Gly Thr Gly
            35                  40                  45

Asn Ser Leu Asp Met Arg His Pro His Val Leu Gln Leu Ile Met Asp
        50                  55                  60

Ser Leu Arg Tyr Trp Val Thr Asp Met His Val Asp Gly Phe Arg Ile
65                  70                  75                  80

Asp Ala

<210> SEQ ID NO 139
<211> LENGTH: 82
<212> TYPE: PRT
<213> ORGANISM: Arabidopsis thaliana

<400> SEQUENCE: 139

Val Tyr Ala Asp Val Phe Asn His Thr Ala Glu Gly Asn His Leu
1               5                   10                  15

Gly Pro Thr Leu Ser Phe Arg Gly Ile Asp Asn Pro Ala Tyr Tyr Arg
                20                  25                  30

Leu Val Pro Asp Lys Gln His Tyr Tyr Asp Thr Thr Gly Thr Gly
            35                  40                  45

Asn Ser Phe Asn Met Ala His Pro His Ala Leu Gln Leu Ile Met Asp
        50                  55                  60

Ser Leu Arg Tyr Trp Val Thr Glu Cys His Val Asp Gly Phe Arg Ile
65                  70                  75                  80

Asp Ala

<210> SEQ ID NO 140
<211> LENGTH: 81
<212> TYPE: PRT
<213> ORGANISM: Arabidopsis thaliana
<220> FEATURE:
<221> NAME/KEY: misc_feature
<222> LOCATION: (22)..(22)
<223> OTHER INFORMATION: Xaa can be any naturally occurring amino acid

<400> SEQUENCE: 140

Val Tyr Ala Asp Val Phe Asn His Thr Cys Glu Gly Asn Glu Gln
1               5                   10                  15

Gly Pro Ile Leu Ser Xaa Lys Gly Leu Glu Asn Arg Val Tyr Tyr Met
                20                  25                  30

Met Ala Asn Gly Gly Ser His Tyr Met Asn Tyr Ser Cys Gly Asn
            35                  40                  45

Thr Val Asn Gly Asn His Pro Ile Val Arg Glu Met Ile Phe His Cys
        50                  55                  60

Leu Arg His Trp Val His Asn Tyr His Ile Asp Gly Phe Arg Ile Asp
65                  70                  75                  80

Ala

<210> SEQ ID NO 141
<211> LENGTH: 82
<212> TYPE: PRT
<213> ORGANISM: Arabidopsis thaliana

<400> SEQUENCE: 141
```

```
Val Tyr Ala Asp Val Val Asn Asn His Thr Cys Glu Gly Asn Gln Met
1               5                   10                  15

Gly Pro Thr Leu Ser Trp Arg Gly Ile Asp Asn Ala Ser Tyr Tyr Arg
                20                  25                  30

Leu Thr Asp Asp Lys Arg Tyr Tyr Met Asp Tyr Thr Gly Cys Gly
            35                  40                  45

Asn Thr Leu Asn Met Thr His Pro Arg Val Leu Gln Leu Ile Met Asp
        50                  55                  60

Ser Leu Arg Tyr Trp Val Thr Glu Met His Val Asp Gly Phe Arg Ile
65                  70                  75                  80

Asp Ala
```

<210> SEQ ID NO 142
<211> LENGTH: 82
<212> TYPE: PRT
<213> ORGANISM: Arabidopsis thaliana

<400> SEQUENCE: 142

```
Val Tyr Ala Asp Val Val Ile Asn His Thr Gly Glu Gly Asn His Gln
1               5                   10                  15

Gly Pro Thr Ile Ser Phe Lys Gly Leu Glu Asn Glu Ala Tyr Tyr Met
                20                  25                  30

Leu Ser Pro Gly Asp Gly Ala Tyr Tyr Met Asn Tyr Ser Gly Cys Gly
            35                  40                  45

Asn Thr Val Asn Ala Asn His Pro Val Val Glu Lys Phe Ile Ala Asp
        50                  55                  60

Cys Leu Gly Tyr Trp Val Glu Glu Met His Val Asp Gly Phe Arg Ile
65                  70                  75                  80

Asp Ala
```

<210> SEQ ID NO 143
<211> LENGTH: 82
<212> TYPE: PRT
<213> ORGANISM: Arabidopsis thaliana
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (71)..(72)
<223> OTHER INFORMATION: Xaa can be any naturally occurring amino acid

<400> SEQUENCE: 143

```
Val Tyr Ala Asp Val Val Ile Asn His Thr Ser Glu Gly Asn His Leu
1               5                   10                  15

Gly Pro Thr Leu Ser Leu Arg Gly Ile Asp Asn Glu Thr Tyr Tyr Arg
                20                  25                  30

Leu Thr Pro Arg Thr Ser Ala Thr Thr Ser Ile Ser Pro Ala Ala Gly
            35                  40                  45

Thr Arg Ser Asn Met Xaa Ser Pro Gln Val Leu Gln Leu Ile Met Asp
        50                  55                  60

Ser Xaa Arg Tyr Trp Val Xaa Xaa Met His Val Asp Gly Phe Arg Ile
65                  70                  75                  80

Asp Ala
```

-continued

```
<210> SEQ ID NO 144
<211> LENGTH: 82
<212> TYPE: PRT
<213> ORGANISM: Arabidopsis thaliana
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid

<400> SEQUENCE: 144

Val Tyr Ala Asp Val Val Phe Asn His Thr Gly Glu Gly Asn His Gln
1               5                   10                  15

Gly Pro Thr Ile Ser Phe Lys Gly Leu Glu Xaa Arg Gly Val Leu His
            20                  25                  30

Ala Leu Ala Gly Arg Arg Gly Val Leu His Glu Leu Leu Arg Leu Arg
        35                  40                  45

Glu His Gly Gln Arg Glu Pro Pro Arg Arg Glu Val His Arg Arg
    50                  55                  60

Leu Pro Gly Leu Leu Gly Arg Xaa Met His Val Asp Gly Phe Arg Ile
65                  70                  75                  80

Asp Ala

<210> SEQ ID NO 145
<211> LENGTH: 82
<212> TYPE: PRT
<213> ORGANISM: Arabidopsis thaliana

<400> SEQUENCE: 145

Val Tyr Ala Asp Val Val Phe Asn His Thr Ala Glu Gly Asn Gln Leu
1               5                   10                  15

Gly Pro Thr Leu Ser Phe Arg Gly Ile Asp Asn Ala Asn Tyr Tyr Arg
            20                  25                  30

Leu Val Asp Glu Asp Lys Lys His Tyr Tyr Asp Thr Thr Gly Thr Gly
        35                  40                  45

Asn Thr Leu Leu Met Lys Ser Pro His Val Leu Gln Leu Ile Met Asp
    50                  55                  60

Ser Leu Arg Tyr Trp Val Thr Glu Met His Val Asp Gly Phe Arg Ile
65                  70                  75                  80

Asp Ala

<210> SEQ ID NO 146
<211> LENGTH: 107
<212> TYPE: PRT
<213> ORGANISM: Triticum aestivum
<220> FEATURE:
<221> NAME/KEY: misc_feature
<222> LOCATION: (16)..(16)
<223> OTHER INFORMATION: Xaa can be any naturally occurring amino acid

<400> SEQUENCE: 146

Val Tyr Ala Asp Val Val Ile Asn His Thr Ser Asp Gln His Pro Xaa
1               5                   10                  15

Phe Gln Glu Ser Arg Gln Asp Arg Thr Asn Pro Lys Ala Asp Trp Tyr
            20                  25                  30

Val Trp Asp Asp Asp Gly Thr Lys Trp Ser Glu Ala Arg Val Ile Phe
        35                  40                  45
```

```
Val Asp Thr Glu Pro Ser Asn Trp Thr Phe Asp Pro Gln Arg Glu Gln
        50                  55                  60

Phe Tyr Trp His Arg Phe Ser His Gln Pro Asp Leu Asn Phe Asp
65                  70                  75                  80

Asn Pro Glu Val Glu Ala Met Phe Asp Val Met Arg Phe Trp Leu
                85                  90                  95

Asp Leu Gly Leu Asp Gly Phe Arg Ile Asp Ala
            100                 105
```

<210> SEQ ID NO 147
<211> LENGTH: 82
<212> TYPE: PRT
<213> ORGANISM: Triticum aestivum
<220> FEATURE:
<221> NAME/KEY: misc_feature
<222> LOCATION: (36)..(37)
<223> OTHER INFORMATION: Xaa can be any naturally occurring amino acid

<400> SEQUENCE: 147

```
Val Tyr Ala Asp Val Val Phe Asn His Thr Gly Glu Gly Asn His Leu
1               5                   10                  15

Gly Leu Thr Leu Ser Phe Lys Gly Leu Asp Asn Pro Thr Tyr Tyr Gln
                20                  25                  30

Leu Lys Arg Xaa Xaa Gln Arg Tyr Tyr Val Asp Tyr Thr Gly Thr Gly
            35                  40                  45

Asn Ser Leu Asn Val His His Pro Gln Val Leu Gln Leu Val Leu Asp
        50                  55                  60

Ser Leu Arg Tyr Trp Val Lys Val Met His Val Asp Gly Phe Arg Ile
65                  70                  75                  80

Asp Ala
```

<210> SEQ ID NO 148
<211> LENGTH: 107
<212> TYPE: PRT
<213> ORGANISM: Sulfolobus shibatae

<400> SEQUENCE: 148

```
Val Tyr Ala Asp Val Val Phe Asn His Ser Ser Asp Arg His Pro Trp
1               5                   10                  15

Phe Val Glu Ser Arg Ser Ser Arg Ala Asn Ala Lys Arg Asp Trp Tyr
                20                  25                  30

Ile Trp Arg Asp Pro Ala Pro Gly Gly Pro Pro Asn Asn Trp Met
            35                  40                  45

Ser Asp Phe Gly Gly Pro Ala Trp Thr Leu Asp Pro Ala Thr Gly Gln
        50                  55                  60

Tyr Tyr Leu His Ala Phe Leu Pro Gln Gln Pro Asp Leu Asn Trp Arg
65                  70                  75                  80

Asn Pro Asp Val Arg Ala Ala Met Met Gly Val Leu Arg Phe Trp Leu
                85                  90                  95

Asp Arg Gly Val Asp Gly Phe Arg Ile Asp Ala
            100                 105
```

<210> SEQ ID NO 149
<211> LENGTH: 71
<212> TYPE: PRT
<213> ORGANISM: Streptomyces coelicolor

<400> SEQUENCE: 149

```
Val Tyr Ala Asp Val Val Phe Asn His Leu Gly Pro Ala Gly Asn Tyr
```

```
                1               5                  10                 15
Leu Pro Arg Phe Ser Arg Ser Tyr Leu Ser His Arg Tyr Ala Asn Glu
                20                 25                 30

Trp Gly Asp Ala Leu Asn Tyr Asp Asp Thr Gly Cys Glu Gly Leu Arg
            35                 40                 45

Glu Leu Val Leu Ser Asn Ile Ala Tyr Trp Val Arg Glu Phe His Leu
        50                 55                 60

Asp Gly Phe Arg Ile Asp Ala
65                  70

<210> SEQ ID NO 150
<211> LENGTH: 82
<212> TYPE: PRT
<213> ORGANISM: Alicyclobacillus acidocaldarius

<400> SEQUENCE: 150

Val Tyr Ala Asp Val Val Phe Asn His Thr Gly Glu Ser Asp Ala Leu
1               5                  10                 15

Gly Pro Thr Leu Ser Leu Arg Gly Leu Asp Asn Arg Ala Tyr Tyr Arg
                20                 25                 30

His Leu Pro Gly Glu Ala Gly Ser Leu Val Asn Asp Thr Gly Thr Gly
            35                 40                 45

Asn Thr Val Ala Cys Asn Tyr Pro Val Val Arg Gly Leu Val Leu Asp
        50                 55                 60

Thr Leu Arg His Phe Val Leu Asn Ala Gly Val Asp Gly Phe Arg Ile
65                  70                 75                 80

Asp Ala

<210> SEQ ID NO 151
<211> LENGTH: 81
<212> TYPE: PRT
<213> ORGANISM: Alicyclobacillus acidocaldarius

<400> SEQUENCE: 151

Val Tyr Ala Asp Val Val Phe Asn His Thr Gly Glu Gly Asn His Leu
1               5                  10                 15

Gly His Pro Arg Val Gln Gly His Arg Gln Gln Gly Val Leu Pro Val
                20                 25                 30

Gly Ala Gly Gln Pro Ala Leu Val His Arg Phe His Gly His Arg Lys
            35                 40                 45

Gln Pro Glu His Ala Ala Ser Ala His Asp Pro Ala His His Gly Leu
        50                 55                 60

Ala Ala Leu Leu Gly Thr Glu Met His Val Asp Gly Phe Arg Ile Asp
65                  70                 75                 80

Ala

<210> SEQ ID NO 152
<211> LENGTH: 82
<212> TYPE: PRT
<213> ORGANISM: Alicyclobacillus acidocaldarius

<400> SEQUENCE: 152

Val Tyr Ala Asp Val Val Phe Asn His Thr Thr Glu Gly Asn His Gln
1               5                  10                 15

Gly Pro Thr Ile Asn Phe Arg Gly Phe Asp Asn Ser Val Tyr Tyr Phe
                20                 25                 30

Thr Val Pro Asp Asp Lys Gln Tyr Tyr Met Asp Tyr Ser Gly Cys Gly
```

```
                  35                  40                  45
Asn Thr Leu Asn Cys Asn His Pro Val Val Glu Lys Met Ile Leu Asp
            50                  55                  60

Cys Leu Glu Phe Trp Val Arg Asp Met His Ile Asp Gly Phe Arg Ile
 65                  70                  75                  80

Asp Ala

<210> SEQ ID NO 153
<211> LENGTH: 82
<212> TYPE: PRT
<213> ORGANISM: Rhizobium tropici

<400> SEQUENCE: 153

Val Tyr Ala Asp Val Val Tyr Asn His Thr Ala Glu Gly Asn His Leu
 1               5                  10                  15

Gly Pro Thr Leu Ser Phe Arg Gly Ile Asp Asn Ala Thr Tyr Tyr Trp
            20                  25                  30

Leu Lys Pro Asp Gln Pro Arg Tyr Glu Asp Phe Thr Gly Cys Gly
            35                  40                  45

Asn Ser Leu Asn Leu Thr His Pro His Val Leu Gln Leu Val Met Asp
            50                  55                  60

Ser Leu Arg Tyr Trp Val Glu Gln Cys His Val Asp Gly Phe Arg Ile
 65                  70                  75                  80

Asp Ala

<210> SEQ ID NO 154
<211> LENGTH: 70
<212> TYPE: PRT
<213> ORGANISM: Rhizobium tropici

<400> SEQUENCE: 154

Val Tyr Ala Asp Val Val Phe Asn His Leu Gly Pro Ala Gly Asn Tyr
 1               5                  10                  15

Leu Arg Glu Phe Gly Pro Tyr Phe Thr Asp Arg Tyr Gly Thr Pro Trp
            20                  25                  30

Gly Asp Ala Val Asn Leu Asp Asp Arg Gly Ser Thr Glu Val Arg Asn
            35                  40                  45

Tyr Phe Phe Asp Asn Ala Leu Gly Trp Leu Glu His Tyr His Leu Asp
            50                  55                  60

Gly Phe Arg Ile Asp Ala
 65                  70

<210> SEQ ID NO 155
<211> LENGTH: 82
<212> TYPE: PRT
<213> ORGANISM: Rhizobium tropici

<400> SEQUENCE: 155

Val Tyr Ala Asp Val Val Phe Asn His Thr Ala Glu Gly Asn His Leu
 1               5                  10                  15

Gly Pro Met Leu Ser Phe Lys Gly Ile Asp Asn Leu Ser Tyr Tyr Arg
            20                  25                  30

Thr Leu Pro Gly Asp Pro Arg Phe Tyr Met Asp Tyr Thr Gly Thr Gly
            35                  40                  45

Asn Ser Leu Asn Val Arg His Pro His Ser Val Gln Leu Ile Met Asp
            50                  55                  60

Ser Leu Arg Tyr Trp Val Thr Glu Met His Val Asp Gly Phe Arg Ile
```

```
65                  70                  75                  80
Asp Ala

<210> SEQ ID NO 156
<211> LENGTH: 70
<212> TYPE: PRT
<213> ORGANISM: Streptomyces coelicolor

<400> SEQUENCE: 156

Val Tyr Ala Asp Val Val Phe Asn His Phe Gly Pro Asp Gly Cys Trp
1               5                   10                  15

Ile Glu Lys Phe Ser Pro His Phe Phe Ser Glu Arg Ala Thr Glu Trp
            20                  25                  30

Gly Arg Ala Ile Asn Phe Asp Gly Glu His Ala Ala Glu Val Arg Ala
        35                  40                  45

Phe Phe Val Ala Asn Ala Ser Tyr Trp Ile Glu Glu Phe His Leu Asp
    50                  55                  60

Gly Phe Arg Ile Asp Ala
65                  70

<210> SEQ ID NO 157
<211> LENGTH: 82
<212> TYPE: PRT
<213> ORGANISM: Streptomyces coelicolor

<400> SEQUENCE: 157

Val Tyr Ala Asp Val Val Ile Asn His Thr Gly Glu Gly Ser His Thr
1               5                   10                  15

Gly Pro Thr Leu Cys Phe Arg Gly Ile Asp Asn Ala Ser Tyr Tyr Arg
            20                  25                  30

Leu Asn Ala Gln Asn Pro Arg Leu Tyr Val Asp Tyr Thr Gly Cys Gly
        35                  40                  45

Asn Thr Leu Asn Met Gln Asn Pro Arg Val Leu Gln Leu Ile Met Asp
    50                  55                  60

Ser Leu Arg Tyr Trp Val Thr Glu Met His Val Asp Gly Phe Arg Ile
65                  70                  75                  80

Asp Ala

<210> SEQ ID NO 158
<211> LENGTH: 81
<212> TYPE: PRT
<213> ORGANISM: Streptomyces coelicolor

<400> SEQUENCE: 158

Val Tyr Ala Asp Val Val Phe Asn His Thr Gly Glu Gly Asn His Leu
1               5                   10                  15

Gly Pro Thr Val Ser Leu Lys Gly Ile Asp Asn Thr Ala Tyr Tyr Arg
            20                  25                  30

Leu Glu Glu Asp Lys Arg Phe Tyr Thr Asp Phe Thr Gly Thr Gly Asn
        35                  40                  45

Ser Leu Asn Met Arg His Pro Arg Thr Ile Gln Leu Ile Met Asp Ser
    50                  55                  60

Leu Arg Tyr Trp Val Thr Glu Met His Val Asp Gly Phe Arg Ile Asp
65                  70                  75                  80

Ala

<210> SEQ ID NO 159
```

```
<211> LENGTH: 82
<212> TYPE: PRT
<213> ORGANISM: Streptomyces coelicolor

<400> SEQUENCE: 159

Val Tyr Ala Asp Val Val Phe Asn His Thr Ser Glu Gly His His Leu
1               5                   10                  15

Gly Pro Thr Leu Ser Tyr Lys Gly Ile Asp Asn Pro Thr Tyr Tyr Arg
            20                  25                  30

Leu Leu Pro Glu Asp Pro Arg Phe Tyr Arg Asp Tyr Thr Gly Thr Gly
        35                  40                  45

Asn Ser Leu Asn Met Arg His Pro Gln Thr Leu Lys Leu Val Met Asp
    50                  55                  60

Ser Leu Arg Tyr Trp Val Leu Glu Met His Val Asp Gly Phe Arg Ile
65                  70                  75                  80

Asp Ala

<210> SEQ ID NO 160
<211> LENGTH: 80
<212> TYPE: PRT
<213> ORGANISM: Sulfolobus solfataricus

<400> SEQUENCE: 160

Val Tyr Ala Asp Val Val Phe Asn His Thr Ala Glu Gly Asn Glu Thr
1               5                   10                  15

Gly Pro Thr Phe Cys Phe Lys Gly Leu Glu Asn Lys Val His Tyr Met
            20                  25                  30

Leu Asn Glu Asn Gly Thr Tyr Lys Asn Phe Ser Gly Cys Gly Asn Thr
        35                  40                  45

Val Asn Gly Asn His Pro Val Met Arg Glu Met Ile Phe His Cys Leu
    50                  55                  60

Arg His Trp Val His Asn Tyr His Ile Asp Gly Phe Arg Ile Asp Ala
65                  70                  75                  80

<210> SEQ ID NO 161
<211> LENGTH: 67
<212> TYPE: PRT
<213> ORGANISM: Sulfolobus solfataricus

<400> SEQUENCE: 161

Val Tyr Ala Asp Val Val Ile Asn His Phe Gly Pro Ala Gly Asn Ser
1               5                   10                  15

His Tyr Ala Phe Ala Pro Glu Ile Lys Ala Pro Thr Met Thr Glu Trp
            20                  25                  30

Gly Asp Ala Leu Asp Tyr Ser Arg Pro Gly Ala Arg Glu Leu Phe Ile
        35                  40                  45

Thr Asn Ala Ala Tyr Trp Ile Arg Glu Phe His Phe Asp Gly Phe Arg
    50                  55                  60

Ile Asp Ala
65

<210> SEQ ID NO 162
<211> LENGTH: 82
<212> TYPE: PRT
<213> ORGANISM: Sulfolobus solfataricus

<400> SEQUENCE: 162

Val Tyr Ala Asp Val Val Asn Asn His Thr Ala Glu Gly Asn His Leu
1               5                   10                  15
```

Gly Pro Met Leu Ser Met Lys Gly Ile Asp Asn Ala Gly Tyr Tyr Arg
            20                  25                  30

Leu Val Asp Asp Lys Arg Phe Tyr Tyr Asp Thr Thr Gly Thr Gly
            35                  40                  45

Asn Ser Leu Asp Met Arg His Pro His Val Leu Gln Leu Ile Met Asp
        50                  55                  60

Ser Leu Arg Tyr Trp Val Thr Glu Met His Val Asp Gly Phe Arg Ile
65                  70                  75                  80

Asp Ala

<210> SEQ ID NO 163
<211> LENGTH: 80
<212> TYPE: PRT
<213> ORGANISM: Sulfolobus solfataricus

<400> SEQUENCE: 163

Val Tyr Ala Asp Val Val Phe Asn His Thr Ala Glu Gly Asp Gln Arg
1               5                   10                  15

Gly Pro Thr Leu Ser Trp Arg Gly Leu Asp Asn Ala Ser Ser Tyr Ala
            20                  25                  30

Leu Asp Gly Ser Gly Gln Tyr Leu Asn Phe Thr Gly Cys Gly Asn Ala
            35                  40                  45

Ile Asn Ala Gly Glu Pro Arg Met Val Gln Phe Val Met Asp Ser Leu
        50                  55                  60

Arg Trp Trp Val Gln Ala Phe Gly Val Asp Gly Phe Arg Ile Asp Ala
65                  70                  75                  80

<210> SEQ ID NO 164
<211> LENGTH: 82
<212> TYPE: PRT
<213> ORGANISM: Sulfolobus solfataricus

<400> SEQUENCE: 164

Val Tyr Ala Asp Val Val Phe Asn His Thr Ala Glu Gly Asn His Leu
1               5                   10                  15

Gly Pro Thr Leu Ser Phe Arg Gly Ile Asp Asn Ala Val Tyr Tyr Lys
            20                  25                  30

Leu Pro Ala Asn Asp Arg Arg His Tyr Trp Asp Ser Thr Gly Thr Gly
            35                  40                  45

Asn Thr Leu Asp Val Asn His Pro Gln Val Leu Lys Met Val Leu Asp
        50                  55                  60

Ser Leu Arg His Trp Val Glu Asp Tyr His Val Asp Gly Phe Arg Ile
65                  70                  75                  80

Asp Ala

<210> SEQ ID NO 165
<211> LENGTH: 82
<212> TYPE: PRT
<213> ORGANISM: Sulfolobus solfataricus

<400> SEQUENCE: 165

Val Tyr Ala Asp Val Val Phe Asn His Thr Ala Glu Gly Asn His Leu
1               5                   10                  15

Gly Pro Thr Leu Ser Phe Arg Gly Ile Asp Asn Ala Ala Tyr Tyr Arg
            20                  25                  30

Leu Val Asp Ser Asp Arg Arg His Tyr Met Asp Tyr Thr Gly Thr Gly
            35                  40                  45

```
Asn Thr Leu Asn Met Arg Asn Pro Phe Pro Leu Gln Leu Leu Met Asp
        50                  55                  60

Ser Leu Arg Tyr Trp Val Thr Glu Cys His Val Asp Gly Phe Arg Ile
65                  70                  75                  80

Asp Ala

<210> SEQ ID NO 166
<211> LENGTH: 82
<212> TYPE: PRT
<213> ORGANISM: Solfolobus solfataricus

<400> SEQUENCE: 166

Val Tyr Ala Asp Val Val Phe Asn His Thr Ala Glu Gly Asn Gln Leu
1               5                   10                  15

Gly Pro Thr Leu Ser Phe Arg Gly Ile Asp Asn Thr Ser Tyr Tyr Trp
                20                  25                  30

Leu Leu Pro Asp Glu Pro Arg Tyr Tyr Asp Asp Phe Thr Gly Cys Gly
                35                  40                  45

Asn Ala Leu Asn Leu Thr His Pro Arg Val Leu Gln Met Val Met Asp
        50                  55                  60

Ser Leu Arg Tyr Trp Val Glu Met Cys Leu Val Asp Gly Phe Arg Ile
65                  70                  75                  80

Asp Ala

<210> SEQ ID NO 167
<211> LENGTH: 82
<212> TYPE: PRT
<213> ORGANISM: Solfolobus solfataricus

<400> SEQUENCE: 167

Val Tyr Ala Asp Val Val Phe Asn His Thr Gly Glu Gly Ser His Thr
1               5                   10                  15

Gly Pro Thr Leu Cys Phe Arg Gly Ile Asp Asn Ala Ser Tyr Tyr Arg
                20                  25                  30

Leu Asn Pro Gln Asn Pro Arg Leu Tyr Val Asp Tyr Thr Gly Cys Gly
                35                  40                  45

Asn Thr Leu Asn Met Gln Asn Pro Arg Val Leu Gln Leu Ile Met Asp
        50                  55                  60

Ser Leu Arg Tyr Trp Val Thr Glu Met His Val Asp Gly Phe Arg Ile
65                  70                  75                  80

Asp Ala

<210> SEQ ID NO 168
<211> LENGTH: 80
<212> TYPE: PRT
<213> ORGANISM: Solfolobus solfataricus

<400> SEQUENCE: 168

Val Tyr Ala Asp Val Val Phe Asn His Thr Ala Glu Gly Asn Glu Thr
1               5                   10                  15

Gly Pro Thr Phe Cys Phe Lys Gly Leu Glu Asn Lys Val Tyr Tyr Met
                20                  25                  30

Leu Asn Glu Asn Gly Thr Tyr Lys Asn Phe Ser Gly Cys Gly Asn Thr
                35                  40                  45

Val Asn Gly Asn His Pro Val Met Arg Glu Met Ile Phe His Cys Leu
        50                  55                  60
```

-continued

Arg His Trp Val His Asn Tyr His Ile Asp Gly Phe Arg Ile Asp Ala
65              70                  75                  80

<210> SEQ ID NO 169
<211> LENGTH: 80
<212> TYPE: PRT
<213> ORGANISM: Solfolobus solfataricus

<400> SEQUENCE: 169

Val Tyr Ala Asp Val Val Phe Asn His Thr Ala Glu Gly Pro Gln Gly
1               5                   10                  15

Gly Pro Ala Leu Cys Trp Arg Gly Leu Ser Glu Met Lys Tyr Tyr Arg
                20                  25                  30

His His Asp Asp Gly Arg Tyr Leu Asp Thr Thr Gly Cys Gly Asn Thr
            35                  40                  45

Val Asn Phe Thr Glu Pro Arg Val Ile Gln Phe Ala Leu Asp Ser Leu
        50                  55                  60

Arg Tyr Trp Val Asp Glu Phe Gly Ile Asp Gly Phe Arg Ile Asp Ala
65              70                  75                  80

<210> SEQ ID NO 170
<211> LENGTH: 71
<212> TYPE: PRT
<213> ORGANISM: Solfolobus solfataricus

<400> SEQUENCE: 170

Val Tyr Ala Asp Val Val Phe Asn His Phe Gly Pro Asp Gly Asn Tyr
1               5                   10                  15

Leu Arg Ala Tyr Ser Asp Asp Tyr Phe Thr Asp Arg Tyr Ala Thr Pro
                20                  25                  30

Trp Gly Glu Ala Ile Asp Tyr Asp Gly Pro Gly Ser Arg Trp Val Arg
            35                  40                  45

Gln Phe Ile Arg Glu Asn Ala Arg Tyr Trp Leu Asp Glu Tyr Arg Leu
        50                  55                  60

Asp Gly Phe Arg Ile Asp Ala
65              70

<210> SEQ ID NO 171
<211> LENGTH: 82
<212> TYPE: PRT
<213> ORGANISM: Solfolobus solfataricus

<400> SEQUENCE: 171

Val Tyr Ala Asp Val Val Tyr Asn His Thr Ala Glu Gly Asn Gln Met
1               5                   10                  15

Gly Pro Thr Leu Ser Leu His Gly Val Asp Asn Val Thr Tyr Tyr Arg
                20                  25                  30

Leu Val Pro His Asp Arg Arg Tyr Tyr Gln Asp Phe Thr Gly Cys Gly
            35                  40                  45

Asn Thr Leu Asn Met Gln Ser Pro Gln Val Leu Gln Leu Ile Met Asp
        50                  55                  60

Ser Leu Arg Tyr Trp Val Leu Glu Met His Val Asp Gly Phe Arg Ile
65              70                  75                  80

Asp Ala

<210> SEQ ID NO 172
<211> LENGTH: 82
<212> TYPE: PRT
<213> ORGANISM: Solfolobus solfataricus

```
<400> SEQUENCE: 172

Val Tyr Ala Asp Val Val Phe Asn His Thr Cys Glu Gly Asn Glu Lys
1               5                   10                  15

Gly Pro Thr Leu Ser Trp Arg Gly Ile Asp Asn Val Ala Tyr Tyr Arg
            20                  25                  30

Leu Ser Lys Glu Asp Pro Arg Tyr Tyr Thr Asp Phe Thr Gly Cys Gly
        35                  40                  45

Asn Thr Leu Asn Met Thr His Pro Arg Val Leu Gln Leu Ile Met Asp
    50                  55                  60

Ser Leu Arg Tyr Trp Val Thr Glu Met His Ile Asp Gly Phe Arg Ile
65                  70                  75                  80

Asp Ala

<210> SEQ ID NO 173
<211> LENGTH: 78
<212> TYPE: PRT
<213> ORGANISM: Solfolobus solfataricus

<400> SEQUENCE: 173

Val Tyr Ala Asp Val Val Ile Asn His Thr Ala Ala Ser Gly Gln Ala
1               5                   10                  15

Gly Thr Ser Val Leu Asp Arg Ile Val Pro Gly Tyr Tyr Gln Arg Leu
            20                  25                  30

Leu Ala Asp Gly Ser Val Ala Asn Ser Thr Cys Cys Ser Asn Thr Ala
        35                  40                  45

Thr Glu Asn Ala Met Met Gly Lys Leu Val Val Asp Ser Val Val Thr
    50                  55                  60

Trp Ala Lys Glu Tyr Lys Val Asp Gly Phe Arg Ile Asp Ala
65                  70                  75

<210> SEQ ID NO 174
<211> LENGTH: 72
<212> TYPE: PRT
<213> ORGANISM: Solfolobus solfataricus

<400> SEQUENCE: 174

Val Tyr Ala Asp Val Val Tyr Asn His Leu Gly Pro Asp Gly Cys Tyr
1               5                   10                  15

Leu Thr Lys Phe Ala Thr Glu Tyr Phe Thr Asp Arg Tyr Lys Asn Glu
            20                  25                  30

Trp Gly Glu Ala Val Lys Leu Arg Arg Arg Glu Leu Cys Ala Gly Ala
        35                  40                  45

Gly Val Leu Leu Arg Arg Thr Ala Ala Tyr Trp Ile Asp Glu Phe His
    50                  55                  60

Leu Asp Gly Phe Arg Ile Asp Ala
65                  70

<210> SEQ ID NO 175
<211> LENGTH: 82
<212> TYPE: PRT
<213> ORGANISM: Streptomyces coelicolor

<400> SEQUENCE: 175

Val Tyr Ala Asp Val Val Phe Asn His Thr Ala Glu Gly Asn His Leu
1               5                   10                  15

Gly Pro Met Leu Ser Phe Lys Gly Ile Asp Asn Ala Ala Tyr Tyr Arg
            20                  25                  30
```

```
Val Ile Gly Asp Asn Arg Arg Tyr Tyr Met Asp Tyr Thr Gly Thr Gly
            35                  40                  45

Asn Thr Leu Asn Met Arg His Pro His Val Leu Gln Leu Met Met Asp
         50                  55                  60

Ser Leu Arg Tyr Phe Val Leu Asp Met His Val Asp Gly Phe Arg Ile
 65                  70                  75                  80

Asp Ala

<210> SEQ ID NO 176
<211> LENGTH: 82
<212> TYPE: PRT
<213> ORGANISM: Corynebacterium glutamicum

<400> SEQUENCE: 176

Val Tyr Ala Asp Val Val Phe Asn His Thr Ser Glu Gly Asn Ala Glu
 1               5                  10                  15

Ser Gly Pro Ala Phe Cys Leu Lys Gly Phe Asp Asn Ser Ile Tyr Tyr
            20                  25                  30

Ile Leu Asp Lys Asp Lys Ser Arg Tyr Ala Asp Tyr Thr Gly Cys Gly
            35                  40                  45

Asn Thr Leu Asn Ser Asn His Pro Ile Val Arg Arg Met Ile Val Asp
         50                  55                  60

Ser Leu Arg Tyr Trp Val Gln Glu Met His Val Asp Gly Phe Arg Ile
 65                  70                  75                  80

Asp Ala

<210> SEQ ID NO 177
<211> LENGTH: 80
<212> TYPE: PRT
<213> ORGANISM: Arthrobacter sp.

<400> SEQUENCE: 177

Val Tyr Ala Asp Val Val Phe Asn His Thr Ala Glu Gly Asn Glu Arg
 1               5                  10                  15

Gly Pro Thr Ile Ser Phe Arg Gly Leu Asp Asn Lys Thr Tyr Tyr Met
            20                  25                  30

Leu Thr Pro Glu Gly Tyr Tyr Phe Asn Phe Ser Gly Thr Gly Asn Thr
            35                  40                  45

Leu Asn Cys Asn Asn Pro Ile Val Arg Asp Met Val Leu Asp Cys Leu
         50                  55                  60

Arg Tyr Trp Ala Ala Glu Tyr His Val Asp Gly Phe Arg Ile Asp Ala
 65                  70                  75                  80

<210> SEQ ID NO 178
<211> LENGTH: 82
<212> TYPE: PRT
<213> ORGANISM: Arthrobacter sp.

<400> SEQUENCE: 178

Val Tyr Ala Asp Val Val Ile Asn His Thr Thr Glu Gly Asn His Gln
 1               5                  10                  15

Gly Pro Ile Val Asn Phe Arg Gly Phe Asp Asn Ser Val Tyr Tyr His
            20                  25                  30

Leu Val Gln Asp Asp Lys Gln Tyr Tyr Met Asp Tyr Ser Gly Cys Gly
            35                  40                  45

Asn Thr Val Asn Cys Asn His Pro Val Val Glu Lys Met Ile Leu Asp
         50                  55                  60
```

```
Cys Leu Glu Phe Trp Val Arg Asp Met His Val Asp Gly Phe Arg Ile
 65                  70                  75                  80

Asp Ala
```

<210> SEQ ID NO 179
<211> LENGTH: 82
<212> TYPE: PRT
<213> ORGANISM: Rhizobium sp

<400> SEQUENCE: 179

```
Val Tyr Ala Asp Val Val Phe Asn His Thr Thr Glu Gly Asn His Gln
  1               5                  10                  15

Gly Pro Ile Val Asn Phe Arg Gly Phe Asp Asn Ser Val Tyr Tyr His
             20                  25                  30

Leu Val Gln Asp Asp Lys Gln Tyr Tyr Met Asp Tyr Ser Gly Cys Gly
         35                  40                  45

Asn Thr Val Asn Cys Asn His Pro Val Val Glu Lys Met Ile Leu Asp
     50                  55                  60

Cys Leu Glu Phe Trp Val Arg Asp Met His Val Asp Gly Phe Arg Ile
 65                  70                  75                  80

Asp Ala
```

<210> SEQ ID NO 180
<211> LENGTH: 80
<212> TYPE: PRT
<213> ORGANISM: Sulfolobus acidocaldarius

<400> SEQUENCE: 180

```
Val Tyr Ala Asp Val Val Phe Asn His Thr Gly Glu Asn Met Glu Val
  1               5                  10                  15

Ala Asp Arg Gly Phe Thr Phe Ser Gly Ile Asp Arg Trp Tyr Tyr Tyr
             20                  25                  30

Arg Met Asn Gln Glu Gly Glu Leu Ile Gly Pro Tyr Gly Asn Glu Ile
         35                  40                  45

Arg Ser Glu Asp Arg Pro Met Val Gln Arg Trp Leu Ile Asp Gln Leu
     50                  55                  60

Arg His Leu Val Asp Ile Phe Gly Val Asp Gly Phe Arg Ile Asp Ala
 65                  70                  75                  80
```

<210> SEQ ID NO 181
<211> LENGTH: 82
<212> TYPE: PRT
<213> ORGANISM: Sulfolobus acidocaldarius

<400> SEQUENCE: 181

```
Val Tyr Ala Asp Val Val Tyr Asn His Thr Cys Glu Gly Asn His Leu
  1               5                  10                  15

Gly Pro Thr Leu Ser Leu Arg Gly Ile Asp Asn Val Ser Tyr Tyr Arg
             20                  25                  30

Leu Ala Glu Asn Glu Arg Arg His Tyr Ala Asp Phe Ser Gly Cys Gly
         35                  40                  45

Asn Thr Leu Asn Leu Glu His Pro Asn Val Leu Gln Leu Val Thr Asp
     50                  55                  60

Ser Leu Arg Tyr Trp Val Glu Val Met His Val Asp Gly Phe Arg Ile
 65                  70                  75                  80

Asp Ala
```

```
<210> SEQ ID NO 182
<211> LENGTH: 82
<212> TYPE: PRT
<213> ORGANISM: Sulfolobus acidocaldarius

<400> SEQUENCE: 182

Val Tyr Ala Asp Val Val Tyr Asn His Thr Cys Glu Gly Asn His Leu
1               5                   10                  15

Gly Pro Thr Leu Ser Leu Arg Gly Ile Asp Asn Val Ser Tyr Tyr Arg
            20                  25                  30

Leu Ala Glu Asn Glu Arg Arg His Tyr Ala Asp Phe Ser Gly Cys Gly
        35                  40                  45

Asn Thr Leu Asn Leu Glu His Pro Asn Val Leu Gln Leu Val Thr Asp
    50                  55                  60

Ser Leu Arg Tyr Trp Val Glu Val Met His Val Asp Gly Phe Arg Ile
65                  70                  75                  80

Asp Ala

<210> SEQ ID NO 183
<211> LENGTH: 80
<212> TYPE: PRT
<213> ORGANISM: Sulfolobus acidocaldarius

<400> SEQUENCE: 183

Val Tyr Ala Asp Val Val Phe Asn His Thr Ala Glu Gly Asn Glu Arg
1               5                   10                  15

Gly Pro His Ile Ser Phe Arg Gly Leu Asp Asn Lys Thr Tyr Tyr Met
            20                  25                  30

Leu Thr Pro Glu Gly Tyr Tyr Phe Asn Phe Ser Gly Thr Gly Asn Thr
        35                  40                  45

Leu Asn Cys Asn Asn Pro Ile Val Arg Ser Met Val Leu Asp Cys Leu
    50                  55                  60

Arg Tyr Trp Ala Ser Glu Tyr His Val Asp Gly Phe Arg Ile Asp Ala
65                  70                  75                  80

<210> SEQ ID NO 184
<211> LENGTH: 82
<212> TYPE: PRT
<213> ORGANISM: Sulfolobus acidocaldarius

<400> SEQUENCE: 184

Val Tyr Ala Asp Val Val Ile Asn His Thr Ala Glu Gly Asn His Leu
1               5                   10                  15

Gly Pro Thr Leu Ser Phe Arg Gly Ile Asp Asn Pro Ala Tyr Tyr Arg
            20                  25                  30

Leu Met Glu Asp Ala Arg Phe Tyr Met Asp Tyr Thr Gly Thr Gly
        35                  40                  45

Asn Thr Leu Asn Val Arg Gln Pro His Ser Leu Gln Leu Ile Met Asp
    50                  55                  60

Ser Leu Arg Tyr Trp Val Thr Glu Met His Val Asp Gly Phe Arg Ile
65                  70                  75                  80

Asp Ala

<210> SEQ ID NO 185
<211> LENGTH: 82
<212> TYPE: PRT
<213> ORGANISM: Sulfolobus acidocaldarius
```

```
<400> SEQUENCE: 185

Val Tyr Ala Asp Val Val Ile Asn His Thr Ala Glu Gly Asn Glu Phe
1               5                   10                  15

Gly Pro Thr Leu Ser Phe Arg Gly Leu Asp Asn Ala Ser Tyr Tyr Arg
            20                  25                  30

Leu Leu Pro Asp Asn Pro Arg His Tyr Ile Asn Asp Thr Gly Thr Gly
            35                  40                  45

Asn Thr Val Asn Leu Ser His Pro Arg Val Leu Gln Thr Val Met Asp
        50                  55                  60

Ser Leu Arg Tyr Trp Val Glu Glu Cys His Val Asp Gly Phe Arg Ile
65                  70                  75                  80

Asp Ala

<210> SEQ ID NO 186
<211> LENGTH: 82
<212> TYPE: PRT
<213> ORGANISM: Sulfolobus acidocaldarius

<400> SEQUENCE: 186

Val Tyr Ala Asp Val Val Tyr Asn His Thr Ala Glu Gly Asp Gln Arg
1               5                   10                  15

Gly Pro Thr Leu Ser Leu Arg Gly Phe Asp Asn Ala Asn Tyr Tyr Arg
            20                  25                  30

Leu Ser Pro His Asp Arg Ser Leu Tyr Glu Asn Phe Ser Gly Thr Gly
            35                  40                  45

Asn Thr Val Ser Phe Asp His Pro Ala Val Arg Ser Leu Val Ile Glu
        50                  55                  60

Cys Leu Arg Tyr Trp Val Ser Asp Met Gly Leu Asp Gly Phe Arg Ile
65                  70                  75                  80

Asp Ala

<210> SEQ ID NO 187
<211> LENGTH: 82
<212> TYPE: PRT
<213> ORGANISM: Sulfolobus acidocaldarius

<400> SEQUENCE: 187

Val Tyr Ala Asp Val Val Tyr Asn His Thr Gly Glu Gly Asn Glu Arg
1               5                   10                  15

Gly Pro Thr Leu Ser Leu Arg Gly Ile Asp Asn Lys Ser Tyr Tyr Arg
            20                  25                  30

Leu Asn Pro Glu Asn Gly Arg His Tyr Val Asp Phe Thr Gly Thr Gly
            35                  40                  45

Asn Thr Leu Asn Met Met Gln Pro Arg Ser Leu Gln Leu Val Thr Asp
        50                  55                  60

Ser Leu Arg Tyr Trp Val Gln Glu Met His Val Asp Gly Phe Arg Ile
65                  70                  75                  80

Asp Ala

<210> SEQ ID NO 188
<211> LENGTH: 82
<212> TYPE: PRT
<213> ORGANISM: Synechocystis sp

<400> SEQUENCE: 188

Val Tyr Ala Asp Val Val Phe Asn His Thr Val Glu Gly Asn His Met
1               5                   10                  15
```

```
Gly Pro Val Leu Ala Met Lys Gly Leu Asp Asn Thr Ala Tyr Tyr Arg
            20                  25                  30

Thr Met Pro Gly Gln Ala Arg Tyr Tyr Met Asp Tyr Thr Gly Thr Gly
        35                  40                  45

Asn Ser Leu His Met Arg His Pro His Val Leu Gln Met Ile Met Asp
        50                  55                  60

Ser Leu Arg Tyr Trp Ile Thr Glu Met His Val Asp Gly Phe Arg Ile
65                  70                  75                  80

Asp Ala

<210> SEQ ID NO 189
<211> LENGTH: 82
<212> TYPE: PRT
<213> ORGANISM: Synechocystis sp

<400> SEQUENCE: 189

Val Tyr Ala Asp Val Val Phe Asn His Thr Ala Glu Gly Asn His Leu
1               5                   10                  15

Gly Pro Thr Leu Ser Leu Arg Gly Ile Asp Asn Ser Ser Tyr Tyr Arg
            20                  25                  30

Leu Leu Pro Asn Asn Pro Arg Tyr Tyr Gln Asp Phe Thr Gly Thr Gly
        35                  40                  45

Asn Thr Leu Asn Met Arg Ser Pro Arg Val Leu Gln Leu Ile Met Asp
        50                  55                  60

Ser Leu Arg Tyr Trp Val Leu Glu Met His Val Asp Gly Phe Arg Ile
65                  70                  75                  80

Asp Ala

<210> SEQ ID NO 190
<211> LENGTH: 81
<212> TYPE: PRT
<213> ORGANISM: Synechocystis sp

<400> SEQUENCE: 190

Val Tyr Ala Asp Val Val Phe Asn His Thr Cys Glu Gly Asn Glu His
1               5                   10                  15

Gly Pro Thr Leu Ser Phe Lys Gly Leu Glu Asn Arg Val Tyr Tyr Met
            20                  25                  30

Leu Ala Gly Gln Gly Glu His Tyr Lys Asn Tyr Ser Gly Cys Gly Asn
        35                  40                  45

Thr Val Asn Gly Asn His Pro Ile Val Arg Glu Met Ile Phe His Cys
        50                  55                  60

Leu Arg His Trp Val His Asn Tyr His Val Asp Gly Phe Arg Ile Asp
65                  70                  75                  80

Ala

<210> SEQ ID NO 191
<211> LENGTH: 69
<212> TYPE: PRT
<213> ORGANISM: Synechocystis sp

<400> SEQUENCE: 191

Ala Asp Val Val Phe Asn His Leu Gly Pro Ser Gly Ala Leu Phe Asp
1               5                   10                  15

Arg Phe Ser Pro His Tyr Phe Thr Asp Arg His Asp Asn Asp Trp Gly
            20                  25                  30
```

-continued

Gln Ala Leu Asn Phe Asp Asp Pro Glu Ser Gly Pro Val Arg Glu Phe
        35                  40                  45

Phe Ile Thr Asp Ala Val His Trp Ile Gly Glu Tyr His Leu Asp Gly
     50                  55                  60

Phe Arg Ile Asp Ala
 65

<210> SEQ ID NO 192
<211> LENGTH: 69
<212> TYPE: PRT
<213> ORGANISM: Synechocystis sp

<400> SEQUENCE: 192

Ala Asp Val Val Phe Asn His Leu Gly Pro Asp Gly Asn Tyr Leu His
 1               5                  10                  15

Ala Phe Thr Gly Ser Tyr Phe Thr Asp Lys His Glu Asn Asp Trp Gly
            20                  25                  30

Arg Ser Ile Asn Phe Asp Asp Leu His Ser Gly Gly Val Arg Glu Phe
        35                  40                  45

Phe Val Ser Asn Ala Arg His Trp Ile Glu Gly Tyr His Phe Asp Gly
     50                  55                  60

Phe Arg Ile Asp Ala
 65

<210> SEQ ID NO 193
<211> LENGTH: 69
<212> TYPE: PRT
<213> ORGANISM: Synechocystis sp

<400> SEQUENCE: 193

Ala Asp Val Val Phe Asn His Leu Gly Pro Glu Gly Asn Tyr Leu His
 1               5                  10                  15

Ala Tyr Ala Cys Glu Phe Phe Thr Asp Arg His Lys Thr Asp Trp Gly
            20                  25                  30

Ala Ala Ile Asn Phe Asp Gly Pro Asp Ser Arg Thr Val Arg Glu Phe
        35                  40                  45

Phe Ile His Asn Ala Leu Tyr Trp Leu Glu Glu Tyr His Phe Asp Gly
     50                  55                  60

Phe Arg Ile Asp Ala
 65

<210> SEQ ID NO 194
<211> LENGTH: 68
<212> TYPE: PRT
<213> ORGANISM: E.coli

<400> SEQUENCE: 194

Ala Asp Val Val Phe Asn His Leu Gly Pro Glu Ser Asn Phe Ala His
 1               5                  10                  15

Glu Phe Gly Pro Tyr Phe Thr Asp Lys Tyr Lys Thr Pro Trp Gly Gln
            20                  25                  30

Ala Ile Asn Tyr Asp Asp Lys Gly Cys Asp Gly Val Arg Asp Trp Val
        35                  40                  45

Leu Asp Asn Val Arg Met Trp Leu Ala Glu Phe His Leu Asp Gly Phe
     50                  55                  60

Arg Ile Asp Ala
 65

```
<210> SEQ ID NO 195
<211> LENGTH: 66
<212> TYPE: PRT
<213> ORGANISM: Sulfolobus solfataricus

<400> SEQUENCE: 195

Ala Asp Val Val Phe Asn His Leu Gly Pro Glu Gly Asn Cys Leu Pro
1               5                   10                  15

Arg Tyr Ala Pro Glu Phe Phe Thr Ser Arg His Ala Thr Pro Trp Gly
            20                  25                  30

Asp Ala Ile Asn Phe Ala His Pro Ile Val Arg Arg Phe Phe Ile Ala
        35                  40                  45

Asn Ala Leu Tyr Trp Leu Glu Glu Tyr Gln Leu Asp Gly Phe Arg Ile
    50                  55                  60

Asp Ala
65

<210> SEQ ID NO 196
<211> LENGTH: 69
<212> TYPE: PRT
<213> ORGANISM: Sulfolobus solfataricus

<400> SEQUENCE: 196

Ala Asp Val Val Phe Asn His Leu Gly Pro Ser Gly Asn Tyr Leu Ala
1               5                   10                  15

Arg Phe Ala Arg Asp Tyr Phe Ser Asp Arg His Ala Thr Asp Trp Gly
            20                  25                  30

Ala Gly Ile Asn Phe Asp Gly Pro Arg Ala Gln His Val Arg Glu Leu
        35                  40                  45

Val Leu Ala Asn Val Glu His Trp Val Arg Glu Phe His Val Asp Gly
    50                  55                  60

Phe Arg Ile Asp Ala
65

<210> SEQ ID NO 197
<211> LENGTH: 68
<212> TYPE: PRT
<213> ORGANISM: Sulfolobus solfataricus

<400> SEQUENCE: 197

Ala Asp Val Val Phe Asn His Phe Gly Pro Asp Gly Asn Tyr Leu Ala
1               5                   10                  15

Gln Phe Ser Arg His Tyr Phe Ala Ala Gln Gln Ser Pro Trp Gly Pro
            20                  25                  30

Ala Ile Asn Leu Asp Gly Pro His Ser Ala Pro Val Arg Glu Phe Leu
        35                  40                  45

Ile Glu Asn Ala Leu His Trp Val His Glu Tyr His Leu Asp Gly Phe
    50                  55                  60

Arg Ile Asp Ala
65

<210> SEQ ID NO 198
<211> LENGTH: 74
<212> TYPE: PRT
<213> ORGANISM: Sulfolobus solfataricus

<400> SEQUENCE: 198

Ala Asp Val Val Phe Asn His Leu Gly Pro Thr Leu Ser Phe Lys Gly
1               5                   10                  15
```

```
Ile Asp Asn Gln Ser Tyr Tyr Arg Leu Met Glu Gly Asp Glu Lys His
            20                  25                  30

Tyr Met Asp Tyr Thr Gly Thr Gly Asn Ser Leu Asn Val Arg Gln Pro
        35                  40                  45

His Ser Leu Gln Leu Leu Met Asp Ser Leu Arg Tyr Trp Val Thr Glu
 50                  55                  60

Met His Val Asp Gly Phe Arg Ile Asp Ala
 65                  70
```

<210> SEQ ID NO 199
<211> LENGTH: 68
<212> TYPE: PRT
<213> ORGANISM: Sulfolobus solfataricus

<400> SEQUENCE: 199

```
Ala Asp Val Val Phe Asn His Gly Pro Glu Gly Asn Tyr Leu Gly
 1               5                  10                  15

Gln Tyr Gly Pro Tyr Phe Thr Asp Arg Tyr Lys Thr Pro Trp Gly Leu
            20                  25                  30

Ala Leu Asn Phe Asp Gly Pro Arg Ser Asp Asp Val Arg Trp Phe Phe
        35                  40                  45

Ile His Asn Ala Leu His Trp Val Asp Glu Phe His Val Asp Gly Phe
    50                  55                  60

Arg Ile Asp Ala
 65
```

<210> SEQ ID NO 200
<211> LENGTH: 69
<212> TYPE: PRT
<213> ORGANISM: Sulfolobus solfataricus
<220> FEATURE:
<221> NAME/KEY: misc_feature
<222> LOCATION: (16)..(16)
<223> OTHER INFORMATION: Xaa can be any naturally occurring amino acid

<400> SEQUENCE: 200

```
Ala Asp Val Val Phe Asn His Phe Gly Pro Thr Gly Asn Tyr Leu Xaa
 1               5                  10                  15

Ala Phe Ser Pro His Tyr Val Ser Lys Lys His Ala Thr Glu Trp Gly
            20                  25                  30

Glu Ser Leu Asn Phe Asp Gly Glu Ser Ala Gly Pro Val Arg Glu Phe
        35                  40                  45

Val Thr Thr Asn Ala Ala His Trp Ile Arg Glu Tyr His Leu Asp Gly
    50                  55                  60

Phe Arg Ile Asp Ala
 65
```

<210> SEQ ID NO 201
<211> LENGTH: 90
<212> TYPE: PRT
<213> ORGANISM: Sulfolobus solfataricus

<400> SEQUENCE: 201

```
Tyr Ala Asp Ala Val Leu Asn His Ser Gly Phe Gln Phe Ala Pro Phe
 1               5                  10                  15

Gln Asp Val Ile Ala Arg Gly Thr Ala Ser Pro Tyr Trp Ser Trp Phe
            20                  25                  30

Leu Val His Gly Asp Arg Val Asp Val Glu Ser Val Asn Tyr Glu Thr
        35                  40                  45
```

```
Phe Ala Thr Arg Leu Arg His Met Pro Lys Leu Asn Leu Ala Glu Pro
    50                  55                  60

Ala Ala Glu Glu Tyr Phe Leu His Val Ala Lys His Tyr Val Leu Glu
65                  70                  75                  80

Cys Asp Ile Asp Gly Phe Arg Ile Asp Ala
                85                  90

<210> SEQ ID NO 202
<211> LENGTH: 91
<212> TYPE: PRT
<213> ORGANISM: Sulfolobus solfataricus

<400> SEQUENCE: 202

Tyr Ala Asp Ala Val Phe Asn His Ser Gly Phe Gln Phe Ala Pro Phe
1               5                   10                  15

Gln Asp Val Ile Ala Arg Gly Thr Ala Ser Pro Tyr Trp Ser Trp Phe
                20                  25                  30

Phe Val His Gly Asp Arg Val Asp Val Glu Ser Val Asn Tyr Glu Thr
            35                  40                  45

Phe Ala Thr Arg Leu Arg His Met Pro Lys Leu Asn Leu Ala Glu Pro
    50                  55                  60

Ala Ala Glu Glu Tyr Phe Leu His Val Ala Lys His Tyr Val Leu Glu
65                  70                  75                  80

Cys Asp Ile Asp Gly Phe Arg Ile Asp Ala Ala
                85                  90

<210> SEQ ID NO 203
<211> LENGTH: 82
<212> TYPE: PRT
<213> ORGANISM: Mycobaterium tuberculosis

<400> SEQUENCE: 203

Tyr Ala Asp Ala Val Phe Asn His Thr Cys Glu Gly Asn Glu Lys Gly
1               5                   10                  15

Pro Thr Leu Ser Trp Arg Gly Ile Asp Asn Val Ala Tyr Tyr Arg Leu
                20                  25                  30

Ser Lys Glu Asp Pro Arg Tyr Tyr Thr Asp Phe Thr Gly Cys Gly Asn
            35                  40                  45

Thr Leu Asn Met Thr Arg Pro Arg Val Leu Gln Leu Ile Met Asp Ser
    50                  55                  60

Leu Arg Tyr Trp Val Thr Glu Met His Ile Asp Gly Phe Arg Ile Asp
65                  70                  75                  80

Ala Ala

<210> SEQ ID NO 204
<211> LENGTH: 70
<212> TYPE: PRT
<213> ORGANISM: Mycobacterium tuberculosis

<400> SEQUENCE: 204

Tyr Ala Asp Ala Val Phe Asn His Leu Gly Pro Ala Gly Asn Tyr Leu
1               5                   10                  15

Asn Arg Phe Gly Pro Tyr Phe Thr Asp Arg Tyr Val Thr Pro Trp Gly
                20                  25                  30

Ala Ala Val Asn Leu Asp Gly Pro Gly Ser Asp Glu Val Arg Ala Phe
            35                  40                  45

Phe Val Asp Asn Ala Leu Met Trp Leu Arg Asp Tyr His Ile Asp Gly
    50                  55                  60
```

Phe Arg Ile Asp Ala Ala
65              70

<210> SEQ ID NO 205
<211> LENGTH: 91
<212> TYPE: PRT
<213> ORGANISM: Mycobacterium tuberculosis

<400> SEQUENCE: 205

Tyr Ala Asp Ala Val Leu Asn His Ser Gly Phe Gln Phe Ala Pro Ser
1               5                   10                  15

Gln Asp Val Ile Ala Arg Gly Thr Ala Ser Pro Tyr Trp Ser Trp Phe
                20                  25                  30

Phe Val His Gly Asp Arg Val Asp Val Glu Ser Val Asn Tyr Glu Thr
            35                  40                  45

Phe Ala Thr Arg Leu Arg His Met Pro Lys Leu Asn Leu Ala Glu Pro
        50                  55                  60

Ala Ala Glu Glu Tyr Phe Leu His Val Ala Lys His Tyr Val Leu Glu
65                  70                  75                  80

Cys Asp Ile Asp Gly Phe Arg Ile Asp Ala Ala
                85                  90

<210> SEQ ID NO 206
<211> LENGTH: 272
<212> TYPE: DNA
<213> ORGANISM: Bacillus flavocaldarius

<400> SEQUENCE: 206
gtacgccgac gccgttttaa atcactcggg ctttcaattt gccccctttc aggacgtcat      60
tgcgcgcggt acggcgtctc cctattggtc ttggttcctc gtgcatgggg accgcgttga     120
cgtcgaatcc gtgaattatg agactttcgc gacgcgcctt cgacatatgc aaaaactgaa     180
cttggcagag cctgctgccg aagaatactt tctgcatgtg gccaaacact atgttctcga     240
gtgcgatatc gacggattta ggatcgacgc cg                                   272

<210> SEQ ID NO 207
<211> LENGTH: 274
<212> TYPE: DNA
<213> ORGANISM: Bacillus flavocaldarius

<400> SEQUENCE: 207
gtacgccgac gccgtcttta atcactcggg ctttcaattt gccccctttc aggacgtcat      60
tgcgcgcggt acggcgtctc cctattggtc ttggttcttc gtgcatgggg accgcgttga     120
cgtcgaatcc gtgaattatg agactttcgc gacgcgcctt cgacatatgc aaaaactgaa     180
cttggcagag cctgctgccg aagaatactt tctgcatgtg gccaaacact atgttctcga     240
gtgcgatatc gacgggttca tgatcgacgc cgcc                                 274

<210> SEQ ID NO 208
<211> LENGTH: 247
<212> TYPE: DNA
<213> ORGANISM: Orysa sativum

<400> SEQUENCE: 208
gtacgccgac gccgtgttta accacacgtg cgaagggaac gagaaaggcc cgacgctctc      60
gtggcgcggg atcgacaacg tcgcgtatta ccgtctgtcg aaggaagatc cgcgctacta     120
cacggatttc accggctgcg gcaacacgct gaacatgacg cgcccgcgcg tgctccagct     180

```
catcatggac tccctgcgct actgggtgac ggagatgcac atcgatggat tcaggatcga    240
cgccgcc                                                              247
```

<210> SEQ ID NO 209
<211> LENGTH: 211
<212> TYPE: DNA
<213> ORGANISM: Orysa sativum

<400> SEQUENCE: 209

```
gtacgccgac gccgttttta atcacctcgg ccctgccggc aactacctga accgcttcgg    60
gccctacttc accgatcgct acgtcacccc ttggggagcg gcggtgaacc tcgacgggcc    120
gggtagcgac gaggtgcggg ccttcttcgt cgacaacgcc ctcatgtggc tgcgggacta    180
ccacatcgac ggattccgga tcgacgccgc c                                   211
```

<210> SEQ ID NO 210
<211> LENGTH: 274
<212> TYPE: DNA
<213> ORGANISM: Orysa sativum

<400> SEQUENCE: 210

```
gtacgccgac gccgttttaa atcactcggg ctttcaattt gccccctctc aggacgtcat    60
tgcgcgcggt acggcgtctc cctattggtc ttggttcttc gtgcatgggg accgcgttga    120
cgtcgaatcc gtgaattatg agactttcgc gacgcgcctt cgacatatgc aaaaactgaa    180
cttggcagag cctgctgccg aagaatactt tctgcatgtg gccaaacact atgttctcga    240
gtgcgatatc gacggcttcc ggatcgacgc cgcc                                274
```

<210> SEQ ID NO 211
<211> LENGTH: 205
<212> TYPE: DNA
<213> ORGANISM: Orysa sativum

<400> SEQUENCE: 211

```
cgacgtggtg ttcaaccatc ttggtccctc aggcgctctc ttcgaccgct tctccccgca    60
ctacttcacc gaccggcatg acaacgactg ggggcaggcg ctcaacttcg acgaccccga    120
atccgtcccc gtccgggagt tcttcatcac cgacgccgtc cactggatcg gcgaatacca    180
cctcgacggg ttccgcatcg acgcc                                          205
```

<210> SEQ ID NO 212
<211> LENGTH: 207
<212> TYPE: DNA
<213> ORGANISM: Arthrobacter sp.

<400> SEQUENCE: 212

```
gccgacgtgg tgttcaatca tctaggcccg gacggcaact acctccacgc ctttaccggg    60
tcctacttca ccgacaagca cgagaacgac tggggccggt cgatcaactt cgacgatctg    120
cactccggcg gcgtgcgcga gttcttcgtg tcgaacgcca ggcactggat cgaggagtat    180
cacttcgacg ggttccgcat cgacgcc                                        207
```

<210> SEQ ID NO 213
<211> LENGTH: 207
<212> TYPE: DNA
<213> ORGANISM: Arthrobacter sp.

<400> SEQUENCE: 213

```
gccgacgtgg tgttcaatca cttggggccg gagggggaact acctgcacgc gtacgcgtgc      60
gagttcttca ccgaccgcca caagaccgac tggggcgcgg cgatcaactt cgacgggccc     120
gactcgcgca ccgtgcgcga gttcttcatc cataacgcgc tctactggct cgaggagtat     180
cacttcgacg gcttccgcat cgacgcc                                         207

<210> SEQ ID NO 214
<211> LENGTH: 204
<212> TYPE: DNA
<213> ORGANISM: Arthrobacter sp.

<400> SEQUENCE: 214
ggcgtcgatg cggaacccgt cgaggtgaaa ctcggcgagc cacatgcgaa cattgtcgag      60
gacccaatca cgaacgccat cgcagccttt gtcgtcgtag ttgatcgcct gcccccaagg     120
cgttttgtat ttgtcggtga agtacggacc gaattcgtga gcgaaattcg attcgggccc     180
taagtggttg aacaccacgt cggc                                            204

<210> SEQ ID NO 215
<211> LENGTH: 198
<212> TYPE: DNA
<213> ORGANISM: Arthrobacter sp.

<400> SEQUENCE: 215
gccgacgtgg tgttcaatca cctaggtccg gaaggcaact gcctgccgcg ttatgcaccc      60
gagttcttca cctcacgcca tgccacaccc tggggcgacg ccatcaattt cgcgcacccg     120
atcgtgcggc gttttttcat tgcgaatgcg ctctattggc tcgaggaata ccaattggac     180
ggcttccgca tcgacgcc                                                   198

<210> SEQ ID NO 216
<211> LENGTH: 205
<212> TYPE: DNA
<213> ORGANISM: Arthrobacter sp.

<400> SEQUENCE: 216
cgacgtggtg ttcaaccatc ttggtccgag cgggaactat ctcgcccggt tcgcgcgcga      60
ctacttcagc gatcgccacg ccaccgactg gggcgcgggc atcaacttcg atgggccgcg     120
tgcgcagcac gtgcgcgagc tcgtgctggc caacgtggag cattgggtgc gcgagttcca     180
cgtcgacggc ttccgcatcg acgcc                                           205

<210> SEQ ID NO 217
<211> LENGTH: 202
<212> TYPE: DNA
<213> ORGANISM: Arthrobacter sp.

<400> SEQUENCE: 217
cgacgtggtg ttcaaccact tggtcccga cggcaactac ctggcgcagt tcagccgcca      60
ctacttcgcg gcgcagcaga gcccgtgggg accggccatc aacctcgacg gccccacag     120 cgcgccggtg cgcgagttcc tcatcgagaa cgcgctgcac tgggtccacg agtaccacct     180
cgacgggttc cgcatcgacg cc                                              202

<210> SEQ ID NO 218
<211> LENGTH: 225
<212> TYPE: DNA
<213> ORGANISM: Arthrobacter sp.

<400> SEQUENCE: 218
```

```
cgacgtggtg ttcaaccacc ttggtcccac cctgtccttc aagggcatcg acaaccagtc    60
ctactaccgg ctgatggagg gcgacgaaaa gcactacatg gactacacgg gaacgggcaa   120
ctcgctcaac gtccgccagc cgcactcgct gcagctgctc atggattcct tgcggtactg   180
ggtcaccgaa atgcatgtgg acgggttccg catcgacgcc aaggg                   225
```

<210> SEQ ID NO 219
<211> LENGTH: 201
<212> TYPE: DNA
<213> ORGANISM: Arthrobacter sp.

<400> SEQUENCE: 219

```
cgacgtggtg ttcaaccact ttggacccga ggggaactac ctcggccagt acggtcccta    60
cttcacggac cgctacaaga cgccgtgggg gctggcactc aacttcgacg gccctcgcag   120
cgacgacgtg cgctggttct tcatccacaa cgcgctgcat gggtcgacg agttccacgt   180 cgacggcttc cgcatcgacg c                                             201
```

<210> SEQ ID NO 220
<211> LENGTH: 204
<212> TYPE: DNA
<213> ORGANISM: Arthrobacter sp.
<220> FEATURE:
<221> NAME/KEY: misc_feature
<222> LOCATION: (43)..(43)
<223> OTHER INFORMATION: n is a, c, g, or t

<400> SEQUENCE: 220

```
gacgtggtgt tcaaccattt cgggccgacg ggaaattacc tgncggcgtt ctcgccccac    60
tatgtgtcca aaagcacgc caccgaatgg ggcgaatcgc tcaacttcga cggcgaatcg   120
gccggccccg tgcgcgagtt cgtcacgaca aatgcggccc actggattcg cgagtaccat   180
ctcgacggct tccgcatcga cgcc                                          204
```

<210> SEQ ID NO 221
<211> LENGTH: 235
<212> TYPE: DNA
<213> ORGANISM: Arthrobacter sp.

<400> SEQUENCE: 221

```
ggtctacgcc gacgtcgtgt tcaaccacac cggcgagggc gacgcgacga aaccgacgtg    60
gacgttccgc ggtctcgacg atcggctgta cctccacgac cgcgacggta cgtacaacga   120
cgacgcgggc tgcggcaacg tcgccgaccc tggtgccgag gaggtgcggc ggctcgtgct   180
cgaggccctc cagcgcttca ctgacctcgg catcgacggg ttccgcatcg acgcc        235
```

<210> SEQ ID NO 222
<211> LENGTH: 243
<212> TYPE: DNA
<213> ORGANISM: Arthrobacter sp.

<400> SEQUENCE: 222

```
ggtctacgcc gacgtcgtct tcaaccacac ggccgaggga aaccgcatgg gcccgacgct    60
gtcgtggcgc gggatcgaca ataccccacta ctaccggctg accgaggaca agcgctatca   120
cctggactac acgggcacgg gcaacgccct gaacatgacg agcccgcgcg tgctccagat   180
gatcatggac agcctgcgct actgggtcat ggagatgcac gtcgacggct tccgcacgac   240
gcc                                                                 243
```

<210> SEQ ID NO 223
<211> LENGTH: 246
<212> TYPE: DNA
<213> ORGANISM: Deinococcus radiodurans

<400> SEQUENCE: 223

| | |
|---|---|
| ggtctacgcc gacgtcgtgt tcaaccacac cggcgagggc aaccacaacg gcccgacgat | 60 |
| cagcttccgg ggccaggcca acgaggccta ctaccacctc gtcgacgagg acaggaagta | 120 |
| ctacatggac tactcgggct gcggcaaac gatcaacgcc aaccacccac tcgtcaccaa | 180 |
| gctgatcatc gagagcctgg agtactgggt caccgagcac acgtcgacg gtccgcatc | 240 |
| gacgcc | 246 |

<210> SEQ ID NO 224
<211> LENGTH: 240
<212> TYPE: DNA
<213> ORGANISM: Deinococcus radiodurans

<400> SEQUENCE: 224

| | |
|---|---|
| ggtctacgcc gacgtcgtgt tcaaccacac ggccgaaggc aacgaaacag gccccacgtt | 60 |
| ctgcttcaag ggcttggaga cgaagtttta ttacatgctg aatgagaacg gcacgtacaa | 120 |
| aaacttctcc ggctgcggca acacggtgaa cggcaaccac cccgtcatgc gcgaaatgat | 180 |
| cttccattgc ctccgtcatt gggtgcacaa ctaccacatc gacggcttcc gcacgacgcc | 240 |

<210> SEQ ID NO 225
<211> LENGTH: 247
<212> TYPE: DNA
<213> ORGANISM: Deinococcus radiodurans

<400> SEQUENCE: 225

| | |
|---|---|
| ggtctacgcc gacgtcgtgt tcaaccacac ctgcgaagga acgagcgcg gcccgacgct | 60 |
| ctgttaccgc gggctcgacg cgccggtctg gtactgggtg daccctgcgc agccgtcgcg | 120 |
| ccacctcgac ttcaccggct gcggcaacag cttcaacatg cgccaccccc aggtgctgaa | 180 |
| gctggcgatg gactcgctgc gctactgggt caccgagatg catgtcgacg ggttccgcat | 240 |
| cgacgcc | 247 |

<210> SEQ ID NO 226
<211> LENGTH: 241
<212> TYPE: DNA
<213> ORGANISM: Deinococcus radiodurans

<400> SEQUENCE: 226

| | |
|---|---|
| ggtctacgcc gacgtcgtgt tcaaccacac ggcagaggag ggtctcggcg gacccaccag | 60 |
| cagcctgcgc ggcatcgaca accggaacta ctaccgccag accccgacg gtgaatacat | 120 |
| cgacgtcacg ggatgcggca actcggtgaa caccgcgacg gaggcgtcgc gacggctcat | 180 |
| cctcgactcc ctcaggtact gggcgaacga ggtgcaggtg gacggcttcc gcatcgacgc | 240 |
| c | 241 |

<210> SEQ ID NO 227
<211> LENGTH: 247
<212> TYPE: DNA
<213> ORGANISM: Deinococcus radiodurans

<400> SEQUENCE: 227

| | |
|---|---|
| ggtctacgcc gacgtcgtgt tcaaccacac ggcggaaggc aatcacatgg ggccgacgct | 60 |

```
gtccttccgc ggcatcgaca acgtttcgta ctaccgcgtc gatcccgcaa acccgcgtct    120
ctacgtcgac tacaccggct gcggcaacac gctcaacatg caaaatccgc gcgtgctgca    180
gctcatcatg gattcgctgc gctactgggt gactgagatg cacgtcgacg gcttccgcat    240
cgacgcc                                                               247

<210> SEQ ID NO 228
<211> LENGTH: 247
<212> TYPE: DNA
<213> ORGANISM: Deinococcus radiodurans

<400> SEQUENCE: 228
ggtctacgcc gacgtcgtga tcaaccacac cgccgagggc aacgagcggg gccccaccct    60
ctccttccgc ggcatcgaca acgcctccta ctaccgtctg gtggacgggg actggcagca    120
ctactacgac accaccggca ccggcaacag cctgctgatg cgccaccccct acgtgctcca    180 gctcatcatg gactcgctgc gctactgggt caccgagatg cacgtcgacg gcttccgcat    240
cgacgcc                                                               247

<210> SEQ ID NO 229
<211> LENGTH: 244
<212> TYPE: DNA
<213> ORGANISM: Deinococcus radiodurans

<400> SEQUENCE: 229
ggtctacgcc gacgtcgtgt acaaccacac cgccgagggc aaccagatgg ggccgacgct    60
gtcgtttcgc ggcatcgaca atgccagcta ttacctgctc ggcgacgacc cgcgctatta    120
tttcgacacg accggatgcg gcaacgcggt caatctgcgc caccagcgcg tgctgcagat    180
ggtcatggat tcgctgcgct actgggtgca ggaatgccat gtcgacgggt ccgcatcga    240 cgcc                                                                  244

<210> SEQ ID NO 230
<211> LENGTH: 247
<212> TYPE: DNA
<213> ORGANISM: Deinococcus radiodurans

<400> SEQUENCE: 230
ggtctacgcc gacgtcgtct tcaaccactc ggccgagggc aaccacatgg gccccacgct    60
cagcttcaag gggttcgaca acccctcta ctaccggctg gtggccgacg agcaggagca    120
ctacttcgac tacaccggca ccggcaacac catgaacatg cgcagcccgc acacgctgca    180
gctggtcatg gacagcctcc ggtggtgggc cacggagatg cacgtcgacg gcttccgcat    240
cgacgcc                                                               247

<210> SEQ ID NO 231
<211> LENGTH: 244
<212> TYPE: DNA
<213> ORGANISM: Deinococcus radiodurans

<400> SEQUENCE: 231
ggtctacgcc gacgtcgtct tcaaccacac ctgcgaaggg aacgaggaag gcccgatcct    60
cagcttcaaa ggactggaga accgcgtcta ctacatgctg gccaacggcg gcagccagta    120
catgaactac tcaggctgcg gcaacacggt caacggcaat cacccgatcg tccgcgagat    180
gatcttccat tgtttgcggc actgggtaca caactaccat atcgacgact tccgcatcga    240
```

-continued cgcc                                                               244

<210> SEQ ID NO 232
<211> LENGTH: 247
<212> TYPE: DNA
<213> ORGANISM: Deinococcus radiodurans

<400> SEQUENCE: 232
ggtctacgcc gacgtcgtgt tcaaccacac cgccgagggc aatcacacgg gcccgatgct      60
gagcttcaag gggatcgaca accaggcgta ctaccgcctg atggaggacg agcccaagta     120
ctacagggac tacacgggca ccggtagctc cctcaacgtg cgccaccccc actcgctgca     180
gctgatcatg gactcgctgc gctactgggt gaccgagatg cacgtcgacg gcttccgcat     240
cgacgcc                                                              247

<210> SEQ ID NO 233
<211> LENGTH: 246
<212> TYPE: DNA
<213> ORGANISM: Deinococcus radiodurans

<400> SEQUENCE: 233
gtctacgccg acgtcgtgtt caaccatacc gccgaaggca accacctcgg gccgagcttc      60
aacctcaagg gcatcgacaa cccgacctac tatcgtctgg ttccgaacga gcctcgctat     120
tacttcgact acacgggcac cggcaacacg ctcaacgtgc ggcaccctca ggtgctggcg     180
ctcatcatgg actcgctgcg ctactgggcg atcgagatgc acgtcgacgg gttccgcatc     240
gacgcc                                                               246

<210> SEQ ID NO 234
<211> LENGTH: 246
<212> TYPE: DNA
<213> ORGANISM: Deinococcus radiodurans

<400> SEQUENCE: 234
gtctacgccg acgtcgtgta caaccacgcg gccgaaggga accacctcgg cccgatgctg      60
tcgttcaagg gctacgacaa cgaggcgtac taccggctcg gccccgacga cccccgctac     120
tacgtcgact acaccggctg cggcaacagc ctcaacatgc gcaacccgca cgtgctgcaa     180
ctgatcatgg acagcctgcg gtactgggtc gaagagatgc acgtcgacgg gttccgcatc     240
gacgcc                                                               246

<210> SEQ ID NO 235
<211> LENGTH: 247
<212> TYPE: DNA
<213> ORGANISM: Pseudomonas aeruginosa

<400> SEQUENCE: 235
ggtctacgcc gacgtcgtct tcaaccacac gagcgagggc aatcacgacg gcccgacgat      60
cagcttcaag ggattcgaga acagcgtcta ctaccatctc acaccgcggg atcgccagta     120
ctacatggac tattcgggtt gcggcaacac ggtcaactgc aaccacccgc tcgtggacaa     180
gttcatcctg gacagcctcg agttctgggt gcacgagatg cacgtcgacg gcttccgcat     240
cgacgcc                                                              247

<210> SEQ ID NO 236
<211> LENGTH: 244
<212> TYPE: DNA
<213> ORGANISM: Pseudomonas aeruginosa

<400> SEQUENCE: 236

| | |
|---|---|
| ggtctacgcc gacgtcgtgt tcaaccacac cgccgagggc aaccacctag gcccggtgct | 60 |
| cgccttcaag ggcatcgaca acgcgtcgta ctatcggctg gcggacgacg cccgttatta | 120 |
| catggacttc accggctgcg gaaatacgtt gaacatgcgc agccctcagg tgttgcagct | 180 |
| gatcatggac agcctgcgct attggcacct tgacatgcac gtcgacgggt tccgcatcga | 240 |
| cgcc | 244 |

<210> SEQ ID NO 237
<211> LENGTH: 247
<212> TYPE: DNA
<213> ORGANISM: Arabidopsis thaliana

<400> SEQUENCE: 237

| | |
|---|---|
| ggtctacgcc gacgtcgtgt tcaaccacac gaccgagggc gacgagcacg gaccgacgct | 60 |
| ttcgtttcgc ggcatcgata accccacgca ttacctgctg aaccccgacg accgcgcgcg | 120 |
| gtacatcgac tacaccggct gcggcaacac tatcagcggc aatcacccca tcgtgcggcg | 180 |
| aatgattctc gacgccctgc gctattgggt cgagcacatg cacgtcgacg gcttccgcat | 240 |
| cgacgcc | 247 |

<210> SEQ ID NO 238
<211> LENGTH: 247
<212> TYPE: DNA
<213> ORGANISM: Arabidopsis thaliana

<400> SEQUENCE: 238

| | |
|---|---|
| ggtctacgcc gacgtcgtgt tcaaccacac cgccgaaggc aatcatctgg ggccggtgct | 60 |
| ctcgttcaag ggtctcgaca acgccgccta ctaccgtctc ctcgccggcg atgcgcgcta | 120 |
| ctacatggac tacacgggca ccggcaacag cctgaacatg cggcatcccc acgtgctgca | 180 |
| gctgctgatg gattcgctcc gctactgggt gctcgaaatg cacgtcgacg gcttccgcat | 240 |
| cgacgcc | 247 |

<210> SEQ ID NO 239
<211> LENGTH: 247
<212> TYPE: DNA
<213> ORGANISM: Arabidopsis thaliana

<400> SEQUENCE: 239

| | |
|---|---|
| ggcgtcgatg cggaagccgt ccacgtgcat gtccagcacc cagtagcgga ggctgtccat | 60 |
| gatcagctgc agcacgtgcg ggtgccgcat gttcaggctg ttcccggtgc ccgtgtagtc | 120 |
| catgtagaac tgcttgtcct cgggcgtcag ccggtagtac gcggcgttgt cgatgcgctt | 180 |
| catggacagc atcgggccca ggtggttgcc ctcggcggtg tggttgttca cgacgtcggc | 240 |
| gtagacc | 247 |

<210> SEQ ID NO 240
<211> LENGTH: 247
<212> TYPE: DNA
<213> ORGANISM: Arabidopsis thaliana

<400> SEQUENCE: 240

| | |
|---|---|
| ggtctacgcc gacgtcgtgt acaaccacac cgtcgagggc gatcagcgcg gcccgacgct | 60 |
| gtcgctgcgc ggcttcgaca acgccaacta ctaccgcctg tcgccgcacg accggtcgct | 120 |

```
gtacgagaac ttctccggga cgggcaacac cgtgagcttc gatcatccgg cggtgcgctc    180
gctcgtgatc gagtgtctgc gctactgggt gagcgacatg ggcttggacg gcttccgcat    240
cgacgcc                                                               247
```

```
<210> SEQ ID NO 241
<211> LENGTH: 241
<212> TYPE: DNA
<213> ORGANISM: Arabidopsis thaliana

<400> SEQUENCE: 241
ggtctacgcc gacgtcgtgt tcaaccacac gtccgaaggc aacgaatcag gccccacgtt     60
cggctttaag ggcctcgaaa accgcgtgta ctacatgctc aacgccgatg gcacgtaccg    120
caactacacc ggctgcggca acaccgtcaa cggcaaccac ccgatcgtcc gcagagatgat   180 cttccactgc ctgcggcatt gggtgcacaa ctaccacatc gacggcttcc gcatcgacgc    240
c                                                                     241
```

```
<210> SEQ ID NO 242
<211> LENGTH: 240
<212> TYPE: DNA
<213> ORGANISM: Arabidopsis thaliana

<400> SEQUENCE: 242
ggcgtcgatg cggaagccgt cgatgtggta gttgtgcacc caatggcgga ggcaatggaa     60
gatcatctcg cgcatcacgg gatgattgcc gttcactgtg ttgccgcagc cggagaagtt    120
tttgtacgtg ccgttgtcgt tcagcatgta atagactttg ttctccaggc ccttgaagca    180
gaaagtggga cctgtctcgt tgccttcggc ggtgtggttg aacacgacgt cggcgtagac    240
```

```
<210> SEQ ID NO 243
<211> LENGTH: 247
<212> TYPE: DNA
<213> ORGANISM: Arabidopsis thaliana

<400> SEQUENCE: 243
ggtctacgcc gacgtcgtct tcaaccacac cgccgagggc aaccatctcg gacccgtgct     60
gtcgctcaag ggaatcgaca acgcggcgta ctaccggctg gtcgccgacc accgccggta    120
ctacatggac tacacgggca ccggcaacag cctgaacatg cgccaccgc acgtgctgca    180 gctcttgatg gattcgctgc ggtactgggt gaccgagatg cacgtggacg ggttccgcat    240
cgacgcc                                                              247
```

```
<210> SEQ ID NO 244
<211> LENGTH: 247
<212> TYPE: DNA
<213> ORGANISM: Arabidopsis thaliana

<400> SEQUENCE: 244
ggtctacgcc gacgtcgtga acaaccacac ggcggaaggg aatcatctcg ggccgaccct     60
gtcgttccgc gggatcgaca acacgagcta ctaccgcctg ctccacgaca cccgcgcta    120 ctacatggac ttcaccgggt gcgggaacac gctgaacatg cagtgcccgc aggtgctgca    180
gctgatcatg gacagcctgc gctactgggt cctcgaaatg cacgtcgacg gcttccgcat    240
cgacgcc                                                              247
```

```
<210> SEQ ID NO 245
<211> LENGTH: 240
```

-continued

<212> TYPE: DNA
<213> ORGANISM: Triticum aestivum

<400> SEQUENCE: 245

| ggtctacgcc | gacgtcgtgt | tcaaccacac | gtcggaaggc | aacgaaacgg | gccccacgtt | 60 |
| cagcttcaaa | ggcctggaga | accgcgtcta | ctacatgctc | aacgacgacg | gcacctaccg | 120 |
| gaactacagc | ggctgcggca | acaccgtcaa | cggcaatcac | ccgatcgtgc | gcagatgat | 180 |
| cttccattgc | ctccgccatt | gggtgcacaa | ctaccacgtc | gacggcttcc | gcacggcgcc | 240 |

<210> SEQ ID NO 246
<211> LENGTH: 246
<212> TYPE: DNA
<213> ORGANISM: Triticum aestivum

<400> SEQUENCE: 246

| ggtctacgcc | gacgtcgtct | tcaaccacac | cgcggaaggg | aatcatctcg | gaccgacgtt | 60 |
| gtccctgcgc | ggcatcgaca | acacctcgtc | ctatcggctg | cagcctcacg | acccgcggtt | 120 |
| ctaccaggac | ttcaccggct | gcggcaacac | gctgaacatg | cgcagcccgc | gcatgctgca | 180 |
| gctgctgatg | gacagcctgc | gctactgggt | gcaggagatg | cacgtggacg | gcttccgcat | 240 |
| cgacgc | | | | | | 246 |

<210> SEQ ID NO 247
<211> LENGTH: 211
<212> TYPE: DNA
<213> ORGANISM: Sulfolobus shibatae

<400> SEQUENCE: 247

| ggtctacgcc | gacgtcgtgt | tcaaccacct | cggccctgcc | ggcaactacc | tgaaccgctt | 60 |
| cgggccctac | ttcaccgatc | gctacgccac | cccttgggga | gcggcggtga | acctcgacgg | 120 |
| gccgggtagc | gacgaggtgc | gggccttctt | cgtcgacaac | gccctcatgt | ggctgcggga | 180 |
| ctaccacatc | gacggcttcc | gcatcgacgc | c | | | 211 |

<210> SEQ ID NO 248
<211> LENGTH: 247
<212> TYPE: DNA
<213> ORGANISM: Streptomyces coelicolor

<400> SEQUENCE: 248

| ggtctacgcc | gacgtcgtca | tcaaccacac | cgccgagggc | aaccatctcg | gcccgaccct | 60 |
| gtcgctgcgc | ggcgtcgata | acgccaccta | ctaccggttg | atgccggacg | accggcgcca | 120 |
| ctacctggat | ttcaccggat | gcgggaacac | gctcaacatg | cagagcccgc | aggtgctgca | 180 |
| gctgatcatg | gacagcctgc | ggtactgggt | gctcgagatg | cacgtcgacg | ggttccgcat | 240 |
| cgacgcc | | | | | | 247 |

<210> SEQ ID NO 249
<211> LENGTH: 244
<212> TYPE: DNA
<213> ORGANISM: Alicyclobacillus acidocaldarius

<400> SEQUENCE: 249

| ggtctacgcc | gacgtcgtca | tcaaccacac | ggccgagggc | aaccacctgg | gcccgacgct | 60 |
| gtccttcaag | ggcctcgaca | accccctcgta | ctaccggctg | gccgacgatc | cccgttacta | 120 |
| cacggacacc | acgggaccg | ggaactccct | gctcatgcgg | tccccgcacg | tactccagat | 180 |

```
gatcatggac tcgctgcggt actgggtcac cgagatgcac gtggacgggt tccgcatcga    240
cgcc                                                                 244

<210> SEQ ID NO 250
<211> LENGTH: 244
<212> TYPE: DNA
<213> ORGANISM: Alicyclobacillus acidocaldarius

<400> SEQUENCE: 250
ggtctacgcc gacgtcgtca tcaaccactc gcgcgagggg aaccactacg ggccgacggt     60
cagcttcaag ggtttggata ataatatcta ttacatgctg gagtcggccc cggaattcta    120
caacgacttc accggctgcg gcaacacgct gaattgcaac catccggtcg tccgcaagtt    180
catcctcgac tgcctccggt actgggtgac cgagatgcac gtcgacgggt tccgcatcga    240
cgcc                                                                 244

<210> SEQ ID NO 251
<211> LENGTH: 241
<212> TYPE: DNA
<213> ORGANISM: Alicyclobacillus acidocaldarius

<400> SEQUENCE: 251
ggtctacgcc gacgtcgtga tcaaccatag cgcggagctg gataaggacg gcccgaccct     60
gtccctgagc ggaatcgaca accgtagcta ttattggtta atggacaacg gcgactatca    120
gaactggacg ggctgcggca atacgctgaa tttgagcacc cccggcgtag tggcccagat    180
gatggattgc ctgcgctact gggtagagag tttccatatt gacgggttcc gcatcgacgc    240
c                                                                    241

<210> SEQ ID NO 252
<211> LENGTH: 247
<212> TYPE: DNA
<213> ORGANISM: Rhizobium tropici

<400> SEQUENCE: 252
ggtctacgcc gacgtcgtct tcaaccacac ggccgagggc aaccacatgg gccccgtcct     60
gtcgatgaag ggcatcgaca acgccggcta ctaccggctg gtcgacagcg acaggcgtta    120
ctactacgac accacgggca ccggcaacag cctcgacatg cgccacccgc acgtcctgca    180
gctcatcatg gacagcctgc ggtactgggt caccgacatg cacgtggacg ggttccgcat    240
cgacgcc                                                              247

<210> SEQ ID NO 253
<211> LENGTH: 247
<212> TYPE: DNA
<213> ORGANISM: Rhizobium tropici

<400> SEQUENCE: 253
ggtctacgcc gacgtcgtct tcaaccacac ggccgagggc aaccacctcg gccccacgct     60
gtcgttccga ggcatcgaca acccggcgta ctaccggctc gtgccggacg acaagcagca    120
ctactacgac accacgggca ccggtaacag cttcaacatg gcccaccccc acgcgctgca    180
gctgatcatg gactcgctgc ggtactgggt caccgagtgc cacgtcgacg gcttccgcat    240
cgacgcc                                                              247

<210> SEQ ID NO 254
<211> LENGTH: 244
```

```
<212> TYPE: DNA
<213> ORGANISM: Rhizobium tropici
<220> FEATURE:
<221> NAME/KEY: misc_feature
<222> LOCATION: (65)..(67)
<223> OTHER INFORMATION: n is a, c, g, or t

<400> SEQUENCE: 254
ggtctacgcc gacgtcgtct tcaaccacac ctgcgaaggg aacgagcagg gaccgatcct      60
cagcnnnaaa gggctggaaa accgcgtcta ttacatgatg gctaacggcg gcagccatta     120
catgaactac tcaggctgcg gcaacacggt caacggcaat cacccgatcg tccgcgagat     180
gatcttccat tgcttgcggc actgggtgca taactaccac atcgacggct tccgcatcga     240
cgcc                                                                  244

<210> SEQ ID NO 255
<211> LENGTH: 247
<212> TYPE: DNA
<213> ORGANISM: Streptomyces coelicolor

<400> SEQUENCE: 255
ggtctacgcc gacgtcgtga acaaccacac ctgcgaaggc aaccagatgg ggccgacgct      60
ttcctggcgc ggcatcgaca acgccagcta ttaccgcctg accgacgacg ataaacgcta     120
ctacatggat tacaccggct gcggcaatac gctcaacatg acccacccgc gcgtgctcca     180
gctcatcatg gacagcctgc ggtattgggt gacagagatg cacgttgacg ggttccgcat     240
cgacgcc                                                               247

<210> SEQ ID NO 256
<211> LENGTH: 246
<212> TYPE: DNA
<213> ORGANISM: Streptomyces coelicolor

<400> SEQUENCE: 256
ggtctacgcc gacgtcgtga tcaaccacac gggcgagggc aaccaccagg gcccgacgat      60
cagcttcaag gtctcgaga acgaggcgta ctacatgctc tcgccgggcg acggggcgta     120
ctacatgaac tactccggct gcgggaacac ggtcaacgcg aaccaccccg tcgtcgagaa     180
gttcatcgcc gactgcctgg gctactgggt cgaggagatg cacgtcgacg ggttccgcat     240
cgcgcc                                                                246

<210> SEQ ID NO 257
<211> LENGTH: 247
<212> TYPE: DNA
<213> ORGANISM: Streptomyces coelicolor
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (214)..(215)
<223> OTHER INFORMATION: n is a, c, g, or t

<400> SEQUENCE: 257
ggtctacgcc gacgtcgtca tcaaccacac ctcggaaggg aatcacctcg ggccgacgtt      60
gtcgctgcgc gggatcgaca acgagaccta ttaccgcctg acgccgagga caagcgctac    120
```

```
tacctcgatt tcaccggctg cgggaacacg ctcaaacatg canagcccgc aggtgctgca      180
gctgatcatg gacagcatnc ggtactgggt gctnnacatg cacgtcgacg gcttccgcat      240
cgacgcc                                                                247
```

```
<210> SEQ ID NO 258
<211> LENGTH: 247
<212> TYPE: DNA
<213> ORGANISM: Streptomyces coelicolor
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (214)..(215)
<223> OTHER INFORMATION: n is a, c, g, or t

<400> SEQUENCE: 258
```

```
ggtctacgcc gacgtcgtct tcaaccacac gggcgagggg aaccaccagg gcccgacgat      60
cagcttcaag ggtctcgagn gacgaggcgt actacatgct ctcgccgggc gacggggcgt     120
actacatgaa ctactccggc tgcgggaaca cggtcaacgc gaaccacccc gtcgtcgaga     180
agttcatcgc cgactgcctg ggctactggg tcgnnagatg cacgtcgacg gcttccgcat     240
cgacgcc                                                              247
```

```
<210> SEQ ID NO 259
<211> LENGTH: 247
<212> TYPE: DNA
<213> ORGANISM: Sulfolobus solfataricus

<400> SEQUENCE: 259
```

```
ggtctacgcc gacgtcgtgt tcaaccacac cgccgagggc aaccagctcg gcccgacgct      60
gtcgttccgc gggatcgaca acgccaacta ctaccgcctc gtggacgagg acaagaagca     120
ctactacgac accacgggca cgggcaacac gctgctcatg aagagccccc acgtgctgca     180
gctgatcatg gactcgctgc gctactgggt gaccgagatg cacgtagacg ggttccgcat     240
cgacgcc                                                              247
```

```
<210> SEQ ID NO 260
<211> LENGTH: 322
<212> TYPE: DNA
<213> ORGANISM: Sulfolobus solfataricus
<220> FEATURE:
<221> NAME/KEY: misc_feature
<222> LOCATION: (47)..(47)
<223> OTHER INFORMATION: n is a, c, g, or t

<400> SEQUENCE: 260
```

```
ggtctacgcc gacgtcgtga tcaaccacac cagcgaccag cacccgnggt tccaggagtc      60
gcgccaggac cgcaccaacc ccaaggccga ctggtacgtg tgggacgacg acggcaccaa     120
gtggtccgag gcccgcgtga tcttcgtcga caccgagccc tcgaactgga cgttcgaccc     180
gcagcgcgag cagttctact ggcaccgctt cttctcgcat cagcccgacc tcaacttcga     240
caaccccgag gtcgaggagg cgatgttcga cgtcatgcgg ttctggctcg acctcggcct     300
cgacggcttc cgcatcgacg cc                                             322
```

```
<210> SEQ ID NO 261
<211> LENGTH: 247
<212> TYPE: DNA
<213> ORGANISM: Sulfolobus solfataricus
```

```
<220> FEATURE:
<221> NAME/KEY: misc_feature
<222> LOCATION: (108)..(110)
<223> OTHER INFORMATION: n is a, c, g, or t

<400> SEQUENCE: 261
ggtctacgcc gacgtcgtgt tcaaccacac cggcgagggc aatcacctcg ggctgacgtt      60
gtccttcaag ggtctagaca acccgaccta ctaccagctg aagcgcgnnn agcagcgcta     120
ctacgtcgac tacaccggca ccggcaacag tctgaacgtg caccacccatc aggtgttgca    180 gctcgtgctc gacagcttgc gctactgggt gaaggtgatg catgtggacg ggttccgcat     240
cgacgcc                                                               247

<210> SEQ ID NO 262
<211> LENGTH: 322
<212> TYPE: DNA
<213> ORGANISM: Sulfolobus solfataricus

<400> SEQUENCE: 262
ggtctacgcc gacgtcgtct tcaaccacag ctccgaccgg cacccatggt tcgtggagag      60
ccgctcgtca cgcgcgaacg ccaaacgcga ctggtatatc tggcgcgacc cggctcccgg     120
gggcgggccg cccaacaatt ggatgagcga tttcggcggg ccggcgtgga cgctcgatcc     180
cgcgaccggg caatattatc tccacgcctt cctgccgcaa cagcccgacc tcaactggcg     240
caatccggac gtgcgcgcgg cgatgatggg cgtgctgcga ttctggctcg accgcggagt     300
cgacgggttc cgcatcgacg cc                                              322

<210> SEQ ID NO 263
<211> LENGTH: 214
<212> TYPE: DNA
<213> ORGANISM: Sulfolobus solfataricus

<400> SEQUENCE: 263
ggtctacgcc gacgtcgtgt tcaaccacct cggcccggcc gggaactacc tgccccggtt      60
ctcgcggtcg tacctcagcc atcgctacgc caacgaatgg ggcgacgcac tcaactacga     120
cgacacggga tgcgaggggc tgcgcgaact ggtgctgtcg aacatcgcct actgggtgcg     180
cgagtttcac ctcgacgggt tccgcatcga cgcc                                 214

<210> SEQ ID NO 264
<211> LENGTH: 247
<212> TYPE: DNA
<213> ORGANISM: Sulfolobus solfataricus

<400> SEQUENCE: 264
ggtctacgcc gacgtcgtgt tcaaccacac cggcgagagc gatgcgctcg gcccgaccct      60
gtcgctgcgc gggctcgaca accgggccta ttaccgccac cttcccggcg aagcggaag     120 cctggtcaat gatacgggaa ccggcaacac ggtcgcctgc aactacccgg tcgtccgggg    180
actcgttctc gatacgctgc gccattttgt gctgaacgcc ggcgtcgacg gcttccgcat    240
cgacgcc                                                              247

<210> SEQ ID NO 265
<211> LENGTH: 246
<212> TYPE: DNA
<213> ORGANISM: Sulfolobus solfataricus

<400> SEQUENCE: 265
```

```
ggtctacgcc gacgtcgtct tcaaccacac gggcgaagga aaccacctcg gccccaccct    60
cgcgttcaag ggcatcgaca acaaggcgta ctaccggttg gagccggaca acccgcactt   120
gtacaccgat ttcacgggca ccggaaacag cctgaacatg cagcatccgc gcacgatcca   180
gctcatcatg gactcgctgc gctactgggt accgagatgc acgtagacgg cttccgcatc   240
gacgcc                                                              246
```

<210> SEQ ID NO 266
<211> LENGTH: 247
<212> TYPE: DNA
<213> ORGANISM: Sulfolobus solfataricus

<400> SEQUENCE: 266

```
ggtctacgcc gacgtcgtgt tcaaccacac gaccgagggg aaccatcagg ggccgacgat    60
caacttcaga ggcttcgaca acagcgtcta ctacttcacg gttcccgacg acaagcagta   120
ctacatggac tacagcgggt gcgggaacac gctgaactgc aacccaccgg tcgtcgagaa   180
gatgatcctg gattgtctcg agttctgggt gcgggacatg cacatcgacg gcttccgcat   240
cgacgcc                                                             247
```

<210> SEQ ID NO 267
<211> LENGTH: 247
<212> TYPE: DNA
<213> ORGANISM: Sulfolobus solfataricus

<400> SEQUENCE: 267

```
ggtctacgcc gacgtcgtgt acatccatac cgccgaaggc aaccacctcg ggcccacgct    60
gtcgttccgc ggtatcgaca acgcgaccta ctactggctg aaaccggacc agccgcgtta   120
ttacgaggat ttcaccggat gcggcaattc gctgaacctg acgcatcctc atgtgttgca   180
gcttgtcatg gattcgctgc gctactgggt ggagcagtgc catgtcgacg gcttccgcat   240
cgacgcc                                                             247
```

<210> SEQ ID NO 268
<211> LENGTH: 211
<212> TYPE: DNA
<213> ORGANISM: Sulfolobus solfataricus

<400> SEQUENCE: 268

```
ggtctacgcc gacgtcgtct tcaaccatct cggacccgcc ggcaactacc tgcgcgaatt    60
cggtccctat ttcaccgaca ggtacgggac gccgtgggggc gatgccgtga atctcgacga   120
cagagggtct accgaagtac gcaactactt tttcgacaac gctcttggat ggttggagca   180
ctaccacctc gacggcttcc gcatcgacgc c                                  211
```

<210> SEQ ID NO 269
<211> LENGTH: 247
<212> TYPE: DNA
<213> ORGANISM: Sulfolobus solfataricus

<400> SEQUENCE: 269

```
ggtctacgcc gacgtcgtgt tcaaccacac ggcggagggg aaccacctcg gcccgatgct    60
ctcgttcaag gggatcgaca acctctccta ctaccggacg ctgcccggcg acccgcgctt   120
ctacatggac tacaccggca ccggcaacag cctcaacgtc cgccacccc actcggtgca   180 gctgatcatg gactcgttgc gctactgggt caccgagatg cacgtcgacg gcttccgcat   240
cgacgcc                                                             247
```

-continued

<210> SEQ ID NO 270
<211> LENGTH: 211
<212> TYPE: DNA
<213> ORGANISM: Sulfolobus solfataricus

<400> SEQUENCE: 270

| | |
|---|---|
| ggtctacgcc gacgtcgtgt tcaaccattt cggtccggac ggctgctgga tcgagaagtt | 60 |
| ttcgccacac ttcttttcgg aacgagccac cgaatggggg cgcgccatca acttcgatgg | 120 |
| cgaacacgcc gctgaggtgc gcgcgttctt cgtcgcgaac gcgtcctatt ggatcgagga | 180 |
| atttcatctc gacgggttcc gcatcgacgc c | 211 |

<210> SEQ ID NO 271
<211> LENGTH: 247
<212> TYPE: DNA
<213> ORGANISM: Sulfolobus solfataricus

<400> SEQUENCE: 271

| | |
|---|---|
| ggtctacgcc gacgtcgtga tcaaccacac gggcgaaggc agccataccg gccccacgct | 60 |
| gtgctttcgg ggcatcgaca acgcgagcta ttaccgcctg aacgcacaga acccgcgcct | 120 |
| ctacgtcgat tacaccggct gcggcaatac gctcaacatg cagaacccgc gggtgctcca | 180 |
| gctcatcatg gattcgctgc gctactgggt caccgaaatg cacgtcgacg ggttccgcat | 240 |
| cgacgcc | 247 |

<210> SEQ ID NO 272
<211> LENGTH: 244
<212> TYPE: DNA
<213> ORGANISM: Sulfolobus solfataricus

<400> SEQUENCE: 272

| | |
|---|---|
| ggtctacgcc gacgtcgtct tcaaccacac cggcgaggga aaccatctgg gtccgacggt | 60 |
| ttcgctcaag ggcatcgaca acacggcgta ttaccggctc gaggaagaca agcggttcta | 120 |
| tacggatttc accggcaccg gtaactcgct caacatgcgc caccccgcgca cgatccagtt | 180 |
| gatcatggac tcgctgcgct actgggtgac ggagatgcac gtcgacggct ccgcatcga | 240 |
| cgcc | 244 |

<210> SEQ ID NO 273
<211> LENGTH: 247
<212> TYPE: DNA
<213> ORGANISM: Sulfolobus solfataricus

<400> SEQUENCE: 273

| | |
|---|---|
| ggtctacgcc gacgtcgtct tcaaccacac ctccgagggg caccacctgg ggccgacgct | 60 |
| gtcgtacaag gggatcgaca atccgaccta ctatcggctt ctgcccgagg acccgcgctt | 120 |
| ctaccgcgac tacaccggca cggggaactc gctgaacatg cggcacccgc aaacgctgaa | 180 |
| gctggtgatg gattcgcttc gctactgggt gctcgagatg cacgtggacg ggttccgcat | 240 |
| cgacgcc | 247 |

<210> SEQ ID NO 274
<211> LENGTH: 241
<212> TYPE: DNA
<213> ORGANISM: Streptomyces coelicolor

<400> SEQUENCE: 274

-continued

```
ggtctacgcc gacgtcgtct tcaaccacac ggccgaaggc aacgaaacag gccccacgtt      60
ctgcttcaag ggcttggaga acaaagttca ttacatgctg aatgaaaacg gcacgtacaa     120
aaacttctcc ggctgcggca acacggtgaa cggcaaccac cccgtcatgc gcgaaatgat     180
cttccattgc ctccgtcatt gggtgcacaa ctaccacatc gacgggttcc gcatcgacgc     240
c                                                                     241
```

<210> SEQ ID NO 275
<211> LENGTH: 202
<212> TYPE: DNA
<213> ORGANISM: Corynebacterium glutamicum

<400> SEQUENCE: 275

```
ggtctacgcc gacgtcgtca tcaaccactt cggtcctgcc ggtaactcgc actacgcgtt      60
cgcaccggag atcaaggccc gacgatgac cgagtggggc gacgccctcg actacagccg     120
ccccggtgca cgcgagctgt tcatcacgaa tgcggcgtac tggatccgcg agttccactt     180
cgacggcttc cgcatcgacg cc                                              202
```

<210> SEQ ID NO 276
<211> LENGTH: 247
<212> TYPE: DNA
<213> ORGANISM: Arthrobacter sp.

<400> SEQUENCE: 276

```
ggtctacgcc gacgtcgtga acaaccacac ggcggagggg aaccacctgg gcccgatgct      60
ctccatgaag gggatcgaca acgccggcta ttaccggctg gtcgacgacg acaaacgctt     120
ctactacgac accacaggaa ccggcaacag cctggacatg cgccaccccc acgtactgca     180
gctgatcatg gacagcctgc gttactgggt cacggagatg catgtcgacg ggttccgcat     240
cgacgcc                                                               247
```

<210> SEQ ID NO 277
<211> LENGTH: 241
<212> TYPE: DNA
<213> ORGANISM: Arthrobacter sp.

<400> SEQUENCE: 277

```
ggtctacgcc gacgtcgtct tcaaccacac cgcggaaggg gaccagcgag gtccgactct      60
cagctggcgc ggcctcgaca acgccagcag ctacgccctg gatggcagcg gcaatatct     120 gaacttcacc ggctgcggca atgcgatcaa tgccggcgag ccgcgcatgg tgcagttcgt     180
gatggacagc ctgcgctggt gggtgcaggc attcggcgtc gacgggttcc gcatcgacgc     240
c                                                                     241
```

<210> SEQ ID NO 278
<211> LENGTH: 247
<212> TYPE: DNA
<213> ORGANISM: Rhizobium sp

<400> SEQUENCE: 278

```
ggtctacgcc gacgtcgtgt tcaaccatac cgccgagggc aatcatctcg gccgacgct      60 gtccttccgc ggcatcgaca acgccgtcta ctacaagttg ccggccaacg accgccgcca     120
ctattgggac agcaccggga cgggcaacac gctcgacgtg aaccatccgc aggtgttgaa     180
gatggtgctc gattcactcc gccactgggt cgaggactac catgtcgacg gcttccgcat     240
cgacgcc                                                               247
```

<210> SEQ ID NO 279
<211> LENGTH: 247
<212> TYPE: DNA
<213> ORGANISM: Sulfolobus acidocaldarius

<400> SEQUENCE: 279

```
ggtctacgcc gacgtcgtct tcaaccacac cgccgaggga aaccatctcg ggccaacact    60
gtcgttccgg ggcatcgaca atgccgccta ttaccgcctc gtcgactccg accgccgcca   120
ctacatggac tacaccggta ccggcaacac cctgaacatg cgcaacccgt tcccgctgca   180
actgctgatg gacagcctgc gctactgggt caccgaatgc cacgtcgacg gcttccgcat   240
cgacgcc                                                             247
```

<210> SEQ ID NO 280
<211> LENGTH: 247
<212> TYPE: DNA
<213> ORGANISM: Sulfolobus acidocaldarius

<400> SEQUENCE: 280

```
ggtctacgcc gacgtcgtct tcaaccatac cgccgaaggc aatcagctcg gccccacgct    60
gagctttcgc ggcatcgaca acacctccta ttactggctc ctgcccgacg agccgcgcta   120
ctacgacgac ttcaccggct gcggcaacgc gctcaacctg acacatccgc gcgtgctgca   180
gatggtgatg gattcgctcc gttactgggt cgagatgtgc ctggtcgacg ggttccgcat   240
cgacgcc                                                             247
```

<210> SEQ ID NO 281
<211> LENGTH: 248
<212> TYPE: DNA
<213> ORGANISM: Sulfolobus acidocaldarius

<400> SEQUENCE: 281

```
gggtctacgc cgacgtcgtg ttcaaccaca cgggcgaagg cagccatacc ggcccgacgc    60
tgtgctttcg aggcatcgac aacgcgagtt attaccgcct gaacccgcag aacccgcgcc   120
tctatgtcga ttacaccggc tgcggcaaca cgctcaacat gcagaacccg cgggtgctcc   180
agctcatcat ggattcgctg cgctactggg tcaccgaaat gcacgtcgac ggcttccgca   240
tcgacgcc                                                            248
```

<210> SEQ ID NO 282
<211> LENGTH: 242
<212> TYPE: DNA
<213> ORGANISM: Sulfolobus acidocaldarius

<400> SEQUENCE: 282

```
cggtctacgc cgacgtcgtg ttcaaccaca cggccgaagg caacgaaaca ggccccacgt    60
tctgcttcaa gggcttggag aacaaagttt attacatgct gaatgaaaac ggcacgtaca   120
aaaacttctc cggctgcggc aacacggtga acggcaacca cccgtcatg cgcgaaatga   180 tcttccattg cctccgtcat tgggtgcaca actaccacat cgacggcttc cgcatcgacg   240
cc                                                                  242
```

<210> SEQ ID NO 283
<211> LENGTH: 241
<212> TYPE: DNA
<213> ORGANISM: Sulfolobus acidocaldarius

<400> SEQUENCE: 283

```
ggtctacgcc gacgtcgtgt tcaaccacac cgccgagggc ccgcagggcg gtcccgcact    60
ctgctggcgc ggactgagcg aaatgaagta ctaccgccat cacgacgacg gccggtacct   120
ggacaccacc ggttgtggaa acacggtcaa cttcactgag ccgcgcgtaa tccagttcgc   180
gctggattcc ctgcggtact gggtcgacga gttcggtatc gacggcttcc gcatcgacgc   240
c                                                                   241
```

<210> SEQ ID NO 284
<211> LENGTH: 214
<212> TYPE: DNA
<213> ORGANISM: Sulfolobus acidocaldarius

<400> SEQUENCE: 284

```
ggtctacgcc gacgtcgtgt tcaaccactt cggtcccgac ggcaactacc tgcgcgccta    60
ttcggacgac tacttcaccg accgctacgc cacccctgg gcgaggcga tcgactacga   120
tggacccggt agtcgctggg tgcgccagtt catccgcgag aacgcccgct actggctcga   180
cgagtaccgg ctcgacgggt tccgcatcga cgcc                                214
```

<210> SEQ ID NO 285
<211> LENGTH: 247
<212> TYPE: DNA
<213> ORGANISM: Sulfolobus acidocaldarius

<400> SEQUENCE: 285

```
ggtctacgcc gacgtcgtgt acaaccacac cgcggaaggc aatcagatgg ggccgacgct    60
gtcgctgcac ggcgtcgaca acgtcaccta ctaccgcctc gtgccgcacg acaggcgcta   120
ctaccaggac ttcaccggct gcggcaacac cctcaacatg cagagcccgc aggtgctgca   180
gctgatcatg gacagcctgc gttactgggt gctcgagatg cacgtcgacg ggttccgcat   240
cgacgcc                                                             247
```

<210> SEQ ID NO 286
<211> LENGTH: 247
<212> TYPE: DNA
<213> ORGANISM: Sulfolobus acidocaldarius

<400> SEQUENCE: 286

```
ggtctacgcc gacgtcgtgt tcaaccacac gtgcgaaggg aacgagaaag gcccgacgct    60
ctcgtggcgc gggatcgaca acgtcgcgta ttaccgtctg tcgaaggaag atccgcgcta   120
ctacacggat ttcaccggct gcggcaacac gctgaacatg acgcacccgc gcgtgctcca   180
gctcatcatg gactccctgc gctactgggt gacggagatg cacatcgacg ggttccgcat   240
cgacgcc                                                             247
```

<210> SEQ ID NO 287
<211> LENGTH: 235
<212> TYPE: DNA
<213> ORGANISM: Synechocystis sp

<400> SEQUENCE: 287

```
ggtctacgcc gacgtcgtga tcaaccacac ggccgccagc ggccaggccg ggaccagcgt    60
cctcgaccgg atcgtgcccg gctactacca gcggctgctc gccgacggct cggtggccaa   120
cagcaccctg ctgctcgaaca ccgccaccga gaacgccatg atgggcaagc tcgtcgtcga   180
ctcggtcgtc acctgggcca aggagtacaa ggtcgacggc ttccgcatcg acgcc         235
```

<210> SEQ ID NO 288
<211> LENGTH: 215
<212> TYPE: DNA
<213> ORGANISM: Synechocystis sp

<400> SEQUENCE: 288

```
ggtctacgcc gacgtcgtct acaaccacct cggtcctgac ggctgctacc tcacgaagtt    60
cgcagactga gtacttcacc gaccggtaca agaacgaatg gggcgaggcc gtgaacttcg   120
acggcgagag ctctgcgccg gtgcgggagt tttttgcgga gaacgccgcg tactggatcg   180
acgagtttca cctggacggg ttccgcatcg acgcc                              215
```

<210> SEQ ID NO 289
<211> LENGTH: 247
<212> TYPE: DNA
<213> ORGANISM: Synechocystis sp

<400> SEQUENCE: 289

```
ggtctacgcc gacgtcgtgt tcaaccacac cgccgaaggc aatcatctcg ggcccatgct    60
gtcgttcaag gggatcgaca acgcggcgta ctaccgcgtc attggggaca accgtcgcta   120
ctacatggac tacaccggca cgggcaacac gctgaacatg cgccatcctc acgtgctgca   180
gctgatgatg gacagccttc gctacttcgt gctcgacatg cacgtggacg ggttccgcat   240
cgacgcc                                                             247
```

<210> SEQ ID NO 290
<211> LENGTH: 247
<212> TYPE: DNA
<213> ORGANISM: Synechocystis sp

<400> SEQUENCE: 290

```
ggtctacgcc gacgtcgtgt tcaaccacac gtcggagggg aacgccgagt ccggtcccgc    60
cttctgcctc aagggggttcg acaacagcat ctactacatc ctcgacaagg acaagtcgcg   120
gtacgccgac tacaccgggt gcgggaacac gctcaactcc aaccatccga tcgtgcgccg   180
catgatcgtg gacagcctgc gctactgggt gcaggagatg cacgtcgacg gcttccgcat   240
cgacgcc                                                             247
```

<210> SEQ ID NO 291
<211> LENGTH: 241
<212> TYPE: DNA
<213> ORGANISM: Synechocystis sp

<400> SEQUENCE: 291

```
ggtctacgcc gacgtcgtgt tcaaccacac cgccgaggga aacgaacgcg ggccgacgat    60
ctcgttccgc ggcctcgaca caagacgta ctacatgctg acgccggagg ggtattactt    120
caacttcagc ggcaccggca acacgctgaa ctgcaacaat cccatcgtgc gcgacatggt   180
gctcgactgc ctgcgctact gggcggcgga gtatcacgtg gacggcttcc gcatcgacgc   240
c                                                                   241
```

<210> SEQ ID NO 292
<211> LENGTH: 247
<212> TYPE: DNA
<213> ORGANISM: Synechocystis sp

<400> SEQUENCE: 292

```
ggtctacgcc gacgtcgtga tcaaccacac gaccgagggg aaccatcagg ggccgatcgt    60
caacttccgc ggcttcgaca acagcgtcta ctaccacctg gtccaggacg acaagcagta   120
ctacatggac tacagcggtt gcggcaacac ggtgaactgc aaccacccgg tcgtcgagaa   180
gatgatcctg gactgcctcg agttctgggt gcgggacatg cacgtcgacg gcttccgcat   240
cgacgcc                                                             247
```

<210> SEQ ID NO 293
<211> LENGTH: 247
<212> TYPE: DNA
<213> ORGANISM: E.coli

<400> SEQUENCE: 293

```
ggtctacgcc gacgtcgtgt tcaaccacac gaccgagggg aaccatcagg ggccgattgt    60
caacttccgc ggcttcgaca acagcgtcta ctaccacctg gtccaggacg acaagcagta   120
ctacatggac tacagcggtt gcggcaacac ggtgaactgc aaccacccgg tcgtcgagaa   180
gatgatcctg gactgcctcg agttctgggt gcgcgacatg cacgtcgacg gcttccgcat   240
cgacgcc                                                             247
```

<210> SEQ ID NO 294
<211> LENGTH: 241
<212> TYPE: DNA
<213> ORGANISM: Sulfolobus solfataricus

<400> SEQUENCE: 294

```
ggtctacgcc gacgtcgtgt tcaaccacac gggcgaaaac atggaggtag cggatcgcgg    60
cttcaccttc agcgggatcg accggtggta ctactaccgg atgaaccagg aggggggagct   120
gatcggaccc tacggcaacg agatccgcag cgaggatcgg ccgatggttc agcgttggct   180
gatcgaccag ctgcgacatc tggtggacat tttcggagtc gacggcttcc gcgtcgacgc   240
c                                                                   241
```

<210> SEQ ID NO 295
<211> LENGTH: 247
<212> TYPE: DNA
<213> ORGANISM: Sulfolobus solfataricus

<400> SEQUENCE: 295

```
ggtctacgcc gacgtcgtgt acaaccacac gtgcgagggc aatcatctcg ggccgacgct    60
gtcgctgcgg gggatcgaca acgtctcgta ttaccgcttg gccgagaacg agcgcaggca   120
ctatgccgac ttcagcggct gcggcaacac gctgaacctc gagcacccga atgtgctgca   180
gctggtgacg gattcgctgc gctactgggt cgaggtgatg cacgtggacg ggttccgcat   240
cgacgcc                                                             247
```

<210> SEQ ID NO 296
<211> LENGTH: 247
<212> TYPE: DNA
<213> ORGANISM: Sulfolobus solfataricus

<400> SEQUENCE: 296

```
ggtctacgcc gacgtcgtgt acaaccacac gtgcgagggc aatcatctcg ggccgacgct    60
gtcgctgcgg gggatcgaca acgtctcgta ttaccgcttg gccgagaacg agcgcaggca   120
ctatgccgac ttcagcggct gcggcaacac gctgaacctc gagcacccga atgtgctgca   180
gctggtgacg gattcgctgc gctactgggt cgaggtgatg cacgtggacg ggttccgcat   240
``` cgacgcc                                                                247

<210> SEQ ID NO 297
<211> LENGTH: 241
<212> TYPE: DNA
<213> ORGANISM: Sulfolobus solfataricus

<400> SEQUENCE: 297
ggtctacgcc gacgtcgtct tcaaccacac ggccgaaggc aacgaacgcg gcccgcacat    60
ctcgttccgc ggcctcgaca caagaccta ctacatgctc acgccggagg ctactactt    120 caacttctcc ggcacgggca acacgctcaa ctgcaacaac ccgatcgtgc gcagcatggt   180
gctcgattgc ctgcgctact gggcgtcgga gtatcacgtc gacggcttcc gcatcgacgc   240
c                                                                    241

<210> SEQ ID NO 298
<211> LENGTH: 247
<212> TYPE: DNA
<213> ORGANISM: Sulfolobus solfataricus

<400> SEQUENCE: 298
ggtctacgcc gacgtcgtca tcaaccacac cgcggagggc aaccacctcg gcccgacgct    60
gtcgttccgg ggcatcgaca acccggcgta ctaccggctg atggaggacg acgcccgctt   120
ctacatggac tacacgggca cgggcaacac cctcaacgtg cgtcagccgc actcgctgca   180
gctgatcatg gactctctgc gctactgggt caccgagatg cacgtggacg gcttccgcat   240
cgacgcc                                                              247

<210> SEQ ID NO 299
<211> LENGTH: 247
<212> TYPE: DNA
<213> ORGANISM: Sulfolobus solfataricus

<400> SEQUENCE: 299
ggtctacgcc gacgtcgtga tcaaccacac cgccgaaggc aacgaattcg gtccgacgct    60
gtcgttccgc ggcctcgata acgccagtta ttaccgactg ctgcccgaca atccgcgcca   120
ctacatcaac gacaccggca ccggcaacac ggtgaacctg tcccacccgc gcgtgctgca   180
gacggtgatg gattcgctgc gctactgggt cgaggaatgc catgtcgacg gcttccgcat   240
cgacgcc                                                              247

<210> SEQ ID NO 300
<211> LENGTH: 247
<212> TYPE: DNA
<213> ORGANISM: Sulfolobus solfataricus

<400> SEQUENCE: 300
ggtctacgcc gacgtcgtgt acaaccacac cgccgagggc gatcagcgcg gcccgacgct    60
gtcgctgcgc ggcttcgaca acgccaacta ctaccgcctg tcgccgcacg accggtcgct   120
gtacgagaac ttctccggga cgggcaacac cgtgagcttc gatcatccgg cggtgcgctc   180
gctcgtgatc gagtgtctgc gctactgggt gagcgacatg ggcttggacg ggttccgcat   240
cgacgcc                                                              247

<210> SEQ ID NO 301
<211> LENGTH: 247
<212> TYPE: DNA

<213> ORGANISM: Sulfolobus solfataricus

<400> SEQUENCE: 301

```
ggtctacgcc gacgtcgtgt acaaccacac cggtgagggc aacgagcggg gaccgacgct    60
gtctttgcgt ggcatcgaca caagtcgta ctaccggctc aaccctgaga acggtcggca   120
ctacgtcgac ttcaccggaa ccggcaacac gctcaacatg atgcagccgc gctcgctgca   180
actcgtcacg gacagcctcc gctactgggt gcaagagatg cacgtcgacg gcttccgcat   240
cgacgcc                                                             247
```

<210> SEQ ID NO 302
<211> LENGTH: 247
<212> TYPE: DNA
<213> ORGANISM: Mycobacterium tuberculosis

<400> SEQUENCE: 302

```
ggtctacgcc gacgtcgtgt tcaaccacac ggtcgagggg aatcacatgg ggccggtgct    60
ggcgatgaaa ggcctcgaca acaccgccta ctaccgcacg atgccgggcc aggcgcggta   120
ctacatggac tacaccggca ccggaaacag cctgcacatg cgccatccgc acgtgctgca   180
gatgatcatg gacagcctgc gctactggat cacggagatg cacgtcgacg gcttccgcat   240
cgacgcc                                                             247
```

<210> SEQ ID NO 303
<211> LENGTH: 247
<212> TYPE: DNA
<213> ORGANISM: Mycobacterium tuberculosis

<400> SEQUENCE: 303

```
ggtctacgcc gacgtcgtgt tcaaccacac cgccgagggc aatcacctcg ggccgacgct    60
gtcgctgcgc ggcatcgaca acagctccta ctatcgcctg ctgccgaaca accgcgcgta   120
ctaccaggac ttcaccggca cgggcaacac gctcaacatg cgcagcccgc gcgtgctgca   180
gctcatcatg gacagcctgc gctactgggt cctcgagatg cacgtggacg gcttccgcat   240
cgacgcc                                                             247
```

<210> SEQ ID NO 304
<211> LENGTH: 244
<212> TYPE: DNA
<213> ORGANISM: Mycobacterium tuberculosis

<400> SEQUENCE: 304

```
ggtctacgcc gacgtcgtgt tcaaccacac gtgcgaaggg aacgagcacg gcccgacgct    60
cagcttcaag ggcctcgaga accgcgtgta ctacatgctc gccggccagg gcgagcacta   120
caagaactac tcgggctgcg gcaacacggt caacggaaac catcccatcg tgcgggagat   180
gatcttccat tgcctccgcc actgggtgca caactaccac gtcgacgggt tccgcatcga   240
cgcc                                                                244
```

<210> SEQ ID NO 305
<211> LENGTH: 123
<212> TYPE: PRT
<213> ORGANISM: Artificial Sequence
<220> FEATURE:
<223> OTHER INFORMATION: Consensus A
<220> FEATURE:
<221> NAME/KEY: MISC_FEATURE
<222> LOCATION: (8)..(8)
<223> OTHER INFORMATION: Xaa = Arg or Thr -continued

```
<220> FEATURE:
<221> NAME/KEY: MISC_FEATURE
<222> LOCATION: (9)..(9)
<223> OTHER INFORMATION: Xaa = Gly or Ile or Val or Thr or Leu or Ala
      or Ser
<220> FEATURE:
<221> NAME/KEY: MISC_FEATURE
<222> LOCATION: (10)..(10)
<223> OTHER INFORMATION: Xaa = Lys or Glu or Arg
<220> FEATURE:
<221> NAME/KEY: MISC_FEATURE
<222> LOCATION: (11)..(11)
<223> OTHER INFORMATION: Xaa = His or Ala or Arg
<220> FEATURE:
<221> NAME/KEY: MISC_FEATURE
<222> LOCATION: (12)..(12)
<223> OTHER INFORMATION: Xaa = Ile or Met or Val or Leu
<220> FEATURE:
<221> NAME/KEY: MISC_FEATURE
<222> LOCATION: (13)..(13)
<223> OTHER INFORMATION: Xaa = His or Asp or Arg or Thr or Pro or Ser or
      Ala or Tyr or Asn or Lys
<220> FEATURE:
<221> NAME/KEY: MISC_FEATURE
<222> LOCATION: (14)..(14)
<223> OTHER INFORMATION: Xaa = Pro or Thr or Asn or Ser or Ala or Arg or
      His or Gln
<220> FEATURE:
<221> NAME/KEY: MISC_FEATURE
<222> LOCATION: (15)..(15)
<223> OTHER INFORMATION: Xaa = Pro or Arg or Thr or Ser or Gly or Ala
      or Asp or Gle or Phe
<220> FEATURE:
<221> NAME/KEY: MISC_FEATURE
<222> LOCATION: (16)..(16)
<223> OTHER INFORMATION: Xaa = Phe or Tyr or Asp
<220> FEATURE:
<221> NAME/KEY: MISC_FEATURE
<222> LOCATION: (17)..(17)
<223> OTHER INFORMATION: Xaa = Leu or Val or Phe or Tyr or Ile or
      Trp or Thr
<220> FEATURE:
<221> NAME/KEY: MISC_FEATURE
<222> LOCATION: (18)..(18)
<223> OTHER INFORMATION: Xaa = Ser or Asn or Ala or Lys or Arg or Gle
      or Cys or Gln or His or Leu
<220> FEATURE:
<221> NAME/KEY: MISC_FEATURE
<222> LOCATION: (19)..(19)
<223> OTHER INFORMATION: Xaa = Arg or Ala or His or Glu or Asp or Trp
      or Asn or Gly or Lys
<220> FEATURE:
<221> NAME/KEY: MISC_FEATURE
<222> LOCATION: (20)..(20)
<223> OTHER INFORMATION: Xaa = Trp or Ile or Val or Phe or Leu
<220> FEATURE:
<221> NAME/KEY: MISC_FEATURE
<222> LOCATION: (21)..(21)
<223> OTHER INFORMATION: Xaa = Phe or Leu or Met or Lys or Arg or
      Val or Asn
<220> FEATURE:
<221> NAME/KEY: MISC_FEATURE
<222> LOCATION: (22)..(22)
<223> OTHER INFORMATION: Xaa = Gln or Asp or Gly or Tyr or Cys or Thr
      or Asn or Ser or Ala or Arg
<220> FEATURE:
<221> NAME/KEY: MISC_FEATURE
<222> LOCATION: (23)..(23)
<223> OTHER INFORMATION: Xaa = Glu or Ala or Lys or His or Leu or Arg or
      Gly or Asp
<220> FEATURE:
<221> NAME/KEY: MISC_FEATURE
<222> LOCATION: (24)..(24)
<223> OTHER INFORMATION: Xaa = Val or Leu or Met or Ala or Ile
<220> FEATURE:
<221> NAME/KEY: MISC_FEATURE
<222> LOCATION: (25)..(25)
<223> OTHER INFORMATION: Xaa = Lys or Arg or Thr or Ser or Gly or Asn or
      His or Ala
```

-continued

```
<220> FEATURE:
<221> NAME/KEY: MISC_FEATURE
<222> LOCATION: (26)..(26)
<223> OTHER INFORMATION: Xaa = Gly or Ala or Gln or Glu or Ser or Thr or
      Val or Asn or Asp or Lys or Arg or Tyr
<220> FEATURE:
<221> NAME/KEY: MISC_FEATURE
<222> LOCATION: (27)..(27)
<223> OTHER INFORMATION: Xaa = Thr or Phe or Glu or Ala or Lys or Asn or
      His or Ser or Gly or Arg
<220> FEATURE:
<221> NAME/KEY: MISC_FEATURE
<222> LOCATION: (28)..(28)
<223> OTHER INFORMATION: Xaa = Ser or Asn or Thr or Phe or Tyr or Gly or
      Asp or Val or His or Ala or Lys or may not be present at all
<220> FEATURE:
<221> NAME/KEY: MISC_FEATURE
<222> LOCATION: (29)..(29)
<223> OTHER INFORMATION: Xaa = Pro or Gly or Lys or Ser or Arg or Ile
      or may not be present at all
<220> FEATURE:
<221> NAME/KEY: MISC_FEATURE
<222> LOCATION: (30)..(30)
<223> OTHER INFORMATION: Xaa = Gly or Lys or Asp or Ala or Ser or His or
      Glu or may not be present at all
<220> FEATURE:
<221> NAME/KEY: MISC_FEATURE
<222> LOCATION: (31)..(31)
<223> OTHER INFORMATION: Xaa = Arg or Pro or Glu or Ala or Leu or Asp
      or may not be present at all
<220> FEATURE:
<221> NAME/KEY: MISC_FEATURE
<222> LOCATION: (32)..(32)
<223> OTHER INFORMATION: Xaa = Gly or may not be present at all
<220> FEATURE:
<221> NAME/KEY: MISC_FEATURE
<222> LOCATION: (33)..(33)
<223> OTHER INFORMATION: Xaa = Arg or may not be present at all
<220> FEATURE:
<221> NAME/KEY: MISC_FEATURE
<222> LOCATION: (34)..(34)
<223> OTHER INFORMATION: Xaa = Pro or Lys or may not be present at all
<220> FEATURE:
<221> NAME/KEY: MISC_FEATURE
<222> LOCATION: (35)..(35)
<223> OTHER INFORMATION: Xaa = Glu or Asn or Ala or Arg or Asp or Pro or
      may not be present at all
<220> FEATURE:
<221> NAME/KEY: MISC_FEATURE
<222> LOCATION: (36)..(36)
<223> OTHER INFORMATION: Xaa = Arg or Leu or Ala or Pro or Val or Phe or
      may not be present at all
<220> FEATURE:
<221> NAME/KEY: MISC_FEATURE
<222> LOCATION: (37)..(37)
<223> OTHER INFORMATION: Xaa = Phe or Tyr or Ile
<220> FEATURE:
<221> NAME/KEY: MISC_FEATURE
<222> LOCATION: (38)..(38)
<223> OTHER INFORMATION: Xaa = Ala or Gly or Lys or Ile or Trp or Val or
      Asn or Gln or Met or Thr
<220> FEATURE:
<221> NAME/KEY: MISC_FEATURE
<222> LOCATION: (39)..(39)
<223> OTHER INFORMATION: Xaa = Val or His or Lys or Phe or Thr or Ile
<220> FEATURE:
<221> NAME/KEY: MISC_FEATURE
<222> LOCATION: (40)..(40)
<223> OTHER INFORMATION: Xaa = Thr or Ser or Gly or Ala or Gln or His or
      Leu or Met
<220> FEATURE:
<221> NAME/KEY: MISC_FEATURE
<222> LOCATION: (42)..(42)
<223> OTHER INFORMATION: Xaa = Phe or Ala or Tyr or His or Val or Thr
      or Ile
<220> FEATURE:
<221> NAME/KEY: MISC_FEATURE
<222> LOCATION: (43)..(43)
<223> OTHER INFORMATION: Xaa = Tyr or Trp or Ile or Phe or Val
```

```
<220> FEATURE:
<221> NAME/KEY: MISC_FEATURE
<222> LOCATION: (44)..(44)
<223> OTHER INFORMATION: Xaa - Asp or Phe or Ser or Glu or Gln or Tyr or
      His or Gly or Pro or Asn
<220> FEATURE:
<221> NAME/KEY: MISC_FEATURE
<222> LOCATION: (45)..(45)
<223> OTHER INFORMATION: Xaa = Gly or Ala or Asp or Arg or Ser or Thr
      or Glu or may not be present at all
<220> FEATURE:
<221> NAME/KEY: MISC_FEATURE
<222> LOCATION: (46)..(46)
<223> OTHER INFORMATION: Xaa = Asn or Lys or Asp or Ser or His or
      Ala or Thr
<220> FEATURE:
<221> NAME/KEY: MISC_FEATURE
<222> LOCATION: (47)..(47)
<223> OTHER INFORMATION: Xaa = Pro or Leu or Val or Ile or Met or Ala or
      Asn or Gly or Asp
<220> FEATURE:
<221> NAME/KEY: MISC_FEATURE
<222> LOCATION: (48)..(48)
<223> OTHER INFORMATION: Xaa = Ala or Asp or Gln or Asn or Glu or Thr
<220> FEATURE:
<221> NAME/KEY: MISC_FEATURE
<222> LOCATION: (49)..(49)
<223> OTHER INFORMATION: Xaa = His or Gln or Leu or Ala or Glu or Asp or
      Val or Pro or Asn
<220> FEATURE:
<221> NAME/KEY: MISC_FEATURE
<222> LOCATION: (50)..(50)
<223> OTHER INFORMATION: Xaa = Leu or Ile or Val or Pro or Thr
<220> FEATURE:
<221> NAME/KEY: MISC_FEATURE
<222> LOCATION: (51)..(51)
<223> OTHER INFORMATION: Xaa = Ala or Thr or His or Asn or Lys or Asp or
      Gln or Arg or Ser or Gly
<220> FEATURE:
<221> NAME/KEY: MISC_FEATURE
<222> LOCATION: (52)..(52)
<223> OTHER INFORMATION: Xaa = Thr or Ala or Asp or Asn or Gly or Lys or
      Ser or Arg or Pro or Gln or Val
<220> FEATURE:
<221> NAME/KEY: MISC_FEATURE
<222> LOCATION: (53)..(53)
<223> OTHER INFORMATION: Xaa = Val or Tyr or Gly or Ser or Thr or Asp or
      Ala or Gln or Asn or Leu or Phe
<220> FEATURE:
<221> NAME/KEY: MISC_FEATURE
<222> LOCATION: (54)..(54)
<223> OTHER INFORMATION: Xaa = Ile or Ala or Leu or Val or Gln or Trp or
      Glu or Asp or Ser or Thr or Arg
<220> FEATURE:
<221> NAME/KEY: MISC_FEATURE
<222> LOCATION: (55)..(55)
<223> OTHER INFORMATION: Xaa = Asp or Lys or Thr or Asn or Ala or Ser
      or Tyr or Glu or Trp or Gly
<220> FEATURE:
<221> NAME/KEY: MISC_FEATURE
<222> LOCATION: (56)..(56)
<223> OTHER INFORMATION: Xaa = Leu or Glu or Ala or Ser or Asp or Lys or
      Thr or Ile or Trp or Phe or Arg
<220> FEATURE:
<221> NAME/KEY: MISC_FEATURE
<222> LOCATION: (57)..(57)
<223> OTHER INFORMATION: Xaa = Tyr or Leu or Ser or Val or Thr or Gly
      or Glu or Phe
<220> FEATURE:
<221> NAME/KEY: MISC_FEATURE
<222> LOCATION: (58)..(58)
<223> OTHER INFORMATION: Xaa = Ala or Gly or Asn or Asp or Glu or Ile or
      Ser or Thr or Val or Leu or Met
<220> FEATURE:
<221> NAME/KEY: MISC_FEATURE
<222> LOCATION: (59)..(59)
<223> OTHER INFORMATION: Xaa = Arg or Asp or Ser or Gly or Asn or Ala
<220> FEATURE:
<221> NAME/KEY: MISC_FEATURE
```

```
-continued

<222> LOCATION: (60)..(60)
<223> OTHER INFORMATION: Xaa = Thr or Asn or may not be present at all
<220> FEATURE:
<221> NAME/KEY: MISC_FEATURE
<222> LOCATION: (61)..(61)
<223> OTHER INFORMATION: Xaa = Ala or may not be present at all
<220> FEATURE:
<221> NAME/KEY: MISC_FEATURE
<222> LOCATION: (62)..(62)
<223> OTHER INFORMATION: Xaa = Ser or Met or may not be present at all
<220> FEATURE:
<221> NAME/KEY: MISC_FEATURE
<222> LOCATION: (63)..(63)
<223> OTHER INFORMATION: Xaa = Asp or Pro or Ala or may not be present
      at all
<220> FEATURE:
<221> NAME/KEY: MISC_FEATURE
<222> LOCATION: (64)..(64)
<223> OTHER INFORMATION: Xaa = Gln or Arg or Ala or Lys or Val or Gly or
      Thr or Met or may not be present at all
<220> FEATURE:
<221> NAME/KEY: MISC_FEATURE
<222> LOCATION: (65)..(65)
<223> OTHER INFORMATION: Xaa = Ser or Thr or Met or Val or Leu or Asp or
      Trp or may not be present at all
<220> FEATURE:
<221> NAME/KEY: MISC_FEATURE
<222> LOCATION: (66)..(66)
<223> OTHER INFORMATION: Xaa = His or Arg or Ser or Lys or Gln or Asp
      or Thr
<220> FEATURE:
<221> NAME/KEY: MISC_FEATURE
<222> LOCATION: (67)..(67)
<223> OTHER INFORMATION: Xaa = Leu or Ala or Val or Thr or Asp
<220> FEATURE:
<221> NAME/KEY: MISC_FEATURE
<222> LOCATION: (68)..(68)
<223> OTHER INFORMATION: Xaa = Phe or His or Asp or Gln or Thr or Leu
      or Tyr
<220> FEATURE:
<221> NAME/KEY: MISC_FEATURE
<222> LOCATION: (69)..(69)
<223> OTHER INFORMATION: Xaa = Asp or Glu or Phe
<220> FEATURE:
<221> NAME/KEY: MISC_FEATURE
<222> LOCATION: (70)..(70)
<223> OTHER INFORMATION: Xaa = Phe or Val or Gly
<220> FEATURE:
<221> NAME/KEY: MISC_FEATURE
<222> LOCATION: (71)..(71)
<223> OTHER INFORMATION: Xaa = Ala or Phe or Val or Arg or Gly or Thr
      or His
<220> FEATURE:
<221> NAME/KEY: MISC_FEATURE
<222> LOCATION: (72)..(72)
<223> OTHER INFORMATION: Xaa = Leu or Tyr or Phe or Val
<220> FEATURE:
<221> NAME/KEY: MISC_FEATURE
<222> LOCATION: (73)..(73)
<223> OTHER INFORMATION: Xaa = His or Gly or Ala or Ser or Phe or Lys
<220> FEATURE:
<221> NAME/KEY: MISC_FEATURE
<222> LOCATION: (74)..(74)
<223> OTHER INFORMATION: Xaa = Phe or Tyr or Ala or Arg or Lys or Ser or
      Asp or Asn or Glu
<220> FEATURE:
<221> NAME/KEY: MISC_FEATURE
<222> LOCATION: (75)..(75)
<223> OTHER INFORMATION: Xaa = Leu or Lys or Arg or Asn or Gly or Asp or
      Ser or His or Gln or Ala
<220> FEATURE:
<221> NAME/KEY: MISC_FEATURE
<222> LOCATION: (76)..(76)
<223> OTHER INFORMATION: Xaa = Leu or Phe or Ile or Val or Ala
<220> FEATURE:
<221> NAME/KEY: MISC_FEATURE
<222> LOCATION: (77)..(77)
<223> OTHER INFORMATION: Xaa = Gln or Tyr or Glu or Met or His or Arg or
      Leu or Phe or Lys or Ala or Ser or Gly or Ile or Val
```

-continued

```
<220> FEATURE:
<221> NAME/KEY: MISC_FEATURE
<222> LOCATION: (78)..(78)
<223> OTHER INFORMATION: Xaa = Arg or Gly or Gln or Glu or Asp or Asn or
      Ala or His or Ser or Thr
<220> FEATURE:
<221> NAME/KEY: MISC_FEATURE
<222> LOCATION: (79)..(79)
<223> OTHER INFORMATION: Xaa = Met or Ala or Gln or Val or Arg or Phe
      or Glu
<220> FEATURE:
<221> NAME/KEY: MISC_FEATURE
<222> LOCATION: (80)..(80)
<223> OTHER INFORMATION: Xaa = Ser or Ala or Phe or Leu or Val
<220> FEATURE:
<221> NAME/KEY: MISC_FEATURE
<222> LOCATION: (81)..(81)
<223> OTHER INFORMATION: Xaa = Ala or Asn or Arg or Lys or Gln or Ser or
      Leu or His or Thr or Gly
<220> FEATURE:
<221> NAME/KEY: MISC_FEATURE
<222> LOCATION: (82)..(82)
<223> OTHER INFORMATION: Xaa = Gly or Asn or Ala or Arg or Lys or Gln or
      Ser or Tyr or Phe
<220> FEATURE:
<221> NAME/KEY: MISC_FEATURE
<222> LOCATION: (83)..(83)
<223> OTHER INFORMATION: Xaa = Asn or Gly or Glu or Gln or Asp or Lys
      or may not be present at all
<220> FEATURE:
<221> NAME/KEY: MISC_FEATURE
<222> LOCATION: (84)..(84)
<223> OTHER INFORMATION: Xaa = Arg or may not be present at all
<220> FEATURE:
<221> NAME/KEY: MISC_FEATURE
<222> LOCATION: (85)..(85)
<223> OTHER INFORMATION: Xaa - Gly or Arg or Lys or Glu or Asn or Gln or
      Asp or Pro or Ala
<220> FEATURE:
<221> NAME/KEY: MISC_FEATURE
<222> LOCATION: (86)..(86)
<223> OTHER INFORMATION: Xaa = Gly or Ala or Met or Asp or Glu or Ser or
      Ile or Leu or Pro
<220> FEATURE:
<221> NAME/KEY: MISC_FEATURE
<222> LOCATION: (87)..(87)
<223> OTHER INFORMATION: Xaa = Phe or Ser or Trp or Tyr or Lys or Ala
      or His
<220> FEATURE:
<221> NAME/KEY: MISC_FEATURE
<222> LOCATION: (88)..(88)
<223> OTHER INFORMATION: Xaa = Asp or Trp or Tyr or Asn or Glu or Pro
<220> FEATURE:
<221> NAME/KEY: MISC_FEATURE
<222> LOCATION: (89)..(89)
<223> OTHER INFORMATION: Xaa = Ile or His or may not be present at all
<220> FEATURE:
<221> NAME/KEY: MISC_FEATURE
<222> LOCATION: (90)..(90)
<223> OTHER INFORMATION: Xaa = Leu or Asp or may not be present at all
<220> FEATURE:
<221> NAME/KEY: MISC_FEATURE
<222> LOCATION: (91)..(91)
<223> OTHER INFORMATION: Xaa = Met or Leu or Ile
<220> FEATURE:
<221> NAME/KEY: MISC_FEATURE
<222> LOCATION: (92)..(92)
<223> OTHER INFORMATION: Xaa = Arg or Gly or Ser or Pro or Thr or Gln or
      Lys or Ala or Asn
<220> FEATURE:
<221> NAME/KEY: MISC_FEATURE
<222> LOCATION: (93)..(93)
<223> OTHER INFORMATION: Xaa = Ser or Asn or Lys or Thr or Arg or Ala
<220> FEATURE:
<221> NAME/KEY: MISC_FEATURE
<222> LOCATION: (94)..(94)
<223> OTHER INFORMATION: Xaa = Leu or Ile or Val or Phe or Tyr
<220> FEATURE:
<221> NAME/KEY: MISC_FEATURE
```

```
<222> LOCATION: (95)..(95)
<223> OTHER INFORMATION: Xaa = Arg or Lys or Leu or Phe or Gly or
      Ala or Tyr
<220> FEATURE:
<221> NAME/KEY: MISC_FEATURE
<222> LOCATION: (96)..(96)
<223> OTHER INFORMATION: Xaa = Phe or Gln or Thr or Asp or Ala or Glu or
      Ser or Pro or Arg
      or Leu
<220> FEATURE:
<221> NAME/KEY: MISC_FEATURE
<222> LOCATION: (97)..(97)
<223> OTHER INFORMATION: Xaa = Gly or Ala or Arg or Asn or Ser or Thr or
      may not be present at all
<220> FEATURE:
<221> NAME/KEY: MISC_FEATURE
<222> LOCATION: (98)..(98)
<223> OTHER INFORMATION: Xaa = Ser or Gly or Thr or Trp or Asp or Leu or
      may not be present at all
<220> FEATURE:
<221> NAME/KEY: MISC_FEATURE
<222> LOCATION: (99)..(99)
<223> OTHER INFORMATION: Xaa = Ser or Gly or Asp or may not be present
      at all
<220> FEATURE:
<221> NAME/KEY: MISC_FEATURE
<222> LOCATION: (100)..(100)
<223> OTHER INFORMATION: Xaa = Asp or Leu or Phe or may not be present
      at all
<220> FEATURE:
<221> NAME/KEY: MISC_FEATURE
<222> LOCATION: (101)..(101)
<223> OTHER INFORMATION: Xaa = Asp or Tyr or Lys or may not be present
      at all
<220> FEATURE:
<221> NAME/KEY: MISC_FEATURE
<222> LOCATION: (102)..(102)
<223> OTHER INFORMATION: Xaa = Gly or Thr or may not be present at all
<220> FEATURE:
<221> NAME/KEY: MISC_FEATURE
<222> LOCATION: (103)..(103)
<223> OTHER INFORMATION: Xaa = Ser or Asn or may not be present at all
<220> FEATURE:
<221> NAME/KEY: MISC_FEATURE
<222> LOCATION: (104)..(104)
<223> OTHER INFORMATION: Xaa = Arg or may not be present at all
<220> FEATURE:
<221> NAME/KEY: MISC_FEATURE
<222> LOCATION: (105)..(105)
<223> OTHER INFORMATION: Xaa = Phe or Leu or Asp or may not be present
      at all
<220> FEATURE:
<221> NAME/KEY: MISC_FEATURE
<222> LOCATION: (106)..(106)
<223> OTHER INFORMATION: Xaa = Leu or Thr or Met or Val or Gly or His
      or Phe
<220> FEATURE:
<221> NAME/KEY: MISC_FEATURE
<222> LOCATION: (107)..(107)
<223> OTHER INFORMATION: Xaa = Glu or Lys or Ala or Gln or Arg or Gly or
      Ser or Tyr or Phe or His or Leu or Asp
<220> FEATURE:
<221> NAME/KEY: MISC_FEATURE
<222> LOCATION: (108)..(108)
<223> OTHER INFORMATION: Xaa = Gln or Ala or Glu or Trp or Asp or Arg or
      Gly or Val or Met or Leu or Ile or Thr or Ser
<220> FEATURE:
<221> NAME/KEY: MISC_FEATURE
<222> LOCATION: (109)..(109)
<223> OTHER INFORMATION: Xaa = His or Asn or Gln or Arg or Phe or Gly or
      Ser or Glu or Thr
<220> FEATURE:
<221> NAME/KEY: MISC_FEATURE
<222> LOCATION: (110)..(110)
<223> OTHER INFORMATION: Xaa = Phe or Gly or Ser or Asn or Glu or
      Ala or Ile
<220> FEATURE:
<221> NAME/KEY: MISC_FEATURE
<222> LOCATION: (111)..(111)
```

-continued

```
<223> OTHER INFORMATION: Xaa = Ala or Lys or Leu or Gln or Thr or Asp or
      Ser or Gly or His or Tyr
<220> FEATURE:
<221> NAME/KEY: MISC_FEATURE
<222> LOCATION: (112)..(112)
<223> OTHER INFORMATION: Xaa = Phe or Leu or Arg or Met or Ser or Val or
      Lys or Gln or Gly or Asn or Ala or Glu
<220> FEATURE:
<221> NAME/KEY: MISC_FEATURE
<222> LOCATION: (113)..(113)
<223> OTHER INFORMATION: Xaa = Ala or Ser or Thr or Leu
<220> FEATURE:
<221> NAME/KEY: MISC_FEATURE
<222> LOCATION: (114)..(114)
<223> OTHER INFORMATION: Xaa = Val or Ala or Met or Gly or Ser or Ile or
      Asn or Leu
<220> FEATURE:
<221> NAME/KEY: MISC_FEATURE
<222> LOCATION: (115)..(115)
<223> OTHER INFORMATION: Xaa = Thr or Val or Ala or Ser
<220> FEATURE:
<221> NAME/KEY: MISC_FEATURE
<222> LOCATION: (116)..(116)
<223> OTHER INFORMATION: Xaa = Tyr or Phe

<400> SEQUENCE: 305

Val Asp Gly Phe Arg Ile Asp Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Glu Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Val Asp Asn His Asp Thr Glu
            115                 120

<210> SEQ ID NO 306
<211> LENGTH: 121
<212> TYPE: PRT
<213> ORGANISM: Artificial Sequence
<220> FEATURE:
<223> OTHER INFORMATION: Consensus D
<220> FEATURE:
<221> NAME/KEY: MISC_FEATURE
<222> LOCATION: (8)..(8)
<223> OTHER INFORMATION: Xaa = Ala or Thr
<220> FEATURE:
<221> NAME/KEY: MISC_FEATURE
<222> LOCATION: (9)..(9)
<223> OTHER INFORMATION: Xaa = Gly or Ile or Val or Thr or Leu
      or Ala or Ser
<220> FEATURE:
<221> NAME/KEY: MISC_FEATURE
<222> LOCATION: (10)..(10)
<223> OTHER INFORMATION: Xaa = Lys or Glu or Arg
<220> FEATURE:
<221> NAME/KEY: MISC_FEATURE
<222> LOCATION: (11)..(11)
<223> OTHER INFORMATION: Xaa = His or Arg
<220> FEATURE:
<221> NAME/KEY: MISC_FEATURE
<222> LOCATION: (12)..(12)
<223> OTHER INFORMATION: Xaa = Ile or Met or Val or Leu
```

-continued

```
<220> FEATURE:
<221> NAME/KEY: MISC_FEATURE
<222> LOCATION: (13)..(13)
<223> OTHER INFORMATION: Xaa = His or Asp or Arg or Thr or Pro or Ser
      or Ala or Asn
<220> FEATURE:
<221> NAME/KEY: MISC_FEATURE
<222> LOCATION: (14)..(14)
<223> OTHER INFORMATION: Xaa = Pro or Thr or Asn or Ser or Ala or Arg
<220> FEATURE:
<221> NAME/KEY: MISC_FEATURE
<222> LOCATION: (15)..(15)
<223> OTHER INFORMATION: Xaa = Pro or Arg or Thr or Ser or Gly or Ala or
      Glu or Asp
<220> FEATURE:
<221> NAME/KEY: MISC_FEATURE
<222> LOCATION: (16)..(16)
<223> OTHER INFORMATION: Xaa = Phe or Tyr or Asp
<220> FEATURE:
<221> NAME/KEY: MISC_FEATURE
<222> LOCATION: (17)..(17)
<223> OTHER INFORMATION: Xaa = Leu or Val or Phe or Tyr or Ile or Trp
<220> FEATURE:
<221> NAME/KEY: MISC_FEATURE
<222> LOCATION: (18)..(18)
<223> OTHER INFORMATION: Xaa = Ser or Asn or Ala or Lys or Arg or Glu or
      Cys or His
<220> FEATURE:
<221> NAME/KEY: MISC_FEATURE
<222> LOCATION: (19)..(19)
<223> OTHER INFORMATION: Xaa = Arg or Ala or His or Glu or Asp or Asn
<220> FEATURE:
<221> NAME/KEY: MISC_FEATURE
<222> LOCATION: (20)..(20)
<223> OTHER INFORMATION: Xaa = Trp or Val or Ile or Phe
<220> FEATURE:
<221> NAME/KEY: MISC_FEATURE
<222> LOCATION: (21)..(21)
<223> OTHER INFORMATION: Xaa = Phe or Leu or Met or Val or Lys or Arg
      or Asn
<220> FEATURE:
<221> NAME/KEY: MISC_FEATURE
<222> LOCATION: (22)..(22)
<223> OTHER INFORMATION: Xaa = Gln or Asp or Gly or Tyr or Cys or Asn or
      Thr or Ser or Ala
<220> FEATURE:
<221> NAME/KEY: MISC_FEATURE
<222> LOCATION: (23)..(23)
<223> OTHER INFORMATION: Xaa = Glu or Ala or Lys or His or Gly or
      Arg or Leu
<220> FEATURE:
<221> NAME/KEY: MISC_FEATURE
<222> LOCATION: (24)..(24)
<223> OTHER INFORMATION: Xaa = Val or Leu or Met or Ile
<220> FEATURE:
<221> NAME/KEY: MISC_FEATURE
<222> LOCATION: (25)..(25)
<223> OTHER INFORMATION: Xaa = Lys or Arg or His or Thr or Ser or
      Gly or Asn
<220> FEATURE:
<221> NAME/KEY: MISC_FEATURE
<222> LOCATION: (26)..(26)
<223> OTHER INFORMATION: Xaa = Gly or Ala or Gln or Glu or Thr or Ser or
      Val of Asn or As or Lys or Arg
<220> FEATURE:
<221> NAME/KEY: MISC_FEATURE
<222> LOCATION: (27)..(27)
<223> OTHER INFORMATION: Xaa = Thr or Pro or Glu or Ala or Lys or His or
      Ser or Gly or Arg
<220> FEATURE:
<221> NAME/KEY: MISC_FEATURE
<222> LOCATION: (28)..(28)
<223> OTHER INFORMATION: Xaa = Ser or Asn or Thr or Phe or Val or Gly
      or Asp or Ala or may not be present at all
<220> FEATURE:
<221> NAME/KEY: MISC_FEATURE
<222> LOCATION: (29)..(29)
<223> OTHER INFORMATION: Xaa = Pro or Gly or Lys or Ser or Arg or may
      not be present at all
```

```
<220> FEATURE:
<221> NAME/KEY: MISC_FEATURE
<222> LOCATION: (30)..(30)
<223> OTHER INFORMATION: Xaa = Gly or Lys or Asp or Ala or His or may
      not be present at all
<220> FEATURE:
<221> NAME/KEY: MISC_FEATURE
<222> LOCATION: (31)..(31)
<223> OTHER INFORMATION: Xaa = Arg or Pro or Glu or Ala or Leu or may
      not be present at all
<220> FEATURE:
<221> NAME/KEY: MISC_FEATURE
<222> LOCATION: (32)..(32)
<223> OTHER INFORMATION: Xaa = Gly or may not be present at all
<220> FEATURE:
<221> NAME/KEY: MISC_FEATURE
<222> LOCATION: (33)..(33)
<223> OTHER INFORMATION: Xaa = Arg or may not be present at all
<220> FEATURE:
<221> NAME/KEY: MISC_FEATURE
<222> LOCATION: (34)..(34)
<223> OTHER INFORMATION: Xaa = Pro or may not be present at all
<220> FEATURE:
<221> NAME/KEY: MISC_FEATURE
<222> LOCATION: (35)..(35)
<223> OTHER INFORMATION: Xaa = Glu or Asn or Ala or Arg or Asp or
      may not be present at all
<220> FEATURE:
<221> NAME/KEY: MISC_FEATURE
<222> LOCATION: (36)..(36)
<223> OTHER INFORMATION: Xaa = Arg or Leu or Ala or Pro or Val or Phe
<220> FEATURE:
<221> NAME/KEY: MISC_FEATURE
<222> LOCATION: (37)..(37)
<223> OTHER INFORMATION: Xaa = Phe or Tyr or Ile
<220> FEATURE:
<221> NAME/KEY: MISC_FEATURE
<222> LOCATION: (38)..(38)
<223> OTHER INFORMATION: Xaa = Ala or Gly or Ile or Val or Leu or
      Trp or Gln
<220> FEATURE:
<221> NAME/KEY: MISC_FEATURE
<222> LOCATION: (39)..(39)
<223> OTHER INFORMATION: Xaa = Val or Thr or Phe or His or Lys
<220> FEATURE:
<221> NAME/KEY: MISC_FEATURE
<222> LOCATION: (40)..(40)
<223> OTHER INFORMATION: Xaa = Thr or Ser or Gly or Ala or Gln or His
<220> FEATURE:
<221> NAME/KEY: MISC_FEATURE
<222> LOCATION: (42)..(42)
<223> OTHER INFORMATION: Xaa = Phe or Ala or Tyr or His or Ile or Val
      or Thr
<220> FEATURE:
<221> NAME/KEY: MISC_FEATURE
<222> LOCATION: (43)..(43)
<223> OTHER INFORMATION: Xaa = Tyr or Trp or Phe or Ile
<220> FEATURE:
<221> NAME/KEY: MISC_FEATURE
<222> LOCATION: (44)..(44)
<223> OTHER INFORMATION: Xaa = Asp or Phe or Ser or Glu or Pro or Gln or
      Tyr or His or Asn
<220> FEATURE:
<221> NAME/KEY: MISC_FEATURE
<222> LOCATION: (45)..(45)
<223> OTHER INFORMATION: Xaa = Gly or Ala or Asp or Arg or Ser
<220> FEATURE:
<221> NAME/KEY: MISC_FEATURE
<222> LOCATION: (46)..(46)
<223> OTHER INFORMATION: Xaa = Asn or Lys or Asp or Ser or His or Ala
      or Thr or may not be present at all
<220> FEATURE:
<221> NAME/KEY: MISC_FEATURE
<222> LOCATION: (47)..(47)
<223> OTHER INFORMATION: Xaa = Pro or Leu or Val or Ile or Ala or Asn
      or Gly or Asp or may not be present at all
<220> FEATURE:
<221> NAME/KEY: MISC_FEATURE
<222> LOCATION: (48)..(48)
```

```
<223> OTHER INFORMATION: Xaa = Ala or Asp or Gln or Asn or Thr or Glu
<220> FEATURE:
<221> NAME/KEY: MISC_FEATURE
<222> LOCATION: (49)..(49)
<223> OTHER INFORMATION: Xaa = His or Gln or Leu or Ala or Glu or Asp
      or Pro or Val
<220> FEATURE:
<221> NAME/KEY: MISC_FEATURE
<222> LOCATION: (50)..(50)
<223> OTHER INFORMATION: Xaa = Leu or Phe or Ile or Val
<220> FEATURE:
<221> NAME/KEY: MISC_FEATURE
<222> LOCATION: (51)..(51)
<223> OTHER INFORMATION: Xaa = Ala or Thr or His or Asn or Lys or Asp
      or Arg or Gln or Ser or Gly
<220> FEATURE:
<221> NAME/KEY: MISC_FEATURE
<222> LOCATION: (52)..(52)
<223> OTHER INFORMATION: Xaa = Thr or Ala or Asp or Asn or Gly or Lys
      or Ser or Arg or Gln or Pro or Val
<220> FEATURE:
<221> NAME/KEY: MISC_FEATURE
<222> LOCATION: (53)..(53)
<223> OTHER INFORMATION: Xaa = Val or Tyr or Asp or Gln or Gly or Ser
      or Thr or Ala or Asn or Leu
<220> FEATURE:
<221> NAME/KEY: MISC_FEATURE
<222> LOCATION: (54)..(54)
<223> OTHER INFORMATION: Xaa = Ile or Ala or Leu or Val or Glu or Asp or
      Gln or Trp or Ser
<220> FEATURE:
<221> NAME/KEY: MISC_FEATURE
<222> LOCATION: (55)..(55)
<223> OTHER INFORMATION: Xaa = Asp or Lys or Thr or Asn or Ala or Ser
      or Tyr or Glu
<220> FEATURE:
<221> NAME/KEY: MISC_FEATURE
<222> LOCATION: (56)..(56)
<223> OTHER INFORMATION: Xaa = Leu or Glu or Ala or Ser or Asp or Lys
      or Tyr or Phe or Thr or Ile
<220> FEATURE:
<221> NAME/KEY: MISC_FEATURE
<222> LOCATION: (57)..(57)
<223> OTHER INFORMATION: Xaa = Tyr or Leu or Ser or Val or Thr or Gly
<220> FEATURE:
<221> NAME/KEY: MISC_FEATURE
<222> LOCATION: (58)..(58)
<223> OTHER INFORMATION: Xaa = Ala or Gly or Asn or Asp or Glu or Thr
      or Ile or Ser or Val
<220> FEATURE:
<221> NAME/KEY: MISC_FEATURE
<222> LOCATION: (59)..(59)
<223> OTHER INFORMATION: Xaa = Arg or Asp or Ser or Gly or Asn
<220> FEATURE:
<221> NAME/KEY: MISC_FEATURE
<222> LOCATION: (60)..(60)
<223> OTHER INFORMATION: Xaa = Thr or may not be present at all
<220> FEATURE:
<221> NAME/KEY: MISC_FEATURE
<222> LOCATION: (61)..(61)
<223> OTHER INFORMATION: Xaa = Ala or may not be present at all
<220> FEATURE:
<221> NAME/KEY: MISC_FEATURE
<222> LOCATION: (62)..(62)
<223> OTHER INFORMATION: Xaa = Ser or Met or may not be present at all
<220> FEATURE:
<221> NAME/KEY: MISC_FEATURE
<222> LOCATION: (63)..(63)
<223> OTHER INFORMATION: Xaa = Asp or Pro or may not be present at all
<220> FEATURE:
<221> NAME/KEY: MISC_FEATURE
<222> LOCATION: (64)..(64)
<223> OTHER INFORMATION: Xaa = Gln or Arg or Ala or Lys or Val or Gly or
      Thr or Met or may not be present at all
<220> FEATURE:
<221> NAME/KEY: MISC_FEATURE
<222> LOCATION: (65)..(65)
<223> OTHER INFORMATION: Xaa = Ser or Thr or Met or Val or Leu or Asp
      or may not be present at all
```

-continued

```
<220> FEATURE:
<221> NAME/KEY: MISC_FEATURE
<222> LOCATION: (66)..(66)
<223> OTHER INFORMATION: Xaa = His or Arg or Ser or Lys or Gln or Asp
      or Thr
<220> FEATURE:
<221> NAME/KEY: MISC_FEATURE
<222> LOCATION: (67)..(67)
<223> OTHER INFORMATION: Xaa = Leu or Ala or Val or Thr
<220> FEATURE:
<221> NAME/KEY: MISC_FEATURE
<222> LOCATION: (68)..(68)
<223> OTHER INFORMATION: Xaa = Phe or Leu or His or Asp or Gln
<220> FEATURE:
<221> NAME/KEY: MISC_FEATURE
<222> LOCATION: (69)..(69)
<223> OTHER INFORMATION: Xaa = Asp or Glu
<220> FEATURE:
<221> NAME/KEY: MISC_FEATURE
<222> LOCATION: (70)..(70)
<223> OTHER INFORMATION: Xaa = Phe or Val
<220> FEATURE:
<221> NAME/KEY: MISC_FEATURE
<222> LOCATION: (71)..(71)
<223> OTHER INFORMATION: Xaa = Ala or Pro or Thr or Val or Arg or Gly
<220> FEATURE:
<221> NAME/KEY: MISC_FEATURE
<222> LOCATION: (72)..(72)
<223> OTHER INFORMATION: Xaa = Leu or Phe or Tyr
<220> FEATURE:
<221> NAME/KEY: MISC_FEATURE
<222> LOCATION: (73)..(73)
<223> OTHER INFORMATION: Xaa = His or Ala or Gly or Phe
<220> FEATURE:
<221> NAME/KEY: MISC_FEATURE
<222> LOCATION: (74)..(74)
<223> OTHER INFORMATION: Xaa = Phe or Tyr or Ala or Asp or Arg or Lys
      or Asn
<220> FEATURE:
<221> NAME/KEY: MISC_FEATURE
<222> LOCATION: (75)..(75)
<223> OTHER INFORMATION: Xaa = Leu or Lys or Arg or Asn or Gln or Asp
      or Gly or Ser or Ala
<220> FEATURE:
<221> NAME/KEY: MISC_FEATURE
<222> LOCATION: (76)..(76)
<223> OTHER INFORMATION: Xaa = Leu or Phe or Val or Ile or Ala
<220> FEATURE:
<221> NAME/KEY: MISC_FEATURE
<222> LOCATION: (77)..(77)
<223> OTHER INFORMATION: Xaa = Gln or Tyr or Glu or Met or His or Arg
      or Leu or Phe or Lys or Ala or Ser
<220> FEATURE:
<221> NAME/KEY: MISC_FEATURE
<222> LOCATION: (78)..(78)
<223> OTHER INFORMATION: Xaa = Arg or Gly or Gln or Glu or Asn or Asp
      or Ala or Ser or Thr or His
<220> FEATURE:
<221> NAME/KEY: MISC_FEATURE
<222> LOCATION: (79)..(79)
<223> OTHER INFORMATION: Xaa = Met or Ala or Gln or Val or Phe
<220> FEATURE:
<221> NAME/KEY: MISC_FEATURE
<222> LOCATION: (80)..(80)
<223> OTHER INFORMATION: Xaa = Ser or Ala or Phe or Leu or Val
<220> FEATURE:
<221> NAME/KEY: MISC_FEATURE
<222> LOCATION: (81)..(81)
<223> OTHER INFORMATION: Xaa = Ala or Asn or Arg or Lys or Gln or Ser
      or Leu or His or Thr
<220> FEATURE:
<221> NAME/KEY: MISC_FEATURE
<222> LOCATION: (82)..(82)
<223> OTHER INFORMATION: Xaa = Gly or Asn or Ala or Arg or Lys or Gln
      or Ser or His
<220> FEATURE:
<221> NAME/KEY: MISC_FEATURE
<222> LOCATION: (83)..(83)
<223> OTHER INFORMATION: Xaa = Asn or Gly or Glu or Gln or may not be
```

```
      present at all
<220> FEATURE:
<221> NAME/KEY: MISC_FEATURE
<222> LOCATION: (84)..(84)
<223> OTHER INFORMATION: Xaa = Arg or may not be present at all
<220> FEATURE:
<221> NAME/KEY: MISC_FEATURE
<222> LOCATION: (85)..(85)
<223> OTHER INFORMATION: Xaa = Gly or Arg or Lys or Glu or Asn or Asp
      or Gln or Pro
<220> FEATURE:
<221> NAME/KEY: MISC_FEATURE
<222> LOCATION: (86)..(86)
<223> OTHER INFORMATION: Xaa = Gly or Ala or Met or Asp or Ser or
      Ile or Leu or Phe
<220> FEATURE:
<221> NAME/KEY: MISC_FEATURE
<222> LOCATION: (87)..(87)
<223> OTHER INFORMATION: Xaa = Phe or Ser or Trp or Tyr or Ala or Lys
<220> FEATURE:
<221> NAME/KEY: MISC_FEATURE
<222> LOCATION: (88)..(88)
<223> OTHER INFORMATION: Xaa = Asp or Asn or Trp or Tyr or Glu
<220> FEATURE:
<221> NAME/KEY: MISC_FEATURE
<222> LOCATION: (89)..(89)
<223> OTHER INFORMATION: Xaa = Met or Leu
<220> FEATURE:
<221> NAME/KEY: MISC_FEATURE
<222> LOCATION: (90)..(90)
<223> OTHER INFORMATION: Xaa = Arg or Gly or Ser or Thr or Gln
      or Lys or Ala
<220> FEATURE:
<221> NAME/KEY: MISC_FEATURE
<222> LOCATION: (91)..(91)
<223> OTHER INFORMATION: Xaa = Ser or Asn or Lys or Thr or Ala
<220> FEATURE:
<221> NAME/KEY: MISC_FEATURE
<222> LOCATION: (92)..(92)
<223> OTHER INFORMATION: Xaa = Leu or Ile or Val or Phe or Tyr
<220> FEATURE:
<221> NAME/KEY: MISC_FEATURE
<222> LOCATION: (93)..(93)
<223> OTHER INFORMATION: Xaa = Arg or Lys or Leu or Phe or Gly
<220> FEATURE:
<221> NAME/KEY: MISC_FEATURE
<222> LOCATION: (94)..(94)
<223> OTHER INFORMATION: Xaa = Phe or Gln or Thr or Asp or Ala or Glu
      or Ser or Pro or Arg
<220> FEATURE:
<221> NAME/KEY: MISC_FEATURE
<222> LOCATION: (95)..(95)
<223> OTHER INFORMATION: Xaa = Gly or Ala or Arg or Asn or Ser or Thr
<220> FEATURE:
<221> NAME/KEY: MISC_FEATURE
<222> LOCATION: (96)..(96)
<223> OTHER INFORMATION: Xaa = Ser or Gly or Thr or Trp or Asp
<220> FEATURE:
<221> NAME/KEY: MISC_FEATURE
<222> LOCATION: (97)..(97)
<223> OTHER INFORMATION: Xaa = Ser or Gly or Asp or may not be
      present at all
<220> FEATURE:
<221> NAME/KEY: MISC_FEATURE
<222> LOCATION: (98)..(98)
<223> OTHER INFORMATION: Xaa = Asp or Leu or Tyr or Phe or His or may
      not be present at all
<220> FEATURE:
<221> NAME/KEY: MISC_FEATURE
<222> LOCATION: (99)..(99)
<223> OTHER INFORMATION: Xaa = Asp or Ser or Tyr or may not be present
      at all
<220> FEATURE:
<221> NAME/KEY: MISC_FEATURE
<222> LOCATION: (100)..(100)
<223> OTHER INFORMATION: Xaa = Gly or Thr or may not be present at all
<220> FEATURE:
<221> NAME/KEY: MISC_FEATURE
<222> LOCATION: (101)..(101)
```

```
<223> OTHER INFORMATION: Xaa = Ser or may not be present at all
<220> FEATURE:
<221> NAME/KEY: MISC_FEATURE
<222> LOCATION: (102)..(102)
<223> OTHER INFORMATION: Xaa = Arg or may not be present at all
<220> FEATURE:
<221> NAME/KEY: MISC_FEATURE
<222> LOCATION: (103)..(103)
<223> OTHER INFORMATION: Xaa = Phe or Leu or Asp or may not be present
     at all
<220> FEATURE:
<221> NAME/KEY: MISC_FEATURE
<222> LOCATION: (104)..(104)
<223> OTHER INFORMATION: Xaa = Leu or Thr or Met or Val or His or may
     not be present at all
<220> FEATURE:
<221> NAME/KEY: MISC_FEATURE
<222> LOCATION: (105)..(105)
<223> OTHER INFORMATION: Xaa = Glu or Lys or Ala or Gln or Arg or Gly
     or Asp or may not be present at all
<220> FEATURE:
<221> NAME/KEY: MISC_FEATURE
<222> LOCATION: (106)..(106)
<223> OTHER INFORMATION: Xaa = Gln or Ala or Glu or Trp or Asp or Arg
     or Gly or Thr or Leu or Val or Met or Ile or Ser
<220> FEATURE:
<221> NAME/KEY: MISC_FEATURE
<222> LOCATION: (107)..(107)
<223> OTHER INFORMATION: Xaa = His or Asn or Gln or Arg or Thr or Pro
     or Gly or Ser or Lys
<220> FEATURE:
<221> NAME/KEY: MISC_FEATURE
<222> LOCATION: (108)..(108)
<223> OTHER INFORMATION: Xaa = Pro or Gly or Glu or Ala or Ser or
     Asn or Ile
<220> FEATURE:
<221> NAME/KEY: MISC_FEATURE
<222> LOCATION: (109)..(109)
<223> OTHER INFORMATION: Xaa = Ala or Lys or Leu or Gln or Thr or Asp
     or Ser or Gly or His
<220> FEATURE:
<221> NAME/KEY: MISC_FEATURE
<222> LOCATION: (110)..(110)
<223> OTHER INFORMATION: Xaa = Phe or Leu or Arg or Met or Ser or Val
     or Lys or Asn or Asp or Gln or Gly or Ala
<220> FEATURE:
<221> NAME/KEY: MISC_FEATURE
<222> LOCATION: (111)..(111)
<223> OTHER INFORMATION: Xaa = Ala or Ser or Thr
<220> FEATURE:
<221> NAME/KEY: MISC_FEATURE
<222> LOCATION: (112)..(112)
<223> OTHER INFORMATION: Xaa = Val or Ala or Asn or Met or Gly
     or Ser or Leu
<220> FEATURE:
<221> NAME/KEY: MISC_FEATURE
<222> LOCATION: (113)..(113)
<223> OTHER INFORMATION: Xaa = Thr or Ser or Val or Ala
<220> FEATURE:
<221> NAME/KEY: MISC_FEATURE
<222> LOCATION: (114)..(114)
<223> OTHER INFORMATION: Xaa = Tyr or Phe

<400> SEQUENCE: 306

Val Asp Gly Phe Arg Ile Asp Xaa Xaa Xaa Xaa Xaa Xaa Xaa Xaa
1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Glu Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80
```

```
Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Val Asp Asn His Asp Thr Glu
        115                 120

<210> SEQ ID NO 307
<211> LENGTH: 109
<212> TYPE: PRT
<213> ORGANISM: Artificial Sequence
<220> FEATURE:
<223> OTHER INFORMATION: Consensus B
<220> FEATURE:
<221> NAME/KEY: MISC_FEATURE
<222> LOCATION: (1)..(1)
<223> OTHER INFORMATION: Xaa = Val or may not be present at all
<220> FEATURE:
<221> NAME/KEY: MISC_FEATURE
<222> LOCATION: (2)..(2)
<223> OTHER INFORMATION: Xaa = Tyr or may not be present at all
<220> FEATURE:
<221> NAME/KEY: MISC_FEATURE
<222> LOCATION: (5)..(5)
<223> OTHER INFORMATION: Xaa = Val or Ala
<220> FEATURE:
<221> NAME/KEY: MISC_FEATURE
<222> LOCATION: (7)..(7)
<223> OTHER INFORMATION: Xaa = Phe or Tyr or Ile or Asn or Leu
<220> FEATURE:
<221> NAME/KEY: MISC_FEATURE
<222> LOCATION: (8)..(8)
<223> OTHER INFORMATION: Xaa = Asn or may not be present at all
<220> FEATURE:
<221> NAME/KEY: MISC_FEATURE
<222> LOCATION: (9)..(9)
<223> OTHER INFORMATION: Xaa = His or may not be present at all
<220> FEATURE:
<221> NAME/KEY: MISC_FEATURE
<222> LOCATION: (10)..(10)
<223> OTHER INFORMATION: Xaa = Leu or Phe or Thr or Ser or Ala or may
      not be present at all
<220> FEATURE:
<221> NAME/KEY: MISC_FEATURE
<222> LOCATION: (11)..(11)
<223> OTHER INFORMATION: Xaa = Gly or Ser or Ala or Cys or Arg or Thr
      or Val or may not be present at all
<220> FEATURE:
<221> NAME/KEY: MISC_FEATURE
<222> LOCATION: (12)..(12)
<223> OTHER INFORMATION: Xaa = Pro or Asp or Glu or Ala or Phe or may
      not be present at all
<220> FEATURE:
<221> NAME/KEY: MISC_FEATURE
<222> LOCATION: (13)..(13)
<223> OTHER INFORMATION: Xaa = Ala or Glu or Asp or Ser or Thr or Gln
      or Arg or Leu or Asn or Gly or may not be present at all
<220> FEATURE:
<221> NAME/KEY: MISC_FEATURE
<222> LOCATION: (14)..(14)
<223> OTHER INFORMATION: Xaa = Gly or Ser or His or Asn or Pro or Asp
      or Met or Phe
<220> FEATURE:
<221> NAME/KEY: MISC_FEATURE
<222> LOCATION: (15)..(15)
<223> OTHER INFORMATION: Xaa = Pro or Ala or Glu or may not be
      present at all
<220> FEATURE:
<221> NAME/KEY: MISC_FEATURE
<222> LOCATION: (16)..(16)
<223> OTHER INFORMATION: Xaa = Trp or His or Ala or Gln or Glu or Arg
      or Lys or Leu or Val or Pro or may not be present at all
<220> FEATURE:
<221> NAME/KEY: MISC_FEATURE
<222> LOCATION: (17)..(17)
```

-continued

```
<223> OTHER INFORMATION: Xaa = Phe or Gln or Leu or Thr or Arg or Gly
      or Ser or Glu or His or Tyr or Asn or Met or Lys or Asp or Ala or
      may not be present at all
<220> FEATURE:
<221> NAME/KEY: MISC_FEATURE
<222> LOCATION: (18)..(18)
<223> OTHER INFORMATION: Xaa = Asn or Ala or Cys or Gln or Val or Gly or
      Lys or Asp
<220> FEATURE:
<221> NAME/KEY: MISC_FEATURE
<222> LOCATION: (19)..(19)
<223> OTHER INFORMATION: Xaa = Tyr or Cys or Phe or Leu or Ser or Trp
      or Glu or Pro or Arg
      or Asp or may not be present at all
<220> FEATURE:
<221> NAME/KEY: MISC_FEATURE
<222> LOCATION: (20)..(20)
<223> OTHER INFORMATION: Xaa = Leu or Ala or Phe or His or Ile or Ser
      or Thr or Met or Gly or Val
<220> FEATURE:
<221> NAME/KEY: MISC_FEATURE
<222> LOCATION: (21)..(21)
<223> OTHER INFORMATION: Xaa = Asn or Arg or His or Pro or Gly or Asp or
      Ala or Thr or Tyr or Glu or Ile or Trp or Leu or Phe or Val or Ser
<220> FEATURE:
<221> NAME/KEY: MISC_FEATURE
<222> LOCATION: (22)..(22)
<223> OTHER INFORMATION: Xaa = Arg or Glu or Ala or Gln or Lys or Ser
      or Thr or Cys or Gly or Asn or Val
<220> FEATURE:
<221> NAME/KEY: MISC_FEATURE
<222> LOCATION: (23)..(23)
<223> OTHER INFORMATION: Xaa = Phe or Tyr or Asp or Ser or Val or Trp
      or Leu or Met or Arg
<220> FEATURE:
<221> NAME/KEY: MISC_FEATURE
<222> LOCATION: (24)..(24)
<223> OTHER INFORMATION: Xaa = Gly or Ala or Ser or Thr or Arg or Lys or
      Gln or His or Asp
<220> FEATURE:
<221> NAME/KEY: MISC_FEATURE
<222> LOCATION: (25)..(25)
<223> OTHER INFORMATION: Xaa = Cys or Pro or Asp or Gly or Arg or Thr or
      Ala or may not be present at all
<220> FEATURE:
<221> NAME/KEY: MISC_FEATURE
<222> LOCATION: (26)..(26)
<223> OTHER INFORMATION: Xaa = Pro or Glu or Asp or His or Ser or Asn
      or Leu or Phe or Gln or Ile or Val or Tyr or Ala
<220> FEATURE:
<221> NAME/KEY: MISC_FEATURE
<222> LOCATION: (27)..(27)
<223> OTHER INFORMATION: Xaa = Tyr or Phe or Glu or His or Pro or Ala or
      Arg or Asp or Ser or Val
<220> FEATURE:
<221> NAME/KEY: MISC_FEATURE
<222> LOCATION: (28)..(28)
<223> OTHER INFORMATION: Xaa = Phe or Val or Leu or Ile or Lys or Gln or
      Asp or Asn or Glu or Ala or Pro or Arg
<220> FEATURE:
<221> NAME/KEY: MISC_FEATURE
<222> LOCATION: (29)..(29)
<223> OTHER INFORMATION: Xaa = Thr or Ser or Ala or Lys or Phe or Arg
      or Gln or Met or Glu or Asn or Pro or Thr or Val or Gly or Trp
      or Tyr or Leu
<220> FEATURE:
<221> NAME/KEY: MISC_FEATURE
<222> LOCATION: (30)..(30)
<223> OTHER INFORMATION: Xaa = Asp or Ser or Lys or Ala or His or Gly or
      Leu or Val or Thr or Ile or Tyr or Trp or Asn
<220> FEATURE:
<221> NAME/KEY: MISC_FEATURE
<222> LOCATION: (31)..(31)
<223> OTHER INFORMATION: Xaa = Arg or Lys or Gln or Pro or Glu or Trp or
      Val or Tyr or Ser or His
<220> FEATURE:
<221> NAME/KEY: MISC_FEATURE
<222> LOCATION: (32)..(32)
<223> OTHER INFORMATION: Xaa = Tyr or His or Gln or Thr or Arg or
```

```
      Leu or Trp
<220> FEATURE:
<221> NAME/KEY: MISC_FEATURE
<222> LOCATION: (33)..(33)
<223> OTHER INFORMATION: Xaa = Ala or Val or Gly or Lys or Asp or Glu
      or Ser or Met or Ile or Pro or Arg or Phe or Leu or Gln or may
      not be present at all
<220> FEATURE:
<221> NAME/KEY: MISC_FEATURE
<222> LOCATION: (34)..(34)
<223> OTHER INFORMATION: Xaa = Thr or Asn or Trp or Ala or Val or Asp
      or Leu or His or Met or Gln or Phe or may not be present at all
<220> FEATURE:
<221> NAME/KEY: MISC_FEATURE
<222> LOCATION: (35)..(35)
<223> OTHER INFORMATION: Xaa = Pro or Asp or Glu or Arg or Leu or Gly
      or His or Asn or Ala or Thr or Val or Ser or Asn or Gln or
      Met or Ile
<220> FEATURE:
<221> NAME/KEY: MISC_FEATURE
<222> LOCATION: (36)..(36)
<223> OTHER INFORMATION: Xaa = Trp or Asp or Ala or Gly or Glu or Asn
      or Pro or Ser or Gln or Lys or His or Arg or may not be
      present at all
<220> FEATURE:
<221> NAME/KEY: MISC_FEATURE
<222> LOCATION: (37)..(37)
<223> OTHER INFORMATION: Xaa = Gly or Asp or Pro or Ser or Asn or Gln or
      Glu or Ala or Arg
      or His
<220> FEATURE:
<221> NAME/KEY: MISC_FEATURE
<222> LOCATION: (38)..(38)
<223> OTHER INFORMATION: Xaa = Ala or Asp or Leu or Glu or Gln or Arg or
      Pro or Gly or Thr
      or His or Asn or may not be present at all
<220> FEATURE:
<221> NAME/KEY: MISC_FEATURE
<222> LOCATION: (39)..(39)
<223> OTHER INFORMATION: Xaa = Thr or Pro or Arg or Gln or Ser or Glu or
      Tyr or Lys or Gly or Ala or Trp or Asp or may not be present at all
<220> FEATURE:
<221> NAME/KEY: MISC_FEATURE
<222> LOCATION: (40)..(40)
<223> OTHER INFORMATION: Xaa = Lys or Gly or Ala or Gln or His or Phe
      or Ser or Arg or Glu or Val or may not be present at all
<220> FEATURE:
<221> NAME/KEY: MISC_FEATURE
<222> LOCATION: (41)..(41)
<223> OTHER INFORMATION: Xaa = Trp or Gly or Val or Leu or Asp or may
      not be present at all
<220> FEATURE:
<221> NAME/KEY: MISC_FEATURE
<222> LOCATION: (42)..(42)
<223> OTHER INFORMATION: Xaa = Ser or Gly or Leu or Val or may not
      be present at all
<220> FEATURE:
<221> NAME/KEY: MISC_FEATURE
<222> LOCATION: (43)..(43)
<223> OTHER INFORMATION: Xaa = Glu or Pro or His or may not
      be present at all
<220> FEATURE:
<221> NAME/KEY: MISC_FEATURE
<222> LOCATION: (44)..(44)
<223> OTHER INFORMATION: Xaa = Ala or Pro or may not be present at all
<220> FEATURE:
<221> NAME/KEY: MISC_FEATURE
<222> LOCATION: (45)..(45)
<223> OTHER INFORMATION: Xaa = Arg or Asn or may not be present at all
<220> FEATURE:
<221> NAME/KEY: MISC_FEATURE
<222> LOCATION: (46)..(46)
<223> OTHER INFORMATION: Xaa = Val or Asn or may not be present at all
<220> FEATURE:
<221> NAME/KEY: MISC_FEATURE
<222> LOCATION: (47)..(47)
<223> OTHER INFORMATION: Xaa = Ile or Trp or Glu or Arg or Thr or Tyr
      or Phe or His or Leu or Ser or may not be present at all
<220> FEATURE:
```

```
<221> NAME/KEY: MISC_FEATURE
<222> LOCATION: (48)..(48)
<223> OTHER INFORMATION: Xaa = Ala or Ser or Gly or Phe or Met or Leu
      or Tyr or Thr or His or Val or may not be present at all
<220> FEATURE:
<221> NAME/KEY: MISC_FEATURE
<222> LOCATION: (49)..(49)
<223> OTHER INFORMATION: Xaa = Val or Ile or Leu or Ser or His or
      Asn or Lys or Arg or Met or Phe or Ala or Gln or Thr or Asp or
      Glu or Trp or Tyr or may not be present at all
<220> FEATURE:
<221> NAME/KEY: MISC_FEATURE
<222> LOCATION: (50)..(50)
<223> OTHER INFORMATION: Xaa = Asn or Asp or Lys or Arg or Gly
      or Ser or Leu
<220> FEATURE:
<221> NAME/KEY: MISC_FEATURE
<222> LOCATION: (51)..(51)
<223> OTHER INFORMATION: Xaa = Leu or Phe or Tyr or Thr or His or Asp
      or Ile or Ser or Trp or Val
<220> FEATURE:
<221> NAME/KEY: MISC_FEATURE
<222> LOCATION: (52)..(52)
<223> OTHER INFORMATION: Xaa = Asp or Ala or Arg or Ser or Glu or Gly
      or Thr
<220> FEATURE:
<221> NAME/KEY: MISC_FEATURE
<222> LOCATION: (53)..(53)
<223> OTHER INFORMATION: Xaa = Gly or Asp or His or Arg or Phe or Glu or
      Lys or Cys or Thr
<220> FEATURE:
<221> NAME/KEY: MISC_FEATURE
<222> LOCATION: (54)..(54)
<223> OTHER INFORMATION: Xaa = Asp or Arg or Lys or Leu or Glu or Thr
      or Ser or His or Gln or Cys or Ala or Tyr or Phe
<220> FEATURE:
<221> NAME/KEY: MISC_FEATURE
<222> LOCATION: (55)..(55)
<223> OTHER INFORMATION: Xaa = Gly or Asp or Arg or Glu or His or Ser
      or Asn or Ala or Pro or may not be present at all
<220> FEATURE:
<221> NAME/KEY: MISC_FEATURE
<222> LOCATION: (56)..(56)
<223> OTHER INFORMATION: Xaa = Ser or Gly or Cys or Ala or Leu or His
      or Trp or Gln or Glu or Asn or Thr or may not be present at all
<220> FEATURE:
<221> NAME/KEY: MISC_FEATURE
<222> LOCATION: (57)..(57)
<223> OTHER INFORMATION: Xaa = Arg or Asp or Ser or Gly or Ala or Gln
      or Cys or Thr or Arg or His or Val or Glu or may not
      be present at all
<220> FEATURE:
<221> NAME/KEY: MISC_FEATURE
<222> LOCATION: (58)..(58)
<223> OTHER INFORMATION: Xaa = Phe or Leu or Glu or Ala or Ile or Val
      or Arg or Met or may not be present at all
<220> FEATURE:
<221> NAME/KEY: MISC_FEATURE
<222> LOCATION: (59)..(59)
<223> OTHER INFORMATION: Xaa = Asp or Ser or Arg or may not be
      present at all
<220> FEATURE:
<221> NAME/KEY: MISC_FEATURE
<222> LOCATION: (60)..(60)
<223> OTHER INFORMATION: Xaa = Asp or may not be present at all
<220> FEATURE:
<221> NAME/KEY: MISC_FEATURE
<222> LOCATION: (61)..(61)
<223> OTHER INFORMATION: Xaa = Gln or Ala or may not be present at all
<220> FEATURE:
<221> NAME/KEY: MISC_FEATURE
<222> LOCATION: (62)..(62)
<223> OTHER INFORMATION: Xaa = Arg or Thr or may not be present at all
<220> FEATURE:
<221> NAME/KEY: MISC_FEATURE
<222> LOCATION: (63)..(63)
<223> OTHER INFORMATION: Xaa = Glu or Gln or may not be present at all
<220> FEATURE:
<221> NAME/KEY: MISC_FEATURE
```

```
<222> LOCATION: (64)..(64)
<223> OTHER INFORMATION: Xaa = Gln or may not be present at all
<220> FEATURE:
<221> NAME/KEY: MISC_FEATURE
<222> LOCATION: (65)..(65)
<223> OTHER INFORMATION: Xaa = Phe or Tyr or may not be present at all
<220> FEATURE:
<221> NAME/KEY: MISC_FEATURE
<222> LOCATION: (66)..(66)
<223> OTHER INFORMATION: Xaa = Tyr or may not be present at all
<220> FEATURE:
<221> NAME/KEY: MISC_FEATURE
<222> LOCATION: (67)..(67)
<223> OTHER INFORMATION: Xaa = Trp or Leu or may not be present at all
<220> FEATURE:
<221> NAME/KEY: MISC_FEATURE
<222> LOCATION: (68)..(68)
<223> OTHER INFORMATION: Xaa = His or may not be present at all
<220> FEATURE:
<221> NAME/KEY: MISC_FEATURE
<222> LOCATION: (69)..(69)
<223> OTHER INFORMATION: Xaa = Arg or Ala or may not be present at all
<220> FEATURE:
<221> NAME/KEY: MISC_FEATURE
<222> LOCATION: (70)..(70)
<223> OTHER INFORMATION: Xaa = Phe or may not be present at all
<220> FEATURE:
<221> NAME/KEY: MISC_FEATURE
<222> LOCATION: (71)..(71)
<223> OTHER INFORMATION: Xaa = Phe or Leu or may not be present at all
<220> FEATURE:
<221> NAME/KEY: MISC_FEATURE
<222> LOCATION: (72)..(72)
<223> OTHER INFORMATION: Xaa = Ser or Phe or may not be present at all
<220> FEATURE:
<221> NAME/KEY: MISC_FEATURE
<222> LOCATION: (73)..(73)
<223> OTHER INFORMATION: Xaa = His or Gln or may not be present at all
<220> FEATURE:
<221> NAME/KEY: MISC_FEATURE
<222> LOCATION: (74)..(74)
<223> OTHER INFORMATION: Xaa = Gln or Met or may not be present at all
<220> FEATURE:
<221> NAME/KEY: MISC_FEATURE
<222> LOCATION: (75)..(75)
<223> OTHER INFORMATION: Xaa = Asp or may not be present at all
<220> FEATURE:
<221> NAME/KEY: MISC_FEATURE
<222> LOCATION: (76)..(76)
<223> OTHER INFORMATION: Xaa = Asp or Lys or may not be present at all
<220> FEATURE:
<221> NAME/KEY: MISC_FEATURE
<222> LOCATION: (77)..(77)
<223> OTHER INFORMATION: Xaa = Leu or may not be present at all
<220> FEATURE:
<221> NAME/KEY: MISC_FEATURE
<222> LOCATION: (78)..(78)
<223> OTHER INFORMATION: Xaa = Asn or Pro or Ala or Asp or Ser or Leu
      or His or may not be present at all
<220> FEATURE:
<221> NAME/KEY: MISC_FEATURE
<222> LOCATION: (79)..(79)
<223> OTHER INFORMATION: Xaa = Phe or Trp or Pro or Ser or Ala or
      Gly or Cys or Met or Leu or Val or Thr or Glu or may
      not be present at all
<220> FEATURE:
<221> NAME/KEY: MISC_FEATURE
<222> LOCATION: (80)..(80)
<223> OTHER INFORMATION: Xaa = Asp or Arg or Ala or Gly or Thr or Asn
      or Gln or Ser or Glu or Met or Lys or may not be present at all
<220> FEATURE:
<221> NAME/KEY: MISC_FEATURE
<222> LOCATION: (81)..(81)
<223> OTHER INFORMATION: Xaa = Axn or Arg or His or Ala or Glu or Cys
      or Ser or Gln or Thr or Tyr or may not be present at all
<220> FEATURE:
<221> NAME/KEY: MISC_FEATURE
<222> LOCATION: (82)..(82)
<223> OTHER INFORMATION: Xaa = Asp or Thr or Arg or Glu or Ala or Pro
```

```
          or Gln or may not be present at all
<220> FEATURE:
<221> NAME/KEY: MISC_FEATURE
<222> LOCATION: (83)..(83)
<223> OTHER INFORMATION: Xaa = Glu or Thr or Ile or Asp or Trp or Gly
      or Pro or His or Arg or Val or Leu or Gln or Asn or Tyr or
      Phe or Ala or Met
<220> FEATURE:
<221> NAME/KEY: MISC_FEATURE
<222> LOCATION: (84)..(84)
<223> OTHER INFORMATION: Xaa = Val or Leu or Ala or Met or Ser
      or Thr or Phe
<220> FEATURE:
<221> NAME/KEY: MISC_FEATURE
<222> LOCATION: (85)..(85)
<223> OTHER INFORMATION: Xaa = Arg or Gly or Glu or His or Val or Ile
      or Asp or Thr or Leu or Gln
<220> FEATURE:
<221> NAME/KEY: MISC_FEATURE
<222> LOCATION: (86)..(86)
<223> OTHER INFORMATION: Xaa = Ala or Asn or Glu or Arg or Trp or Gln
      or Asp or Val or His or Ser or Lys
<220> FEATURE:
<221> NAME/KEY: MISC_FEATURE
<222> LOCATION: (87)..(87)
<223> OTHER INFORMATION: Xaa = Phe or Tyr or Trp or Leu or Ala or Arg or
      Gly or Met or Gln
<220> FEATURE:
<221> NAME/KEY: MISC_FEATURE
<222> LOCATION: (88)..(88)
<223> OTHER INFORMATION: Xaa = Phe or Ile or Val or Leu or Met or Ala
<220> FEATURE:
<221> NAME/KEY: MISC_FEATURE
<222> LOCATION: (89)..(89)
<223> OTHER INFORMATION: Xaa = Val or Phe or Ile or Arg or Leu or Thr
      or Met or Pro or Ala
<220> FEATURE:
<221> NAME/KEY: MISC_FEATURE
<222> LOCATION: (90)..(90)
<223> OTHER INFORMATION: Xaa = Asp or His or Ala or Glu or Thr or
      Ser or Arg or Gly
<220> FEATURE:
<221> NAME/KEY: MISC_FEATURE
<222> LOCATION: (91)..(91)
<223> OTHER INFORMATION: Xaa = Asn or Asp or Thr or Val or Leu or Ala
      or Ser or Cys or Gln
<220> FEATURE:
<221> NAME/KEY: MISC_FEATURE
<222> LOCATION: (92)..(92)
<223> OTHER INFORMATION: Xaa = Ala or Val or Ile or Met or Leu
<220> FEATURE:
<221> NAME/KEY: MISC_FEATURE
<222> LOCATION: (93)..(93)
<223> OTHER INFORMATION: Xaa = Leu or Arg or Val or Ala or Glu or
      Ser or Gly or Gln or Lys
<220> FEATURE:
<221> NAME/KEY: MISC_FEATURE
<222> LOCATION: (94)..(94)
<223> OTHER INFORMATION: Xaa = Met or Gly or Tyr or His or Phe or Arg
      or Trp or Thr or may not be present at all
<220> FEATURE:
<221> NAME/KEY: MISC_FEATURE
<222> LOCATION: (95)..(95)
<223> OTHER INFORMATION: Xaa = Trp or Phe or Leu or Tyr or may not be
      present at all
<220> FEATURE:
<221> NAME/KEY: MISC_FEATURE
<222> LOCATION: (96)..(96)
<223> OTHER INFORMATION: Xaa = Leu or Val or Ile or Ala or His or may
      not be present at all
<220> FEATURE:
<221> NAME/KEY: MISC_FEATURE
<222> LOCATION: (97)..(97)
<223> OTHER INFORMATION: Xaa = Arg or Glu or Asp or Ala or Gly or His or
      Leu or Thr or Gln or Ser or Lys or Ile or Met
<220> FEATURE:
<221> NAME/KEY: MISC_FEATURE
<222> LOCATION: (98)..(98)
<223> OTHER INFORMATION: Xaa = Asp or His or Glu or Ala or Asn or Met or
```

```
            Gln or Val or Ser or Ile
<220> FEATURE:
<221> NAME/KEY: MISC_FEATURE
<222> LOCATION: (99)..(99)
<223> OTHER INFORMATION: Xaa = Tyr or Phe or Leu or Arg or Met or Cys
      or Ala or Val
<220> FEATURE:
<221> NAME/KEY: MISC_FEATURE
<222> LOCATION: (100)..(100)
<223> OTHER INFORMATION: Xaa = His or Gln or Arg or Gly or Leu or
      Lys or Asp
<220> FEATURE:
<221> NAME/KEY: MISC_FEATURE
<222> LOCATION: (101)..(101)
<223> OTHER INFORMATION: Xaa = Ile or Leu or Phe or Val
<220> FEATURE:
<221> NAME/KEY: MISC_FEATURE
<222> LOCATION: (109)..(109)
<223> OTHER INFORMATION: Xaa = Ala or may not be present at all

<400> SEQUENCE: 307

Xaa Xaa Ala Asp Xaa Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Asp Gly Phe Arg Ile Asp Ala Xaa
            100                 105

<210> SEQ ID NO 308
<211> LENGTH: 78
<212> TYPE: PRT
<213> ORGANISM: Artificial Sequence
<220> FEATURE:
<223> OTHER INFORMATION: Consensus C
<220> FEATURE:
<221> NAME/KEY: MISC_FEATURE
<222> LOCATION: (1)..(1)
<223> OTHER INFORMATION: Xaa = Val or may not be present at all
<220> FEATURE:
<221> NAME/KEY: MISC_FEATURE
<222> LOCATION: (2)..(2)
<223> OTHER INFORMATION: Xaa = Tyr or may not be present at all
<220> FEATURE:
<221> NAME/KEY: MISC_FEATURE
<222> LOCATION: (7)..(7)
<223> OTHER INFORMATION: Xaa = Phe or Ile
<220> FEATURE:
<221> NAME/KEY: MISC_FEATURE
<222> LOCATION: (10)..(10)
<223> OTHER INFORMATION: Xaa = Phe or Leu or Thr
<220> FEATURE:
<221> NAME/KEY: MISC_FEATURE
<222> LOCATION: (11)..(11)
<223> OTHER INFORMATION: Xaa = Gly or Ala
<220> FEATURE:
<221> NAME/KEY: MISC_FEATURE
<222> LOCATION: (12)..(12)
<223> OTHER INFORMATION: Xaa = Pro or Ala
<220> FEATURE:
<221> NAME/KEY: MISC_FEATURE
<222> LOCATION: (13)..(13)
<223> OTHER INFORMATION: Xaa = Thr or Asp or Ala or Glu or Ser
<220> FEATURE:
```

-continued

```
<221> NAME/KEY: MISC_FEATURE
<222> LOCATION: (14)..(14)
<223> OTHER INFORMATION: Xaa = Gly or Ser
<220> FEATURE:
<221> NAME/KEY: MISC_FEATURE
<222> LOCATION: (15)..(15)
<223> OTHER INFORMATION: Xaa = Gln or may not be present at all
<220> FEATURE:
<221> NAME/KEY: MISC_FEATURE
<222> LOCATION: (16)..(16)
<223> OTHER INFORMATION: Xaa = Ala or may not be present at all
<220> FEATURE:
<221> NAME/KEY: MISC_FEATURE
<222> LOCATION: (17)..(17)
<223> OTHER INFORMATION: Xaa = Gly or may not be present at all
<220> FEATURE:
<221> NAME/KEY: MISC_FEATURE
<222> LOCATION: (18)..(18)
<223> OTHER INFORMATION: Xaa = Thr or may not be present at all
<220> FEATURE:
<221> NAME/KEY: MISC_FEATURE
<222> LOCATION: (19)..(19)
<223> OTHER INFORMATION: Xaa = Asn or Cys or Ser
<220> FEATURE:
<221> NAME/KEY: MISC_FEATURE
<222> LOCATION: (20)..(20)
<223> OTHER INFORMATION: Xaa = Tyr or Trp or Phe or Val
<220> FEATURE:
<221> NAME/KEY: MISC_FEATURE
<222> LOCATION: (21)..(21)
<223> OTHER INFORMATION: Xaa = Leu or Ile or Ala
<220> FEATURE:
<221> NAME/KEY: MISC_FEATURE
<222> LOCATION: (22)..(22)
<223> OTHER INFORMATION: Xaa = Glu or Ala or Arg or His or Gly or Asp
<220> FEATURE:
<221> NAME/KEY: MISC_FEATURE
<222> LOCATION: (23)..(23)
<223> OTHER INFORMATION: Xaa = Ala or Lys or Gln or Glu or Arg
<220> FEATURE:
<221> NAME/KEY: MISC_FEATURE
<222> LOCATION: (24)..(24)
<223> OTHER INFORMATION: Xaa = Phe or Tyr or Ile
<220> FEATURE:
<221> NAME/KEY: MISC_FEATURE
<222> LOCATION: (25)..(25)
<223> OTHER INFORMATION: Xaa = Ser or Gly or Thr or Ala or Val
<220> FEATURE:
<221> NAME/KEY: MISC_FEATURE
<222> LOCATION: (26)..(26)
<223> OTHER INFORMATION: Xaa = Pro or Arg or Gly or Cys or may not be
      present at all
<220> FEATURE:
<221> NAME/KEY: MISC_FEATURE
<222> LOCATION: (27)..(27)
<223> OTHER INFORMATION: Xaa = His or Pro or Ser or Glu or Asp or Gly
<220> FEATURE:
<221> NAME/KEY: MISC_FEATURE
<222> LOCATION: (28)..(28)
<223> OTHER INFORMATION: Xaa = Tyr or Phe
<220> FEATURE:
<221> NAME/KEY: MISC_FEATURE
<222> LOCATION: (29)..(29)
<223> OTHER INFORMATION: Xaa = Val or Phe or Tyr
<220> FEATURE:
<221> NAME/KEY: MISC_FEATURE
<222> LOCATION: (30)..(30)
<223> OTHER INFORMATION: Xaa = Ser or Ala or Thr or Gln
<220> FEATURE:
<221> NAME/KEY: MISC_FEATURE
<222> LOCATION: (31)..(31)
<223> OTHER INFORMATION: Xaa = Lys or Glu or Ala or Asp or Arg
<220> FEATURE:
<221> NAME/KEY: MISC_FEATURE
<222> LOCATION: (32)..(32)
<223> OTHER INFORMATION: Xaa = Lys or Arg or Gln or Leu
<220> FEATURE:
<221> NAME/KEY: MISC_FEATURE
<222> LOCATION: (33)..(33)
```

```
<223> OTHER INFORMATION: Xaa = His or Tyr or Leu or may not be
      present at all
<220> FEATURE:
<221> NAME/KEY: MISC_FEATURE
<222> LOCATION: (34)..(34)
<223> OTHER INFORMATION: Xaa = Ala or Gln or Gly or Lys or Glu
<220> FEATURE:
<221> NAME/KEY: MISC_FEATURE
<222> LOCATION: (35)..(35)
<223> OTHER INFORMATION: Xaa = Thr or Ser or Asn or Asp
<220> FEATURE:
<221> NAME/KEY: MISC_FEATURE
<222> LOCATION: (36)..(36)
<223> OTHER INFORMATION: Xaa = Glu or Pro or Asp or Gly
<220> FEATURE:
<221> NAME/KEY: MISC_FEATURE
<222> LOCATION: (37)..(37)
<223> OTHER INFORMATION: Xaa = Trp or Ser
<220> FEATURE:
<221> NAME/KEY: MISC_FEATURE
<222> LOCATION: (38)..(38)
<223> OTHER INFORMATION: Xaa = Gly or Val
<220> FEATURE:
<221> NAME/KEY: MISC_FEATURE
<222> LOCATION: (39)..(39)
<223> OTHER INFORMATION: Xaa = Glu or Arg or Pro or Asp or Gln or
      Leu or Ala
<220> FEATURE:
<221> NAME/KEY: MISC_FEATURE
<222> LOCATION: (40)..(40)
<223> OTHER INFORMATION: Xaa = Ser or Ala or Gly or Asn
<220> FEATURE:
<221> NAME/KEY: MISC_FEATURE
<222> LOCATION: (41)..(41)
<223> OTHER INFORMATION: Xaa = Leu or Ile or Val or Ser
<220> FEATURE:
<221> NAME/KEY: MISC_FEATURE
<222> LOCATION: (42)..(42)
<223> OTHER INFORMATION: Xaa = Asn or Thr
<220> FEATURE:
<221> NAME/KEY: MISC_FEATURE
<222> LOCATION: (43)..(43)
<223> OTHER INFORMATION: Xaa = Phe or Leu or Tyr or Cys
<220> FEATURE:
<221> NAME/KEY: MISC_FEATURE
<222> LOCATION: (44)..(44)
<223> OTHER INFORMATION: Xaa = Asp or Cys
<220> FEATURE:
<221> NAME/KEY: MISC_FEATURE
<222> LOCATION: (45)..(45)
<223> OTHER INFORMATION: Xaa = Gly or Asp or Ser
<220> FEATURE:
<221> NAME/KEY: MISC_FEATURE
<222> LOCATION: (46)..(46)
<223> OTHER INFORMATION: Xaa = Glu or Pro or Arg or Lys or Leu or Asn
<220> FEATURE:
<221> NAME/KEY: MISC_FEATURE
<222> LOCATION: (47)..(47)
<223> OTHER INFORMATION: Xaa = Ser or His or Gly or Arg or Asp or Thr
<220> FEATURE:
<221> NAME/KEY: MISC_FEATURE
<222> LOCATION: (48)..(48)
<223> OTHER INFORMATION: Xaa = Ala or Ser or Cys
<220> FEATURE:
<221> NAME/KEY: MISC_FEATURE
<222> LOCATION: (49)..(49)
<223> OTHER INFORMATION: Xaa = Gly or Ala or Thr or Asp or Arg or Gln
<220> FEATURE:
<221> NAME/KEY: MISC_FEATURE
<222> LOCATION: (50)..(50)
<223> OTHER INFORMATION: Xaa = Pro or Gly or Asp or Glu or Thr or His
<220> FEATURE:
<221> NAME/KEY: MISC_FEATURE
<222> LOCATION: (51)..(51)
<223> OTHER INFORMATION: Xaa = Asn or may not be present at all
<220> FEATURE:
<221> NAME/KEY: MISC_FEATURE
<222> LOCATION: (52)..(52)
<223> OTHER INFORMATION: Xaa = Ala or may not be present at all
```

```
<220> FEATURE:
<221> NAME/KEY: MISC_FEATURE
<222> LOCATION: (53)..(53)
<223> OTHER INFORMATION: Xaa = Met or may not be present at all
<220> FEATURE:
<221> NAME/KEY: MISC_FEATURE
<222> LOCATION: (54)..(54)
<223> OTHER INFORMATION: Xaa = Val or Met
<220> FEATURE:
<221> NAME/KEY: MISC_FEATURE
<222> LOCATION: (55)..(55)
<223> OTHER INFORMATION: Xaa = Arg or Gly
<220> FEATURE:
<221> NAME/KEY: MISC_FEATURE
<222> LOCATION: (56)..(56)
<223> OTHER INFORMATION: Xaa = Glu or Ala or Asn or Asp or Trp or Lys
<220> FEATURE:
<221> NAME/KEY: MISC_FEATURE
<222> LOCATION: (57)..(57)
<223> OTHER INFORMATION: Xaa = Phe or Tyr or Trp or Leu
<220> FEATURE:
<221> NAME/KEY: MISC_FEATURE
<222> LOCATION: (58)..(58)
<223> OTHER INFORMATION: Xaa = Val or Phe or Leu
<220> FEATURE:
<221> NAME/KEY: MISC_FEATURE
<222> LOCATION: (59)..(59)
<223> OTHER INFORMATION: Xaa = Thr or Val or Ile or Phe or Leu
<220> FEATURE:
<221> NAME/KEY: MISC_FEATURE
<222> LOCATION: (60)..(60)
<223> OTHER INFORMATION: Xaa = Thr or Ala or Glu or Asp or His or Ser
<220> FEATURE:
<221> NAME/KEY: MISC_FEATURE
<222> LOCATION: (61)..(61)
<223> OTHER INFORMATION: Xaa = Asn or Ser
<220> FEATURE:
<221> NAME/KEY: MISC_FEATURE
<222> LOCATION: (62)..(62)
<223> OTHER INFORMATION: Xaa = Ala or Val
<220> FEATURE:
<221> NAME/KEY: MISC_FEATURE
<222> LOCATION: (63)..(63)
<223> OTHER INFORMATION: Xaa = Ala or Ser or Leu or Arg or Glu or Val
<220> FEATURE:
<221> NAME/KEY: MISC_FEATURE
<222> LOCATION: (64)..(64)
<223> OTHER INFORMATION: Xaa = His or Tyr or Gly or Met or Thr
<220> FEATURE:
<221> NAME/KEY: MISC_FEATURE
<222> LOCATION: (66)..(66)
<223> OTHER INFORMATION: Xaa = Ile or Val or Ala
<220> FEATURE:
<221> NAME/KEY: MISC_FEATURE
<222> LOCATION: (67)..(67)
<223> OTHER INFORMATION: Xaa = Arg or Glu or His or Ala or Asp or Lys
<220> FEATURE:
<221> NAME/KEY: MISC_FEATURE
<222> LOCATION: (68)..(68)
<223> OTHER INFORMATION: Xaa = Glu or His
<220> FEATURE:
<221> NAME/KEY: MISC_FEATURE
<222> LOCATION: (69)..(69)
<223> OTHER INFORMATION: Xaa = Tyr or Phe
<220> FEATURE:
<221> NAME/KEY: MISC_FEATURE
<222> LOCATION: (70)..(70)
<223> OTHER INFORMATION: Xaa = His or Lys
<220> FEATURE:
<221> NAME/KEY: MISC_FEATURE
<222> LOCATION: (71)..(71)
<223> OTHER INFORMATION: Xaa = Leu or Val or Phe

<400> SEQUENCE: 308

Xaa Xaa Ala Asp Val Val Xaa Asn His Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
```

-continued

```
                 20                  25                  30
Xaa Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa
         50                  55                  60

Trp Xaa Xaa Xaa Xaa Xaa Xaa Asp Gly Phe Arg Ile Asp Ala
65                  70                  75
```

<210> SEQ ID NO 309
<211> LENGTH: 27
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (20)..(21)
<223> OTHER INFORMATION: w = a or t

<400> SEQUENCE: 309
ggtctacgcc gacgtcgtsw wcaacca                                      27

<210> SEQ ID NO 310
<211> LENGTH: 24
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (16)..(16)
<223> OTHER INFORMATION: s = c or g
<220> FEATURE:
<221> NAME/KEY: misc_feature
<222> LOCATION: (23)..(23)
<223> OTHER INFORMATION: r = a or g

<400> SEQUENCE: 310
cgtcgacggc ttccgsatcg acrc                                         24

<210> SEQ ID NO 311
<211> LENGTH: 21
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (16)..(16)
<223> OTHER INFORMATION: s = c or g

<400> SEQUENCE: 311
ggcgtcgatg cggaasccgt c                                            21

<210> SEQ ID NO 312
<211> LENGTH: 25
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (20)..(20)
<223> OTHER INFORMATION: s = c or g
<220> FEATURE:
<221> NAME/KEY: misc_feature
<222> LOCATION: (24)..(24)
<223> OTHER INFORMATION: w = a or t

```
<400> SEQUENCE: 312
gctcggtgtc gtggttgtcs acgwa                                25

<210> SEQ ID NO 313
<211> LENGTH: 24
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (16)..(16)
<223> OTHER INFORMATION: n = a, c, g or t
<220> FEATURE:
<221> NAME/KEY: misc_feature
<222> LOCATION: (17)..(17)
<223> OTHER INFORMATION: w = a or t
<220> FEATURE:
<221> NAME/KEY: misc_feature
<222> LOCATION: (19)..(19)
<223> OTHER INFORMATION: h = a or c or t
<220> FEATURE:
<221> NAME/KEY: misc_feature
<222> LOCATION: (22)..(22)
<223> OTHER INFORMATION: y = c or t

<400> SEQUENCE: 313
gtacgccgac gccgtnwtha ayca                                 24

<210> SEQ ID NO 314
<211> LENGTH: 29
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (16)..(16)
<223> OTHER INFORMATION: n = a, c, g or t
<220> FEATURE:
<221> NAME/KEY: misc_feature
<222> LOCATION: (17)..(17)
<223> OTHER INFORMATION: r = a or g
<220> FEATURE:
<221> NAME/KEY: misc_feature
<222> LOCATION: (20)..(20)
<223> OTHER INFORMATION: n = a, c, g or t
<220> FEATURE:
<221> NAME/KEY: misc_feature
<222> LOCATION: (23)..(23)
<223> OTHER INFORMATION: r = a or g

<400> SEQUENCE: 314
gggcggcgtc gatcckraan ccrtcrvrs                            29

<210> SEQ ID NO 315
<211> LENGTH: 27
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (19)..(20)
<223> OTHER INFORMATION: y = c or t
<220> FEATURE:
<221> NAME/KEY: misc_feature
<222> LOCATION: (22)..(22)
<223> OTHER INFORMATION: n = a, c, g or t
<220> FEATURE:
<221> NAME/KEY: misc_feature
<222> LOCATION: (25)..(25)
<223> OTHER INFORMATION: n = a, c, g or t
```

```
<400> SEQUENCE: 315
cgacgtggtg ttcaaccayy tnggncc                                        27

<210> SEQ ID NO 316
<211> LENGTH: 26
<212> TYPE: DNA
<213> ORGANISM: Artificial Sequence
<220> FEATURE:
<223> OTHER INFORMATION: PCR Primer
<220> FEATURE:
<221> NAME/KEY: misc_feature
<222> LOCATION: (18)..(18)
<223> OTHER INFORMATION: y = c or t
<220> FEATURE:
<221> NAME/KEY: misc_feature
<222> LOCATION: (21)..(22)
<223> OTHER INFORMATION: y = c or t
<220> FEATURE:
<221> NAME/KEY: misc_feature
<222> LOCATION: (24)..(24)
<223> OTHER INFORMATION: n = a, c, g or t

<400> SEQUENCE: 316
gccgacgtgg tgttcaayca yytngg                                         26

<210> SEQ ID NO 317
<211> LENGTH: 16
<212> TYPE: DNA
<213> ORGANISM: Artificial Sequence
<220> FEATURE:
<223> OTHER INFORMATION: M13 forward primer

<400> SEQUENCE: 317
gtaaaacgac ggccag                                                    16

<210> SEQ ID NO 318
<211> LENGTH: 17
<212> TYPE: DNA
<213> ORGANISM: Artificial Sequence
<220> FEATURE:
<223> OTHER INFORMATION: M13 reverse primer

<400> SEQUENCE: 318
caggaaacag ctatgac                                                   17

<210> SEQ ID NO 319
<211> LENGTH: 20
<212> TYPE: DNA
<213> ORGANISM: Artificial Sequence
<220> FEATURE:
<223> OTHER INFORMATION: TopoF primer

<400> SEQUENCE: 319
gctcggatcc actagtaacg                                                20

<210> SEQ ID NO 320
<211> LENGTH: 19
<212> TYPE: DNA
<213> ORGANISM: Artificial Sequence
<220> FEATURE:
<223> OTHER INFORMATION: TopoR primer

<400> SEQUENCE: 320
ctctagatgc atgctcgag                                                 19
```